US012735496B2

(12) United States Patent
Orengo et al.

(10) Patent No.: US 12,735,496 B2
(45) Date of Patent: Sep. 15, 2026

(54) METHODS OF TREATING AN INTERLEUKIN-2 RECEPTOR GAMMA-MEDIATED DISEASE OR CONDITION BY ADMINISTERING AN IL2 RECEPTOR GAMMA ANTIBODY

(71) Applicant: Regeneron Pharmaceuticals, Inc., Tarrytown, NY (US)

(72) Inventors: Jamie M. Orengo, Cortlandt Manor, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 712 days.

(21) Appl. No.: 18/169,345

(22) Filed: Feb. 15, 2023

(65) Prior Publication Data

US 2023/0279131 A1 Sep. 7, 2023

Related U.S. Application Data

(62) Division of application No. 16/776,928, filed on Jan. 30, 2020, now Pat. No. 11,629,195.

(60) Provisional application No. 62/799,851, filed on Feb. 1, 2019.

(51) Int. Cl.

| | |
|---|---|
| ***C07K 16/28*** | (2006.01) |
| ***A61K 9/00*** | (2006.01) |
| ***A61K 39/395*** | (2006.01) |
| ***A61P 37/06*** | (2006.01) |
| ***C12N 15/63*** | (2006.01) |

(52) U.S. Cl.

CPC ........ *C07K 16/2866* (2013.01); *A61K 9/0019* (2013.01); *A61K 39/3955* (2013.01); *A61P 37/06* (2018.01); *C12N 15/63* (2013.01); *C07K 2317/31* (2013.01); *C07K 2317/565* (2013.01); *C07K 2317/92* (2013.01)

(58) Field of Classification Search

CPC ............ C07K 16/2866; C07K 2317/31; C07K 2317/565; C07K 2317/92; C07K 2317/21; C07K 2317/33; C07K 2317/76; A61K 9/0019; A61K 39/3955; A61K 2039/505; A61K 45/06; A61P 37/06; C12N 15/63

See application file for complete search history.

(56) References Cited

U.S. PATENT DOCUMENTS

| | | | |
|---|---|---|---|
| 4,399,216 | A | 8/1983 | Axel et al. |
| 4,740,461 | A | 4/1988 | Kaufman |
| 4,816,567 | A | 3/1989 | Cabilly et al. |
| 4,912,040 | A | 3/1990 | Kaufman et al. |
| 4,952,496 | A | 8/1990 | Studier et al. |
| 4,959,455 | A | 9/1990 | Clark et al. |
| 5,168,062 | A | 12/1992 | Stinski |
| 5,385,839 | A | 1/1995 | Stinski |
| 5,510,259 | A | 4/1996 | Sugamura et al. |
| 5,693,489 | A | 12/1997 | Studier et al. |
| 6,323,027 | B1 | 11/2001 | Burkly et al. |
| 6,576,236 | B1 | 6/2003 | Boussiotis et al. |
| 6,596,541 | B2 | 7/2003 | Murphy et al. |
| 6,770,745 | B2 | 8/2004 | Burkly et al. |
| 7,816,091 | B2 | 10/2010 | Ruben et al. |
| 8,697,396 | B2 | 4/2014 | Dall'Acqua et al. |
| 2002/0028202 | A1 | 3/2002 | Burkly et al. |
| 2011/0250213 | A1 | 10/2011 | Tso et al. |
| 2014/0134162 | A1 | 5/2014 | Stavenhagen et al. |
| 2014/0171623 | A1 | 6/2014 | Dall'Acqua et al. |
| 2014/0243504 | A1 | 8/2014 | Davis et al. |

FOREIGN PATENT DOCUMENTS

| | | | |
|---|---|---|---|
| EP | 3172227 | A2 | 5/2017 |
| KR | 20080032046 | A | 4/2008 |
| WO | 1996001122 | A1 | 1/1996 |
| WO | 1997017360 | A2 | 5/1997 |
| WO | 1997043416 | A1 | 11/1997 |
| WO | 2001077288 | A2 | 10/2001 |
| WO | 2012096994 | A2 | 7/2012 |
| WO | 2014043361 | A1 | 3/2014 |
| WO | 2015109212 | A1 | 7/2015 |
| WO | 2017021540 | A1 | 2/2017 |
| WO | 2017220989 | A1 | 12/2017 |
| WO | 2018156649 | A1 | 8/2018 |

OTHER PUBLICATIONS

R&D Systems(TM) (2015) "Common gamma-Chain Family Cytokines Play a Pivotal Role in Regulating Immune System Functions". (https://www.mdsystems.com/resources/posters/common-gamma-chain-family-cytokines-play-pivotal-role-regulating-immune-system-functions).*

Remington's Pharmaceutical Sciences and U.S. Pharmacopeia: National Formulary, Mack Publishing Company, Easton, Pa. (1984).

Rochman et al., "New insights into the regulation of T cells by gamma(c) family cytokines". Nat Rev Immunol. (2009), 9(7): 480-90.

Rudikoff et al., "Single amino acid substitution altering antigen-binding specificity", Proc. Natl. Acad. Sco, USA, (1982), 79(6):1979-1983.

Schwartz et al., "Matrices for detecting distant relationships." in Atlas of Protein Sequence and Structure, (1978) 5 (suppl. 3): 353-58, .M. O. Dayhoff (ed.), Natl. Biomed. Res. Found., Washington, D.C.

States et al., "Improved Sensitivity of Nucleic Acid Database Searches Using Application-Specific Scoring Matrices", Methods (1991), 3: 66-70.

Studier et al., "Use of bacteriophage T7 RNA polymerase to direct selective high-level expression of cloned genes", J. Mol. Biol. (1986), 189(1): 113-30.

(Continued)

*Primary Examiner* — Robert S Landsman

(74) *Attorney, Agent, or Firm* — Fox Rothschild LLP; Lisa D. Flanagan

(57) ABSTRACT

The present invention provides antibodies and antigen-binding fragments (e.g., human antibodies) that bind specifically to human IL2 receptor gamma (IL2Rγ). Methods for treating or preventing diseases mediated by IL2Rγ (e.g., graft vs host disease) using the antibodies and fragments are also provided along with methods of making the antibodies and fragments.

25 Claims, 23 Drawing Sheets

Specification includes a Sequence Listing.

(56) References Cited

OTHER PUBLICATIONS

Takeshita et al., "Cloning of the Gamma Chain of the Human IL-2 Receptor", Science (1992), 257(5068): 379-382.
Tashkin et al., "Role of eosinophils in airway inflammation of chronic obstructive pulmonary disease", Int J Chron Obstruct Pulmon Dis. (2018), 13: 335-349.
Thomson Healthcare; 57th edition (Nov. 1, 2002).
Tomer et al., "Characterization of a Discontinuous Epitope of the Human Immunodeficiency Virus (HIV) Core Protein 624 by Epitope Excision and Differential Chemical Modification Followed by Mass Spectrometric Peptide Mapping Analysis", Prot. Sci. (2000), 9: 487-496.
Viia-Komaroff et al., "A bacterial clone synthesizing proinsulin", Proc. Natl. Acad. Sci. USA (1978), 75:3727-3731 (Abstract).
Villa-Komaroff, "Useful proteins from recombinant bacteria", Sci Am (1980), 242: 74-94.
Wagner et al., "Nucleotide sequence of the thymidine kinase gene of herpes simplex virus type 1", Proc. Natl. Acad. Sci. USA (1981), 78:1441-1445.
Watson et al., "Molecular Biology of the Gene" (4th Ed.), The Benjamin/Cummings Pub. Co., (1987) p. 224.
Weiner et al., "Excipient Toxicity and Safety", Marcel Dekker, Inc., (2000) New York, N.Y.
Wootton et al., "Statistics of Local Complexity in Amino Acid Sequences and Sequence Databases", Comput. Chem. (1993), 17: 149-163.
Yamamoto et al., "Identification of a functional promoter in the long terminal repeat of Rous sarcoma virus", Cell (1980), 22:787-797 (Abstract).
Yang et al., "Therapeutic potential of IL-15 in rheumatoid arthritis", Hum Immunol. (2015), 76(11): 812-8.
Zhang et al., "PowerBLAST: A New Network BLAST Application of INteractive or Automated Sequence Analysis and Annotation" Genome Res. (1997), 7: 649-656.
Altschul et al., "Protein Databse Searches Using Compositionally Adjusted Substitution Matrices", (2005) FEBS J. 272(20): 5101-5109.
Altschul, "Evaluating the statistical significance of multiple distinct local alignments." in Theoretical and Computational Methods in Genome Research (S. Suhai, ed.), (1997) pp. 1-14, Plenum, N.Y.
Altschul, "Amino acid substitution matrices from an information theoretic perspective", J. Mol. Biol. (1991), 219: 555-565.
Altschul et al., "Basic local alignment search tool", (1990) J. Mol. Biol. 215: 403-410.
Altschul et al., "Gapped BLAST and PSI-BLAST: a new generation of protein database search programs", (1997) Nucleic Acids Res. 25: 3389-3402.
Altschul et al.,, "A Protein Alignment Scoring System Sensitve at All Evolutionary Distances", (1993) J. Mol. Evol. 36: 290-300.
Angal et al. A single amino acid substitution abolishes the heterogeneity of chimeric mouse/human (lgG4) antibody, Mol Immunol. (1993), 30(1): 105-108.
Avis et al. (eds.) "Pharmaceutical Dosage Forms: Parenteral Medications", (1993) Marcel Dekker, NY (Synopsis only).
Baldassari & Rose, "Daclizumab: Development, Clinical Trials, and Practical Aspects of Use in Multiple Sclerosis", Neurotherapeutics (2017), 14(4): 842-858.
Benoist et al., "In vivo sequence requirements of the SV40 early promoter region", Nature (1981), 290: 304-310 (Abstract).
Brinster et al., "Regulation of metallothionein—thymidine kinase fusion plasmids injected into mouse eggs", Nature (1992), 296: 39-42 (Abstract).
Brorson et al., "Mutational Analysis of Avidity and Fine Specificity of Anti-Levan Antibodies", J. Immunol (1999), 163: 6694-6701.
Brummell et al., "Probing the combining stie of an anti-carbohydrate antibody by saturation-mutagenesis: role of the heavy-chain CDR3 residues", Biochemistry (1993), 32(4): 1180-87.
Buzney et al., "Asthma and Atopic Dermatitis: A Review of Targeted Inhibition of Interleukin-4 and Interleukin-13 as Therapy for Atopic Disease", J Drugs Dermatol. (2016), 15(2):165-71.
Casset et al., "A peptide mimetic of an anti-CD4 monoclonal anitbody by rational design", Biochemical and Biophysical Research Communications (2003), 307:198-205.
Coleman, "Effects of amino acid sequence changes on antibody-antigen interactions", Research In Immunol. (1994), 145-33-36.
Dantas et al., "Increased Serum Interleukin-9 Levels in Rheumatoid Arthritis and Systemic Lupus Erythematosus: Pathogenic Role or Just an Epiphenomenon?", Dis Markers. (2015), 2015:2015: 519638.
Dayhoff et al., "A model of evolutionary change in proteins." in Atlas of Protein Sequence and Structure, (1978) 5 (suppl. 3): 345-52. M. O. Dayhoff (ed.), Natl. Biomed. Res. Found., Washington, D.C.
Deboer et al., "The tac promoter: a functional hybrid derived from the trp and lac promoters" Proc. Natl. Acad. Sci. USA (1983), 80:21-25.
Dembo et al., "Limit Distribution of Maximal Non-Aligned Two-Sequence Segmental Score", Ann. Prob. (1994), 22: 2022-2039.
Dinesh et al., "Multifaceted role of IL-21 in rheumatoid arthritis: Current understanding and future perspectives", J Cell Physiol. (2018), 233(5): 3918-3928.
Ehring, "Hydrogen Enchange/Electrospray Ionization Mass Spectrometry Studies of Structural Features of Proteins and Protein/Protein Interactions", Analytical Biochemistry (1999), 267: 252-259.
Engen et al., "Investigating protein structure and dynamics by hydrogen exchange MS", Anal. Chem. (2001), 73: 256A-265A.
Generoso et al., "Prospects for Monoclonal Antibody Therapy in Pediatric Asthma", Curr Allergy Asthma Rep. (2018), 18(9):45.
Gennaro "Remington: The Science and Practice of Pharmacy", (2000) Lippincott, Williams, and Wilkins, New York, N.Y. (Abstract).
Gish et al., "Identification of protein coding regions by database similarity search", Nature Genet (1993),. 3: 266-272 (Abstract).
Goldsby, "Immunlogy", 5th ed, 2003, pp. 82-84.
Gonnet et al., "Exhaustive Matching of the Entire Protein Sequence Database", Science (1992), 256: 1443-45.
Hancock et al., "SIMPLE34: an improved and enhanced implementation for VAX and Sun computers of the SIMPLE algorithm for analysis of clustered repetitive motifs in nucleotide sequences", Comput. Appl. Biosci. (1994), 10: 67-70 (Abstract).
Hardman et al., "Goodman & Gilman's The Pharmacological Basis of Therapeutics", 10th Edition, McGraw-Hill, NY (2001) (Abstract).
He et al., "Expression and Function of the Gamma Subunit of the IL-2, IL-4, and IL-7 Receptors", J. of Immunology, American Assoc of Immunologists, US (1995), 154(4): 1596-1605.
Hechinger et al., "Therapeutic Activity of Multiple Common g-Chain Cytokine Inhibition in Acute and Chronic GVHD", Blood (2015), 125(3): 570-580.
Henikoff et al., "Amino Acid Substitution Matrices From Protein Blocks", Proc. Natl. Acad. Sci. USA (1992), 89:10915-10919.
Holm et al., "Evaluating IL-21 as a Potential Therapeutic Target in Crohn's Disease", Gastroenterol Res Pract. (2018) 2018: 5962624.
Hughes-Austin et al., "Multiple cytokines and chemokines are associated with rheumatoid arthritis-related autoimmunity in first-degree relatives without rheumatoid arthritis: Studies of the Aetiology of Rheumatoid Arthritis (SERA)", Ann Rheum Dis (2013),;72(6): 901-7.
International Search Report and Written Opinion dated Jul. 20, 2020 for PCT/US2020/015841.
Karlin et al., "Applications and Statistics for Multiple High-Scoring Segments in Molecular Sequences", Proc. Natl. Acad. Sci. USA (1993), 90: 5873-5877.
Karlin et al., "Methods for Assessing the Statistical Significance of Molecular Sequence Features by Using General Scoring Schemes", Proc. Natl. Acad. Sci. USA (1990), 87: 2264-2268.
Kobayashi et al., Tryptophan H33 plays an important role in pyrimidine (6-4) pyrimidone photoproduct binding by a high-affinity antibody, Protein Engineering (1999), 12(10): 879-884.
Lesiak et al., "Are interleukin-15 and -22 a new pathogenic factor in pustular palmoplantar psoriasis?", Postepy Dermatol Alergol. (2016), 33(5): 336-339.
Lieberman et al. (eds.) "Pharmaceutical Dosage Forms: Disperse Systems" (1990) Marcel Dekker, NY.

(56) References Cited

OTHER PUBLICATIONS

Lieberman, et al. (eds.) "Pharmaceutical Dosage Forms: Tablets", (1990) Marcel Dekker, NY (Abstract).
Lloyd et al.. , "Epigenetic Control of Interleukin-9 in Asthma", N Engl J Med. (2018), 379(1): 87-89.
Madden et al., "Applications of network BLAST server", Meth. Enzymol. (1996), 266: 131-141.
Neurath et al., "IL-9 signaling as key driver of chronic inflammation in mucosal immunity", Cytokine Growth Factor Rev. (2016), 29: 93-9.
Olosz et al., "Structural basis for binding multiple ligands by the common cytokine receptor gamma-chain", J Biol Chem. (2002), 277(14): 12047-52.
Pathak, "The expanding role of IL-7 and thymic stromal lymphopoietin as therapeutic target for rheumatoid arthritis" Expert Opin Ther Targets (2014), 18(5): 581-94.
Paul, "Fundamental Immulonogy" (1993) 3rd Ed, pp. 292-295.
Raeber et al.., "The role of cytokines in T-cell memory in health and disease", Immunol Rev. (2018), 283(1):176-193.
Reineke, "Antibody Epitope Mapping Using Arrays of Synthetic Peptides", Methods Mol. Biol. (2004), 248: 443-63.
Noguchi et al., "Interleukin-2 Receptor y Chain: A Functional Component of the Interleukin-7 Receptor," Science (1993), 262: 1877-80.

* cited by examiner

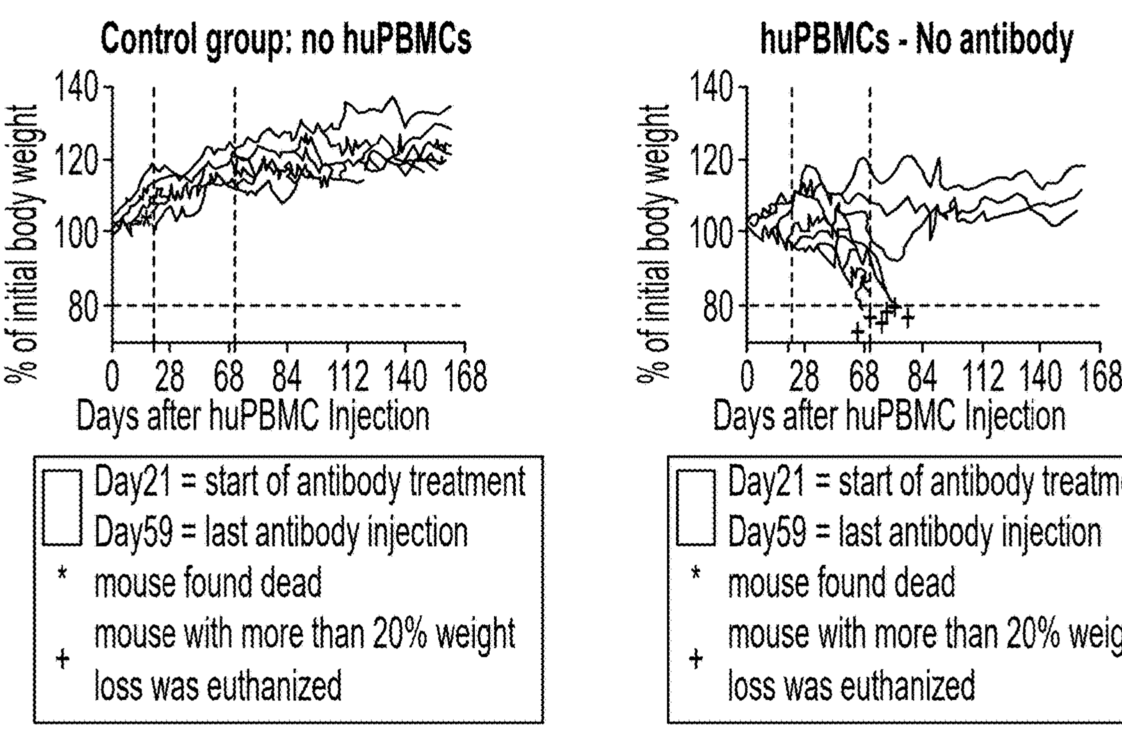
FIG. 3A
FIG. 3B
huPBMCs - Isotype control antibody
140
120
100
80
% of initial body weight
0 28 68 84 112 140 168
Days after huPBMC Injection
Day21 = start of antibody treatment
Day59 = last antibody injection
* mouse found dead
+ mouse with more than 20% weight loss was euthanized
FIG. 3C
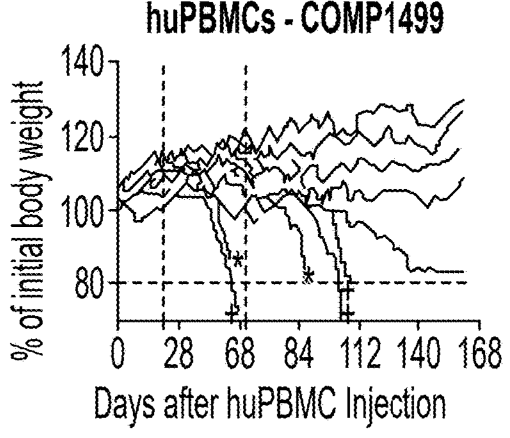
Day21 = start of antibody treatment
Day59 = last antibody injection
* mouse found dead
+ mouse with more than 20% weight loss was euthanized
FIG. 3D Day21 = start of antibody treatment
Day59 = last antibody injection
* mouse found dead
+ mouse with more than 20% weight loss was euthanized Day21 = start of antibody treatment
Day59 = last antibody injection
* mouse found dead
+ mouse with more than 20% weight loss was euthanized

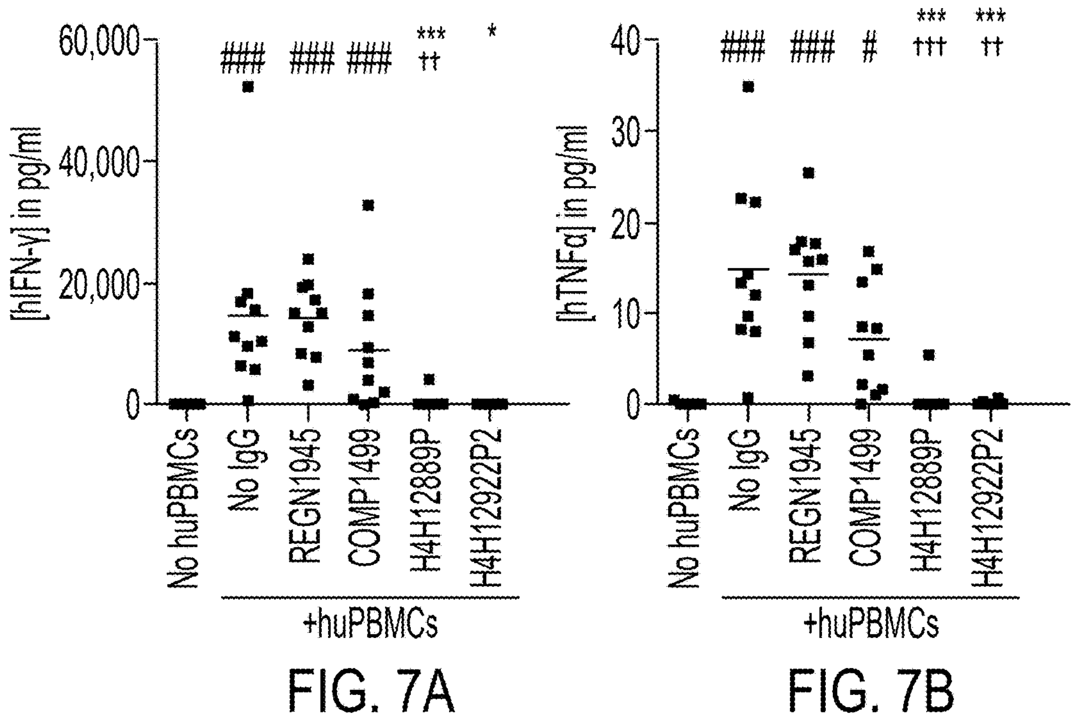
FIG. 7A
FIG. 7B
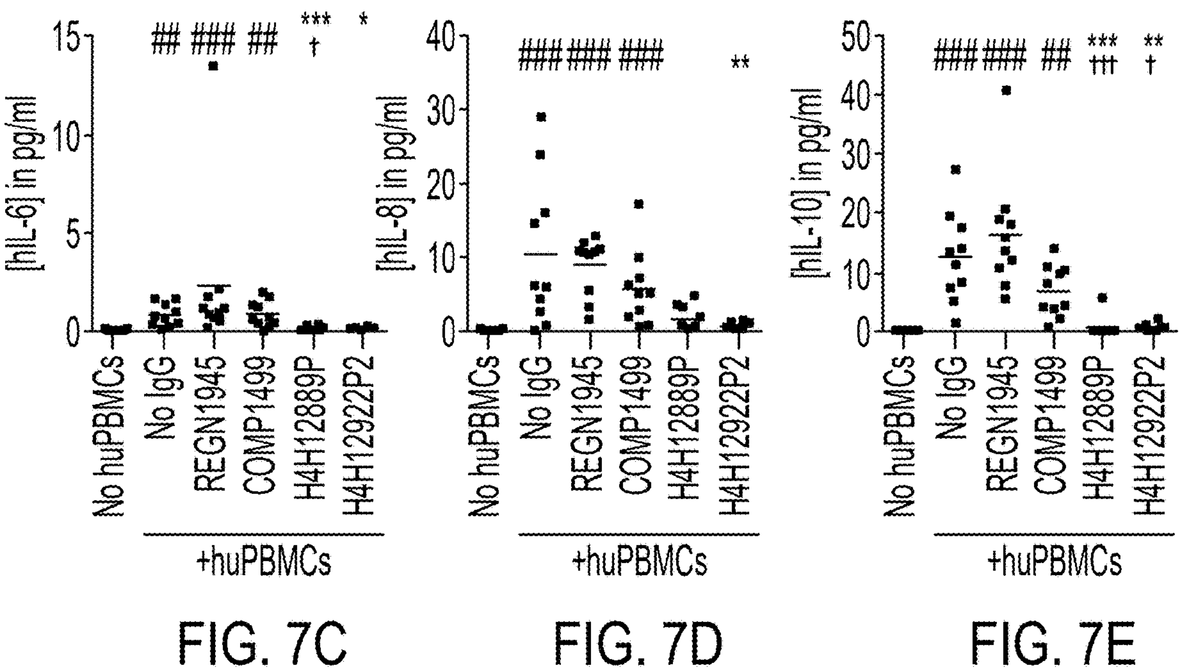
FIG. 7C
FIG. 7D
FIG. 7E

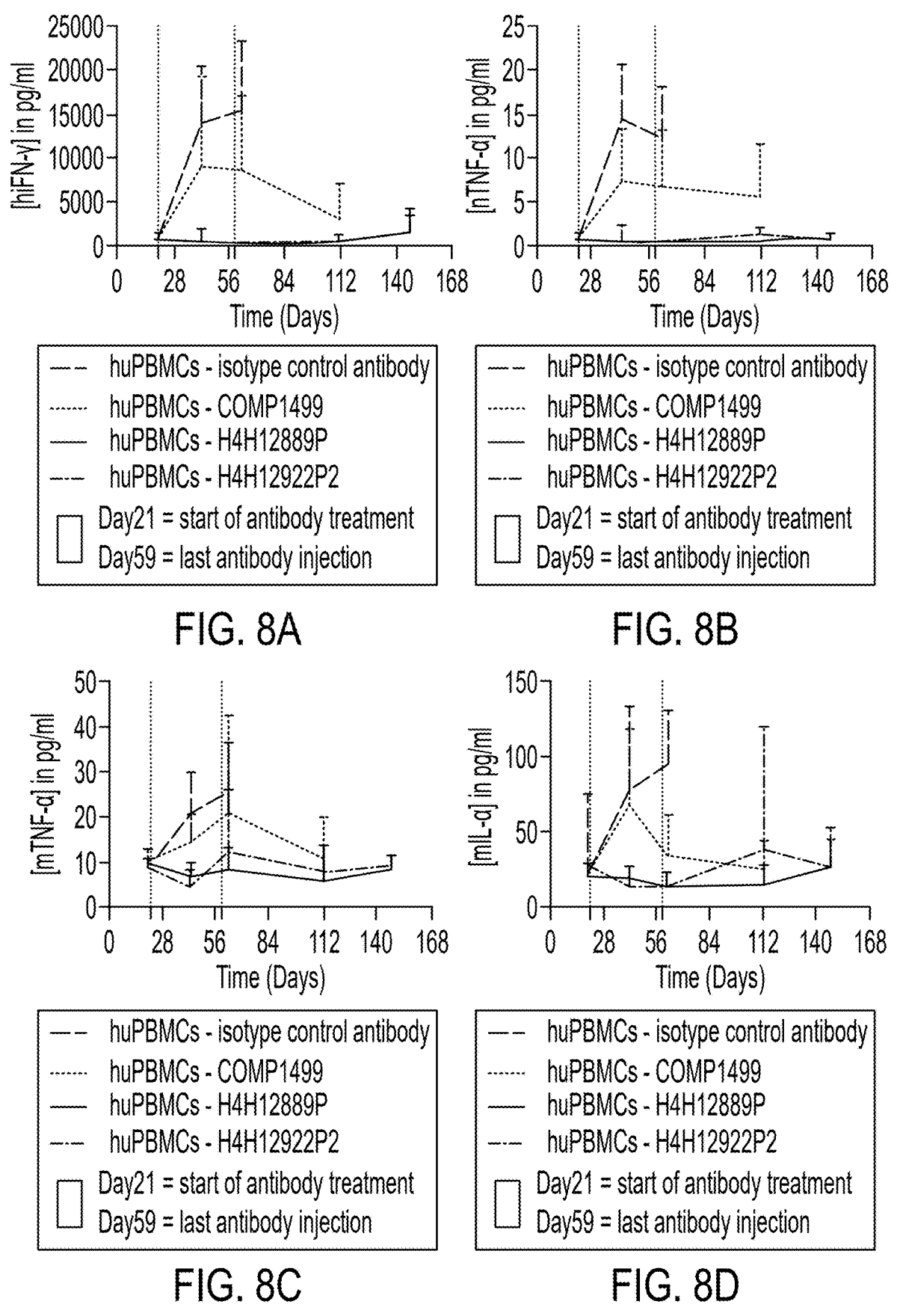

[hIFN-γ] in pg/ml
25000
20000
15000
10000
5000
0
0 28 56 84 112 140 168
Time (Days)

huPBMCs - isotype control antibody
huPBMCs - COMP1499
huPBMCs - H4H12889P
huPBMCs - H4H12922P2
Day21 = start of antibody treatment
Day59 = last antibody injection

FIG. 8A

[hTNF-α] in pg/ml
25
20
15
10
5
0
0 28 56 84 112 140 168
Time (Days)

huPBMCs - isotype control antibody
huPBMCs - COMP1499
huPBMCs - H4H12889P
huPBMCs - H4H12922P2
Day21 = start of antibody treatment
Day59 = last antibody injection

FIG. 8B

[mTNF-α] in pg/ml
50
40
30
20
10
0
0 28 56 84 112 140 168
Time (Days)

huPBMCs - isotype control antibody
huPBMCs - COMP1499
huPBMCs - H4H12889P
huPBMCs - H4H12922P2
Day21 = start of antibody treatment
Day59 = last antibody injection

FIG. 8C

[mIL-α] in pg/ml
150
100
50
0
0 28 56 84 112 140 168
Time (Days)

huPBMCs - isotype control antibody
huPBMCs - COMP1499
huPBMCs - H4H12889P
huPBMCs - H4H12922P2
Day21 = start of antibody treatment
Day59 = last antibody injection

FIG. 8D

****, significantly different from group where mice received REGN1945 (Isotype control)

****, significantly different from group where mice received REGN1945 (Isotype control)

MdFI=Median Fluorescence Intensity

- No Antibody (No mAb)
- REGN1945 25mg/kg (Isotype)
- REGN7257 25mg/kg ( IL2Rg)
- Non-engrafted WT VG mouse (VG WT)
- Non-engrafted BALB/cJ mouse (BALB/cJ)

METHODS OF TREATING AN INTERLEUKIN-2 RECEPTOR GAMMA-MEDIATED DISEASE OR CONDITION BY ADMINISTERING AN IL2 RECEPTOR GAMMA ANTIBODY

CROSS-REFERENCE TO RELATED APPLICATIONS

This application is a divisional of U.S. patent application Ser. No. 16/776,928 filed Jan. 30, 2020 (now U.S. Pat. No. 11,629,195), which claims the benefit of priority to U.S. Provisional Patent Appl. No. 62/799,851, filed Feb. 1, 2019, the disclosures of which are hereby incorporated by reference in their entireties.

FIELD OF THE INVENTION

The present invention relates to antibodies that bind to the anti-IL2 receptor gamma protein and method of use thereof, e.g., to treat or prevent diseases.

BACKGROUND OF THE INVENTION

The common cytokine receptor gamma chain (γc) was first identified as the third chain of the interleukin-2 (IL-2) receptor complex and named IL-2Rγ. The same subunit was identified as part of several other cytokine receptors complexes: IL-4, IL-7, IL-9, IL-15, and IL-21, and therefore may be referred to as γc (common cytokine receptor gamma chain). The γc is involved in the signal transduction of these cytokine receptors as well as ligand binding.

Binding of a cytokine to its receptor activates Janus kinase (JAK)-family protein tyrosine kinases JAK1 and JAK3 and triggers the transphosphorylation of JAK1 and JAK3 on tyrosines. JAK1 is associated with the unique a or B chain and JAK3 with the γc of the receptor. The phosphorylated JAKs can in turn activate the signal transducer and activator of transcription (STAT) proteins, which together form the JAK/STAT signaling pathway. The phosphorylation of STATs causes dimerization of STATs, which now adopt a high-affinity DNA-binding activity and translocate to the nucleus. Here, they act as transcription factors inducing the transcription of target genes.

The γc gene (IL2RG) is located on chromosome Xq13. IL-2Rγ is mutated in patients with X-linked severe combined immunodeficiency (X-SCID). Patients with this disease present with profound immunodeficiency due to lack of T, NK and fully mature B cells.

IL-7, -9 and -15 have been linked to psoriasis and rheumatoid arthritis (Pathak, The expanding role of IL-7 and thymic stromal lymphopoietin as therapeutic target for rheumatoid arthritis. Expert Opin Ther Targets. 18(5): 581-94 (2014); Hughes-Austin et al., Multiple cytokines and chemokines are associated with rheumatoid arthritis-related autoimmunity in first-degree relatives without rheumatoid arthritis: Studies of the Aetiology of Rheumatoid Arthritis (SERA), Ann Rheum Dis.; 72(6): 901-7 (2013); Dantas et al., Increased Serum Interleukin-9 Levels in Rheumatoid Arthritis and Systemic Lupus Erythematosus: Pathogenic Role or Just an Epiphenomenon?, Dis Markers. 2015; 2015: 519638; Yang et al., Therapeutic potential of IL-15 in rheumatoid arthritis, Hum Immunol. 2015 November; 76(11): 812-8; Lesiak et al., Are interleukin-15 and -22 a new pathogenic factor in pustular palmoplantar psoriasis?, Postepy Dermatol Alergol. 33(5): 336-339 (2016); Raeber et al., The role of cytokines in T-cell memory in health and disease, Immunol Rev. 283(1): 176-193 (2018)).

IL-4 and IL-9 blockade have been shown to improve asthma symptoms in mice (Generoso et al., Prospects for Monoclonal Antibody Therapy in Pediatric Asthma, Curr Allergy Asthma Rep. 18(9): 45 (2018); Tashkin & Wechsler, Role of eosinophils in airway inflammation of chronic obstructive pulmonary disease, Int J Chron Obstruct Pulmon Dis. 13:335-349 (2018); Buzney et al., Asthma and Atopic Dermatitis: A Review of Targeted Inhibition of Interleukin-4 and Interleukin-13 As Therapy for Atopic Disease, J Drugs Dermatol. 15(2): 165-71 (2016); Lloyd & Harker, Epigenetic Control of Interleukin-9 in Asthma, N Engl J Med. 379(1): 87-89 (2018); Neurath & Finotto, IL-9 signaling as key driver of chronic inflammation in mucosal immunity, Cytokine Growth Factor Rev. 29:93-9 (2016)). IL-21 is connected with various inflammatory disorders including Crohn's disease and rheumatoid arthritis. (Holm et al., Evaluating IL-21 as a Potential Therapeutic Target in Crohn's Disease, Gastroenterol Res Pract. 2018:5962624 (2018); Dinesh & Rasool Multifaceted role of IL-21 in rheumatoid arthritis: Current understanding and future perspectives, J Cell Physiol. 233(5): 3918-3928 (2018)).

SUMMARY OF THE INVENTION

The present invention provides isolated antigen-binding proteins (e.g., antibodies or antigen-binding fragments thereof, for example, which are monospecific or multispecific) characterized by one or more of the following: Binds to human IL2Rγ at 25° C. with a $K_D$ of about $2.75\times10^{-9}$ M to about $3.36\times10^{-7}$ M; Binds to human IL2Rγ at 37° C. with a $K_D$ of about $6.42\times10^{-9}$ M to about $3.53\times10^{-7}$ M; or binds with a $K_D$ of less than about $3.53\times10^{-7}$ M; Binds to *Macaca fascicularis* IL-2Rγ at 25° C. with a $K_D$ of about $3.18\times10^{-9}$ M to about $2.38\times10^{-7}$ M; Binds to *Macaca fascicularis* IL-2Rγ at 37° C. with a $K_D$ of about $8.29\times10^{-9}$ M to about $3.20\times10^{-7}$ M; or binds with a $K_D$ of less than about $3.20\times10^{-7}$ M; Binds to human IL2Rγ at 25° C. with a $K_D$ of about $2.45\times10^{-9}$ M to about $1.20\times10^{-8}$ M; or binds with a $K_D$ of less than about $1.20\times10^{-8}$ M; Binds to human IL2Rγ at 37° C. with a $K_D$ of about $1.86\times10^{-11}$ M to about $3.00\times10^{-8}$ M; or binds with a $K_D$ of less than about $3.00\times10^{-8}$ M; Binds to mouse IL2Rγ at 25° C. with a $K_D$ of about $1.84\times10^{-8}$ M, $3.76\times10^{-9}$ M, $1.08\times10^{-7}$ M, $2.17\times10^{-8}$ M, $6.02\times10^{-9}$ M or $7.93\times10^{-8}$ M; or does not bind detectably; Binds to mouse IL2Rγ at 37° C. with a $K_D$ of about $5.59\times10^{-8}$ M, $6.11\times10^{-9}$ M, $3.87\times10^{-7}$ M, $5.16\times10^{-8}$ M, $8.70\times10^{-9}$ M or $2.15\times10^{-7}$ M; or does not bind detectably; Binds to human IL2Rγ domain 1 at 25° C. with a $K_D$ of about $3.32\times10^{-9}$ M to about $1.97\times10^{-7}$ M; or does not bind detectably; Binds to human IL2Rγ domain 1 at 37° C. with a $K_D$ of about $4.13\times10^{-9}$ M to about $2.25\times10^{-7}$ M; or does not bind detectably; Binds to human IL2Rγ domain 2 at 25° C. with a $K_D$ of about $2.91\times10^{-7}$ M to about $5.35\times10^{-10}$; or does not bind detectably; Binds to human IL2Rγ domain 2 at 37° C. with a $K_D$ of about $1.14\times10^{-8}$ or about $1.27\times10^{-8}$; or does not bind detectably; Blocks STAT phosphorylation in T-cells which is induced by IL-2, IL-4, IL7, IL-15 and/or IL-21; Blocks STAT phosphorylation in mast cells which is induced by IL-9; Reduces the number of human immune cells which were injected into a mouse; Reduces the levels of serum human cytokines and/or mouse serum cytokines in mice having human immune cells; Does not bind detectably to mouse or rat IL2Rγ; Protects mice from weight loss and/or death due to GvHD in a GvHD mouse model; Blocks binding of a hybrid receptor comprising IL2Rγ complexed with a cytokine-specific receptor subunit from binding to IL-2, IL-4, IL-7, IL-9, IL-15 and/or IL-21; and/or reduces the number of CD45+ cells, B-cells, T-cells and/or NK cells (but, optionally, not, for example, neutrophils) in the blood or serum of a subject. Antibodies and antigen-binding fragments that bind specifically to IL2Rγ, which are variants of any of the antibodies or fragments whose sequences are specifically set forth herein, and which are characterized by one or more of the traits set forth above, form part of the present invention.

The present invention also provides an isolated antigen-binding protein, e.g., which is an antibody or antigen-binding fragment thereof, that (i) specifically binds to the same epitope on IL2Rγ as a reference antibody or antigen-binding fragment thereof; or (ii) competes for binding to IL2Rγ polypeptide with a reference antibody or antigen-binding fragment thereof, wherein the reference antibody or antigen-binding fragment thereof comprises: (a) a heavy chain immunoglobulin or variable region thereof that comprises CDR-H1, CDR-H2 and CDR-H3 of a heavy chain immunoglobulin or variable region thereof that comprises the amino acid sequence set forth in SEQ ID NO: 2, 18, 22, 38, 42, 58, 62, 77, 81, 97, 101, 115, 119, 134, 138, 152, 156, 170, 174, 186, 190, 198, 200, 208, 210, 216, 218, 234, 238, 254, 258, 272, 276, 284, 286, 294, 296, 311, 315, 331, 335, 343, 345, 357, 361 and/or 376; or a variant thereof; and/or (b) a light chain immunoglobulin or variable region thereof that comprises CDR-L1, CDR-L2 and CDR-L3 of a light chain immunoglobulin or variable region thereof that comprises the amino acid sequence set forth in SEQ ID NO: 10, 20, 30, 40, 50, 60, 70, 79, 89, 99, 109, 117, 127, 136, 146, 154, 164, 172, 182, 188, 226, 236, 246, 256, 266, 274, 304, 313, 323, 333, 353, 359, 368 and/or 378; or a variant thereof. In an embodiment of the invention, the reference antibody or fragment is pre-bound to the IL2Rg antigen before the antigen-binding protein is added and evaluated for binding. In an embodiment of the invention, antigen-binding protein is pre-bound to the antigen before the reference antibody or fragment is added and evaluated for binding.

The present invention also provides an isolated antigen-binding protein (e.g., antibody or antigen-binding fragment thereof) comprising: (a) a heavy chain immunoglobulin or variable region thereof that comprises CDR-H1, CDR-H2 and CDR-H3 of a heavy chain immunoglobulin or variable region thereof that comprises the amino acid sequence set forth in SEQ ID NO: 2, 18, 22, 38, 42, 58, 62, 77, 81, 97, 101, 115, 119, 134, 138, 152, 156, 170, 174, 186, 190, 198, 200, 208, 210, 216, 218, 234, 238, 254, 258, 272, 276, 284, 286, 294, 296, 311, 315, 331, 335, 343, 345, 357, 361 and/or 376; or a variant thereof; and/or (b) a light chain immunoglobulin or variable region thereof that comprises CDR-L1, CDR-L2 and CDR-L3 of a light chain immunoglobulin or variable region thereof that comprises the amino acid sequence set forth in SEQ ID NO: 10, 20, 30, 40, 50, 60, 70, 79, 89, 99, 109, 117, 127, 136, 146, 154, 164, 172, 182, 188, 226, 236, 246, 256, 266, 274, 304, 313, 323, 333, 353, 359, 368 and/or 378; or a variant thereof.

In an embodiment of the invention comprises (a) a heavy chain immunoglobulin or variable region thereof comprising an amino acid sequence having at least 90% amino acid sequence identity to the amino acid sequence set forth in SEQ ID NO: 2, 18, 22, 38, 42, 58, 62, 77, 81, 97, 101, 115, 119, 134, 138, 152, 156, 170, 174, 186, 190, 198, 200, 208, 210, 216, 218, 234, 238, 254, 258, 272, 276, 284, 286, 294, 296, 311, 315, 331, 335, 343, 345, 357, 361 and/or 376; and/or (b) a light chain immunoglobulin or variable region thereof comprising an amino acid sequence having at least 90% amino acid sequence identity to the amino acid sequence set forth in SEQ ID NO: 10, 20, 30, 40, 50, 60, 70, 79, 89, 99, 109, 117, 127, 136, 146, 154, 164, 172, 182, 188, 226, 236, 246, 256, 266, 274, 304, 313, 323, 333, 353, 359, 368 and/or 378. For example, in an embodiment of the invention, the antigen-binding protein comprises (a) a heavy chain immunoglobulin or variable region thereof comprising the CDR-H1, CDR-H2 and CDR-H3 of a heavy chain immunoglobulin or variable region thereof comprising an amino acid sequence set forth in SEQ ID NO: 2, 18, 22, 38, 42, 58, 62, 77, 81, 97, 101, 115, 119, 134, 138, 152, 156, 170, 174, 186, 190, 198, 200, 208, 210, 216, 218, 234, 238, 254, 258, 272, 276, 284, 286, 294, 296, 311, 315, 331, 335, 343, 345, 357, 361 and/or 376 and at least 90% amino acid sequence identity to the amino acid sequence set forth in SEQ ID NO: 2, 18, 22, 38, 42, 58, 62, 77, 81, 97, 101, 115, 119, 134, 138, 152, 156, 170, 174, 186, 190, 198, 200, 208, 210, 216, 218, 234, 238, 254, 258, 272, 276, 284, 286, 294, 296, 311, 315, 331, 335, 343, 345, 357, 361 and/or 376; and/or (b) an light chain immunoglobulin or variable region thereof comprising the CDR-L1, CDR-L2 and CDR-L3 of a light chain immunoglobulin or variable region thereof comprising an amino acid sequence set forth in SEQ ID NO: 10, 20, 30, 40, 50, 60, 70, 79, 89, 99, 109, 117, 127, 136, 146, 154, 164, 172, 182, 188, 226, 236, 246, 256, 266, 274, 304, 313, 323, 333, 353, 359, 368 and/or 378 and at least 90% amino acid sequence identity to the amino acid sequence set forth in SEQ ID NO: 10, 20, 30, 40, 50, 60, 70, 79, 89, 99, 109, 117, 127, 136, 146, 154, 164, 172, 182, 188, 226, 236, 246, 256, 266, 274, 304, 313, 323, 333, 353, 359, 368 and/or 378.

In an embodiment of the invention, the antigen-binding protein comprises:

(i) the heavy chain set of CDRs: CDR-H1 comprising the amino acid sequence set forth in SEQ ID NO: 4; CDR-H2 comprising the amino acid sequence set forth in SEQ ID NO: 6; and CDR-H3 comprising the amino acid sequence set forth in SEQ ID NO: 8; and/or CDR-H1 comprising the amino acid sequence set forth in SEQ ID NO: 24; CDR-H2 comprising the amino acid sequence set forth in SEQ ID NO: 26; and CDR-H3 comprising the amino acid sequence set forth in SEQ ID NO: 28; and/or CDR-H1 comprising the amino acid sequence set forth in SEQ ID NO: 44; CDR-H2 comprising the amino acid sequence set forth in SEQ ID NO: 46; and CDR-H3 comprising the amino acid sequence set forth in SEQ ID NO: 48; and/or CDR-H1 comprising the amino acid sequence set forth in SEQ ID NO: 64; CDR-H2 comprising the amino acid sequence set forth in SEQ ID NO: 66; and CDR-H3 comprising the amino acid sequence set forth in SEQ ID NO: 68; and/or CDR-H1 comprising the amino acid sequence set forth in SEQ ID NO: 83; CDR-H2 comprising the amino acid sequence set forth in SEQ ID NO: 85; and CDR-H3 comprising the amino acid sequence set forth in SEQ ID NO: 87; and/or CDR-H1 comprising the amino acid sequence set forth in SEQ ID NO: 103; CDR-H2 comprising the amino acid sequence set forth in SEQ ID NO: 105; and CDR-H3 comprising the amino acid sequence set forth in SEQ ID NO: 107; and/or CDR-H1 comprising the amino acid sequence set forth in SEQ ID NO: 121; CDR-H2 comprising the amino acid sequence set forth in SEQ ID NO: 123; and CDR-H3 comprising the amino acid sequence set forth in SEQ ID NO: 125; and/or CDR-H1 comprising the amino acid sequence set forth in SEQ ID NO: 140; CDR-H2 comprising the amino acid sequence set forth in SEQ ID NO: 142; and CDR-H3 comprising the amino acid sequence set forth in SEQ ID NO: 144; and/or CDR-H1 comprising the amino acid sequence set forth in SEQ ID NO: 158; CDR-H2 comprising the amino acid sequence set forth in SEQ ID NO: 160; and CDR-H3 comprising the amino acid sequence set forth in SEQ ID NO: 162; and/or CDR-H1 comprising the amino acid sequence set forth in SEQ ID NO: 176; CDR-H2 comprising the amino acid sequence set forth in SEQ ID NO: 178; and CDR-H3 comprising the amino acid sequence set forth in SEQ ID NO: 180; and/or CDR-H1 comprising the amino acid sequence set forth in SEQ ID NO: 192; CDR-H2 comprising the amino acid sequence set forth in SEQ ID NO: 194; and CDR-H3 comprising the amino acid sequence set forth in SEQ ID NO: 196; and/or CDR-H1 comprising the amino acid sequence set forth in SEQ ID NO: 202; CDR-H2 comprising the amino acid sequence set forth in SEQ ID NO: 204; and CDR-H3 comprising the amino acid sequence set forth in SEQ ID NO: 206; and/or CDR-H1 comprising the amino acid sequence set forth in SEQ ID NO: 176; CDR-H2 comprising the amino acid sequence set forth in SEQ ID NO: 212; and CDR-H3 comprising the amino acid sequence set forth in SEQ ID NO: 214; and/or CDR-H1 comprising the amino acid sequence set forth in SEQ ID NO: 220; CDR-H2 comprising the amino acid sequence set forth in SEQ ID NO: 222; and CDR-H3 comprising the amino acid sequence set forth in SEQ ID NO: 224; and/or CDR-H1 comprising the amino acid sequence set forth in SEQ ID NO: 240; CDR-H2 comprising the amino acid sequence set forth in SEQ ID NO: 242; and CDR-H3 comprising the amino acid sequence set forth in SEQ ID NO: 244; and/or CDR-H1 comprising the amino acid sequence set forth in SEQ ID NO: 260; CDR-H2 comprising the amino acid sequence set forth in SEQ ID NO: 262; and CDR-H3 comprising the amino acid sequence set forth in SEQ ID NO: 264; and/or CDR-H1 comprising the amino acid sequence set forth in SEQ ID NO: 278; CDR-H2 comprising the amino acid sequence set forth in SEQ ID NO: 280; and CDR-H3 comprising the amino acid sequence set forth in SEQ ID NO: 282; and/or CDR-H1 comprising the amino acid sequence set forth in SEQ ID NO: 288; CDR-H2 comprising the amino acid sequence set forth in SEQ ID NO: 290; and CDR-H3 comprising the amino acid sequence set forth in SEQ ID NO: 292; and/or CDR-H1 comprising the amino acid sequence set forth in SEQ ID NO: 298; CDR-H2 comprising the amino acid sequence set forth in SEQ ID NO: 300; and CDR-H3 comprising the amino acid sequence set forth in SEQ ID NO: 302; and/or CDR-H1 comprising the amino acid sequence set forth in SEQ ID NO: 317; CDR-H2 comprising the amino acid sequence set forth in SEQ ID NO: 319; and CDR-H3 comprising the amino acid sequence set forth in SEQ ID NO: 321; and/or CDR-H1 comprising the amino acid sequence set forth in SEQ ID NO: 337; CDR-H2 comprising the amino acid sequence set forth in SEQ ID NO: 339; and CDR-H3 comprising the amino acid sequence set forth in SEQ ID NO: 341; and/or CDR-H1 comprising the amino acid sequence set forth in SEQ ID NO: 347; CDR-H2 comprising the amino acid sequence set forth in SEQ ID NO: 349; and CDR-H3 comprising the amino acid sequence set forth in SEQ ID NO: 351; and/or CDR-H1 comprising the amino acid sequence set forth in SEQ ID NO: 363; CDR-H2 comprising the amino acid sequence set forth in SEQ ID NO: 66; and CDR-H3 comprising the amino acid sequence set forth in SEQ ID NO: 366; and/or (ii) the light chain set of CDRs: CDR-L1 comprising the amino acid sequence set forth in SEQ ID NO: 12; CDR-L2 comprising the amino acid sequence set forth in SEQ ID NO: 14; and CDR-L3 comprising the amino acid sequence set forth in SEQ ID NO: 16; and/or CDR-L1 comprising the amino acid sequence set forth in SEQ ID NO: 32; CDR-L2 comprising the amino acid sequence set forth in SEQ ID NO: 34; and CDR-L3 comprising the amino acid sequence set forth in SEQ ID NO: 36; and/or CDR-L1 comprising the amino acid sequence set forth in SEQ ID NO: 52; CDR-L2 comprising the amino acid sequence set forth in SEQ ID NO: 54; and CDR-L3 comprising the amino acid sequence set forth in SEQ ID NO: 56; and/or CDR-L1 comprising the amino acid sequence set forth in SEQ ID NO: 72; CDR-L2 comprising the amino acid sequence set forth in SEQ ID NO: 54; and CDR-L3 comprising the amino acid sequence set forth in SEQ ID NO: 75; and/or CDR-L1 comprising the amino acid sequence set forth in SEQ ID NO: 91; CDR-L2 comprising the amino acid sequence set forth in SEQ ID NO: 93; and CDR-L3 comprising the amino acid sequence set forth in SEQ ID NO: 95; and/or CDR-L1 comprising the amino acid sequence set forth in SEQ ID NO: 111; CDR-L2 comprising the amino acid sequence set forth in SEQ ID NO: 54; and CDR-L3 comprising the amino acid sequence set forth in SEQ ID NO: 113; and/or CDR-L1 comprising the amino acid sequence set forth in SEQ ID NO: 129; CDR-L2 comprising the amino acid sequence set forth in SEQ ID NO: 54; and CDR-L3 comprising the amino acid sequence set forth in SEQ ID NO: 132; and/or CDR-L1 comprising the amino acid sequence set forth in SEQ ID NO: 148; CDR-L2 comprising the amino acid sequence set forth in SEQ ID NO: 54; and CDR-L3 comprising the amino acid sequence set forth in SEQ ID NO: 150; and/or CDR-L1 comprising the amino acid sequence set forth in SEQ ID NO: 166; CDR-L2 comprising the amino acid sequence set forth in SEQ ID NO: 14; and CDR-L3 comprising the amino acid sequence set forth in SEQ ID NO: 168; and/or CDR-L1 comprising the amino acid sequence set forth in SEQ ID NO: 72; CDR-L2 comprising the amino acid sequence set forth in SEQ ID NO: 54; and CDR-L3 comprising the amino acid sequence set forth in SEQ ID NO: 184; and/or CDR-L1 comprising the amino acid sequence set forth in SEQ ID NO: 72; CDR-L2 comprising the amino acid sequence set forth in SEQ ID NO: 54; and CDR-L3 comprising the amino acid sequence set forth in SEQ ID NO: 184; and/or CDR-L1 comprising the amino acid sequence set forth in SEQ ID NO: 72; CDR-L2 comprising the amino acid sequence set forth in SEQ ID NO: 54; and CDR-L3 comprising the amino acid sequence set forth in SEQ ID NO: 184; and/or CDR-L1 comprising the amino acid sequence set forth in SEQ ID NO: 72; CDR-L2 comprising the amino acid sequence set forth in SEQ ID NO: 54; and CDR-L3 comprising the amino acid sequence set forth in SEQ ID NO: 184; and/or CDR-L1 comprising the amino acid sequence set forth in SEQ ID NO: 228; CDR-L2 comprising the amino acid sequence set forth in SEQ ID NO: 230; and CDR-L3 comprising the amino acid sequence set forth in SEQ ID NO: 232; and/or CDR-L1 comprising the amino acid sequence set forth in SEQ ID NO: 248; CDR-L2 comprising the amino acid sequence set forth in SEQ ID NO: 250; and CDR-L3 comprising the amino acid sequence set forth in SEQ ID NO: 252; and/or CDR-L1 comprising the amino acid sequence set forth in SEQ ID NO: 268; CDR-L2 comprising the amino acid sequence set forth in SEQ ID NO: 54; and CDR-L3 comprising the amino acid sequence set forth in SEQ ID NO: 270; and/or CDR-L1 comprising the amino acid sequence set forth in SEQ ID NO: 72; CDR-L2 comprising the amino acid sequence set forth in SEQ ID NO: 54; and CDR-L3 comprising the amino acid sequence set forth in SEQ ID NO: 184; and/or CDR-L1 comprising the amino acid sequence set forth in SEQ ID NO: 72; CDR-L2 comprising the amino acid sequence set forth in SEQ ID NO: 54; and CDR-L3 comprising the amino acid sequence set forth in SEQ ID NO: 184; and/or CDR-L1 comprising the amino acid sequence set forth in SEQ ID NO: 306; CDR-L2 comprising the amino acid sequence set forth in SEQ ID NO: 230; and CDR-L3 comprising the amino acid sequence set forth in SEQ ID NO: 309; and/or CDR-L1 comprising the amino acid sequence set forth in SEQ ID NO: 325; CDR-L2 comprising the amino acid sequence set forth in SEQ ID NO: 327; and CDR-L3 comprising the amino acid sequence set forth in SEQ ID NO: 329; and/or CDR-L1 comprising the amino acid sequence set forth in SEQ ID NO: 72; CDR-L2 comprising the amino acid sequence set forth in SEQ ID NO: 54; and CDR-L3 comprising the amino acid sequence set forth in SEQ ID NO: 184; and/or CDR-L1 comprising the amino acid sequence set forth in SEQ ID NO: 72; CDR-L2 comprising the amino acid sequence set forth in SEQ ID NO: 54; and CDR-L3 comprising the amino acid sequence set forth in SEQ ID NO: 355; and/or CDR-L1 comprising the amino acid sequence set forth in SEQ ID NO: 370; CDR-L2 comprising the amino acid sequence set forth in SEQ ID NO: 372; and CDR-L3 comprising the amino acid sequence set forth in SEQ ID NO: 374.

In an embodiment of the invention, the antigen-binding protein of the present invention comprises the heavy chain set of CDRs and the light chain set of CDRs as follows:

(i) a heavy chain variable region comprising a CDR-H1 comprising the amino acid sequence set forth in SEQ ID NO: 4; a CDR-H2 comprising the amino acid sequence set forth in SEQ ID NO: 6; and a CDR-H3 comprising the amino acid sequence set forth in SEQ ID NO: 8; and a light chain variable region comprising a CDR-L1 comprising the amino acid sequence set forth in SEQ ID NO: 12; a CDR-L2 comprising the amino acid sequence set forth in SEQ ID NO: 14; and a CDR-L3 comprising the amino acid sequence set forth in SEQ ID NO: 16; (ii) a heavy chain variable region comprising a CDR-H1 comprising the amino acid sequence set forth in SEQ ID NO: 24; a CDR-H2 comprising the amino acid sequence set forth in SEQ ID NO: 26; and a CDR-H3 comprising the amino acid sequence set forth in SEQ ID NO: 28; and a light chain variable region comprising a CDR-L1 comprising the amino acid sequence set forth in SEQ ID NO: 32; a CDR-L2 comprising the amino acid sequence set forth in SEQ ID NO: 34; and a CDR-L3 comprising the amino acid sequence set forth in SEQ ID NO: 36; (iii) a heavy chain variable region comprising a CDR-H1 comprising the amino acid sequence set forth in SEQ ID NO: 44; a CDR-H2 comprising the amino acid sequence set forth in SEQ ID NO: 46; and a CDR-H3 comprising the amino acid sequence set forth in SEQ ID NO: 48; and a light chain variable region comprising a CDR-L1 comprising the amino acid sequence set forth in SEQ ID NO: 52; a CDR-L2 comprising the amino acid sequence set forth in SEQ ID NO: 54; and a CDR-L3 comprising the amino acid sequence set forth in SEQ ID NO: 56; (iv) a heavy chain variable region comprising a CDR-H1 comprising the amino acid sequence set forth in SEQ ID NO: 64; a CDR-H2 comprising the amino acid sequence set forth in SEQ ID NO: 66; and a CDR-H3 comprising the amino acid sequence set forth in SEQ ID NO: 68; and a light chain variable region comprising a CDR-L1 comprising the amino acid sequence set forth in SEQ ID NO: 72; a CDR-L2 comprising the amino acid sequence set forth in SEQ ID NO: 54; and a CDR-L3 comprising the amino acid sequence set forth in SEQ ID NO: 75; (v) a heavy chain variable region comprising a CDR-H1 comprising the amino acid sequence set forth in SEQ ID NO: 83; a CDR-H2 comprising the amino acid sequence set forth in SEQ ID NO: 85; and a CDR-H3 comprising the amino acid sequence set forth in SEQ ID NO: 87; and a light chain variable region comprising a CDR-L1 comprising the amino acid sequence set forth in SEQ ID NO: 91; a CDR-L2 comprising the amino acid sequence set forth in SEQ ID NO: 93; and a CDR-L3 comprising the amino acid sequence set forth in SEQ ID NO: 95; (vi) a heavy chain variable region comprising a CDR-H1 comprising the amino acid sequence set forth in SEQ ID NO: 103; a CDR-H2 comprising the amino acid sequence set forth in SEQ ID NO: 105; and a CDR-H3 comprising the amino acid sequence set forth in SEQ ID NO: 107; and a light chain variable region comprising a CDR-L1 comprising the amino acid sequence set forth in SEQ ID NO: 111; a CDR-L2 comprising the amino acid sequence set forth in SEQ ID NO: 54; and a CDR-L3 comprising the amino acid sequence set forth in SEQ ID NO: 113; (vi) a heavy chain variable region comprising a CDR-H1 comprising the amino acid sequence set forth in SEQ ID NO: 121; a CDR-H2 comprising the amino acid sequence set forth in SEQ ID NO: 123; and a CDR-H3 comprising the amino acid sequence set forth in SEQ ID NO: 125; and a light chain variable region comprising a CDR-L1 comprising the amino acid sequence set forth in SEQ ID NO: 129; a CDR-L2 comprising the amino acid sequence set forth in SEQ ID NO: 54; and a CDR-L3 comprising the amino acid sequence set forth in SEQ ID NO: 132; (vii) a heavy chain variable region comprising a CDR-H1 comprising the amino acid sequence set forth in SEQ ID NO: 140; a CDR-H2 comprising the amino acid sequence set forth in SEQ ID NO: 142; and a CDR-H3 comprising the amino acid sequence set forth in SEQ ID NO: 144; and a light chain variable region comprising a CDR-L1 comprising the amino acid sequence set forth in SEQ ID NO: 148; a CDR-L2 comprising the amino acid sequence set forth in SEQ ID NO: 54; and a CDR-L3 comprising the amino acid sequence set forth in SEQ ID NO: 150; (viii) a heavy chain variable region comprising a CDR-H1 comprising the amino acid sequence set forth in SEQ ID NO: 158; a CDR-H2 comprising the amino acid sequence set forth in SEQ ID NO: 160; and a CDR-H3 comprising the amino acid sequence set forth in SEQ ID NO: 162; and a light chain variable region comprising a CDR-L1 comprising the amino acid sequence set forth in SEQ ID NO: 166; a CDR-L2 comprising the amino acid sequence set forth in SEQ ID NO: 14; and a CDR-L3 comprising the amino acid sequence set forth in SEQ ID NO: 168; (ix) a heavy chain variable region comprising a CDR-H1 comprising the amino acid sequence set forth in SEQ ID NO: 176; a CDR-H2 comprising the amino acid sequence set forth in SEQ ID NO: 178; and a CDR-H3 comprising the amino acid sequence set forth in SEQ ID NO: 180; and a light chain variable region comprising a CDR-L1 comprising the amino acid sequence set forth in SEQ ID NO: 72; a CDR-L2 comprising the amino acid sequence set forth in SEQ ID NO: 54; and a CDR-L3 comprising the amino acid sequence set forth in SEQ ID NO: 184; (x) a heavy chain variable region comprising a CDR-H1 comprising the amino acid sequence set forth in SEQ ID NO: 192; a CDR-H2 comprising the amino acid sequence set forth in SEQ ID NO: 194; and a CDR-H3 comprising the amino acid sequence set forth in SEQ ID NO: 196; and a light chain variable region comprising a CDR-L1 comprising the amino acid sequence set forth in SEQ ID NO: 72; a CDR-L2 comprising the amino acid sequence set forth in SEQ ID NO: 54; and a CDR-L3 comprising the amino acid sequence set forth in SEQ ID NO: 184; (xi) a heavy chain variable region comprising a CDR-H1 comprising the amino acid sequence set forth in SEQ ID NO: 202; a CDR-H2 comprising the amino acid sequence set forth in SEQ ID NO: 204; and a CDR-H3 comprising the amino acid sequence set forth in SEQ ID NO: 206; and a light chain variable region comprising a CDR-L1 comprising the amino acid sequence set forth in SEQ ID NO: 72; a CDR-L2 comprising the amino acid sequence set forth in SEQ ID NO: 54; and a CDR-L3 comprising the amino acid sequence set forth in SEQ ID NO: 184; (xii) a heavy chain variable region comprising a CDR-H1 comprising the amino acid sequence set forth in SEQ ID NO: 176; a CDR-H2 comprising the amino acid sequence set forth in SEQ ID NO: 212; and a CDR-H3 comprising the amino acid sequence set forth in SEQ ID NO: 214; and a light chain variable region comprising a CDR-L1 comprising the amino acid sequence set forth in SEQ ID NO: 72; a CDR-L2 comprising the amino acid sequence set forth in SEQ ID NO: 54; and a CDR-L3 comprising the amino acid sequence set forth in SEQ ID NO: 184; (xiii) a heavy chain variable region comprising a CDR-H1 comprising the amino acid sequence set forth in SEQ ID NO: 220; a CDR-H2 comprising the amino acid sequence set forth in SEQ ID NO: 222; and a CDR-H3 comprising the amino acid sequence set forth in SEQ ID NO: 224; and a light chain variable region comprising a CDR-L1 comprising the amino acid sequence set forth in SEQ ID NO: 228; a CDR-L2 comprising the amino acid sequence set forth in SEQ ID NO: 230; and a CDR-L3 comprising the amino acid sequence set forth in SEQ ID NO: 232; (xiv) a heavy chain variable region comprising a CDR-H1 comprising the amino acid sequence set forth in SEQ ID NO: 240; a CDR-H2 comprising the amino acid sequence set forth in SEQ ID NO: 242; and a CDR-H3 comprising the amino acid sequence set forth in SEQ ID NO: 244; and a light chain variable region comprising a CDR-L1 comprising the amino acid sequence set forth in SEQ ID NO: 248; a CDR-L2 comprising the amino acid sequence set forth in SEQ ID NO: 250; and a CDR-L3 comprising the amino acid sequence set forth in SEQ ID NO: 252; (xv) a heavy chain variable region comprising a CDR-H1 comprising the amino acid sequence set forth in SEQ ID NO: 260; a CDR-H2 comprising the amino acid sequence set forth in SEQ ID NO: 262; and a CDR-H3 comprising the amino acid sequence set forth in SEQ ID NO: 264; and a light chain variable region comprising a CDR-L1 comprising the amino acid sequence set forth in SEQ ID NO: 268; a CDR-L2 comprising the amino acid sequence set forth in SEQ ID NO: 54; and a CDR-L3 comprising the amino acid sequence set forth in SEQ ID NO: 270; (xvi) a heavy chain variable region comprising a CDR-H1 comprising the amino acid sequence set forth in SEQ ID NO: 278; a CDR-H2 comprising the amino acid sequence set forth in SEQ ID NO: 280; and a CDR-H3 comprising the amino acid sequence set forth in SEQ ID NO: 282; and a light chain variable region comprising a CDR-L1 comprising the amino acid sequence set forth in SEQ ID NO: 72; a CDR-L2 comprising the amino acid sequence set forth in SEQ ID NO: 54; and a CDR-L3 comprising the amino acid sequence set forth in SEQ ID NO: 184; (xvii) a heavy chain variable region comprising a CDR-H1 comprising the amino acid sequence set forth in SEQ ID NO: 288; a CDR-H2 comprising the amino acid sequence set forth in SEQ ID NO: 290; and a CDR-H3 comprising the amino acid sequence set forth in SEQ ID NO: 292; and a light chain variable region comprising a CDR-L1 comprising the amino acid sequence set forth in SEQ ID NO: 72; a CDR-L2 comprising the amino acid sequence set forth in SEQ ID NO: 54; and a CDR-L3 comprising the amino acid sequence set forth in SEQ ID NO: 184; (xviii) a heavy chain variable region comprising a CDR-H1 comprising the amino acid sequence set forth in SEQ ID NO: 298; a CDR-H2 comprising the amino acid sequence set forth in SEQ ID NO: 300; and a CDR-H3 comprising the amino acid sequence set forth in SEQ ID NO: 302; and a light chain variable region comprising a CDR-L1 comprising the amino acid sequence set forth in SEQ ID NO: 306; a CDR-L2 comprising the amino acid sequence set forth in SEQ ID NO: 230; and a CDR-L3 comprising the amino acid sequence set forth in SEQ ID NO: 309; (xix) a heavy chain variable region comprising a CDR-H1 comprising the amino acid sequence set forth in SEQ ID NO: 317; a CDR-H2 comprising the amino acid sequence set forth in SEQ ID NO: 319; and a CDR-H3 comprising the amino acid sequence set forth in SEQ ID NO: 321; and a light chain variable region comprising a CDR-L1 comprising the amino acid sequence set forth in SEQ ID NO: 325; a CDR-L2 comprising the amino acid sequence set forth in SEQ ID NO: 327; and a CDR-L3 comprising the amino acid sequence set forth in SEQ ID NO: 329; (xx) a heavy chain variable region comprising a CDR-H1 comprising the amino acid sequence set forth in SEQ ID NO: 337; a CDR-H2 comprising the amino acid sequence set forth in SEQ ID NO: 339; and a CDR-H3 comprising the amino acid sequence set forth in SEQ ID NO: 341; and a light chain variable region comprising a CDR-L1 comprising the amino acid sequence set forth in SEQ ID NO: 72; a CDR-L2 comprising the amino acid sequence set forth in SEQ ID NO: 54; and a CDR-L3 comprising the amino acid sequence set forth in SEQ ID NO: 184; (xxi) a heavy chain variable region comprising a CDR-H1 comprising the amino acid sequence set forth in SEQ ID NO: 347; a CDR-H2 comprising the amino acid sequence set forth in SEQ ID NO: 349; and a CDR-H3 comprising the amino acid sequence set forth in SEQ ID NO: 351; and a light chain variable region comprising a CDR-L1 comprising the amino acid sequence set forth in SEQ ID NO: 72; a CDR-L2 comprising the amino acid sequence set forth in SEQ ID NO: 54; and a CDR-L3 comprising the amino acid sequence set forth in SEQ ID NO: 355; (xxii) a heavy chain variable region comprising a CDR-H1 comprising the amino acid sequence set forth in SEQ ID NO: 363; a CDR-H2 comprising the amino acid sequence set forth in SEQ ID NO: 66; and a CDR-H3 comprising the amino acid sequence set forth in SEQ ID NO: 366; and a light chain variable region comprising a CDR-L1 comprising the amino acid sequence set forth in SEQ ID NO: 370; a CDR-L2 comprising the amino acid sequence set forth in SEQ ID NO: 372; and a CDR-L3 comprising the amino acid sequence set forth in SEQ ID NO: 374.

Complexes including an antigen-binding protein of the present invention bound to an IL2Rγ polypeptide or antigenic fragment thereof are also part of the present invention.

The present invention also provides a method for making an antigen-binding protein (e.g., antibody or antigen-binding fragment thereof) or an immunoglobulin chain thereof (e.g., $V_H$, $V_L$, HC or LC) comprising: (a) introducing one or more polynucleotides (or a vector comprising such a polynucleotide) encoding one or more immunoglobulin chains of said antigen-binding protein into a host cell (e.g., a CHO cell); (b) culturing the host cell under conditions favorable to expression of the polynucleotide; and (c) optionally, isolating the antigen-binding protein or immunoglobulin chain from the host cell and/or medium in which the host cell is grown. An antigen-binding protein or immunoglobulin chain which is a product of such a method also forms part of the present invention.

The present invention also provides a polypeptide comprising: (a) CDR-H1, CDR-H2, and CDR-H3 of a heavy chain immunoglobulin or variable region thereof that comprises the amino acid sequence set forth in SEQ ID NO: 2, 18, 22, 38, 42, 58, 62, 77, 81, 97, 101, 115, 119, 134, 138, 152, 156, 170, 174, 186, 190, 198, 200, 208, 210, 216, 218, 234, 238, 254, 258, 272, 276, 284, 286, 294, 296, 311, 315, 331, 335, 343, 345, 357, 361 and/or 376, or a variant thereof; and/or (b) CDR-L1, CDR-L2, and CDR-L3 of a light chain immunoglobulin or variable region thereof that comprises the amino acid sequence set forth in SEQ ID NO: 10, 20, 30, 40, 50, 60, 70, 79, 89, 99, 109, 117, 127, 136, 146, 154, 164, 172, 182, 188, 226, 236, 246, 256, 266, 274, 304, 313, 323, 333, 353, 359, 368 and/or 378, or a variant thereof; or (c) the amino acid sequence set forth in a member selected from the group consisting of SEQ ID NO: 1-378, or a variant thereof. The present invention also provides a polynucleotide encoding one or more of such polypeptides or a vector comprising such a polynucleotide (e.g., a plasmid).

The present invention also provides a host cell (e.g., a CHO cell) comprising the antigen-binding protein (e.g., antibody or antigen-binding fragment thereof) or immunoglobulin chain (e.g., $V_H$, $V_L$, HC or LC) or polypeptide or polynucleotide or vector set forth herein.

The present invention also provides a composition or kit comprising one or more of the antigen-binding proteins set forth herein (e.g., antibody or antigen-binding fragment thereof) optionally in association with a further therapeutic agent (e.g., anti-inflammatory agent, an anti-TNFα antibody or binding protein, infliximab, adalimumab, etanercept, golimumab, a corticoid, prednisolone, methylprednisolone, antithymocyte globulin, alemtuzumab, dacluzimab, extracorporeal photophoresis, mycophenolate mofetil, sirolimus, pentostatin, mesenchyman stem cells, inolimomab, denileukin or basiliximab).

The present invention further provides a pharmaceutical formulation comprising the antigen-binding protein set forth herein (e.g., antibody or antigen-binding fragment thereof) and a pharmaceutically acceptable carrier and, optionally, a further therapeutic agent (e.g., anti-inflammatory agent, an anti-TNFα antibody or binding protein, infliximab, adalimumab, etanercept, golimumab, a corticoid, prednisolone, methylprednisolone, antithymocyte globulin, alemtuzumab, daclizumab, extracorporeal photophoresis, mycophenolate mofetil, tacrolimus, cyclosporine, sirolimus, pentostatin, mesenchyman stem cells, inolimomab, denileukin or basiliximab).

The present invention also provides a vessel or injection device (e.g., a vial, syringe, pre-filled syringe or autoinjector) comprising the antigen-binding protein or composition (e.g., pharmaceutical formulation) set forth herein.

The present invention also provides a method for administering antigen-binding protein or composition set forth herein to a subject (e.g., a human) comprising introducing, e.g., injecting (e.g., subcutaneously, intravenously or intramuscularly), said antigen-binding protein or composition into the body of the subject. The present invention also provides a method for treating or preventing an IL2Rγ-mediated disease or condition (e.g., graft-versus-host disease, organ transplant rejection, skin transplant rejection, heart transplant rejection, lung transplant rejection, kidney transplant rejection, liver transplant rejection, birdshot chorioretinopathy, multiple sclerosis, uveitis, an autoimmune disease, Type I diabetes, multiple sclerosis, rheumatoid arthritis, systemic lupus erythematosus, and/or myasthenia gravis), in a subject in need thereof, comprising administering, e.g., injecting, an effective amount of antigen-binding protein or composition set forth herein.

The present invention also provides a method for: blocking STAT phosphorylation in an peripheral blood mononuclear cell (e.g., a T-cell) induced by a cytokine (e.g., IL-2, IL-4, IL-7, IL-15 and/or IL-21); blocking STAT (e.g., STAT3) phosphorylation in a mast cell induced by a cytokine (e.g., IL-9); reducing serum levels of interferon-gamma, tumor necrosis factor-alpha, IL-6, IL-8, IL-10 and/or mKC/GRO (e.g., in a subject that has received a transplant); blocking JAK-STAT-mediated (e.g., STAT3) intracellular signaling (e.g., in an NK cell), induced by a cytokine in the IL2Rγ family (e.g., IL-2, IL-4, IL-7, IL-9, IL-15 and/or IL-21); and/or reducing the serum levels of CD45+ immune cells, NK cells, T-cells and/or B-cells (e.g., excluding neutrophils), in a subject, comprising administering, to the subject, an effective amount of anti-IL2Rγ antigen-binding protein set forth herein or composition thereof or formulation thereof. In an embodiment of the invention, the subject suffers from an IL2Rγ-mediated disease or condition, e.g., graft-versus-host disease, organ transplant rejection, b-islet cell graft rejection, skin transplant rejection, heart transplant rejection, lung transplant rejection, kidney transplant rejection, liver transplant rejection, birdshot chorioretinopathy, multiple sclerosis, uveitis, an autoimmune disease, Type I diabetes, multiple sclerosis, rheumatoid arthritis, systemic lupus erythematosus, myasthenia gravis, aplastic anemia, atopic dermatitis, asthma, a mast cell activation disorder, mast cell activation syndrome (MCAS), systemic mastocytosis (SM) and/or mast cell leukemia (MCL).

BRIEF DESCRIPTION OF THE FIGURES

FIG. 3(A) is a graph showing percentage of initial body weight of mice in control experiments of mice not having human PBMCs.

FIG. 3(B) is a graph showing percentage of initial body weight of mice, having human PBMCs, in control experiments of mice administered no antibody.

FIG. 3(C) is a graph showing percentage of initial body weight of mice, having human PBMCs, in control experiments of mice administered isotype control antibody over time. The start of antibody injection on day 21 and the end of antibody injection on day 59 are indicated by dashed lines.

FIG. 3(D) is a graph showing percentage of initial body weight of mice, having human PBMCs, administered antibody COMP1499 over time. The start of antibody injection on day 21 and the end of antibody injection on day 59 are indicated by dashed lines.

FIG. 6(A) is a graph showing blood counts of human CD45+ cells over time in mice administered anti-IL2R gamma antibody H4H12889P or H4H12922P2; or COMP1499 or isotype control antibody. The start of antibody injection on day 21 and the end of antibody injection on day 59 are indicated by dashed lines.

FIG. 6(B) is a graph showing blood counts of human T cells over time in mice administered anti-IL2R gamma antibody H4H12889P or H4H12922P2; or COMP1499 or isotype control antibody. The start of antibody injection on day 21 and the end of antibody injection on day 59 are indicated by dashed lines.

FIG. 6(C) is a graph showing blood counts of human CD4+ T cells over time in mice administered anti-IL2R gamma antibody H4H12889P or H4H12922P2; or COMP1499 or isotype control antibody. The start of antibody injection on day 21 and the end of antibody injection on day 59 are indicated by dashed lines.

FIG. 6(D) is a graph showing blood counts of human CD8+ T cells over time in mice administered anti-IL2R gamma antibody H4H12889P or H4H12922P2; or COMP1499 or isotype control antibody. The start of antibody injection on day 21 and the end of antibody injection on day 59 are indicated by dashed lines.

FIG. 7(A) is a graph showing serum levels of human interferon-gamma cytokine at day 42 post-huPBMC injection in mice administered no antibody (No IgG), REGN1945, COMP1499 or anti-IL2Rgamma antibody H4H12889P or H4H12922P2 or in mice with no human PBMCs. #, significantly different from group "No huPBMCs"; †, significantly different from group "huPBMCs-No IgG"; *, significantly different from group "huPBMCs-REGN1945". Each symbol represents a mouse.

FIG. 7(B) is a graph showing serum levels of human TNF-alpha cytokine at day 42 post-huPBMC injection in mice administered no antibody (No IgG), REGN1945, COMP1499 or anti-IL2Rgamma antibody H4H12889P or H4H12922P2 or in mice with no human PBMCs. #, significantly different from group "No huPBMCs"; †, significantly different from group "huPBMCs-No IgG"; *, significantly different from group "huPBMCs-REGN1945". Each symbol represents a mouse.

FIG. 7(C) is a graph showing serum levels of human IL-6 cytokine at day 42 post-huPBMC injection in mice administered no antibody (No IgG), REGN1945, COMP1499 or anti-IL2Rgamma antibody H4H12889P or H4H12922P2 or in mice with no human PBMCs. #, significantly different from group "No huPBMCs"; †, significantly different from group "huPBMCs-No IgG"; *, significantly different from group "huPBMCs-REGN1945". Each symbol represents a mouse.

FIG. 7(D) is a graph showing serum levels of human IL-8 cytokine at day 42 post-huPBMC injection in mice administered no antibody (No IgG), REGN1945, COMP1499 or anti-IL2Rgamma antibody H4H12889P or H4H12922P2 or in mice with no human PBMCs. #, significantly different from group "No huPBMCs"; †, significantly different from group "huPBMCs-No IgG"; *, significantly different from group "huPBMCs-REGN1945". Each symbol represents a mouse.

FIG. 7(E) is a graph showing serum levels of human IL-10 cytokine at day 42 post-huPBMC injection in mice administered no antibody (No IgG), REGN1945, COMP1499 or anti-IL2Rgamma antibody H4H12889P or H4H12922P2 or in mice with no human PBMCs. #, significantly different from group "No huPBMCs"; †, significantly different from group "huPBMCs-No IgG"; *, significantly different from group "huPBMCs-REGN1945". Each symbol represents a mouse.

FIG. 8(A) is a graph showing serum levels of human IFN-γ over time in mice administered anti-IL2R gamma antibody H4H12889P or H4H12922P2; or COMP1499 or isotype control antibody.

FIG. 8(B) is a graph showing serum levels of human TNFα over time in mice administered anti-IL2R gamma antibody H4H12889P or H4H12922P2; or COMP1499 or isotype control antibody.

FIG. 8(C) is a graph showing serum levels of mouse TNFα over time in mice administered anti-IL2R gamma antibody H4H12889P or H4H12922P2; or COMP1499 or isotype control antibody.

FIG. 8(D) is a graph showing serum levels of mouse IL-6 over time in mice administered anti-IL2R gamma antibody H4H12889P or H4H12922P2; or COMP1499 or isotype control antibody.

DETAILED DESCRIPTION OF THE INVENTION

Figure 1A:
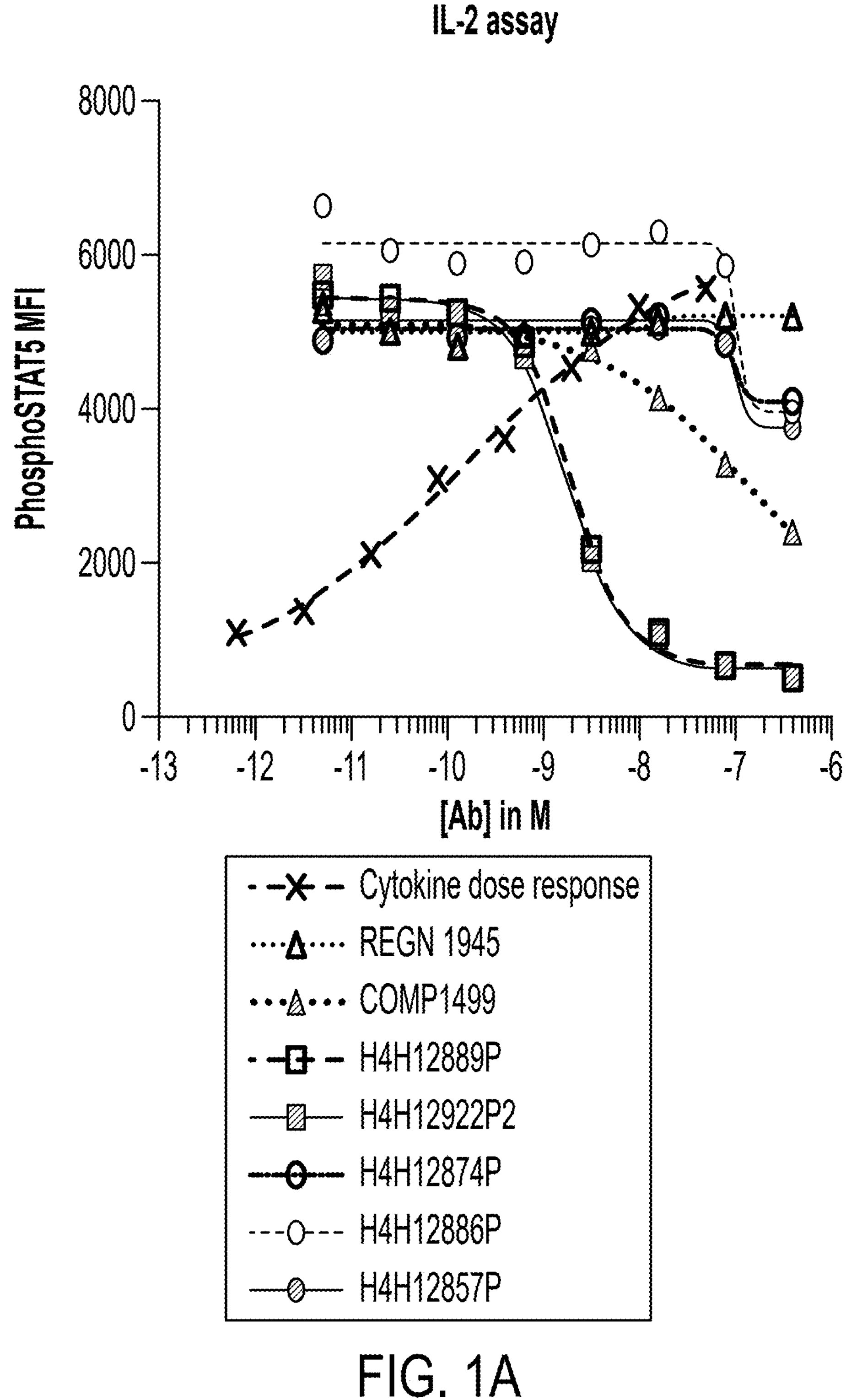
FIG. 1(A) is a graph showing blocking of human IL-2-induced STAT phosphorylation in human CD4+ T cells by various concentrations of anti-IL-2R gamma antibodies H4H12857P, H4H12874P, H4H12886P, H4H12889P and H4H12922P2; and antibodies REGN1945 and COMP1499.
Figure 1B:
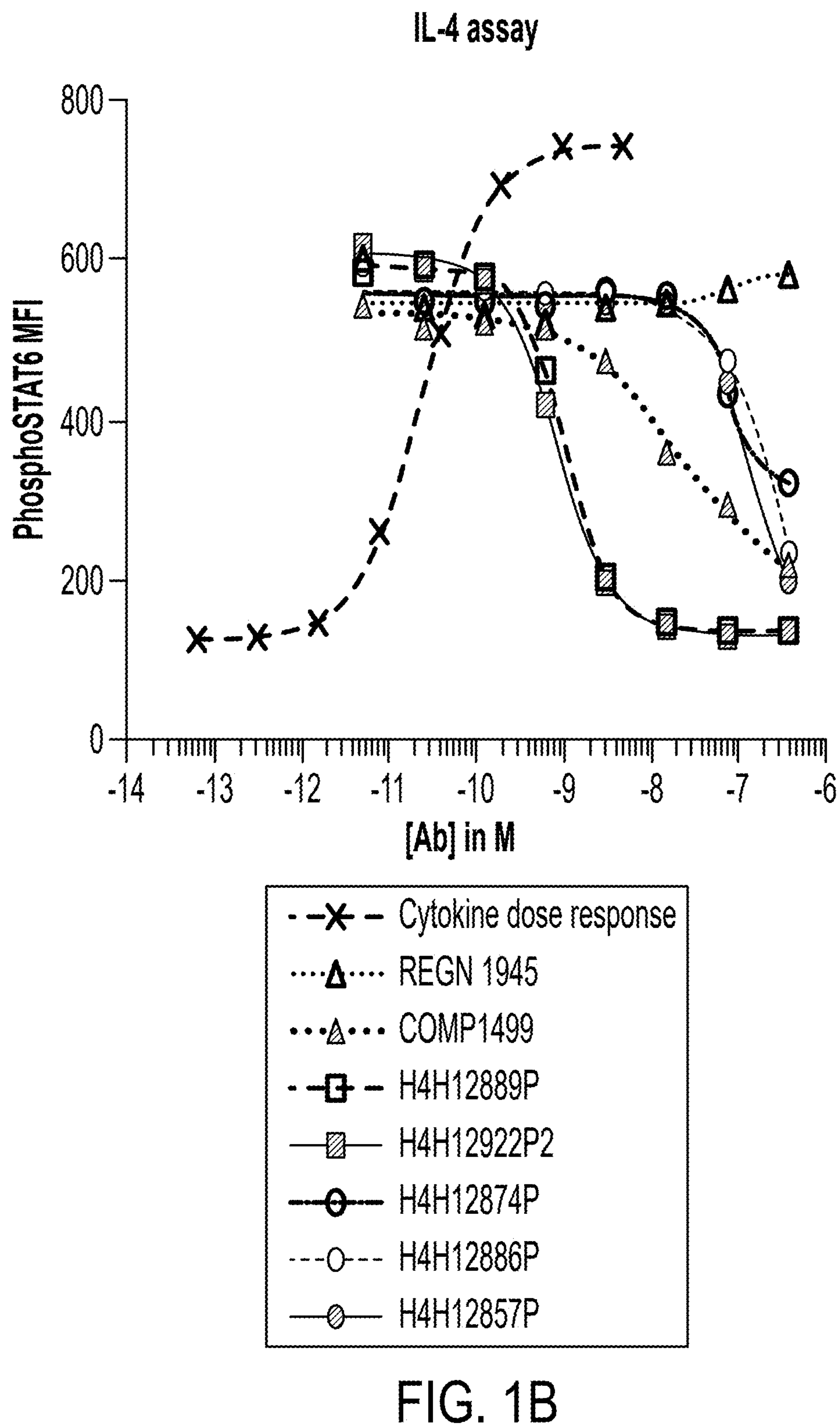
FIG. 1(B) is a graph showing blocking of human IL-4-induced STAT phosphorylation in human CD4+ T cells by various concentrations of anti-IL-2R gamma antibodies H4H12857P, H4H12874P, H4H12886P, H4H12889P and H4H12922P2; and antibodies REGN1945 and COMP1499.
Figure 1C:
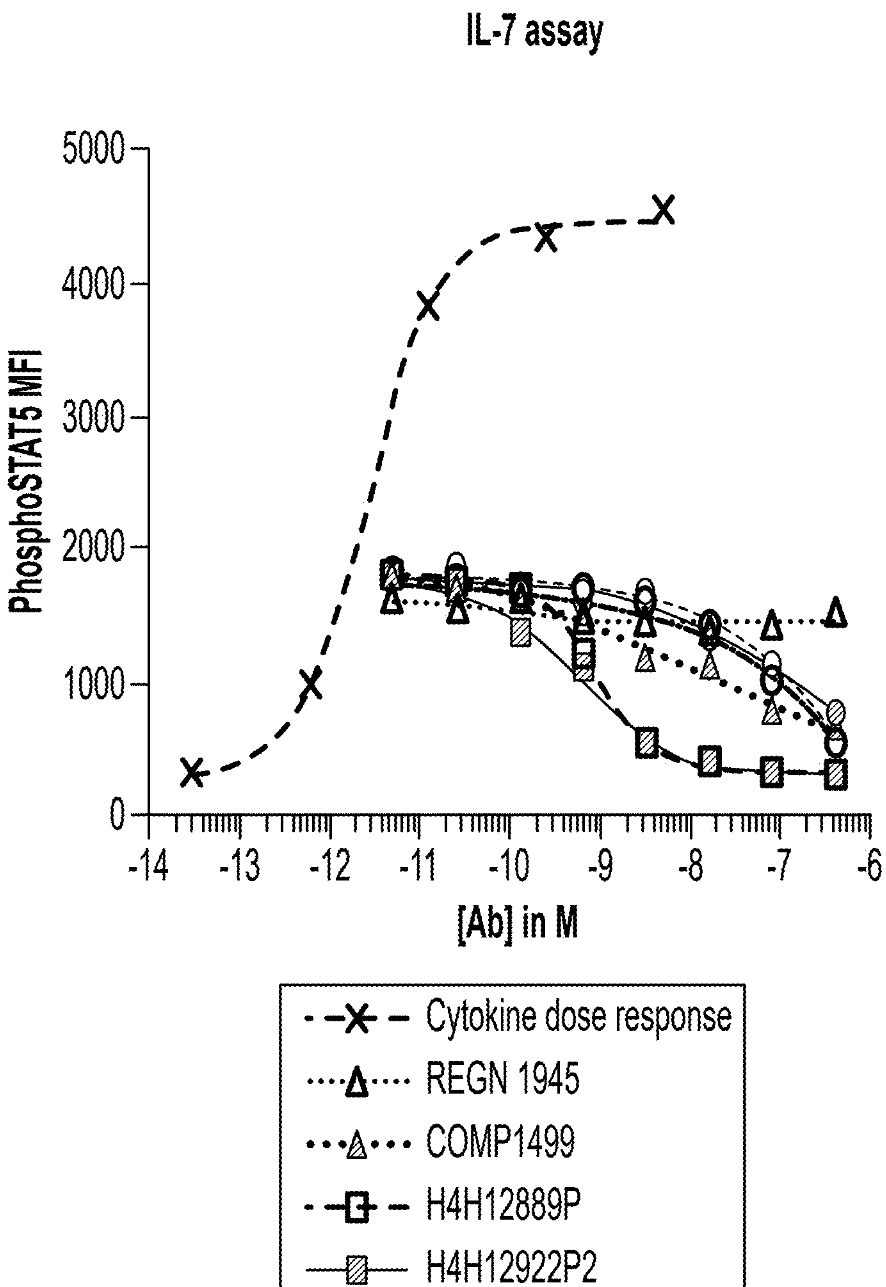
FIG. 1(C) is a graph showing blocking of human IL-7-induced STAT phosphorylation in human CD4+ T cells by various concentrations of anti-IL-2R gamma antibodies H4H12857P, H4H12874P, H4H12886P, H4H12889P and H4H12922P2; and antibodies REGN1945 and COMP1499.
Figure 1D:
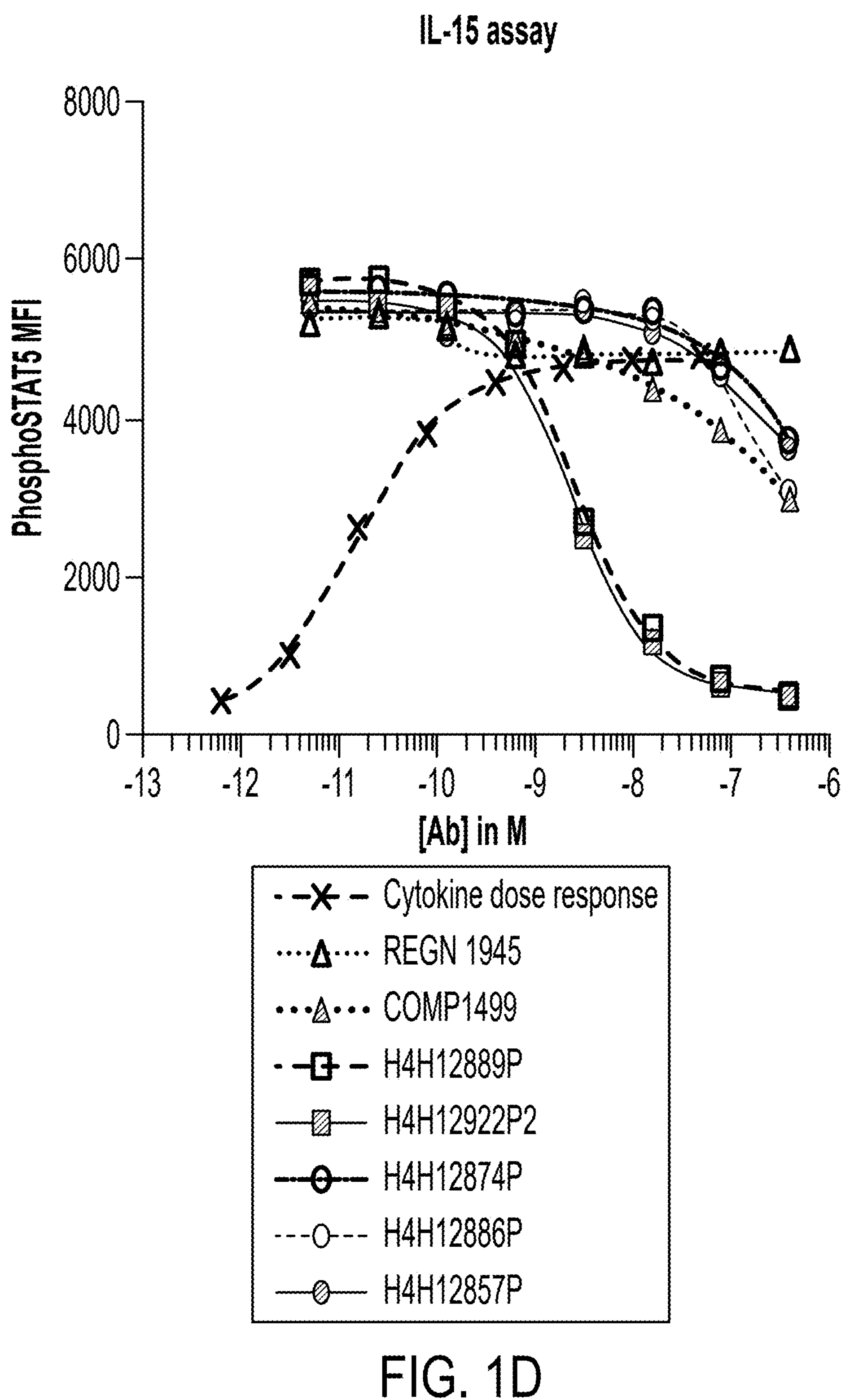
FIG. 1(D) is a graph showing blocking of human IL-15-induced STAT phosphorylation in human CD4+ T cells by various concentrations of anti-IL-2R gamma antibodies H4H12857P, H4H12874P, H4H12886P, H4H12889P and H4H12922P2; and antibodies REGN1945 and COMP1499.
Figure 1E:
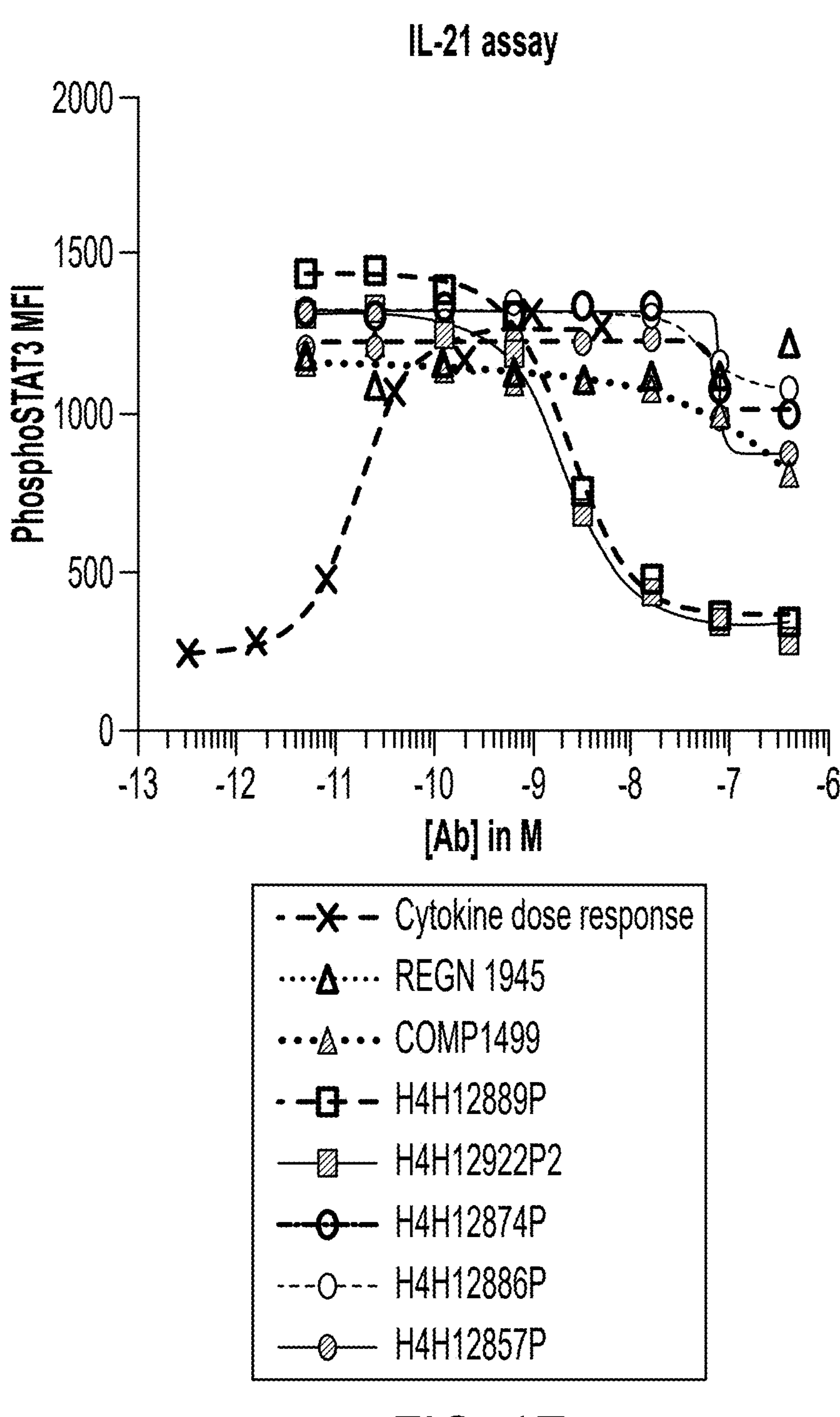
FIG. 1(E) is a graph showing blocking of human IL-21-induced STAT phosphorylation in human CD4+ T cells by various concentrations of anti-IL-2R gamma antibodies H4H12857P, H4H12874P, H4H12886P, H4H12889P and H4H12922P2; and antibodies REGN1945 and COMP1499.

The present invention provides antibodies and antigen-binding fragments thereof that specifically bind to human and *Macaca fascicularis* IL2Rγ and exhibit exceptional biological activity, especially with respect to blockage of cytokine-induced STAT phosphorylation in T-cells and blockage of graft-versus-host disease in an applicable mouse model.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook, et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984); F. M. Ausubel, et al. (eds.), Current Protocols in Molecular Biology, John Wiley & Sons, Inc. (1994).

IL-2Rγ

Interleukin-2 receptor subunit gamma is also known as CD132; common cytokine receptor γc-chain; IL-2RG; IL-2Rg; IL2Rgamma; IL-2Rγ, IMD4; P64: SCIDX; or SCIDX1. IL2Rγ is a subunit which is common to several interleukin receptors including IL-2R, IL-4R, IL-7R, IL-9R, IL-15R and IL21R.

In an embodiment of the invention, human IL2Rγ is encoded by the nucleotide sequence set forth under Genbank accession no. NM_000206. In an embodiment of the invention, human IL2Rγ comprises the amino acid sequence set forth under Genbank accession no. NP_000197.

Antigen-Binding Proteins

The present invention provides antigen-binding proteins, such as antibodies (e.g., human antibodies, monoclonal antibodies and recombinant antibodies) and antigen-binding fragments thereof, that specifically bind to IL2Rγ protein or an antigenic fragment thereof (e.g., the extracellular domain of IL2Rγ). Antigen-binding proteins that bind to the same epitope on IL2Rγ as, or compete for binding to IL2Rγ with any of the antigen-binding proteins set forth herein, are also part of the present invention.

The present invention also provides any polypeptide that includes an amino acid sequence set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 75, 77, 79, 81, 83, 85, 87, 89, 91, 93, 95, 97, 99, 101, 103, 105, 107, 109, 111, 113, 115, 117, 119, 121, 123, 125, 127, 129, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 309, 311, 313, 315, 317, 319, 321, 323, 325, 327, 329, 331, 333, 335, 337, 339, 341, 343, 345, 347, 349, 351, 353, 355, 357, 359, 361, 363, 366, 368, 370, 372, 374, 376 and/or 378 or a variant thereof. Optionally, the polypeptide is fused to one or more other polypeptides, e.g., a human Fc (e.g., a human IgG such as an IgG1 or IgG4 (e.g., comprising a S108P mutation)).

The term "antibody", as used herein, refers to immunoglobulin molecules comprising four polypeptide chains, two heavy chains (HCs) and two light chains (LCs) inter-connected by disulfide bonds (i.e., "full antibody molecules") (e.g. IgG)—for example H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2. In an embodiment of the invention, each antibody heavy chain (HC) comprises a heavy chain variable region ("HCVR" or "$V_H$") (e.g., SEQ ID NO: 2, 22, 42, 62, 81, 101, 119, 138, 156, 174, 190, 200, 210, 218, 238, 258, 276, 286, 296, 315, 335, 345 or 361 or a variant thereof) and a heavy chain constant region (including domains $C_H1$, $C_H2$ and $C_H3$); and each antibody light chain (LC) comprises a light chain variable region ("LCVR or "$V_L$") (e.g., SEQ ID NO: 10, 30, 50, 70, 89, 109, 127, 146, 164, 182, 226, 246, 266, 304, 323, 353 or 368 or a variant thereof) and a light chain constant region (CL). The $V_H$ and $V_L$ regions can be further subdivided into regions of hypervariability, termed complementarity determining regions (CDR), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) are identical to the human germline sequences or are naturally or artificially modified.

Typically, the variable domains of both the heavy and light immunoglobulin chains comprise three hypervariable regions, also called complementarity determining regions (CDRs), located within relatively conserved framework regions (FR). In general, from N-terminal to C-terminal, both light and heavy chains variable domains comprise FR1, CDR1, FR2, CDR2, FR3, CDR3 and FR4. In an embodiment of the invention, the assignment of amino acids to each domain is in accordance with the definitions of Sequences of Proteins of Immunological Interest, Kabat, et al.; National Institutes of Health, Bethesda, Md.; 5th ed.; NIH Publ. No. 91-3242 (1991); Kabat (1978) Adv. Prot. Chem. 32:1-75; Kabat, et al., (1977) J. Biol. Chem. 252:6609-6616; Chothia, et al., (1987) J Mol. Biol. 196:901-917 or Chothia, et al., (1989) Nature 342:878-883. Thus, the present invention includes antibodies and antigen-binding fragments including the CDRs of a $V_H$ and the CDRs of a $V_L$, which $V_H$ and $V_L$ comprise amino acid sequences as set forth herein (or a variant thereof), wherein the CDRs are as defined according to Kabat and/or Chothia.

The terms "antigen-binding portion" or "antigen-binding fragment" of an antibody or antigen-binding protein, and the like, as used herein, include any naturally occurring, enzymatically obtainable, synthetic, or genetically engineered polypeptide or glycoprotein that specifically binds an antigen to form a complex. Non-limiting examples of antigen-binding fragments include: (i) Fab fragments; (ii) $F(ab')_2$ fragments; (iii) Fd fragments (heavy chain portion of a Fab fragment cleaved with papain); (iv) Fv fragments (a $V_H$ or $V_L$); and (v) single-chain Fv (scFv) molecules; consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies and small modular immunopharmaceuticals (SMIPs), are also encompassed within the expression "antigen-binding fragment," as used herein. In an embodiment of the invention, the antigen-binding fragment comprises three or more CDRs of H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2 (e.g., CDR-H1, CDR-H2 and CDR-H3; or CDR-L1, CDR-L2 and CDR-L3).

In an embodiment of the invention, an antigen-binding protein of the present invention (e.g., an antibody or antigen-binding fragment thereof) includes a heavy chain immunoglobulin that comprises a $V_H$ (e.g., an HC) including the combination of heavy chain CDRs (CDR-H1, CDR-H2 and CDR-H3) set forth below in Table A.

TABLE A

Heavy Chain CDRs in Immunoglobulins of the Present Invention.

| CDR-H combination | CDR-H1 | CDR-H2 | CDR-H3 |
|---|---|---|---|
| 1 | 4 | 6 | 8 |
| 2 | 24 | 26 | 28 |
| 3 | 44 | 46 | 48 |
| 4 | 64 | 66 | 68 |
| 5 | 83 | 85 | 87 |
| 6 | 103 | 105 | 107 |
| 7 | 121 | 123 | 125 |
| 8 | 140 | 142 | 144 |
| 9 | 158 | 160 | 162 |
| 10 | 176 | 178 | 180 |
| 11 | 192 | 194 | 196 |
| 12 | 202 | 204 | 206 |
| 13 | 176 | 212 | 214 |
| 14 | 220 | 222 | 224 |
| 15 | 240 | 242 | 244 |
| 16 | 260 | 262 | 264 |
| 17 | 278 | 280 | 282 |
| 18 | 288 | 290 | 292 |
| 19 | 298 | 300 | 302 |
| 20 | 317 | 319 | 321 |
| 21 | 337 | 339 | 341 |

TABLE A-continued

Heavy Chain CDRs in Immunoglobulins of the Present Invention.

| CDR-H combination | CDR-H1 | CDR-H2 | CDR-H3 |
|---|---|---|---|
| 22 | 347 | 349 | 351 |
| 23 | 363 | 66 | 366 |

*Numbers correspond to an amino acid sequence set forth in that SEQ ID NO and/or a light chain immunoglobulin that comprises a $V_L$ (e.g., a LC) including the combination of light chain CDRs (CDR-L1, CDR-L2 and CDR-L3) set forth below in Table B.

TABLE B

Light Chain CDRs in Immunoglobulins of the Present Invention.

| CDR-L combination | CDR-L1 | CDR-L2 | CDR-L3 |
|---|---|---|---|
| 1 | 12 | 14 | 16 |
| 2 | 32 | 34 | 36 |
| 3 | 52 | 54 | 56 |
| 4 | 72 | 54 | 75 |
| 5 | 91 | 93 | 95 |
| 6 | 111 | 54 | 113 |
| 7 | 129 | 54 | 132 |
| 8 | 148 | 54 | 150 |
| 9 | 166 | 14 | 168 |
| 10 | 72 | 54 | 184 |
| 11 | 228 | 230 | 232 |
| 12 | 248 | 250 | 252 |
| 13 | 268 | 54 | 270 |
| 14 | 306 | 230 | 309 |
| 15 | 325 | 327 | 329 |
| 16 | 72 | 54 | 355 |
| 17 | 370 | 372 | 374 |

*Numbers correspond to an amino acid sequence set forth in that SEQ ID NO

In an embodiment of the invention, an antigen-binding protein of the present invention (e.g., an antibody or antigen-binding fragment thereof) includes a heavy and light chain immunoglobulin that comprises a $V_H$ (e.g., an HC) and a $V_L$ (e.g., a LC), respectively, including the combination of heavy and light chain CDRs (CDR-H1, CDR-H2 and CDR-H3; and CDR-L1, CDR-L2 and CDR-L3) set forth below in Table C.

TABLE C

Heavy and Light Chain CDRs in Immunoglobulins of the Present Invention.

| CDR combination | CDR-H1 | CDR-H2 | CDR-H3 | CDR-L1 | CDR-L2 | CDR-L3 |
|---|---|---|---|---|---|---|
| 1 | 4 | 6 | 8 | 12 | 14 | 16 |
| 2 | 24 | 26 | 28 | 32 | 34 | 36 |
| 3 | 44 | 46 | 48 | 52 | 54 | 56 |
| 4 | 64 | 66 | 68 | 72 | 54 | 75 |
| 5 | 83 | 85 | 87 | 91 | 93 | 95 |
| 6 | 103 | 105 | 107 | 111 | 54 | 113 |
| 7 | 121 | 123 | 125 | 129 | 54 | 132 |
| 8 | 140 | 142 | 144 | 148 | 54 | 150 |
| 9 | 158 | 160 | 162 | 166 | 14 | 168 |
| 10 | 176 | 178 | 180 | 72 | 54 | 184 |
| 11 | 192 | 194 | 196 | 72 | 54 | 184 |
| 12 | 202 | 204 | 206 | 72 | 54 | 184 |
| 13 | 176 | 212 | 214 | 72 | 54 | 184 |
| 14 | 220 | 222 | 224 | 228 | 230 | 232 |
| 15 | 240 | 242 | 244 | 248 | 250 | 252 |
| 16 | 260 | 262 | 264 | 268 | 54 | 270 |
| 17 | 278 | 280 | 282 | 72 | 54 | 184 |
| 18 | 288 | 290 | 292 | 72 | 54 | 184 |
| 19 | 298 | 300 | 302 | 306 | 230 | 309 |
| 20 | 317 | 319 | 321 | 325 | 327 | 329 |
| 21 | 337 | 339 | 341 | 72 | 54 | 184 |
| 22 | 347 | 349 | 351 | 72 | 54 | 355 |
| 23 | 363 | 66 | 366 | 370 | 372 | 374 |

*Numbers correspond to an amino acid sequence set forth in that SEQ ID NO

The present invention includes an antigen-binding protein (e.g., an antibody or antigen-binding fragment thereof) comprising polypeptide pairs that comprise the following $V_H$ and $V_L$ amino acid sequences:

SEQ ID NO: 2 and SEQ ID NO: 10;
SEQ ID NO: 22 and SEQ ID NO: 30;
SEQ ID NO: 42 and SEQ ID NO: 50;
SEQ ID NO: 62 and SEQ ID NO: 70;
SEQ ID NO: 81 and SEQ ID NO: 89;
SEQ ID NO: 101 and SEQ ID NO: 109;
SEQ ID NO: 119 and SEQ ID NO: 127;
SEQ ID NO: 138 and SEQ ID NO: 146;
SEQ ID NO: 156 and SEQ ID NO: 164;
SEQ ID NO: 174 and SEQ ID NO: 182;
SEQ ID NO: 190 and SEQ ID NO: 182;
SEQ ID NO: 200 and SEQ ID NO: 182;
SEQ ID NO: 210 and SEQ ID NO: 182;
SEQ ID NO: 218 and SEQ ID NO: 226;
SEQ ID NO: 238 and SEQ ID NO: 246;
SEQ ID NO: 258 and SEQ ID NO: 266;
SEQ ID NO: 276 and SEQ ID NO: 182;
SEQ ID NO: 286 and SEQ ID NO: 182;
SEQ ID NO: 296 and SEQ ID NO: 304;
SEQ ID NO: 315 and SEQ ID NO: 323;
SEQ ID NO: 335 and SEQ ID NO: 182;
SEQ ID NO: 345 and SEQ ID NO: 353; or
SEQ ID NO: 361 and SEQ ID NO: 368.

The present invention includes an antigen-binding protein (e.g., an antibody or antigen-binding fragment thereof) comprising the following amino acid sequence pairs encoding a HC and LC:

SEQ ID NO: 18 and SEQ ID NO: 20;
SEQ ID NO: 38 and SEQ ID NO: 40;
SEQ ID NO: 58 and SEQ ID NO: 60;
SEQ ID NO: 77 and SEQ ID NO: 79;
SEQ ID NO: 97 and SEQ ID NO: 99;
SEQ ID NO: 115 and SEQ ID NO: 117;
SEQ ID NO: 134 and SEQ ID NO: 136;
SEQ ID NO: 152 and SEQ ID NO: 154;
SEQ ID NO: 170 and SEQ ID NO: 172;
SEQ ID NO: 186 and SEQ ID NO: 188;
SEQ ID NO: 198 and SEQ ID NO: 188;
SEQ ID NO: 208 and SEQ ID NO: 188;
SEQ ID NO: 216 and SEQ ID NO: 188;
SEQ ID NO: 234 and SEQ ID NO: 236;
SEQ ID NO: 254 and SEQ ID NO: 256;
SEQ ID NO: 272 and SEQ ID NO: 274;
SEQ ID NO: 284 and SEQ ID NO: 188;
SEQ ID NO: 294 and SEQ ID NO: 188;
SEQ ID NO: 311 and SEQ ID NO: 313;
SEQ ID NO: 331 and SEQ ID NO: 333;
SEQ ID NO: 343 and SEQ ID NO: 188;
SEQ ID NO: 357 and SEQ ID NO: 359; or
SEQ ID NO: 376 and SEQ ID NO: 378.

Embodiments of the present invention also include antigen-binding proteins, e.g., anti-IL2Rγ antibodies and antigen-binding fragments thereof, that comprise immunoglobulin $V_H$s and $V_L$s; or HCs and LCs, which comprise a variant amino acid sequence having 70% or more (e.g., 80%, 85%, 90%, 95%, 97% or 99%) overall amino acid sequence identity or similarity to the amino acid sequences of the corresponding $V_H$s, $V_L$s, HCs or LCs specifically set forth herein, but wherein the CDR-L1, CDR-L2, CDR-L3, CDR-H1, CDR-H2 and CDR-H3 of such immunoglobulins are not variants and comprise the amino acid sequences set forth herein. Thus, in such embodiments, the CDRs within variant antigen-binding proteins are not, themselves, variants.

The present invention includes monoclonal anti-IL2Rγ antigen-binding proteins, e.g., antibodies and antigen-binding fragments thereof, as well as monoclonal compositions comprising a plurality of isolated monoclonal antigen-binding proteins. The term "monoclonal antibody" or "mAb", as used herein, refers to a member of a population of substantially homogeneous antibodies, i.e., the antibody molecules comprising the population are identical in amino acid sequence except for possible naturally occurring mutations that may be present in minor amounts. A "plurality" of such monoclonal antibodies and fragments in a composition refers to a concentration of identical (i.e., as discussed above, in amino acid sequence except for possible naturally occurring mutations that may be present in minor amounts) antibodies and fragments which is above that which would normally occur in nature, e.g., in the blood of a host organism such as a mouse or a human.

In an embodiment of the invention, an anti-IL2Rγ antigen-binding protein, e.g., antibody or antigen-binding fragment comprises a heavy chain constant domain, e.g., of the type IgA (e.g., IgA1 or IgA2), IgD, IgE, IgG (e.g., IgG1, IgG2, IgG3 and IgG4 (e.g., comprising a S228P and/or S108P mutation)) or IgM. In an embodiment of the invention, an antigen-binding protein, e.g., antibody or antigen-binding fragment, comprises a light chain constant domain, e.g., of the type kappa or lambda. The present invention includes antigen-binding proteins comprising the variable domains set forth herein (e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2) which are linked to a heavy and/or light chain constant domain, e.g., as set forth above.

The term "human" antigen-binding protein, such as an antibody or antigen-binding fragment, as used herein, includes antibodies and fragments having variable and constant regions derived from human germline immunoglobulin sequences whether in a human cell or grafted into a non-human cell, e.g., a mouse cell. See e.g., U.S. Pat. No. 8,502,018, 6,596,541 or 5,789,215. The human antibodies and antigen-binding fragments of the invention may, in an embodiment of the invention, include amino acid residues not encoded by human germline immunoglobulin sequences (e.g., having mutations introduced by random or site-specific mutagenesis in vitro or by somatic mutation in vivo), for example in the CDRs and, in particular, CDR3. However, the term "human antibody", as used herein, is not intended to include mAbs in which CDR sequences derived from the germline of another mammalian species (e.g., mouse) have been grafted onto human FR sequences. The term includes antibodies recombinantly produced in a non-human mammal or in cells of a non-human mammal. The term is not intended to include antibodies isolated from or generated in a human subject. The present invention includes human antigen-binding proteins (e.g., antibodies or antigen-binding fragments thereof such as H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2).

The present invention includes anti-IL2Rγ chimeric antigen-binding proteins, e.g., antibodies and antigen-binding fragments thereof, and methods of use thereof. As used herein, a "chimeric antibody" is an antibody having the variable domain from a first antibody and the constant domain from a second antibody, where the first and second antibodies are from different species. (see e.g., U.S. Pat. No. 4,816,567; and Morrison et al., (1984) Proc. Natl. Acad. Sci. USA 81:6851-6855). The present invention includes chimeric antibodies comprising the variable domains which are set forth herein (e.g., from H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2).

The term "recombinant" antigen-binding proteins, such as antibodies or antigen-binding fragments thereof, refers to such molecules created, expressed, isolated or obtained by technologies or methods known in the art as recombinant DNA technology which include, e.g., DNA splicing and transgenic expression. The term includes antibodies expressed in a non-human mammal (including transgenic non-human mammals, e.g., transgenic mice), or a host cell (e.g., Chinese hamster ovary (CHO) cell) or cellular expression system or isolated from a recombinant combinatorial human antibody library. The present invention includes recombinant antigen-binding proteins as set forth herein (e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2).

An antigen-binding fragment of an antibody will, in an embodiment of the invention, comprise at least one variable domain. The variable domain may be of any size or amino acid composition and will generally comprise at least one (e.g., 3) CDR(s), which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$—$V_H$, $V_H$-$V_L$ or $V_L$-$V_L$ dimers. Alternatively, the antigen-binding fragment of an antibody may contain a monomeric $V_H$ and/or $V_L$ domain which are bound non-covalently.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-CL; (viii) $V_L$-$C_H1$; (IX) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-CL. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)). The present invention includes an antigen-binding fragment of an antigen-binding protein set forth herein, for example, H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2.

Antigen-binding proteins (e.g., antibodies and antigen-binding fragments) may be monospecific or multi-specific (e.g., bispecific). Multispecific antigen-binding proteins are discussed further herein. The present invention includes monospecific as well as multispecific (e.g., bispecific) antigen-binding fragments comprising one or more variable domains from an antigen-binding protein that is specifically set forth herein (e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2).

The term "specifically binds" or "binds specifically" refers to those antigen-binding proteins (e.g., antibodies or antigen-binding fragments thereof) having a binding affinity to an antigen, such as IL2Rγ protein, expressed as $K_D$, of at least about $10^{-7}$ M (e.g., $10^{-8}$ M, $10^{-9}$ M, $10^{-10}$M, $10^{-11}$ M or $10^{-12}$ M), as measured by real-time, label free bio-layer interferometry assay, for example, at 25° C. or 37° C., e.g., an OCTET HTX biosensor, or by surface plasmon resonance, e.g., BIACORE (biosensor assay), or by solution-affinity ELISA. The present invention includes antigen-binding proteins that specifically bind to IL2Rγ protein. In an embodiment of the invention, an anti-IL2Rγ antigen-binding protein comprises a $K_D$ value, for binding to human and/or mouse and/or *Macaca fascicularis* and/or rat IL2Rγ or a domain thereof, which value is set forth in any of Tables 3-1 to 3-12. "Anti-IL2Rgamma" refers to an antigen-binding protein (or other molecule), for example an antibody or antigen-binding fragment thereof, that binds specifically to IL2Rgamma.

"Isolated" antigen-binding proteins (e.g., antibodies or antigen-binding fragments thereof), polypeptides, polynucleotides and vectors, are at least partially free of other biological molecules from the cells or cell culture from which they are produced. Such biological molecules include nucleic acids, proteins, other antibodies or antigen-binding fragments, lipids, carbohydrates, or other material such as cellular debris and growth medium. An isolated antigen-binding protein may further be at least partially free of expression system components such as biological molecules from a host cell or of the growth medium thereof. Generally, the term "isolated" is not intended to refer to a complete absence of such biological molecules (e.g., minor or insignificant amounts of impurity may remain) or to an absence of water, buffers, or salts or to components of a pharmaceutical formulation that includes the antigen-binding proteins (e.g., antibodies or antigen-binding fragments).

The present invention includes antigen-binding proteins, e.g., antibodies or antigen-binding fragments, that bind to the same epitope as an antigen-binding protein of the present invention (e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2;

H4H12924P2; H4H12926P2; H4H12927P2; H4H12934P2; H4H13538P; H4H13541P; H4H13544P2; or H4H13545P2).

An antigen is a molecule, such as a peptide (e.g., IL2R gamma or a fragment thereof (an antigenic fragment)), to which, for example, an antibody binds. The specific region on an antigen that an antibody recognizes and binds to is called the epitope. Antigen-binding proteins (e.g., antibodies) of the present invention that specifically bind to such antigens are part of the present invention.

The term "epitope" refers to an antigenic determinant (e.g., on IL2Rγ) that interacts with a specific antigen-binding site of an antigen-binding protein, e.g., a variable region of an antibody molecule, known as a paratope. A single antigen may have more than one epitope. Thus, different antibodies may bind to different areas on an antigen and may have different biological effects. The term "epitope" may also refer to a site on an antigen to which B and/or T cells respond and/or to a region of an antigen that is bound by an antibody. Epitopes may be defined as structural or functional. Functional epitopes are generally a subset of the structural epitopes and have those residues that directly contribute to the affinity of the interaction. Epitopes may be linear or conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. Epitopes to which antigen-binding proteins of the present invention bind may be included in fragments of IL2Rγ, e.g., human IL2Rγ, for example the ectodomain, domain 1 or domain 2 thereof. Antigen-binding proteins (e.g., antibodies) of the present invention that bind to such epitopes are part of the present invention.

Methods for determining the epitope of an antigen-binding protein, e.g., antibody or fragment or polypeptide, include alanine scanning mutational analysis, peptide blot analysis (Reineke (2004) Methods Mol. Biol. 248:443-63), peptide cleavage analysis, crystallographic studies and NMR analysis. In addition, methods such as epitope excision, epitope extraction and chemical modification of antigens can be employed (Tomer (2000) Prot. Sci. 9:487-496). Another method that can be used to identify the amino acids within a polypeptide with which an antigen-binding protein (e.g., antibody or fragment or polypeptide) interacts is hydrogen/deuterium exchange detected by mass spectrometry. See, e.g., Ehring (1999) Analytical Biochemistry 267: 252-259; Engen and Smith (2001) Anal. Chem. 73: 256A-265A.

The present invention includes antigen-binding proteins that compete for binding to IL2Rγ, e.g., a variant IL2Rγ epitope as discussed herein, with an antigen-binding protein of the present invention, e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2. The term "competes" as used herein, refers to an antigen-binding protein (e.g., antibody or antigen-binding fragment thereof) that binds to an antigen (e.g., IL2Rγ) and inhibits or blocks the binding of another antigen-binding protein (e.g., antibody or antigen-binding fragment thereof) to the antigen. Unless otherwise stated, the term also includes competition between two antigen-binding proteins e.g., antibodies, in both orientations, i.e., a first antibody that binds antigen and blocks binding by a second antibody and vice versa. Thus, in an embodiment of the invention, competition occurs in one such orientation. In certain embodiments, the first antigen-binding protein (e.g., antibody) and second antigen-binding protein (e.g., antibody) may bind to the same epitope. Alternatively, the first and second antigen-binding proteins (e.g., antibodies) may bind to different, but, for example, overlapping or non-overlapping epitopes, wherein binding of one inhibits or blocks the binding of the second antibody, e.g., via steric hindrance. Competition between antigen-binding proteins (e.g., antibodies) may be measured by methods known in the art, for example, by a real-time, label-free bio-layer interferometry assay. Also, binding competition between anti-IL2Rγ antigen-binding proteins (e.g., monoclonal antibodies (mAbs)) can be determined using a real time, label-free bio-layer interferometry assay on an OCTET RED384 biosensor (Pall ForteBio Corp.).

Typically, an antibody or antigen-binding fragment of the invention which is modified in some way retains the ability to specifically bind to IL2Rγ, e.g., retains at least 10% of its IL2Rγ binding activity (when compared to the parental antibody) when that activity is expressed on a molar basis. Preferably, an antibody or antigen-binding fragment of the invention retains at least 20%, 50%, 70%, 80%, 90%, 95% or 100% or more of the IL2Rγ binding affinity as the parental antibody. It is also intended that an antibody or antigen-binding fragment of the invention may include conservative or non-conservative amino acid substitutions (referred to as "conservative variants" or "function conserved variants" of the antibody) that do not substantially alter its biologic activity.

A "variant" of a polypeptide, such as an immunoglobulin chain (e.g., an H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2 $V_H$, $V_L$, HC or LC or CDR thereof comprising the amino acid sequence specifically set forth herein), refers to a polypeptide comprising an amino acid sequence that is at least about 70-99.9% (e.g., at least 70, 72, 74, 75, 76, 79, 80, 81, 82, 83, 84, 85, 86, 87, 88, 89, 90, 91, 92, 93, 94, 95, 96, 97, 98, 99, 99.5 or 99.9%) identical or similar to a referenced amino acid sequence that is set forth herein (e.g., any of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 75, 77, 79, 81, 83, 85, 87, 89, 91, 93, 95, 97, 99, 101, 103, 105, 107, 109, 111, 113, 115, 117, 119, 121, 123, 125, 127, 129, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 309, 311, 313, 315, 317, 319, 321, 323, 325, 327, 329, 331, 333, 335, 337, 339, 341, 343, 345, 347, 349, 351, 353, 355, 357, 359, 361, 363, 366, 368, 370, 372, 374, 376 or 378); when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLO- SUM 62 matrix; gap costs: existence 11, extension 1; conditional compositional score matrix adjustment).

Moreover, a variant of a polypeptide may include a polypeptide such as an immunoglobulin chain (e.g., an H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2 $V_H$, $V_L$, HC or LC or CDR thereof) which may include the amino acid sequence of the reference polypeptide whose amino acid sequence is specifically set forth herein but for one or more (e.g., 1, 2, 3, 4, 5, 6, 7, 8, 9 or 10) mutations, e.g., one or more missense mutations (e.g., conservative substitutions), non-sense mutations, deletions, or insertions. For example, the present invention includes anti-IL2Rγ antigen-binding proteins which include an immunoglobulin light chain (or $V_L$) variant comprising the amino acid sequence set forth in SEQ ID NO: 10 but having one or more of such mutations and/or an immunoglobulin heavy chain (or $V_H$) variant comprising the amino acid sequence set forth in SEQ ID NO: 2 but having one or more of such mutations. In an embodiment of the invention, an anti-IL2Rγ antigen-binding protein includes an immunoglobulin light chain variant comprising CDR-L1, CDR-L2 and CDR-L3 wherein one or more (e.g., 1 or 2 or 3) of such CDRs has one or more of such mutations (e.g., conservative substitutions) and/or an immunoglobulin heavy chain variant comprising CDR-H1, CDR-H2 and CDR-H3 wherein one or more (e.g., 1 or 2 or 3) of such CDRs has one or more of such mutations (e.g., conservative substitutions).

The following references relate to BLAST algorithms often used for sequence analysis: BLAST ALGORITHMS: Altschul et al. (2005) FEBS J. 272(20): 5101-5109; Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y.

A "conservatively modified variant" or a "conservative substitution", e.g., of an immunoglobulin chain set forth herein, refers to a variant wherein there is one or more substitutions of amino acids in a polypeptide with other amino acids having similar characteristics (e.g. charge, side-chain size, hydrophobicity/hydrophilicity, backbone conformation and rigidity, etc.). Such changes can frequently be made without significantly disrupting the biological activity of the antibody or fragment. Those of skill in this art recognize that, in general, single amino acid substitutions in non-essential regions of a polypeptide do not substantially alter biological activity (see, e.g., Watson et al. (1987) Molecular Biology of the Gene, The Benjamin/Cummings Pub. Co., p. 224 ($4^{th}$ Ed.)). In addition, substitutions of structurally or functionally similar amino acids are less likely to significantly disrupt biological activity. The present invention includes anti-IL2Rγ antigen-binding proteins comprising such conservatively modified variant immunoglobulin chains.

Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Alternatively, a conservative replacement is any change having a positive value in the PAM250 log-likelihood matrix disclosed in Gonnet et al. (1992) Science 256:1443-45.

Anti-IL2Rγ antigen-binding proteins set forth herein, e.g., comprising variant immunoglobulin chains, may exhibit one or more of the following properties:

- Binds to human IL2Rγ (e.g., a fusion thereof such as a myc-myc-His6 fusion) at 25° C. with a $K_D$ of about $2.75\times10^{-9}$ M to about $3.36\times10^{-7}$ M;
- Binds to human IL2Rγ (e.g., a fusion thereof such as a myc-myc-His6 fusion) at 37° C. with a $K_D$ of about $6.42\times10^{-9}$ M to about $3.53\times10^{-7}$ M (or binds with a $K_D$ of less than about $3.53\times10^{-7}$ M);
- Binds to *Macaca fascicularis* IL-2Rγ (e.g., a fusion thereof such as a myc-myc-His6 fusion) at 25° C. with a $K_D$ of about $3.18\times10^{-9}$ M to about $2.38\times10^{-7}$ M;
- Binds to *Macaca fascicularis* IL-2Rγ (e.g., a fusion thereof such as a myc-myc-His6 fusion) at 37° C. with a $K_D$ of about $8.29\times10^{-9}$ M to about $3.20\times10^{-7}$M (or binds with a $K_D$ of less than about 3.20× 10-7 M);
- Binds to human IL2Rγ (e.g., a fusion thereof such as to a C-terminal mouse IgG2a Fc tag) at 25° C. with a $K_D$ of about $2.45\times10^{-9}$ M to about $1.20\times10^{-8}$ M (or binds with a $K_D$ of less than about $1.20\times10^{-8}$ M);
- Binds to human IL2Rγ (e.g., a fusion thereof such as to a C-terminal mouse IgG2a Fc tag) at 37° C. with a $K_D$ of about $1.86\times10^{-11}$ M to about $3.00\times10^{-8}$ M (or binds with a $K_D$ of less than about $3.00\times10^{-8}$ M);
- Binds to mouse IL2Rγ (e.g., a fusion thereof such as a myc-myc-His6 fusion) at 25° C. with a $K_D$ of about $1.84\times10^{-8}$ M, $3.76\times10^{-9}$ M, $1.08\times10^{-7}$ M, $2.17\times10^{-8}$ M, $6.02\times10^{-9}$ M or $7.93\times10^{-8}$ M (or binds does not bind);
- Binds to mouse IL2Rγ (e.g., a fusion thereof such as a myc-myc-His6 fusion) at 37° C. with a $K_D$ of about $5.59\times10^{-8}$ M, $6.11\times10^{-9}$ M, $3.87\times10^{-7}$ M, $5.16\times10^{-8}$ M, $8.70\times10^{-9}$ M or $2.15\times10^{-7}$ M (or binds does not bind);
- Binds to human IL2Rγ domain 1 (e.g., a fusion thereof such as a myc-myc-His6 fusion) at 25° C. with a $K_D$ of about $3.32\times10^{-9}$ M to about $1.97\times10^{-7}$ M (or binds does not bind);

Binds to human IL2Rγ domain 1 (e.g., a fusion thereof such as a myc-myc-His6 fusion) at 37° C. with a $K_D$ of about $4.13\times10^{-9}$ M to about $2.25\times10^{-7}$ M (or binds does not bind);

Binds to human IL2Rγ domain 2 (e.g., a fusion thereof such as a myc-myc-His6 fusion) at 25° C. with a $K_D$ of about $2.91\times10^{-7}$ M to about $5.35\times10^{-10}$ (or binds does not bind);

Binds to human IL2Rγ domain 2 (e.g., a fusion thereof such as a myc-myc-His6 fusion) at 37° C. with a $K_D$ of about $1.14\times10^{-8}$ or about $1.27\times10^{-8}$ (or binds does not bind);

Blocks STAT phosphorylation in T-cells (e.g., human $CD4^+$ T cells), for example which is induced by IL-2 (e.g., at about 10 nM), IL-4 (e.g., at about 50 pM), IL7 (e.g., at about 1 pM), IL-15 (e.g., at about 0.5 nM) and/or IL-21 (e.g., at about 50 pM), e.g. at an $IC_{50}$ of about 1 nM to about 0.5 nM;

Blocks STAT phosphorylation in mast cells (e.g., differentiated human mast cells), for example which is induced by IL-9 (e.g., at about 2 nM), e.g., with an $IC_{50}$ of about $4\times10^{-10}$ M;

Reduces the number of human immune cells (e.g., human PBMCs (peripheral blood mononuclear cells), for example, human CD45+ cells, human T cells, human CD4+ T cells and/or human CD8+ T cells) in a mouse after injection with human peripheral blood mononuclear cells (PBMCs) (e.g., NOD-scid IL2rγ null (NSG) mouse);

Reduces the levels of serum human cytokines (e.g., human IFN-γ, human TNFα, human IL-6, human IL-8 and/or human IL-10) and/or mouse cytokines (e.g., mouse TNFα, mouse IL-6, mouse KC/GRO and/or mouse IL-10) in mice (e.g., NOD-scid IL2rγ null (NSG) mouse) in a mouse after injection with human peripheral blood mononuclear cells (PBMCs);

Competes for binding to human IL-2Rγ, for example, on a cell surface (e.g., tagged with a C-terminal myc-myc-hexahistidine tag), with any one or more anti-IL2Rγ antibodies set forth herein;

Binds to the same epitope on IL2Rγ, for example, on a cell surface (e.g., tagged with a C-terminal myc-myc-hexahistidine tag) as any one or more anti-IL2Rγ antibodies set forth herein;

Does not bind detectably to mouse or rat IL2Rγ (e.g., as measured by Biacore at 37° C.);

Protects mice from weight loss and/or death due to GvHD in a GvHD mouse model;

Blocks binding of a hybrid receptor comprising IL2Rγ complexed with a cytokine-specific receptor subunit from binding to a cytokine such as IL-2, IL-4, IL-7, IL-9, IL-15 and/or IL-21; and/or Inhibits IL2Rγ intracellular signaling (e.g., in a human B-lymphocyte cell or human natural killer cell) through the JAK-STAT pathway, e.g., which is induced by IL2, IL4, IL7, IL9, IL15 and/or IL21, for example, as measured by luciferase expression in a cell including a luciferase gene operably linked to a STAT3 response element.

"H4H12857P"; "H4H12858P"; "H4H12859P"; "H4H12863P"; "H4H12874P"; "H4H12871P"; "H4H12884P"; "H4H12886P"; "H4H12889P"; "H4H12890P"; "H4H12899P"; "H4H12900P"; "H4H12908P"; "H4H12913P2"; "H4H12922P2"; "H4H12924P2"; "H4H12926P2"; "H4H12927P2"; "H4H12934P2"; "H4H13538P"; "H4H13541P"; "H4H13544P2"; or "H4H13545P2", unless otherwise stated, refer to anti-IL2Rγ antigen-binding proteins, e.g., antibodies and antigen-binding fragments thereof (including multispecific antigen-binding proteins), comprising an immunoglobulin heavy chain or variable region thereof ($V_H$) comprising the amino acid sequence specifically set forth herein for H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2 (e.g., SEQ ID NO: 2, 18, 22, 38, 42, 58, 62, 77, 81, 97, 101, 115, 119, 134, 138, 152, 156, 170, 174, 186, 190, 198, 200, 208, 210, 216, 218, 234, 238, 254, 258, 272, 276, 284, 286, 294, 296, 311, 315, 331, 335, 343, 345, 357, 361 or 376) (or a variant thereof), and/or an immunoglobulin light chain or variable region thereof ($V_L$) comprising the amino acid sequence specifically set forth herein for H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2 (e.g., SEQ ID NO: 10, 20, 30, 40, 50, 60, 70, 79, 89, 99, 109, 117, 127, 136, 146, 154, 164, 172, 182, 188, 226, 236, 246, 256, 266, 274, 304, 313, 323, 333, 353, 359, 368 or 378) (or a variant thereof), respectively; and/or that comprise a heavy chain or $V_H$ that comprises the CDRs thereof (CDR-H1 (or a variant thereof), CDR-H2 (or a variant thereof) and CDR-H3 (or a variant thereof)) and/or a light chain or $V_L$ that comprises the CDRs thereof (CDR-L1 (or a variant thereof), CDR-L2 (or a variant thereof) and CDR-L3 (or a variant thereof)). In an embodiment of the invention, the $V_H$ is linked to an IgG constant heavy chain domain, for example, human IgG constant heavy chain domain (e.g., IgG1 or IgG4 (e.g., comprising the S228P and/or S108P mutation)) and/or the $V_L$ is linked to a light chain constant domain, for example a human light chain constant domain (e.g., lambda or kappa constant light chain domain). Polynucleotides encoding one or more of any such immunoglobulin chains (e.g., $V_H$, $V_L$, HC and/or LC) forms part of the present invention.

The present invention includes "neutralizing" or "antagonist" anti-IL2Rγ antigen-binding proteins (e.g., antibody or antigen-binding fragment) which includes molecules that inhibit an activity of IL2Rγ (e.g., binding of a hybrid receptor comprising IL2Rγ complexed with a cytokine-specific receptor subunit from binding to a cytokine such as IL-2, IL-4, IL-7, IL-9, IL-15 and/or IL-21) to any detectable degree.

Antibodies and antigen-binding fragments of the present invention (e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2) comprise immunoglobulin chains including the amino acid sequences specifically set forth herein (and variants thereof) as well as cellular and in vitro post-translational modifications to the antibody or fragment. For example, the present invention includes antibodies and antigen-binding fragments thereof that specifically bind to IL2Rγ comprising heavy and/or light chain amino acid sequences set forth herein as well as antibodies and fragments wherein one or more asparagine, serine and/or threonine residues is glycosylated, one or more asparagine residues is deamidated, one or more residues (e.g., Met, Trp and/or His) is oxidized, the N-terminal glutamine is pyroglutamate (pyroE) and/or the C-terminal lysine or other amino acid is missing.

The present invention provides a vessel (e.g., a plastic or glass vial, e.g., with a cap or a chromatography column, hollow bore needle or a syringe cylinder) comprising an anti-IL2Rγ antigen-binding protein of the present invention, e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2.

The present invention also provides an injection device comprising one or more antigen-binding proteins (e.g., antibody or antigen-binding fragment) that bind specifically to IL2Rγ, e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2, or a pharmaceutical formulation thereof. The injection device may be packaged into a kit. An injection device is a device that introduces a substance into the body of a subject via a parenteral route, e.g., intraocular, intravitreal, intramuscular, subcutaneous or intravenous. For example, an injection device may be a syringe or an auto-injector (e.g., pre-filled with the pharmaceutical formulation) which, for example, includes a cylinder or barrel for holding fluid to be injected (e.g., comprising the antibody or fragment or a pharmaceutical formulation thereof), a needle for piecing skin, blood vessels or other tissue for injection of the fluid; and a plunger for pushing the fluid out of the cylinder and through the needle bore and into the body of the subject.

The present invention further provides methods for administering an anti-IL2Rγ antigen-binding protein of the present invention, e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2, to a subject, comprising introducing the antigen-binding protein into the body of the subject (e.g., a human), for example, parenterally. For example, the method comprises piercing the body of the subject with a needle of a syringe and injecting the antigen-binding protein into the body of the subject, e.g., into the vein, artery, eye, muscular tissue or subcutis of the subject.

Polynucleotides and Methods of Making

A polynucleotide includes DNA and RNA. The present invention includes any polynucleotide of the present invention, for example, encoding an immunoglobulin $V_H$, $V_L$, CDR-H, CDR-L, HC or LC of H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2, optionally, which is operably linked to a promoter or other expression control sequence. For example, the present invention provides any polynucleotide (e.g., DNA) that includes a nucleotide sequence set forth in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 74, 76, 78, 80, 82, 84, 86, 88, 90, 92, 94, 96, 98, 100, 102, 104, 106, 108, 110, 112, 114, 116, 118, 120, 122, 124, 126, 128, 130, 131, 133, 135, 137, 139, 141, 143, 145, 147, 149, 151, 153, 155, 157, 159, 161, 163, 165, 167, 169, 171, 173, 175, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 308, 310, 312, 314, 316, 318, 320, 322, 324, 326, 328, 330, 332, 334, 336, 338, 340, 342, 344, 346, 348, 350, 352, 354, 356, 358, 360, 362, 364, 365, 367, 369, 371, 373, 375 or 377. In an embodiment of the invention, a polynucleotide of the present invention is fused to a secretion signal sequence. Polypeptides encoded by such polynucleotides are also within the scope of the present invention.

In general, a "promoter" or "promoter sequence" is a DNA regulatory region capable of binding an RNA polymerase in a cell (e.g., directly or through other promoter-bound proteins or substances) and initiating transcription of a coding sequence. A promoter may be operably linked to other expression control sequences, including enhancer and repressor sequences and/or with a polynucleotide of the invention. Promoters which may be used to control gene expression include, but are not limited to, cytomegalovirus (CMV) promoter (U.S. Pat. Nos. 5,385,839 and 5,168,062), the SV40 early promoter region (Benoist, et al., (1981) Nature 290:304-310), the promoter contained in the 3' long terminal repeat of Rous sarcoma virus (Yamamoto, et al., (1980) Cell 22:787-797), the herpes thymidine kinase promoter (Wagner, et al., (1981) Proc. Natl. Acad. Sci. USA 78:1441-1445), the regulatory sequences of the metallothionein gene (Brinster, et al., (1982) Nature 296:39-42); prokaryotic expression vectors such as the beta-lactamase promoter (VIIIa-Komaroff, et al., (1978) Proc. Natl. Acad. Sci. USA 75:3727-3731), or the tac promoter (DeBoer, et al., (1983) Proc. Natl. Acad. Sci. USA 80:21-25); see also "Useful proteins from recombinant bacteria" in Scientific American (1980) 242:74-94; and promoter elements from yeast or other fungi such as the Gal4 promoter, the ADC (alcohol dehydrogenase) promoter, PGK (phosphoglycerol kinase) promoter or the alkaline phosphatase promoter.

A polynucleotide encoding a polypeptide is "operably linked" to a promoter or other expression control sequence when, in a cell or other expression system, the sequence directs RNA polymerase mediated transcription of the coding sequence into RNA, preferably mRNA, which then may be RNA spliced (if it contains introns) and, optionally, translated into a protein encoded by the coding sequence.

The present invention includes a polynucleotide comprising the following polynucleotide pairs encoding a $V_H$ and $V_L$:

SEQ ID NO: 1 and SEQ ID NO: 9;
SEQ ID NO: 21 and SEQ ID NO: 29;
SEQ ID NO: 41 and SEQ ID NO: 49;
SEQ ID NO: 61 and SEQ ID NO: 69;
SEQ ID NO: 80 and SEQ ID NO: 88;
SEQ ID NO: 100 and SEQ ID NO: 108;
SEQ ID NO: 118 and SEQ ID NO: 126;
SEQ ID NO: 137 and SEQ ID NO: 145;
SEQ ID NO: 155 and SEQ ID NO: 163;
SEQ ID NO: 173 and SEQ ID NO: 181;
SEQ ID NO: 189 and SEQ ID NO: 181;
SEQ ID NO: 199 and SEQ ID NO: 181;
SEQ ID NO: 209 and SEQ ID NO: 181;
SEQ ID NO: 217 and SEQ ID NO: 225;
SEQ ID NO: 237 and SEQ ID NO: 245;

SEQ ID NO: 257 and SEQ ID NO: 265;
SEQ ID NO: 275 and SEQ ID NO: 181;
SEQ ID NO: 285 and SEQ ID NO: 181;
SEQ ID NO: 295 and SEQ ID NO: 303;
SEQ ID NO: 314 and SEQ ID NO: 322;
SEQ ID NO: 334 and SEQ ID NO: 181;
SEQ ID NO: 344 and SEQ ID NO: 352; or
SEQ ID NO: 360 and SEQ ID NO: 367.

The present invention includes a polynucleotide comprising the following polynucleotide sets which encode a CDR-H1, CDR-H2, CDR-H3, CDR-L1, CDR-L2 and CDR-L3:

SEQ ID NOs: 3, 5, 7, 11, 13 and 15;
SEQ ID NOs: 23, 25, 27, 31, 33 and 35;
SEQ ID NOs: 43, 45, 47, 51, 53 and 55;
SEQ ID NOs: 63, 65, 67, 71, 73 and 74;
SEQ ID NOs: 82, 84, 86, 90, 92 and 94;
SEQ ID NOs: 102, 104, 106, 110, 73 and 112;
SEQ ID NOs: 120, 122, 124, 128, 130 and 131;
SEQ ID NOs: 139, 141, 143, 147, 73 and 149;
SEQ ID NOs: 157, 159, 161, 165, 13 and 167;
SEQ ID NOs: 175, 177, 179, 71, 73 and 183;
SEQ ID NOs: 191, 193, 195, 71, 73 and 183;
SEQ ID NOs: 201, 203, 205, 71, 73 and 183;
SEQ ID NOs: 175, 211, 213, 71, 73 and 183;
SEQ ID NOs: 219, 221, 223, 227, 229 and 231;
SEQ ID NOs: 239, 241, 243, 247, 249 and 251;
SEQ ID NOs: 259, 261, 263, 267, 73 and 269;
SEQ ID NOs: 277, 279, 281, 71, 73 and 183;
SEQ ID NOs: 287, 289, 291, 71, 73 and 183;
SEQ ID NOs: 297, 299, 301, 305, 307 and 308;
SEQ ID NOs: 316, 318, 320, 324, 326 and 328;
SEQ ID NOs: 336, 338, 340, 71, 73 and 183;
SEQ ID NOs: 346, 348, 350, 71, 73 and 354; or
SEQ ID NOs: 362, 364, 365, 369, 371 and 373.

The present invention includes a polynucleotide comprising the following polynucleotide pairs encoding a HC and LC:

SEQ ID NO: 17 and SEQ ID NO: 19;
SEQ ID NO: 37 and SEQ ID NO: 39;
SEQ ID NO: 57 and SEQ ID NO: 59;
SEQ ID NO: 76 and SEQ ID NO: 78;
SEQ ID NO: 96 and SEQ ID NO: 98;
SEQ ID NO: 114 and SEQ ID NO: 116;
SEQ ID NO: 133 and SEQ ID NO: 135;
SEQ ID NO: 151 and SEQ ID NO: 153;
SEQ ID NO: 169 and SEQ ID NO: 171;
SEQ ID NO: 185 and SEQ ID NO: 187;
SEQ ID NO: 197 and SEQ ID NO: 187;
SEQ ID NO: 207 and SEQ ID NO: 187;
SEQ ID NO: 215 and SEQ ID NO: 187;
SEQ ID NO: 233 and SEQ ID NO: 235;
SEQ ID NO: 253 and SEQ ID NO: 255;
SEQ ID NO: 271 and SEQ ID NO: 273;
SEQ ID NO: 283 and SEQ ID NO: 187;
SEQ ID NO: 293 and SEQ ID NO: 187;
SEQ ID NO: 310 and SEQ ID NO: 312;
SEQ ID NO: 330 and SEQ ID NO: 332;
SEQ ID NO: 342 and SEQ ID NO: 187;
SEQ ID NO: 356 and SEQ ID NO: 358; or
SEQ ID NO: 375 and SEQ ID NO: 377.

The present invention includes polynucleotides encoding immunoglobulin polypeptide chains which are variants of those whose nucleotide sequence is specifically set forth herein. A "variant" of a polynucleotide refers to a polynucleotide comprising a nucleotide sequence that is at least about 70-99.9% (e.g., 70, 72, 74, 75, 76, 79, 80, 81, 82, 83, 84, 85, 86, 87, 88, 89, 90, 91, 92, 93, 94, 95, 96, 97, 98, 99, 99.5, 99.9%) identical to a referenced nucleotide sequence that is set forth herein; when the comparison is performed by a BLAST algorithm wherein the parameters of the algorithm are selected to give the largest match between the respective sequences over the entire length of the respective reference sequences (e.g., expect threshold: 10; word size: 28; max matches in a query range: 0; match/mismatch scores: 1, −2; gap costs: linear). In an embodiment of the invention, a variant of a nucleotide sequence specifically set forth herein comprises one or more (e.g., 1, 2, 3, 4, 5, 6, 7, 8, 9, 10, 11 or 12) point mutations, insertions (e.g., in frame insertions) or deletions (e.g., in frame deletions) of one or more nucleotides. Such mutations may, in an embodiment of the invention, be missense or nonsense mutations. In an embodiment of the invention, such a variant polynucleotide encodes an immunoglobulin polypeptide chain which can be incorporated into an anti-IL2Rγ antigen-binding protein, i.e., such that the protein retains specific binding to IL2Rγ.

Eukaryotic and prokaryotic host cells, including mammalian cells, may be used as hosts for expression of an anti-IL2Rγ antigen-binding protein (e.g., antibody or antigen-binding fragment thereof). Such host cells are well known in the art and many are available from the American Type Culture Collection (ATCC). These host cells include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Other cell lines that may be used are insect cell lines (e.g., *Spodoptera frugiperda* or *Trichoplusia ni*), amphibian cells, bacterial cells, plant cells and fungal cells. Fungal cells include yeast and filamentous fungus cells including, for example, *Pichia, Pichia pastoris, Pichia finlandica, Pichia trehalophila, Pichia koclamae, Pichia membranaefaciens, Pichia minuta* (*Ogataea minuta, Pichia lindneri*), *Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa*. The present invention includes an isolated host cell (e.g., a CHO cell or any type of host cell set forth above) comprising an antigen-binding protein, a $V_H$, $V_L$, HC, LC or CDRs thereof (or variant thereof), such as H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2; and/or a polynucleotide encoding one or more immunoglobulin chains thereof (e.g., as discussed herein).

The present invention also includes a cell which is expressing IL2Rγ or an antigenic fragment or fusion thereof (e.g., $His_6$, Fc and/or myc) which is bound by an antigen-binding protein of the present invention (e.g., an antibody or antigen-binding fragment thereof), for example, H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P;

H4H13541P; H4H13544P2; or H4H13545P2, for example, wherein the cell is in the body of a subject or is in vitro.

In addition, the present invention also provides a complex comprising an anti-IL2Rγ antigen-binding protein, e.g., antibody or antigen-binding fragment thereof, as discussed herein complexed with IL2Rγ polypeptide or an antigenic fragment thereof or fusion thereof and/or with a secondary antibody or antigen-binding fragment thereof (e.g., detectably labeled secondary antibody) that binds specifically to the anti-IL2Rγ antibody or fragment. In an embodiment of the invention, the complex is in vitro (e.g., is immobilized to a solid substrate) or is in the body of a subject.

Recombinant anti-IL2Rγ antigen-binding proteins, e.g., antibodies and antigen-binding fragments, disclosed herein may also be produced in an *E. coli*/T7 expression system. In this embodiment, polynucleotides encoding the anti-IL2Rγ antibody immunoglobulin molecules of the invention (e.g., HC, LC, $V_H$ and/or $V_L$ or CDRs thereof of H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2) may be inserted into a pET-based plasmid and expressed in the *E. coli*/T7 system. For example, the present invention includes methods for expressing an antibody or antigen-binding fragment thereof or immunoglobulin chain thereof in a host cell (e.g., bacterial host cell such as *E. coli* such as BL21 or BL21DE3) comprising expressing T7 RNA polymerase in the cell which also includes a polynucleotide encoding an immunoglobulin chain (e.g., including the nucleotide sequence in any one or more of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 74, 76, 78, 80, 82, 84, 86, 88, 90, 92, 94, 96, 98, 100, 102, 104, 106, 108, 110, 112, 114, 116, 118, 120, 122, 124, 126, 128, 130, 131, 133, 135, 137, 139, 141, 143, 145, 147, 149, 151, 153, 155, 157, 159, 161, 163, 165, 167, 169, 171, 173, 175, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 308, 310, 312, 314, 316, 318, 320, 322, 324, 326, 328, 330, 332, 334, 336, 338, 340, 342, 344, 346, 348, 350, 352, 354, 356, 358, 360, 362, 364, 365, 367, 369, 371, 373, 375 or 377; or a variant thereof) that is operably linked to a T7 promoter. For example, in an embodiment of the invention, a bacterial host cell, such as an *E. coli*, includes a polynucleotide encoding the T7 RNA polymerase gene operably linked to a lac promoter and expression of the polymerase and the chain is induced by incubation of the host cell with IPTG (isopropyl-beta-D-thiogalactopyranoside). See U.S. Pat. Nos. 4,952,496 and 5,693,489 or Studier & Moffatt, Use of bacteriophage T7 RNA polymerase to direct selective high-level expression of cloned genes, J. Mol. Biol. 1986 May 5; 189(1): 113-30.

There are several methods by which to produce recombinant antibodies which are known in the art. One example of a method for recombinant production of antibodies is disclosed in U.S. Pat. No. 4,816,567.

Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040; 4,740,461 and 4,959,455. Thus, the present invention includes recombinant methods for making an anti-IL2Rγ antigen-binding protein, such as an antibody or antigen-binding fragment thereof of the present invention, or an immunoglobulin chain thereof, comprising (i) introducing, into a host cell, one or more polynucleotides (e.g., including the nucleotide sequence in any one or more of SEQ ID NOs: 1, 9, 17, 19, 21, 29, 37, 39, 41, 49, 57, 59, 61, 69, 76, 78, 80, 88, 96, 98, 100, 108, 114, 116, 118, 126, 133, 135, 137, 145, 151, 153, 155, 163, 169, 171, 173, 181, 185, 187, 189, 197, 199, 207, 209, 215, 217, 225, 233, 235, 237, 245, 253, 255, 257, 265, 271, 273, 275, 283, 285, 293, 295, 303, 310, 312, 314, 322, 330, 332, 334, 342, 344, 352, 356, 358, 360, 367, 375 or 377; or a variant thereof) encoding light and/or heavy immunoglobulin chains of the antigen-binding protein, e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2, for example, wherein the polynucleotide is in a vector; and/or integrates into the host cell chromosome and/or is operably linked to a promoter; (ii) culturing the host cell (e.g., CHO or *Pichia* or *Pichia pastoris*) under conditions favorable to expression of the polynucleotide and, (iii) optionally, isolating the antigen-binding protein (e.g., antibody or antigen-binding fragment) or chain from the host cell and/or medium in which the host cell is grown. When making an antigen-binding protein (e.g., antibody or antigen-binding fragment) comprising more than one immunoglobulin chain, e.g., an antibody that comprises two heavy immunoglobulin chains and two light immunoglobulin chains, co-expression of the chains in a single host cell leads to association of the chains, e.g., in the cell or on the cell surface or outside the cell if such chains are secreted, so as to form the antigen-binding protein (e.g., antibody or antigen-binding fragment). The methods of the present invention include those wherein only a heavy immunoglobulin chain or only a light immunoglobulin chain or both (e.g., any of those discussed herein including mature fragments and/or variable domains thereof) are expressed in a cell. Such single chains are useful, for example, as intermediates in the expression of an antibody or antigen-binding fragment that includes such a chain. For example, the present invention also includes anti-IL2Rγ antigen-binding proteins, such as antibodies and antigen-binding fragments thereof which are the product of the production methods set forth herein, and, optionally, the purification methods set forth herein.

In an embodiment of the invention, a method for making an anti-IL2Rγ antigen-binding protein, e.g., antibody or antigen-binding fragment thereof, includes a method of purifying the antigen-binding protein, e.g., by column chromatography, precipitation and/or filtration. As discussed, the product of such a method also forms part of the present invention.

Preparation of Human Antibodies

The anti-IL2Rγ antibodies of the present invention can be fully human antibodies. Methods for generating monoclonal antibodies, including fully human monoclonal antibodies are known in the art. Any such known methods can be used in the context of the present invention to make human antibodies that specifically bind to human IL2Rγ.

Using VELOCIMMUNE technology (producing optimized fully human monoclonal antibodies), for example, or any other similar known method for generating fully human monoclonal antibodies, high affinity chimeric antibodies to IL2Rγ are initially isolated having a human variable region and a mouse constant region. As in the experimental section below, the antibodies are characterized and selected for desirable characteristics, including affinity, ligand blocking activity, selectivity, epitope, etc. If necessary, mouse constant regions are replaced with a desired human constant region, for example wild-type or modified IgG1 or IgG4, to generate a fully human anti-IL2Rγ antibody. While the constant region selected may vary according to specific use, high affinity antigen-binding and target specificity characteristics reside in the variable region. In certain instances, fully human anti-IL2Rγ antibodies are isolated directly from antigen-positive B cells. See, for example, U.S. Pat. No. 6,596,541, Regeneron Pharmaceuticals, VELOCIMMUNE.

Anti-IL2Rγ Antibodies Comprising Fc Variants

According to certain embodiments of the present invention, anti-IL2Rγ antibodies are provided comprising an Fc domain comprising one or more mutations which enhance or diminish antibody binding to the FcRn receptor, e.g., at acidic pH as compared to neutral pH. For example, the present invention includes anti-IL2Rγ antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal.

Non-limiting examples of such Fc modifications include, e.g., a modification at position:

250 (e.g., E or Q);
250 and 428 (e.g., L or F);
252 (e.g., L/Y/F/W or T),
254 (e.g., S or T), and/or
256 (e.g., S/R/Q/E/D or T);

and/or a modification at position:

428 and/or 433 (e.g., H/L/R/S/P/Q or K), and/or
434 (e.g., H/F or Y);

and/or a modification at position:

250 and/or 428;

and/or a modification at position:

307 or 308 (e.g., 308F, V308F), and/or
434.

In an embodiment of the invention, the modification comprises:

a 428L (e.g., M428L) and 434S (e.g., N434S) modification;

a 428L, 2591 (e.g., V2591), and 308F (e.g., V308F) modification;

a 433K (e.g., H433K) and a 434 (e.g., 434Y) modification;

a 252, 254, and 256 (e.g., 252Y, 254T, and 256E) modification;

a 250Q and 428L modification (e.g., T250Q and M428L); and/or.

a 307 and/or 308 modification (e.g., 308F or 308P).

For example, the present invention includes anti-IL2Rγ antibodies comprising an Fc domain comprising one or more pairs or groups of mutations selected from the group consisting of:

250Q and 248L (e.g., T250Q and M248L);
252Y, 254T and 256E (e.g., M252Y, S254T and T256E);
428L and 434S (e.g., M428L and N434S); and
433K and 434F (e.g., H433K and N434F).

In an embodiment of the invention, the heavy chain constant domain is γ4 comprising an S228P and/or S108P mutation. See Angal et al. A single amino acid substitution abolishes the heterogeneity of chimeric mouse/human (IgG4) antibody, Mol Immunol. 1993 January; 30(1): 105-108.

All possible combinations of the foregoing Fc domain mutations, and other mutations within the antibody variable domains disclosed herein, are contemplated within the scope of the present invention.

The anti-IL2Rγ antibodies of the present invention may comprise a modified Fc domain having reduced effector function. As used herein, a "modified Fc domain having reduced effector function" means any Fc portion of an immunoglobulin that has been modified, mutated, truncated, etc., relative to a wild-type, naturally occurring Fc domain such that a molecule comprising the modified Fc exhibits a reduction in the severity or extent of at least one effect selected from the group consisting of cell killing (e.g., ADCC and/or CDC), complement activation, phagocytosis and opsonization, relative to a comparator molecule comprising the wild-type, naturally occurring version of the Fc portion. In certain embodiments, a "modified Fc domain having reduced effector function" is an Fc domain with reduced or attenuated binding to an Fc receptor (e.g., FcγR).

In certain embodiments of the present invention, the modified Fc domain is a variant IgG1 Fc or a variant IgG4 Fc comprising a substitution in the hinge region. For example, a modified Fc for use in the context of the present invention may comprise a variant IgG1 Fc wherein at least one amino acid of the IgG1 Fc hinge region is replaced with the corresponding amino acid from the IgG2 Fc hinge region. Alternatively, a modified Fc for use in the context of the present invention may comprise a variant IgG4 Fc wherein at least one amino acid of the IgG4 Fc hinge region is replaced with the corresponding amino acid from the IgG2 Fc hinge region. Non-limiting, exemplary modified Fc regions that can be used in the context of the present invention are set forth in US Patent Application Publication No. 2014/0243504, the disclosure of which is hereby incorporated by reference in its entirety, as well as any functionally equivalent variants of the modified Fc regions set forth therein.

Other modified Fc domains and Fc modifications that can be used in the context of the present invention include any of the modifications as set forth in US2014/0171623; U.S. Pat. No. 8,697,396; US2014/0134162; WO2014/043361, the disclosures of which are hereby incorporated by reference in their entireties. Methods of constructing antibodies or other antigen-binding fusion proteins comprising a modified Fc domain as described herein are known in the art.

Multispecific Antigen-Binding Proteins

The present invention includes anti-IL2Rγ antigen-binding proteins, e.g., antibodies and antigen-binding fragments thereof, as well as methods of use thereof and methods of making such antigen-binding proteins. The term "anti-IL2Rγ" or "anti-IL2Rgamma" antigen-binding protein, e.g., antibodies or antigen-binding fragments, includes multispecific (e.g., bispecific or biparatopic) molecules that include at least one first antigen-binding domain that specifically binds to IL2Rγ (e.g., an antigen-binding domain from H4H12857P; H4H12858P; H4H12859P; H4H12863P; H4H12874P; H4H12871P; H4H12884P; H4H12886P; H4H12889P; H4H12890P; H4H12899P; H4H12900P;

H4H12908P; H4H12913P2; H4H12922P2; H4H12924P2; H4H12926P2; H4H12927P2; H4H12934P2; H4H13538P; H4H13541P; H4H13544P2; or H4H13545P2) and at least one second antigen-binding domain that binds to a different antigen or to an epitope in IL2Rγ which is different from that of the first antigen-binding domain. In an embodiment of the invention, the first and second epitopes overlap. In another embodiment of the invention, the first and second epitopes do not overlap.

Multispecific binding refers to binding to two or more different epitopes which may be on the same or on different antigens. Multispecific includes bispecific, trispecific and tetraspecific.

"H4H12857P"; "H4H12858P"; "H4H12859P"; "H4H12863P"; "H4H12874P"; "H4H12871P"; "H4H12884P"; "H4H12886P"; "H4H12889P"; "H4H12890P"; "H4H12899P"; "H4H12900P"; "H4H12908P"; "H4H12913P2"; "H4H12922P2"; "H4H12924P2"; "H4H12926P2"; "H4H12927P2"; "H4H12934P2"; "H4H13538P"; "H4H13541P"; "H4H13544P2"; or "H4H13545P2" includes multispecific molecules, e.g., antibodies or antigen-binding fragments, that include the HCDRs and LCDRs, $V_H$ and $V_L$, or HC and LC of "H4H12857P"; "H4H12858P"; "H4H12859P"; "H4H12863P"; "H4H12874P"; "H4H12871P"; "H4H12884P"; "H4H12886P"; "H4H12889P"; "H4H12890P"; "H4H12899P"; "H4H12900P"; "H4H12908P"; "H4H12913P2"; "H4H12922P2"; "H4H12924P2"; "H4H12926P2"; "H4H12927P2"; "H4H12934P2"; "H4H13538P"; "H4H13541P"; "H4H13544P2"; or "H4H13545P2", respectively and one or more antigen-binding domains that bind to a different epitope.

In an embodiment of the invention, an antigen-binding domain that bind specifically to IL2Rγ, which may be included in a multispecific molecule, comprise:

(1)

- (i) a heavy chain variable domain ($V_H$) sequence that comprises CDR-H1, CDR-H2 and CDR-H3 from an immunoglobulin heavy chain comprising an amino acid sequence selected from: SEQ ID NOs: 2, 22, 42, 62, 81, 101, 119, 138, 156, 174, 190, 200, 210, 218, 238, 258, 276, 286, 296, 315, 335, 345 and 361 (or a variant thereof), and
- (ii) a light chain variable domain ($V_L$) sequence that comprises CDR-L1, CDR-L2 and CDR-L3 from an immunoglobulin light chain comprising an amino acid sequence selected from: SEQ ID NOs: 10, 30, 50, 70, 89, 109, 127, 146, 164, 182, 226, 246, 266, 304, 323, 353 and 368 (or a variant thereof);

or, (2)

- (i) a heavy chain variable domain ($V_H$) comprising an amino acid sequence selected from: SEQ ID NOs: 2, 22, 42, 62, 81, 101, 119, 138, 156, 174, 190, 200, 210, 218, 238, 258, 276, 286, 296, 315, 335, 345 and 361 (or a variant thereof); and
- (ii) a light chain variable domain ($V_L$) comprising an amino acid sequence selected from: SEQ ID NOs: 10, 30, 50, 70, 89, 109, 127, 146, 164, 182, 226, 246, 266, 304, 323, 353 and 368 (or a variant thereof);

and one or more antigen-binding domains that bind to a different epitope.

In one embodiment of the invention, a bispecific antigen-binding fragment comprises a first scFv (e.g., comprising $V_H$ and $V_L$ of H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2) having binding specificity for a first epitope (e.g., IL2Rγ) and a second scFv having binding specificity for a second, different epitope. For example, in an embodiment of the invention, the first and second scFv are tethered with a linker, e.g., a peptide linker (e.g., a GS linker such as $(GGGGS)_n$ (SEQ ID NO: 386) wherein n is, for example, 1, 2, 3, 4, 5, 6, 7, 8, 9 or 10).

Other bispecific antigen-binding fragments include an F (ab) 2 of a bispecific IgG antibody which comprises the heavy and light chain CDRs of H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2 and of another antibody that binds to a different epitope.

Immunoconjugates

The invention encompasses anti-IL2Rγ antigen-binding proteins, e.g., antibodies or antigen-binding fragments, conjugated to another moiety, e.g., a therapeutic moiety (an "immunoconjugate"). In an embodiment of the invention, an anti-IL2Rγ antigen-binding protein, e.g., antibody or antigen-binding fragment, is conjugated to any of the further therapeutic agents set forth herein. As used herein, the term "immunoconjugate" refers to an antigen-binding protein, e.g., an antibody or antigen-binding fragment, which is chemically or biologically linked to another antigen-binding protein, a drug, a radioactive agent, a reporter moiety, an enzyme, a peptide, a protein or a therapeutic agent.

Administration and Treatment

The present invention provides methods for treating or preventing an IL2Rγ-mediated disease or condition, in a subject, comprising administering a therapeutically effective dose of anti-IL2Rg antigen-binding protein (H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2) to the subject.

An "IL2Rγ-mediated disease or condition" any disease condition whose symptoms are mediated by the activities of one or more of the cytokines IL-2, IL-4, IL-7, IL-9, IL-15 and IL-21 and/or receptors which bind such cytokines; for example, autoimmunity and/or inflammation mediated by such cytokines and/or receptors. For example, IL2Rγ-mediated diseases or conditions include graft-versus-host disease (GvHD), organ transplant rejection (e.g., transplant of skin (skin graft), b-islet cell graft, transplant of heart, transplant of lung, transplant of kidney and/or transplant of liver), birdshot chorioretinopathy, multiple sclerosis, uveitis, autoimmune diseases (e.g., Type I diabetes, multiple sclerosis, rheumatoid arthritis, systemic lupus erythematosus, and myasthenia gravis), aplastic anemia; atopic dermatitis; asthma; and mast cell activation disorders (e.g., mast cell activation syndrome (MCAS), systemic mastocytosis (SM) or mast cell leukemia (MCL)).

The present invention also includes a method for administering an antigen-binding protein (e.g., antibody or antigen-binding fragment thereof) that binds specifically to IL2Rγ, such as H4H12857P; H4H12858P; H4H12859P;

H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2, to a subject, e.g., with an IL2Rγ-mediated disease or condition, comprising introducing the antigen-binding protein into the body of the subject, e.g., by injection.

GvHD is a condition that might occur after an allogeneic transplant. For example, in GvHD, donated bone marrow or peripheral blood stem cells may view the recipient's body as foreign, and the donated cells/bone marrow attack the body. GvHD may occur, for example, following hematopoietic cell transplantation (HCT; e.g., in a subject suffering from acute myeloid leukemia (AML) or acute lymphocytic leukemia (ALL)) and/or a myelodysplastic syndrome or a myeloproliferative neoplasm), a transfusion, thymus transplantation or in patients with thymoma. Types of GvHD include steroid-refractory GvHD, acute graft-versus-host disease (aGvHD) and chronic graft-versus-host disease (cGvHD). An allogeneic transplant recipient might experience either aGvHD or cGvHD or both forms, or neither. The present invention includes methods for treating or preventing GvHD (of any kind), in a subject, comprising administering a therapeutically effective dosage of an anti-IL2Rγ antigen-binding protein to the subject.

Symptoms of aGvHD may include skin rash or reddened areas on the skin (signs of aGvHD of the skin); yellow discoloration of the skin and/or eyes, and abnormal blood test results (signs of aGvHD of the liver); nausea, vomiting, diarrhea, or abdominal cramping (signs of aGvHD in the gastrointestinal tract, or "gut"); and/or increased dryness/irritation of the eyes (signs of GvHD of the eyes).

Symptoms of cGvHD may include rash, raised, or discolored areas, skin thickening or tightening (signs of cGvHD of the skin); abdominal swelling, yellow discoloration of the skin and/or eyes, and abnormal blood test results (signs of cGvHD of the liver); dry eyes or vision changes (signs of cGvHD of the eyes); dry mouth, white patches inside the mouth, pain or sensitivity to spicy foods (signs of oral cGvHD, of the mouth); shortness of breath or changes seen on your chest X-ray (signs of dry cough pulmonary cGvHD—of the lungs); difficulty swallowing, pain with swallowing, or weight loss (signs of cGvHD of the gastrointestinal tract or "gut"); fatigue, muscle weakness, or pain (signs of neuromuscular cGvHD, of the nerves and muscles); and/or increased need to urinate (urinary frequency), burning or bleeding with urination, vaginal dryness/tightening, or penile dysfunction (signs of cGvHD of the genitourinary system, bladder, or sexual organs).

Organ transplant rejection is the rejection of a transplanted organ by the immune system of the recipient. Hyper-acute rejection occurs within a few minutes of transplant, acute rejection office within a week to 3 months after transplant and chronic rejection takes place over many years. Organs which are transplanted include, for example, solid organs such as skin, pancreas, kidney, liver, heart and lung. The present invention includes methods for treating or preventing organ transplant (of any kind), in a subject, comprising administering a therapeutically effective dosage of an anti-IL2Rγ antigen-binding protein to the subject.

Birdshot chorioretinopathy is a rare form of posterior uveitis—an inflammation of the uvea, the part of the eye that provides the retina with most of its blood supply. Birdshot chorioretinopathy may be caused by autoimmunity. Symptoms of birdshot chorioretinopathy may include night blindness, problems with color vision, sensitivity to bright lights, seeing flashing lights, distortions in vision, pain in the eyes and loss of depth perception and/or peripheral vision. The present invention includes methods for treating or preventing birdshot chorioretinopathy or uveitis, in a subject, comprising administering a therapeutically effective dosage of an anti-IL2Rγ antigen-binding protein to the subject, e.g., by intraocular administration, e.g., intravitreal injection.

The present invention also provides a method for treating or preventing any autoimmune disease or condition by inhibiting IL2Rγ. Blocking of signaling of one or more cytokines in the γc family may be beneficial in patients suffering from autoimmunity due to inhibitor effects on secretion of inflammatory cytokines and production of autoantibodies. Multiple sclerosis (MS) is a disease of the brain and spinal cord (central nervous system (CNS)), wherein the immune system attacks the nerve fiber myelin sheath and causes communication problems between your brain and the rest of your body. Eventually, the disease can cause the nerves themselves to deteriorate or become permanently damaged. Rheumatoid arthritis (RA) is an autoimmune disease in which the body's immune system attacks the joints. This creates inflammation that causes the tissue that lines the inside of joints (the synovium) to thicken, resulting in swelling and pain in and around the joints. Psoriasis is an autoimmune disease with a primary presentation affecting the skin. Inflammation can also affect the joints, vascular system, and eyes of people with psoriasis. Type 1 diabetes is an autoimmune disease wherein the immune system attacks the insulin-producing beta cells in the pancreas and destroys them. The pancreas then produces little or no insulin. Systemic lupus erythematosus (SLE) is a systemic autoimmune disease that occurs when the body's immune system attacks its own tissues and organs. Inflammation caused by lupus can affect many different body systems—including your joints, skin, kidneys, blood cells, brain, heart and lungs. Myasthenia gravis is an autoimmune disease wherein antibodies block the receptors for acetylcholine at the neuromuscular junction, which prevents the muscle from contracting. In most individuals with myasthenia gravis, this is caused by antibodies to the acetylcholine receptor itself. However, antibodies to other proteins, such as MuSK (Muscle-Specific Kinase) protein, can also lead to impaired transmission at the neuromuscular junction. The present invention includes methods for treating or preventing an autoimmune disorder or condition (e.g., multiple sclerosis or any other central nervous system inflammation, rheumatoid arthritis, psoriasis, Type I diabetes, systemic lupus erythematosus and/or myasthenia gravis), in a subject, comprising administering a therapeutically effective dosage of an anti-IL2Rγ antigen-binding protein to the subject.

An effective or therapeutically effective dose of anti-IL2Rγ antigen-binding protein, e.g., antibody or antigen-binding fragment, for treating or preventing an IL2Rγ-mediated disease or condition refers to the amount of the antigen-binding protein sufficient to alleviate one or more signs and/or symptoms of the disease or condition in the treated subject, whether by inducing the regression or elimination of such signs and/or symptoms or by inhibiting the progression of such signs and/or symptoms. In an embodiment of the invention, an effective or therapeutically effective dose of anti-IL2Rγ antigen-binding protein is about 0.05-50 mg/kg of body weight. The dose amount may vary depending upon the age and the size of a subject to be administered, target disease, conditions, route of administration, and the like. In certain embodiments, the initial dose may be followed by administration of a second or a plurality of subsequent doses of antigen-binding protein in an amount that can be approximately the same or less or more than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

As used herein, the term "subject" refers to a mammal (e.g., rat, mouse, cat, dog, cow, sheep, horse, goat, rabbit), preferably a human, for example, in need of prevention and/or treatment of an IL2Rγ-mediated disease. The subject may have an IL2Rγ-mediated disease or be predisposed to developing such a disease.

"Preventing" an IL2Rγ-mediated disease or condition refers, as it relates to use of an anti-IL2Rγ antigen-binding protein of the present invention, to administration to a subject prior to manifestation of the disease or condition in the body of the subject so as to stop such manifestation from occurring.

Combinations and Pharmaceutical Formulation

The present invention provides compositions that include anti-IL2Rγ antigen-binding proteins in association with one or more ingredients; as well as methods of use thereof and methods of making such compositions. Pharmaceutic formulations comprising an anti-IL2Rγ antigen-binding protein and a pharmaceutically acceptable carrier or excipient are part of the present invention.

To prepare pharmaceutical formulations of the anti-IL2Rγ antigen-binding proteins, e.g., antibodies and antigen-binding fragments thereof (e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2), antigen-binding protein is admixed with a pharmaceutically acceptable carrier or excipient. See, e.g., Remington's Pharmaceutical Sciences and U.S. Pharmacopeia: National Formulary, Mack Publishing Company, Easton, Pa. (1984); Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y. In an embodiment of the invention, the pharmaceutical formulation is sterile. Such compositions are part of the present invention.

Pharmaceutical formulations of the present invention include an anti-IL2Rγ antigen-binding protein and a pharmaceutically acceptable carrier including, for example, water, buffering agents, preservatives and/or detergents.

The scope of the present invention includes desiccated, e.g., freeze-dried, compositions comprising an anti-IL2Rγ antigen-binding protein, e.g., antibody or antigen-binding fragment thereof (e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2), or a pharmaceutical formulation thereof that includes a pharmaceutically acceptable carrier but substantially lacks water.

In a further embodiment of the invention, a further therapeutic agent that is administered to a subject in association with an anti-IL2Rγ antigen-binding protein, e.g., antibody or antigen-binding fragment thereof (e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2), disclosed herein is administered to the subject in accordance with the Physicians' Desk Reference 2003 (Thomson Healthcare; 57th edition (Nov. 1, 2002)).

The mode of administration of an anti-IL2Rγ antigen-binding protein or composition thereof can vary. Routes of administration include parenteral, non-parenteral, oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, intraocular, intravitreal, transdermal or intra-arterial.

The present invention provides methods for administering an anti-IL2Rγ antigen-binding protein, e.g., antibody or antigen-binding fragment thereof (e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2) to a subject, comprising introducing the protein or a pharmaceutical formulation thereof into the body of the subject. For example, in an embodiment of the invention, the method comprises piercing the body of the subject, e.g., with a needle of a syringe, and injecting the antigen-binding protein or a pharmaceutical formulation thereof into the body of the subject, e.g., into the eye, vein, artery, muscular tissue or subcutis of the subject.

The present invention provides a vessel (e.g., a plastic or glass vial, e.g., with a cap or a chromatography column, hollow bore needle or a syringe cylinder) comprising any of the anti-IL2Rγ antigen-binding proteins, e.g., antibodies or antigen-binding fragments thereof (e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2), or a pharmaceutical formulation comprising a pharmaceutically acceptable carrier thereof.

The present invention includes combinations including an anti-IL2Rγ antigen-binding protein, e.g., antibody or antigen-binding fragment thereof of the present invention (e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2), in association with one or more further therapeutic agents. The anti-IL2Rγ antigen-binding protein and the further therapeutic agent can be in a single composition or in separate compositions. For example, in an embodiment of the invention, the further therapeutic agent is an immunosuppressive drug. In an embodiment of the invention, the further therapeutic agent is an anti-TNFα antibody or binding protein (e.g., infliximab, adalimumab, etanercept or golimumab), tacrolimus, cyclosporine, a corticoid, prednisolone, methylprednisolone, antithymocyte globulin, alemtuzumab, daclizumab, extracorporeal photophoresis, mycophenolate mofetil, sirolimus, pentostatin, mesenchyman stem cells, inolimomab, denileukin, a multispecific (e.g., bispecific) antibody or antigen-binding fragment thereof that binds BCMA (B-cell maturation antigen) and CD3 and/or basiliximab.

Methods for treating or preventing an IL2Rγ-mediated disease in a subject in need of said treatment or prevention by administering an anti-IL2Rγ antigen-binding protein, e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2, in association with a further therapeutic agent are part of the present invention.

The term "in association with" indicates that components, an anti-IL2Rγ antigen-binding protein, e.g., antibody or antigen-binding fragment thereof of the present invention, along with another agent such as methotrexate, can be formulated into a single composition, e.g., for simultaneous delivery, or formulated separately into two or more compositions (e.g., a kit including each component). Components administered in association with each another can be administered to a subject at a different time than when the other component is administered; for example, each administration may be given non-simultaneously (e.g., separately or sequentially) at intervals over a given period of time. Separate components administered in association with each another may also be administered sequentially, though essentially simultaneously, during the same administration session. Moreover, the separate components administered in association with each another may be administered to a subject by the same or by a different route.

EXAMPLES

The following examples are put forth so as to provide those of ordinary skill in the art with a complete disclosure and description of how to make and use the methods and compositions of the invention, and are not intended to limit the scope of what the inventors regard as their invention.

Example 1: Identification and Isolation of Anti-IL2Rγ Antibodies

Anti-IL2Rγ antibodies were obtained by immunizing a VELOCIMMUNE mouse (i.e., an engineered mouse comprising DNA encoding human immunoglobulin heavy and kappa light chain variable regions) with an IL2Rγ protein immunogen comprising the extracellular sequence (ecto domain) of IL2Rγ.

Specifically, the immunogen, human IL2Rg ecto-mmh, comprised:

- Amino acids (1-240): Human IL2Rg ecto (L23-A262 of NP_000197.1), and
- Amino acids (241-268): Myc-Myc-Hexahistadine tag (underlined);

comprising the amino acid sequence:

```
                                            (SEQ ID NO: 379)
LNTTILTPNGNEDTTADFFLTTMPTDSLSVSTLPLPEVQCFVFNVEYMNC

TWNSSSEPQPTNLTLHYWYKNSDNDKVQKCSHYLFSEEITSGCQLQKKEI

HLYQTFVVQLQDPREPRRQATQMLKLQNLVIPWAPENLTLHKLSESQLEL

NWNNRFLNHCLEHLVQYRTDWDHSWTEQSVDYRHKFSLPSVDGQKRYTFR

VRSRFNPLCGSAQHWSEWSHPIHWGSNTSKENPFLFALEAEQKLISEEDL

GGEQKLISEEDLHHHHHH
*Expressed with mROR signal sequence
```

The antibody immune response was monitored by a IL2Rγ-specific immunoassay. Fully human anti-IL2Rγ antibodies were isolated and purified.

TABLE 1-1

Anti-IL2Rγ VH, VK and CDR Amino Acid Sequence Summary*.

| Name | VH | | CDR1 | | CDR2 | | CDR3 | | VK | |
|---|---|---|---|---|---|---|---|---|---|---|
| | DNA | PEP | DNA | PEP | DNA | PEP | DNA | PEP | DNA | PEP |
| H4H12859P | 1 | 2 | 3 | 4 | 5 | 6 | 7 | 8 | 9 | 10 |
| H4H12863P | 21 | 22 | 23 | 24 | 25 | 26 | 27 | 28 | 29 | 30 |
| H4H12874P | 41 | 42 | 43 | 44 | 45 | 46 | 47 | 48 | 49 | 50 |
| H4H12884P | 61 | 62 | 63 | 64 | 65 | 66 | 67 | 68 | 69 | 70 |
| H4H12886P | 80 | 81 | 82 | 83 | 84 | 85 | 86 | 87 | 88 | 89 |
| H4H12890P | 100 | 101 | 102 | 103 | 104 | 105 | 106 | 107 | 108 | 109 |
| H4H12899P | 118 | 119 | 120 | 121 | 122 | 123 | 124 | 125 | 126 | 127 |
| H4H12900P | 137 | 138 | 139 | 140 | 141 | 142 | 143 | 144 | 145 | 146 |
| H4H12908P | 155 | 156 | 157 | 158 | 159 | 160 | 161 | 162 | 163 | 164 |
| H4H12913P2 | 173 | 174 | 175 | 176 | 177 | 178 | 179 | 180 | 181 | 182 |
| H4H12924P2 | 189 | 190 | 191 | 192 | 193 | 194 | 195 | 196 | 181 | 182 |
| H4H12926P2 | 199 | 200 | 201 | 202 | 203 | 204 | 205 | 206 | 181 | 182 |
| H4H12927P2 | 209 | 210 | 175 | 176 | 211 | 212 | 213 | 214 | 181 | 182 |
| H4H12934P2 | 217 | 218 | 219 | 220 | 221 | 222 | 223 | 224 | 225 | 226 |
| H4H13538P | 237 | 238 | 239 | 240 | 241 | 242 | 243 | 244 | 245 | 246 |
| H4H13541P | 257 | 258 | 259 | 260 | 261 | 262 | 263 | 264 | 265 | 266 |
| H4H13544P2 | 275 | 276 | 277 | 278 | 279 | 280 | 281 | 282 | 181 | 182 |
| H4H13545P2 | 285 | 286 | 287 | 288 | 289 | 290 | 291 | 292 | 181 | 182 |
| REGN9432 (H4H12857P) | 295 | 296 | 297 | 298 | 299 | 300 | 301 | 302 | 303 | 304 |
| REGN9433 (H4H12858P) | 314 | 315 | 316 | 317 | 318 | 319 | 320 | 321 | 322 | 323 |

TABLE 1-1-continued

Anti-IL2Rγ VH, VK and CDR Amino Acid Sequence Summary*.

| | | | | | | | | | | |
|---|---|---|---|---|---|---|---|---|---|---|
| REGN7256 (H4H12922P2) | 334 | 335 | 336 | 337 | 338 | 339 | 340 | 341 | 181 | 182 |
| REGN7257 (H4H12889P) | 344 | 345 | 346 | 347 | 348 | 349 | 350 | 351 | 352 | 353 |
| REGN9434 (H4H12871P) | 360 | 361 | 362 | 363 | 364 | 66 | 365 | 366 | 367 | 368 |

| | CDR1 | | CDR2 | | CDR3 | | HC | | LC | |
|---|---|---|---|---|---|---|---|---|---|---|
| Name | DNA | PEP | DNA | PEP | DNA | PEP | DNA | PEP | DNA | PEP |
| H4H12859P | 11 | 12 | 13 | 14 | 15 | 16 | 17 | 18 | 19 | 20 |
| H4H12863P | 31 | 32 | 33 | 34 | 35 | 36 | 37 | 38 | 39 | 40 |
| H4H12874P | 51 | 52 | 53 | 54 | 55 | 56 | 57 | 58 | 59 | 60 |
| H4H12884P | 71 | 72 | 73 | 54 | 74 | 75 | 76 | 77 | 78 | 79 |
| H4H12886P | 90 | 91 | 92 | 93 | 94 | 95 | 96 | 97 | 98 | 99 |
| H4H12890P | 110 | 111 | 73 | 54 | 112 | 113 | 114 | 115 | 116 | 117 |
| H4H12899P | 128 | 129 | 130 | 54 | 131 | 132 | 133 | 134 | 135 | 136 |
| H4H12900P | 147 | 148 | 73 | 54 | 149 | 150 | 151 | 152 | 153 | 154 |
| H4H12908P | 165 | 166 | 13 | 14 | 167 | 168 | 169 | 170 | 171 | 172 |
| H4H12913P2 | 71 | 72 | 73 | 54 | 183 | 184 | 185 | 186 | 187 | 188 |
| H4H12924P2 | 71 | 72 | 73 | 54 | 183 | 184 | 197 | 198 | 187 | 188 |
| H4H12926P2 | 71 | 72 | 73 | 54 | 183 | 184 | 207 | 208 | 187 | 188 |
| H4H12927P2 | 71 | 72 | 73 | 54 | 183 | 184 | 215 | 216 | 187 | 188 |
| H4H12934P2 | 227 | 228 | 229 | 230 | 231 | 232 | 233 | 234 | 235 | 236 |
| H4H13538P | 247 | 248 | 249 | 250 | 251 | 252 | 253 | 254 | 255 | 256 |
| H4H13541P | 267 | 268 | 73 | 54 | 269 | 270 | 271 | 272 | 273 | 274 |
| H4H13544P2 | 71 | 72 | 73 | 54 | 183 | 184 | 283 | 284 | 187 | 188 |
| H4H13545P2 | 71 | 72 | 73 | 54 | 183 | 184 | 293 | 294 | 187 | 188 |
| REGN9432 (H4H12857P) | 305 | 306 | 307 | 230 | 308 | 309 | 310 | 311 | 312 | 313 |
| REGN9433 (H4H12858P) | 324 | 325 | 326 | 327 | 328 | 329 | 330 | 331 | 332 | 333 |
| REGN7256 (H4H12922P2) | 71 | 72 | 73 | 54 | 183 | 184 | 342 | 343 | 187 | 188 |
| REGN7257 (H4H12889P) | 71 | 72 | 73 | 54 | 354 | 355 | 356 | 357 | 358 | 359 |
| REGN9434 (H4H12871P) | 369 | 370 | 371 | 372 | 373 | 374 | 375 | 376 | 377 | 378 |

*Numbers refer to SEQ ID NOs corresponding to the indicated sequence.

TABLE 1-2

Anti-IL2Rγ Heavy Chain and Light Chain Amino Acid Sequence Summary*.

| | HC | | LC | |
|---|---|---|---|---|
| Name | DNA | PEP | DNA | PEP |
| H4H12859P | 17 | 18 | 19 | 20 |
| H4H12863P | 37 | 38 | 39 | 40 |
| H4H12874P | 57 | 58 | 59 | 60 |
| H4H12884P | 76 | 77 | 78 | 79 |
| H4H12886P | 96 | 97 | 98 | 99 |
| H4H12890P | 114 | 115 | 116 | 117 |
| H4H12899P | 133 | 134 | 135 | 136 |
| H4H12900P | 151 | 152 | 153 | 154 |
| H4H12908P | 169 | 170 | 171 | 172 |
| H4H12913P2 | 185 | 186 | 187 | 188 |
| H4H12924P2 | 197 | 198 | 187 | 188 |
| H4H12926P2 | 207 | 208 | 187 | 188 |
| H4H12927P2 | 215 | 216 | 187 | 188 |
| H4H12934P2 | 233 | 234 | 235 | 236 |

TABLE 1-2-continued

Anti-IL2Rγ Heavy Chain and Light Chain Amino Acid Sequence Summary*.

| | HC | | LC | |
|---|---|---|---|---|
| Name | DNA | PEP | DNA | PEP |
| H4H13538P | 253 | 254 | 255 | 256 |
| H4H13541P | 271 | 272 | 273 | 274 |
| H4H13544P2 | 283 | 284 | 187 | 188 |
| H4H13545P2 | 293 | 294 | 187 | 188 |
| REGN9432 (H4H12857P) | 310 | 311 | 312 | 313 |
| REGN9433 (H4H12858P) | 330 | 331 | 332 | 333 |
| REGN7256 (H4H12922P2) | 342 | 343 | 187 | 188 |
| REGN7257 (H4H12889P) | 356 | 357 | 358 | 359 |
| REGN9434 (H4H12871P) | 375 | 376 | 377 | 378 |

*Numbers refer to SEQ ID NOs corresponding to the indicated sequence.

The amino acid sequences of anti-IL2Rγ antibody heavy and light immunoglobulin chains are set forth below (CDRs underscored; variable regions in bold font).

H4H12857P
Heavy chain (SEQ ID NO: 311)

EVQLVESGGGVVRPGGSLRLSCAASGFTFDDFDMSWVRQGPGKGLEWVSGINWHGSSTGYADSVKGRFTISRDNAKNSLY

LQMSSLRAEDTALYHCVRGGTIVGATTPLDYWGQGTLVTVSSASTKGPSVFPLAPCSRSTSESTAALGCLVKDYFPEPVT

VSWNSGALTSGVHTFPAVLQSSGLYSLSSVVTVPSSSLGTKTYTCNVDHKPSNTKVDKRVESKYGPPCPPCPAPEFLGGP

-continued

SVFLFPPKPKDTLMISRTPEVTCVVVDVSQEDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSLGK

Light chain (SEQ ID NO: 313)

DIQMTQSPSSLSASVGDRVTMTCRASRTISSYLSWYQQKSGKVPNLLIFGASSLQSGVPSRFSASGSGTDFTLIISSLQP

EDFATYYCQQSYSSPLTFGGGTKVEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

H4H12858P
Heavy chain (SEQ ID NO: 331)

EVQLVESGGDLVQPGGSLRLSCTASGFIFRNYAMNWVRQAPGKGLEWLSGILGSNDNTYYVDSVKGRFTISRDNSRNTLY

LQMNSLRAEDSAVYYCAKGDAGGFDYWGQGTLVTVSSASTKGPSVFPLAPCSRSTSESTAALGCLVKDYFPEPVTVSWNS

GALTSGVHTFPAVLQSSGLYSLSSVVTVPSSSLGTKTYTCNVDHKPSNTKVDKRVESKYGPPCPPCPAPEFLGGPSVFLF

PPKPKDTLMISRTPEVTCVVVDVSQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESNGQPENNYKTTPPVLDSDGS

FFLYSRLTVDKSRWQEGNVFSCSVMHEALHNHYTQKSLSLSLGK

Light chain (SEQ ID NO: 333)

DVVMTQSPLSLPVILGQPASISCRSSQSLVSSDGNTYLNWFQQRPGQSPRRLIYKVSNRDSGVPDRFSGSGSGTDFTLKI

SRVEAEDVGAYYCMQGSYWPPTFGQGTKLEIKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC

H4H12859P
Heavy chain (SEQ ID NO: 18)

QVQLVQSGAEVKKPGASVRVSCKASGYTFTDYDIHWVRQAPGHGLEWMGWINPNSGGTNYAQKFQGRVTMTRDTSISTVY

MDLSRLRSDDTAVYYCARADYSSSYYYYGMDVWGQGTTVTVSSASTKGPSVFPLAPCSRSTSESTAALGCLVKDYFPEPV

TVSWNSGALTSGVHTFPAVLQSSGLYSLSSVVTVPSSSLGTKTYTCNVDHKPSNTKVDKRVESKYGPPCPPCPAPEFLGG

PSVFLFPPKPKDTLMISRTPEVTCVVVDVSQEDPEVQFNWYVDGVEVHNAKTKPREEQFNSTYRVVSVLTVLHQDWLNGK

EYKCKVSNKGLPSSIEKTISKAKGQPREPQVYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLGK

Light chain (SEQ ID NO: 20)

DIVMTQSPDSLAVSLGERATINCKSSQSVLYSSKNKNYLSWYQQKPGQPPKLLIYWASTREFGVPDRFSGRGSGTDFTLT

ISSLQAEDVAVYYCQQYYTTPYTFGQGTKLEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC

H4H12863P
Heavy chain (SEQ ID NO: 38)

QVQLVESGGGVVQPGRSLRLSCTASGFTFRSYDMYWVRQAPGKGLEWVSVITYDGNNKYYADSVKGRFTISRDNSKNTLF

LQMSSLRPEDTAVYYCAKRGLIWVGESFDYWGQGTLVTVSSASTKGPSVFPLAPCSRSTSESTAALGCLVKDYFPEPVTV

SWNSGALTSGVHTFPAVLQSSGLYSLSSVVTVPSSSLGTKTYTCNVDHKPSNTKVDKRVESKYGPPCPPCPAPEFLGGPS

VFLFPPKPKDTLMISRTPEVTCVVVDVSQEDPEVQFNWYVDGVEVHNAKTKPREEQFNSTYRVVSVLTVLHQDWLNGKEY

KCKVSNKGLPSSIEKTISKAKGQPREPQVYTLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK

-continued

Light chain (SEQ ID NO: 40)

DIQMTQSPSTLSASVGDRVTITCRASQSINSWLAWYQQKPGKAPNLLIYKASSLESGVPSRFSGSGSGTEFTLTISSLQP

DDFATYYCQQYKSYSWTFGQGTKVEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

H4H12874P
Heavy chain (SEQ ID NO: 58)

QVQLVESGGGVVQPGRSLRLSCAASGFNFRNFGMHWVRQAPGKGLEWVAGILYDGSSKYYADSVKDRFTISRDNSKNTLF

LQMNSLRAEDTAMYYCAKEEDTAMVPFDSWGPGTLVTVSSASTKGPSVFPLAPCSRSTSESTAALGCLVKDYFPEPVTVS

WNSGALTSGVHTFPAVLQSSGLYSLSSVVTVPSSSLGTKTYTCNVDHKPSNTKVDKRVESKYGPPCPPCPAPEFLGGPSV

FLFPPKPKDTLMISRTPEVTCVVVDVSQEDPEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK

Light chain (SEQ ID NO: 60)

DIQLTQSPSFLSASVGDRVTITCWASQGISSYLAWYQQKPGKAPTLLIYAASTLQSGVPSRFSGSGSGTEFTLTISSLQP

EDFASYYCQQLKSYPLTFGGGTKVEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

H4H12871P
Heavy chain (SEQ ID NO: 376)

QVQLQESGPGLVKPSQTLSLTCTVSGGSITSGGYYWSWIRQYPGQGLEWIGYIYYSGKTYYNPSFTSRITISVDTSKKQF

SLKMSSVTAADTAVYYCARAGFTSSNGWFDPWGQGTLVTVSSASTKGPSVFTLAPCSRSTSESTAALGCLVKDYFPEPVT

VSWNSGALTSGVHTFPAVLQSSGLYSLSSVVTVPSSSLGTKTYTCNVDHKPSNTKVDKRVESKYGPPCPPCPAPEFLGGP

SVFLFPPKPKDTLMISRTPEVTCVVVDVSQEDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSLGK

Light chain (SEQ ID NO: 378)

DIQMTQSPSSLSASVGDRVTITCRASQNIRSYLNWYQQKPGKAPKLLIYSASSLQSGVPSRFSGSGSGTDFTLTISSLQP

EDFPTYYCQQTYSSPWTFGPGTKVEIKRTVAAPSVFIFPPSDEQLKSGTASVVCLLNNEYPREAKVQWKVDNALQSGNSQ

ESVTEQDSKDSTYSLSSTLTLSKADYEKHKVYACEVTHQGLSSPVTKSFNRGEC

H4H12884P
Heavy chain (SEQ ID NO: 77)

QVQLQESGPGLVKPSQTLSLTCTVSGGSISSGGYYWSWIRQHPGKGLEWIGFIYYSGKTYYNPSLKSRLTISVDTSKSQF

SLKLRSVTAADTAVYYCARLGYTNSAGWFDPWGQGTLVTVSSASTKGPSVFPLAPCSRSTSESTAALGCLVKDYFPEPVT

VSWNSGALTSGVHTFPAVLQSSGLYSLSSVVTVPSSSLGTKTYTCNVDHKPSNTKVDKRVESKYGPPCPPCPAPEFLGGP

SVFLFPPKPKDTLMISRTPEVTCVVVDVSQEDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSLGK

Light chain (SEQ ID NO: 79)

DIQMTQSPSSLSASVGDRVTITCRASQSISSYLNWYQQKPGKAPNLLIYAASSLQSGVPSRFSGSGSGTDFTLTISSLQP

EDLATYYCQQSYTTPFTFGPGTKVDIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

-continued

H4H12886P
Heavy chain (SEQ ID NO: 97)

EVQLVESGGGLVKPGGSLRLSCAASGFTFSTAWMSWVRQSPGRGLEWVGRMKSKTDGGTTFYAAPVKGRFTISRDDSKNT

LYLQMNSLKTEDTAVYYCTTGLVPAFYKYYGVDVWGQGTTVTVSSASTKGPSVFTLAPCSRSTSESTAALGCLVKDYFPE

PVTVSWNSGALTSGVHTFPAVLQSSGLYSLSSVVTVPSSSLGTKTYTCNVDHKPSNTKVDKRVESKYGPPCPPCPAPEFL

GGPSVFLFPPKPKDTLMISRTPEVTCVVVDVSQEDPEVQFNWYVDGVEVHNAKTKPREEQFNSTYRVVSVLTVLHQDWLN

GKEYKCKVSNKGLPSSIEKTISKAKGQPREPQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSLGK

Light chain (SEQ ID NO: 99)

DIQMTQSPSSLSASVGDRITITCQASQDITNYLNWYQQKPGKAPNLLIYDASNLVTGVPSRFSGSGSGTDFTFTILSLQP

EDIATYYCQQYDSLLTFGPGTKVDIKRTVAAPSVFIFPPSDEQLKSGTASVVCLLNNFYPREAKVQWKVDNALQSGNSQE

SVTEQDSKDSTYSLSSTLTLSKADYEKHKVYACEVTHQGLSSPVTKSFNRGEC

H4H12889P
Heavy chain (SEQ ID NO: 357)

EVQLVESGGGLVQPGGSLRLSCAASGFIFSSYEMHWVRQAPGKGLEWISYISSSGTTIYYADSVKGRFTISRDNAKNSLY

LHMNSLRAEDTAVYYCTRARITGTFDVFDIWGQGTMVTVSSASTKGPSVFPLAPCSRSTSESTAALGCLVKDYFPEPVTV

SWNSGALTSGVHTFPAVLQSSGLYSLSSVVTVPSSSLGTKTYTCNVDHKPSNTKVDKRVESKYGPPCPPCPAPEFLGGPS

VFLFPPKPKDTLMISRTPEVTCVVVDVSQEDPEVQFNWYVDGVEVHNAKTKPREEQFNSTYRVVSVLTVLHQDWLNGKEY

KCKVSNKGLPSSIEKTISKAKGQPREPQVYTLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK

Light chain (SEQ ID NO: 359)

DIQMTQSPSSLSASVGDRVTITCRASQSISSYLNWYQQKPGKAPKLLIFAASNLQSGVPSRFSGSRSGTDFTLTISSLQP

EDFATYYCQQNYNIPYTFGQGTKLEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

H4H12890P
Heavy chain (SEQ ID NO: 115)

EVQLVESGGGLVQPGGSLRLSCAASGFTFNNYAMHWVRQAPGKGLEYVSSISSSGGSTYYEDSVKGRFTISRDNSKNTLY

LQMGSLRAEDMAVYYCARSFYGSGTYYDTFDMWGQGTMVTVSSASTKGPSVFTLAPCSRSTSESTAALGCLVKDYFPEPV

TVSWNSGALTSGVHTFPAVLQSSGLYSLSSVVTVPSSSLGTKTYTCNVDHKPSNTKVDKRVESKYGPPCPPCPAPEFLGG

PSVFLFPPKPKDTLMISRTPEVTCVVVDVSQEDPEVQFNWYVDGVEVHNAKTKPREEQFNSTYRVVSVLTVLHQDWLNGK

EYKCKVSNKGLPSSIEKTISKAKGQPREPQVYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLGK

Light chain (SEQ ID NO: 117)

DIQMTQSPSSLSASIGDRVTITCRASQSISRYLNWYQQKPGKAPKLLIYAASSLQSGVPSRFSASGSGTDFTLTISSLQP

EDFATYYCQQSYSTPFTFGQGTKLEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

H4H12899P
Heavy chain (SEQ ID NO: 134)

QVQLVESGGDLVKPGGSLRLSCATSGFTFSDFYMTWIRQAPGKGLEWISYISNSGSIVKYADSVKGRFTISRDNAKNSLY

LQMNSLRAEDTAIYYCARFYGDRWGQGTLVTVSSASTKGPSVFPLAPCSRSTSESTAALGCLVKDYFPEPVTVSWNSGAL

TSGVHTFPAVLQSSGLYSLSSVVTVPSSSLGTKTYTCNVDHKPSNTKVDKRVESKYGPPCPPCPAPEFLGGPSVFLFPPK

PKDTLMISRTPEVTCVVVDVSQEDPEVQFNWYVDGVEVHNAKTKPREEQFNSTYRVVSVLTVLHQDWLNGKEYKCKVSNK

GLPSSIEKTISKAKGQPREPQVYTLPPSQEEMTKNQVSLTCLVKGFYPSDIAVEWESNGQPENNYKTTPPVLDSDGSFFL

-continued

YSRLTVDKSRWQEGNVFSCSVMHEALHNHYTQKSLSLSLGK

Light chain (SEQ ID NO: 136)

DIQLTQSPSFLSASVGDRVTITCWASQGISTFLAWYQQKPGKAPKLLIYAASTLQSGVPSRFSGSGSGTDFTLTISSLQP

EDFATYHCQQLNNYPWTFGQGTKVEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

H4H12900P
Heavy chain (SEQ ID NO: 152)

QVQLVESGGGLVKPGGSLRLSCEASGFTFNDFYMTWIRQAPGKGLEWIAYISKSGDKMRYADSVKGRFSTSRDNAKNSLS

LQMNSLRAEDTAVYYCARFYGDIWGQGTLVTVSSASTKGPSVFPLAPCSRSTSESTAALGCLVKDYFPEPVTVSWNSGAL

TSGVHTFPAVLQSSGLYSLSSVVTVPSSSLGTKTYTCNVDHKPSNTKVDKRVESKYGPPCPPCPAPEFLGGPSVFLFPPK

PKDTLMISRTPEVTCVVVDVSQEDPEVQFNWYVDGVEVHNAKTKPREEQFNSTYRVVSVLTVLHQDWLNGKEYKCKVSNK

GLPSSIEKTISKAKGQPREPQVYTLPPSQEEMTKNQVSLTCLVKGFYPSDIAVEWESNGQPENNYKTTPPVLDSDGSFFL

YSRLTVDKSRWQEGNVFSCSVMHEALHNHYTQKSLSLSLGK

Light chain (SEQ ID NO: 154)

DIQLTQSPSFLSASVGDRVTITCWASQDISSFLVWYQQKPGKAPNLLIYAASALQSGVPSRFSGSGSGTEFTLTISSLQP

EDFASYYCEQLNNYPWTFGQGTKVEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

H4H12908P
Heavy chain (SEQ ID NO: 170)

EVQLVESGGRLVQPGGSLRLSCEASGFTFSNYGMTWVRQAPGKGLEWVSVISGSDNRKYYAESVKGRFTISRDNSKNTLY

LQMNSLRAEDTAVYYCAKLGYSRSSKDFYYGMDVWGQGTTVTVSSASTKGPSVFPLAPCSRSTSESTAALGCLVKDYFPE

PVTVSWNSGALTSGVHTFPAVLQSSGLYSLSSVVTVPSSSLGTKTYTCNVDHKPSNTKVDKRVESKYGPPCPPCPAPEFL

GGPSVFLFPPKPKDTLMISRTPEVTCVVVDVSQEDPEVQFNWYVDGVEVHNAKTKPREEQFNSTYRVVSVLTVLHQDWLN

GKEYKCKVSNKGLPSSIEKTISKAKGQPREPQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSLGK

Light chain (SEQ ID NO: 172)

DIVMTQSPDSLAVSLGERATINCKSSQSVLYNSNNRNYLVWYQQKPGQSPKLLIYWASTRESGVPDRFSGSGSGTDFTLT

ISSLQAEDVAVYYCQQYYNVPYTFGQGTKLEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC

H4H12913P2
Heavy chain (SEQ ID NO: 186)

EVQLVESGGGVVRPGGSLRLSCAASGFTFDDYGMSWVRQAPGKGLEWISSINRNGGSADYADSVKGRFTISRDNAKNSLF

LQMSSLRAEDTALYHCASGEFRFDYWGQGTLVTVSSASTKGPSVFPLAPCSRSTSESTAALGCLVKDYFPEPVTVSWNSG

ALTSGVHTFPAVLQSSGLYSLSSVVTVPSSSLGTKTYTCNVDHKPSNTKVDKRVESKYGPPCPPCPAPEFLGGPSVFLFP

PKPKDTLMISRTPEVTCVVVDVSQEDPEVQFNWYVDGVEVHNAKTKPREEQFNSTYRVVSVLTVLHQDWLNGKEYKCKVS

NKGLPSSIEKTISKAKGQPREPQVYTLPPSQEEMTKNQVSLTCLVKGFYPSDIAVEWESNGQPENNYKTTPPVLDSDGSF

FLYSRLTVDKSRWQEGNVFSCSVMHEALHNHYTQKSLSLSLGK

-continued

Light chain (SEQ ID NO: 188)

DIQMTQSPSSLSASVGDRVTITCRASQSISSYLNWYQQKPGKAPKLLIYAASSLQSGVPSRFSGSGSGTDFTLTISSLQP

EDFATYYCQQSYSTPPITFGQGTRLEIKRTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGEC

H4H12922P2
Heavy chain (SEQ ID NO: 343)

QVQLVESGGGVVKPGGSLRLSCAASGFTFSNSGIHWVRQAPGKGLEWVALISYAGSNKYYADSVKGRFTISRDNSKNTLS

LQMNSLRAEDTAVYYCAKEVWTGTYDSFDMWGRGTMVTVSSASTKGPSVFPLAPCSRSTSESTAALGCLVKDYFPEPVTV

SWNSGALTSGVHTFPAVLQSSGLYSLSSVVTVPSSSLGTKTYTCNVDHKPSNTKVDKRVESKYGPPCPPCPAPEFLGGPS

VFLFPPKPKDTLMISRTPEVTCVVVDVSQEDPEVQFNWYVDGVEVHNAKTKPREEQFNSTYRVVSVLTVLHQDWLNGKEY

KCKVSNKGLPSSIEKTISKAKGQPREPQVYTLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK

Light chain (SEQ ID NO: 188)

DIQMTQSPSSLSASVGDRVTITCRASQSISSYLNWYQQKPGKAPKLLIYAASSLQSGVPSRFSGSGSGTDFTLTISSLQP

EDFATYYCQQSYSTPPITFGQGTRLEIKRTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGEC

H4H12924P2
Heavy chain (SEQ ID NO: 198)

EVQLVESGGGLVQPGRSLRLSCAASGFTLEDYAMHWVRQAPGKGLEWVSGISWNRGSTGYADSVKGRFTISRDNAKNSLY

LQMTSLRAEDTALYYCAKGFYSMDVWGQGTTVTVSSASTKGPSVFPLAPCSRSTSESTAALGCLVKDYFPEPVTVSWNSG

ALTSGVHTFPAVLQSSGLYSLSSVVTVPSSSLGTKTYTCNVDHKPSNTKVDKRVESKYGPPCPPCPAPEFLGGPSVFLFP

PKPKDTLMISRTPEVTCVVVDVSQEDPEVQFNWYVDGVEVHNAKTKPREEQFNSTYRVVSVLTVLHQDWLNGKEYKCKVS

NKGLPSSIEKTISKAKGQPREPQVYTLPPSQEEMTKNQVSLTCLVKGFYPSDIAVEWESNGQPENNYKTTPPVLDSDGSF

FLYSRLTVDKSRWQEGNVFSCSVMHEALHNHYTQKSLSLSLGK

Light chain (SEQ ID NO: 188)

DIQMTQSPSSLSASVGDRVTITCRASQSISSYLNWYQQKPGKAPKLLIYAASSLQSGVPSRFSGSGSGTDFTLTISSLQP

EDFATYYCQQSYSTPPITFGQGTRLEIKRTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGEC

H4H12926P2
Heavy chain (SEQ ID NO: 208)

QVQLQQSGPGLVKPSQTLSLTCAISGDSVSSNIAAWNWIRLSPSRGLEWLGRTFFRSTWFYDYSLSVKGRITINPDTSKN

QFSLHLNSVTPEDAAVYYCARTGRRWSLDYWGQGTLVTVSSASTKGPSVFPLAPCSRSTSESTAALGCLVKDYFPEPVTV

SWNSGALTSGVHTFPAVLQSSGLYSLSSVVTVPSSSLGTKTYTCNVDHKPSNTKVDKRVESKYGPPCPPCPAPEFLGGPS

VFLFPPKPKDTLMISRTPEVTCVVVDVSQEDPEVQFNWYVDGVEVHNAKTKPREEQFNSTYRVVSVLTVLHQDWLNGKEY

KCKVSNKGLPSSIEKTISKAKGQPREPQVYTLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK

Light chain (SEQ ID NO: 188)

DIQMTQSPSSLSASVGDRVTITCRASQSISSYLNWYQQKPGKAPKLLIYAASSLQSGVPSRFSGSGSGTDFTLTISSLQP

EDFATYYCQQSYSTPPITFGQGTRLEIKRTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGEC

-continued

H4H12927P2
Heavy chain (SEQ ID NO: 216)

EVQLVESGGGVVRPGGSLRLSCATSGFTFDDYGMSWVRQVPGKGLEWVSSVNRNGGTTDYADSVKGRFTISRDNAKRSLF

LQMNSLRAEDTALYHCATGELFFDYWGQGTLVTVSSASTKGPSVFPLAPCSRSTSESTAALGCLVKDYFPEPVTVSWNSG

ALTSGVHTFPAVLQSSGLYSLSSVVTVPSSSLGTKTYTCNVDHKPSNTKVDKRVESKYGPPCPPCPAPEFLGGPSVFLFP

PKPKDTLMISRTPEVTCVVVDVSQEDPEVQFNWYVDGVEVHNAKTKPREEQFNSTYRVVSVLTVLHQDWLNGKEYKCKVS

NKGLPSSIEKTISKAKGQPREPQVYTLPPSQEEMTKNQVSLTCLVKGFYPSDIAVEWESNGQPENNYKTTPPVLDSDGSF

FLYSRLTVDKSRWQEGNVFSCSVMHEALHNHYTQKSLSLSLGK

Light chain (SEQ ID NO: 188)

DIQMTQSPSSLSASVGDRVTITCRASQSISSYLNWYQQKPGKAPKLLIYAASSLQSGVPSRFSGSGSGTDFTLTISSLQP

EDFATYYCQQSYSTPPITFGQGTRLEIKRTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGEC

H4H12934P2
Heavy chain (SEQ ID NO: 234)

QVQLVQSGAEVKKPGASVKVSCKASGYTFTGHYMHWVRQAPGQGLEWMGWIYPHSGHTNYAKRFQGRVTMTRDTSITTAY

MELIRLRSDDTAVYYCARRSGRSWYFDLWGRGTLVTVSSASTKGPSVFPLAPCSRSTSESTAALGCLVKDYFPEPVTVSW

NSGALTSGVHTFPAVLQSSGLYSLSSVVTVPSSSLGTKTYTCNVDHKPSNTKVDKRVESKYGPPCPPCPAPEFLGGPSVF

LFPPKPKDTLMISRTPEVTCVVVDVSQEDPEVQFNWYVDGVEVHNAKTKPREEQFNSTYRVVSVLTVLHQDWLNGKEYKC

KVSNKGLPSSIEKTISKAKGQPREPQVYTLPPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGK

Light chain (SEQ ID NO: 236)

EIVLTQSPGTLSLSPGERATLSCRASQSVSSSYLAWYQQKPGQAPRLLIYGASSRATGIPDRFSGSGSGTDFTLTISRLE

PEDFAVYYCQQYGSSPWTFGQGTKVEIKRTVAAPSVFIFPPSDEQLKSGTASVVCLLNNFYPREAKVQWKVDNALQ SGN S

QESVTEQDSKDSTYSLSSTLTLSKADYEKHKVYACEVTHQGLSSPVTKSFNRGEC

H4H13538P
Heavy chain (SEQ ID NO: 254)

EVQLVESGGGLVQPGGSLGLSCAASGFTFSNYAMSWVRQAPGKGLEWVSAVSGGGGGTYYADSVKGRFTISRDNSKNTVL

LQMNSLRAEDTAVYYCARGRTGGLDYWGPGTLVTVSSASTKGPSVFPLAPCSRSTSESTAALGCLVKDYFPEPVTVSWNS

GALTSGVHTFPAVLQSSGLYSLSSVVTVPSSSLGTKTYTCNVDHKPSNTKVDKRVESKYGPPCPPCPAPEFLGGPSVFLF

PPKPKDTLMISRTPEVTCVVVDVSQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESNGQPENNYKTTPPVLDSDGS

FFLYSRLTVDKSRWQEGNVFSCSVMHEALHNHYTQKSLSLSLGK

Light chain (SEQ ID NO: 256)

DVVMTQSPLSLPVIFGQPASISCRSSQSLVDSDGNTYLNWLQQRPGQSPRRLIYEVSNRDSGVPDRFSGSGSGTDFTLTI

SRVEAEDVGIYYCMQGTRWPPTFGGGTKVEIKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC

H4H13541P
Heavy chain (SEQ ID NO: 272)

EVQLVESGGGVVRPGGSLRLSCAASGFIFDDYDMSWVRQPPGRGLEWVSGIDWFGGTRGYADSMKGRFTISRDNAKNSLY

LQMNSLRVEDTAFYYCARGGAIVGAVTPFDYWGQGTLVTVSSASTKGPSVFPLAPCSRSTSESTAALGCLVKDYFPEPVT

VSWNSGALTSGVHTFPAVLQSSGLYSLSSVVTVPSSSLGTKTYTCNVDHKPSNTKVDKRVESKYGPPCPPCPAPEFLGGP

SVFLFPPKPKDTLMISRTPEVTCVVVDVSQEDPEVQFNWYVDGVEVHNAKTKPREEQFNSTYRVVSVLTVLHQDWLNGKE

-continued

YKCKVSNKGLPSSIEKTISKAKGQPREPQVYTLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSLGK

Light chain (SEQ ID NO: 274)

DIQMTQSPSSLSASVGNRVTLSCRASQSINTYLSWYQQRPGKAPKLLIYAASSLQSGVPSRFSGSGAGTDFTLTISSLQP

EDFATYYCQQSYSAPLTFGGGTKVEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

H4H13544P2
Heavy chain (SEQ ID NO: 284)

QLQLQESGPGLVKPSETLSLTCTVSGGSISIKNYYWGWIRQPPGKGLEWIGSIYYSGTTYYNPSLKSRVTISVDTSKNQF

SLKLSSVTAADTAVYHCARHGYSYGHGWFDPWGQGTLVTVSSASTKGPSVFTLAPCSRSTSESTAALGCLVKDYFPEPVT

VSWNSGALTSGVHTFPAVLQSSGLYSLSSVVTVPSSSLGTKTYTCNVDHKPSNTKVDKRVESKYGPPCPPCPAPEFLGGP

SVFLFPPKPKDTLMISRTPEVTCVVVDVSQEDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSLGK

Light chain (SEQ ID NO: 188)

DIQMTQSPSSLSASVGDRVTITCRASQSISSYLNWYQQKPGKAPKLLIYAASSLQSGVPSRFSGSGSGTDFTLTISSLQP

EDFATYYCQQSYSTPPITFGQGTRLEIKRTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGEC

H4H13545P2
Heavy chain (SEQ ID NO: 294)

QVQLQQSGPGLVKPSQTLSLTCDISGDSVSSNIATWNWIRQSPSRGLEWLGRTYYRSKWYKDYAVSVKSRITINPDTSKN

QFSLQVNSVTPEDTAVYYCARMTGPRYYFEYWGQGTLVTVSSASTKGPSVFTLAPCSRSTSESTAALGCLVKDYFPEPVT

VSWNSGALTSGVHTFPAVLQSSGLYSLSSVVTVPSSSLGTKTYTCNVDHKPSNTKVDKRVESKYGPPCPPCPAPEFLGGP

SVFLFPPKPKDTLMISRTPEVTCVVVDVSQEDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSLGK

Light chain (SEQ ID NO: 188)

DIQMTQSPSSLSASVGDRVTITCRASQSISSYLNWYQQKPGKAPKLLIYAASSLQSGVPSRFSGSGSGTDFTLTISSLQP

EDFATYYCQQSYSTPPITFGQGTRLEIKRTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGEC

*Antibodies referred to in these Example are those having immunoglobulin chains with the amino acid sequences specifically set forth in Example 1.

Example 2: Surface Plasmon Resonance Binding Assays

The dissociation rate constant (kd) for binding of IL-2Rγ reagents to purified anti-IL2Rγ monoclonal antibodies was determined using a real-time surface plasmon resonance based BIACORE 4000 biosensor platform. All binding studies were performed at 25° C. and 37° C. using two running buffers, (i) 1.9 mM NaH2PO4, 8.1 mM Na2HPO4, 2.7 mM KCl, 137 mM NaCl, 0.03% NaN3, 0.05% v/v Surfactant Tween-20, pH7.4 (PBS-T-pH7.4), and (ii) 8.8 mM NaH2PO4, 1.2 mM Na2HPO4, 2.7 mM KCl, 137 mM NaCl, 0.03% NaN3, 0.05% v/v Surfactant Tween-20, pH6.0 (PBS-T-pH6.0). The CM5 BIACORE sensor surface derivatized by amine coupling with monoclonal mouse anti-human Fc antibody (GE, Catalog #BR-1008-39) was used to capture anti-IL2Rγ monoclonal antibodies expressed with human IgG4 Fc. All the IL2Rγ reagents were expressed with a C-terminal myc-myc-hexahistidine tag (subsequently referred to with a -MMH suffix). Different concentrations of human IL2Rγ extracellular domain expressed with a C-terminal myc-myc-hexahistidine tag (hIL-2Rg-MMH; SEQ ID NO: 379) or *Macaca fascicularis* IL2Rγ extracellular domain expressed with a C-terminal myc-myc-hexahistidine tag (mfIL-2Rg-MMH; SEQ ID NO: 380) were prepared in PBS-T-pH7.4 running buffer (100 nM-11.11 nM; 3-fold serial dilution) and injected for 4 minutes at a flow rate of 30 μL/minute. The dissociation of bound IL-2Rg-MMH was performed in PBS-T-pH7.4 or PBS-T-pH6.0 running buffers for 6 minutes.

Dissociation rate constants ($k_d$) in two running buffers were determined by fitting the real-time binding sensorgrams to a 1:1 binding model using Scrubber 2.0c curve-fitting software. Values of dissociation rate for anti-Hemojuvelin mAb binding to hIL-2RG-MMH and mfIL-2RG-MMH at 25° C. and 37° C. in PBS-T-pH7.4 and PBS-T-pH6.0 is shown in Table 2-1 through Table 2-8.

TABLE 2-1

Dissociation Rate Constants of Anti-IL-2Rγ mAbs Binding to hIL-2Rg-MMH at 25° C. in PBS-T-pH 7.4.

| mAb Captured | mAb Capture Level (RU) | 100 nM Ag Bound (RU) | kd (1/s) | t½ (min) |
|---|---|---|---|---|
| H4H13538P | 167 ± 0.3 | 82 | 1.39E−04 | 83 |
| H4H13541P | 195 ± 0.7 | 72 | 1.65E−04 | 70 |
| H4H13544P2 | 273 ± 0.2 | 57 | 6.02E−04 | 19 |
| H4H13545P2 | 319 ± 0.1 | 15 | 2.13E−02 | 0.5 |
| H4H12924P2 | 331 ± 0.4 | 124 | 4.79E−04 | 24 |
| H4H12926P2 | 413 ± 0.6 | 29 | 1.33E−02 | 0.9 |
| H4H12913P2 | 218 ± 0.6 | 56 | 3.03E−04 | 38 |
| H4H12922P2 | 408 ± 1.1 | 164 | 2.04E−04 | 57 |
| H4H12857P | 266 ± 0.4 | 79 | 1.70E−04 | 68 |
| H4H12858P | 272 ± 1.8 | 111 | 1.84E−04 | 63 |
| H4H12859P | 344 ± 0.7 | 54 | 1.11E−03 | 10 |
| H4H12863P | 422 ± 0.8 | 151 | 1.72E−04 | 67 |
| H4H12871P | 413 ± 0.6 | 121 | 5.96E−04 | 19 |
| H4H12874P | 275 ± 0.3 | 72 | 1.62E−04 | 71 |
| H4H12884P | 530 ± 1.4 | 161 | 6.40E−04 | 18 |
| H4H12886P | 303 ± 0.7 | 113 | 1.55E−04 | 75 |
| H4H12889P | 360 ± 0.7 | 118 | 1.38E−04 | 84 |
| H4H12890P | 336 ± 0.6 | 72 | 1.92E−04 | 60 |
| H4H12899P | 327 ± 2.2 | 118 | 1.74E−04 | 66 |
| H4H12900P | 348 ± 1.9 | 130 | 1.75E−04 | 66 |
| H4H12908P | 402 ± 1.5 | 31 | 1.77E−04 | 65 |
| H4H12927P2 | 271 ± 0.5 | 36 | 1.63E−03 | 7 |
| H4H12934P2 | 602 ± 1.4 | 87 | 3.41E−03 | 3.4 |

TABLE 2-2

Dissociation Rate Constants of Anti-IL-2Rg mAbs Binding to hIL-2Rg-MMH at 25° C. in PBS-T-pH 6.0.

| mAb Captured | mAb Capture Level (RU) | 100 nM Ag Bound (RU) | kd (1/s) | t½ (min) |
|---|---|---|---|---|
| H4H13538P | 203 ± 1.5 | 93 | 4.17E−04 | 28 |
| H4H13541P | 192 ± 0.3 | 66 | 4.69E−04 | 25 |
| H4H13544P2 | 259 ± 0.3 | 45 | 1.75E−03 | 7 |
| H4H13545P2 | 278 ± 0.9 | 11 | 3.34E−02 | 0.3 |
| H4H12924P2 | 381 ± 1 | 136 | 3.67E−03 | 3 |
| H4H12926P2 | 410 ± 0.6 | 24 | 2.97E−02 | 0.4 |
| H4H12913P2 | 203 ± 0.4 | 43 | 1.05E−03 | 11 |
| H4H12922P2 | 349 ± 0.7 | 126 | 1.18E−03 | 10 |
| H4H12857P | 318 ± 1.2 | 88 | 5.49E−04 | 21 |
| H4H12858P | 265 ± 0.7 | 103 | 3.77E−04 | 31 |
| H4H12859P | 324 ± 1 | 39 | 5.03E−03 | 2.3 |
| H4H12863P | 366 ± 0.8 | 116 | 7.62E−04 | 15 |
| H4H12871P | 454 ± 1.2 | 129 | 1.36E−03 | 8 |
| H4H12874P | 272 ± 0.7 | 66 | 7.24E−04 | 16 |
| H4H12884P | 516 ± 1 | 135 | 1.99E−03 | 6 |
| H4H12886P | 250 ± 1.3 | 84 | 6.34E−04 | 18 |
| H4H12889P | 409 ± 1.2 | 130 | 4.37E−04 | 26 |
| H4H12890P | 330 ± 0.5 | 64 | 6.36E−04 | 18 |
| H4H12899P | 301 ± 2.2 | 96 | 5.68E−04 | 20 |
| H4H12900P | 280 ± 1 | 101 | 6.92E−04 | 17 |
| H4H12908P | 450 ± 5.3 | 34 | 5.05E−04 | 23 |
| H4H12927P2 | 267 ± 0.5 | 30 | 4.99E−03 | 2.3 |
| H4H12934P2 | 601 ± 1.6 | 71 | 1.32E−02 | 0.9 |

TABLE 2-3

Dissociation Rate Constants of Anti-IL-2Rγ mAbs Binding to hIL-2Rg-MMH at 37° C. in PBS-T-pH 7.4.

| mAb Captured | mAb Capture Level (RU) | 100 nM Ag Bound (RU) | kd (1/s) | t½ (min) |
|---|---|---|---|---|
| H4H13538P | 255 ± 1.2 | 110 | 5.99E−04 | 19 |
| H4H13541P | 281 ± 1.8 | 98 | 5.32E−04 | 22 |
| H4H13544P2 | 371 ± 1.5 | 54 | 4.10E−03 | 2.8 |
| H4H13545P2 | 408 ± 2.2 | 7 | IC | IC |
| H4H12924P2 | 463 ± 1.2 | 133 | 3.02E−03 | 4 |
| H4H12926P2 | 533 ± 0.5 | 14 | 3.08E−02 | 0.4 |
| H4H12913P2 | 318 ± 0.2 | 82 | 1.16E−03 | 10 |
| H4H12922P2 | 552 ± 0.7 | 184 | 7.73E−04 | 15 |
| H4H12857P | 388 ± 2.1 | 117 | 6.21E−04 | 19 |
| H4H12858P | 378 ± 3.4 | 141 | 6.61E−04 | 17 |
| H4H12859P | 476 ± 2 | 55 | 4.54E−03 | 2.5 |
| H4H12863P | 544 ± 2 | 176 | 6.72E−04 | 17 |
| H4H12871P | 536 ± 0.8 | 139 | 1.11E−03 | 10 |
| H4H12874P | 381 ± 0.3 | 99 | 5.72E−04 | 20 |
| H4H12884P | 691 ± 1.9 | 171 | 1.51E−03 | 8 |
| H4H12886P | 420 ± 0.6 | 146 | 5.19E−04 | 22 |
| H4H12889P | 502 ± 1.6 | 147 | 6.36E−04 | 18 |
| H4H12890P | 450 ± 1.4 | 90 | 6.61E−04 | 17 |
| H4H12899P | 460 ± 3.5 | 158 | 6.68E−04 | 17 |
| H4H12900P | 475 ± 3.3 | 162 | 7.11E−04 | 16 |
| H4H12908P | 530 ± 3.3 | 54 | 6.71E−04 | 17 |
| H4H12927P2 | 377 ± 1.8 | 23 | 9.82E−03 | 1.2 |
| H4H12934P2 | 763 ± 1.3 | 63 | 1.61E−02 | 0.7 |

TABLE 2-4

Dissociation Rate Constants of Anti-IL-2Rγ mAbs Binding to hIL-2Rg-MMH at 37° C. in PBS-T-pH 6.0.

| mAb Captured | mAb Capture Level (RU) | 100 nM Ag Bound (RU) | kd (1/s) | t½ (min) |
|---|---|---|---|---|
| H4H13538P | 284 ± 1.4 | 120 | 1.48E−03 | 8 |
| H4H13541P | 284 ± 0.7 | 95 | 1.58E−03 | 7 |
| H4H13544P2 | 335 ± 1.6 | 39 | 8.27E−03 | 1.4 |
| H4H13545P2 | 364 ± 1 | 6 | IC | IC |
| H4H12924P2 | 506 ± 1.2 | 133 | 1.43E−02 | 0.8 |
| H4H12926P2 | 549 ± 0.4 | 14 | 3.12E−02 | 0.4 |
| H4H12913P2 | 277 ± 1.1 | 59 | 3.83E−03 | 3 |
| H4H12922P2 | 486 ± 3.2 | 147 | 3.74E−03 | 3 |
| H4H12857P | 429 ± 1.7 | 123 | 2.07E−03 | 6 |
| H4H12858P | 372 ± 2.6 | 136 | 1.72E−03 | 7 |
| H4H12859P | 424 ± 1.4 | 36 | 1.32E−02 | 0.9 |
| H4H12863P | 485 ± 0.5 | 145 | 2.26E−03 | 5 |
| H4H12871P | 566 ± 1.1 | 141 | 2.46E−03 | 5 |
| H4H12874P | 381 ± 0.4 | 91 | 2.61E−03 | 4 |
| H4H12884P | 634 ± 3.1 | 136 | 3.79E−03 | 3.0 |
| H4H12886P | 350 ± 1.6 | 115 | 2.16E−03 | 5 |
| H4H12889P | 538 ± 1.2 | 153 | 1.88E−03 | 6 |
| H4H12890P | 447 ± 1 | 82 | 2.86E−03 | 4 |
| H4H12899P | 400 ± 2.9 | 125 | 2.19E−03 | 5 |
| H4H12900P | 393 ± 1.8 | 133 | 2.71E−03 | 4 |
| H4H12908P | 566 ± 4.2 | 52 | 1.63E−03 | 7 |
| H4H12927P2 | 374 ± 0.9 | 19 | 2.39E−02 | 0.5 |
| H4H12934P2 | 712 ± 3.7 | 51 | 2.97E−02 | 0.4 |

TABLE 2-5

Dissociation Rate Constants of Anti-IL-2Rγ mAbs Binding to mfIL-2Rg-MMH at 25° C. in PBS-T-pH 7.4.

| mAb Captured | mAb Capture Level (RU) | 100 nM Ag Bound (RU) | kd (1/s) | t½ (min) |
|---|---|---|---|---|
| H4H13538P | 167 ± 0.7 | 94 | 1.79E−04 | 65 |
| H4H13541P | 194 ± 0.3 | 80 | 2.22E−04 | 52 |
| H4H13544P2 | 272 ± 0.8 | 67 | 5.84E−04 | 20 |
| H4H13545P2 | 317 ± 0.5 | 30 | 7.51E−03 | 1.5 |
| H4H12924P2 | 330 ± 0.2 | 130 | 3.85E−04 | 30 |

TABLE 2-5-continued

Dissociation Rate Constants of Anti-IL-2Rγ mAbs Binding to mfIL-2Rg-MMH at 25° C. in PBS-T-pH 7.4.

| mAb Captured | mAb Capture Level (RU) | 100 nM Ag Bound (RU) | kd (1/s) | t½ (min) |
|---|---|---|---|---|
| H4H12926P2 | 411 ± 1.4 | 43 | 7.82E−03 | 1.5 |
| H4H12913P2 | 218 ± 0.2 | 57 | 2.72E−04 | 43 |
| H4H12922P2 | 406 ± 0.1 | 168 | 1.91E−04 | 61 |
| H4H12857P | 264 ± 0.8 | 80 | 1.81E−04 | 64 |
| H4H12858P | 269 ± 0.7 | 111 | 1.71E−04 | 68 |
| H4H12859P | 342 ± 0.6 | 51 | 8.71E−04 | 13 |
| H4H12863P | 418 ± 1 | 155 | 1.94E−04 | 59 |
| H4H12871P | 411 ± 0.9 | 125 | 4.81E−04 | 24 |
| H4H12874P | 276 ± 0.6 | 73 | 1.64E−04 | 70 |
| H4H12884P | 528 ± 0.6 | 160 | 5.16E−04 | 22 |
| H4H12886P | 302 ± 0.4 | 113 | 1.75E−04 | 66 |
| H4H12889P | 358 ± 0.5 | 123 | 1.57E−04 | 74 |
| H4H12890P | 335 ± 1.2 | 71 | 2.03E−04 | 57 |
| H4H12899P | 325 ± 0.8 | 117 | 1.67E−04 | 69 |
| H4H12900P | 345 ± 0.4 | 129 | 1.75E−04 | 66 |
| H4H12908P | 399 ± 1.2 | 37 | 2.08E−04 | 56 |
| H4H12927P2 | 270 ± 0.3 | 38 | 9.84E−04 | 12 |
| H4H12934P2 | 601 ± 0.7 | 89 | 3.05E−03 | 3.8 |

TABLE 2-6

Dissociation Rate Constants of Anti-IL-2Rγ mAbs Binding to mfIL-2Rg-MMH at 25° C. in PBS-T-pH 6.0.

| mAb Captured | mAb Capture Level (RU) | 100 nM Ag Bound (RU) | kd (1/s) | t½ (min) |
|---|---|---|---|---|
| H4H13538P | 202 ± 0.2 | 96 | 4.39E−04 | 26 |
| H4H13541P | 192 ± 0.5 | 69 | 4.97E−04 | 23 |
| H4H13544P2 | 258 ± 0.5 | 52 | 1.70E−03 | 7 |
| H4H13545P2 | 278 ± 1.1 | 20 | 9.35E−03 | 1.2 |
| H4H12924P2 | 381 ± 0.7 | 131 | 3.05E−03 | 4 |
| H4H12926P2 | 410 ± 1.1 | 32 | 1.85E−02 | 0.6 |
| H4H12913P2 | 203 ± 0.8 | 44 | 9.92E−04 | 12 |
| H4H12922P2 | 349 ± 0.7 | 129 | 1.11E−03 | 10 |
| H4H12857P | 317 ± 1 | 80 | 5.01E−04 | 23 |
| H4H12858P | 263 ± 0.6 | 100 | 3.85E−04 | 30 |
| H4H12859P | 323 ± 0.5 | 37 | 4.13E−03 | 2.8 |
| H4H12863P | 365 ± 1.9 | 118 | 7.61E−04 | 15 |
| H4H12871P | 455 ± 3.6 | 128 | 1.16E−03 | 10 |
| H4H12874P | 272 ± 0.6 | 64 | 7.29E−04 | 16 |
| H4H12884P | 513 ± 2.1 | 133 | 1.59E−03 | 7 |
| H4H12886P | 251 ± 0.2 | 83 | 6.82E−04 | 17 |
| H4H12889P | 408 ± 1.6 | 126 | 4.34E−04 | 27 |
| H4H12890P | 329 ± 0.5 | 60 | 6.68E−04 | 17 |
| H4H12899P | 300 ± 0.7 | 95 | 7.03E−04 | 16 |
| H4H12900P | 280 ± 0.4 | 100 | 6.71E−04 | 17 |
| H4H12908P | 445 ± 0.8 | 34 | 4.88E−04 | 24 |
| H4H12927P2 | 267 ± 0.1 | 30 | 3.20E−03 | 3.6 |
| H4H12934P2 | 597 ± 2.5 | 64 | 1.01E−02 | 1.1 |

TABLE 2-7

Dissociation Rate Constants of Anti-IL-2Rγ mAbs Binding to mfIL-2Rg-MMH at 37° C. in PBS-T-pH 7.4.

| mAb Captured | mAb Capture Level (RU) | 100 nM Ag Bound (RU) | kd (1/s) | t½ (min) |
|---|---|---|---|---|
| H4H13538P | 254 ± 0.3 | 119 | 5.10E−04 | 23 |
| H4H13541P | 280 ± 0.6 | 100 | 5.12E−04 | 23 |
| H4H13544P2 | 368 ± 1.1 | 58 | 3.62E−03 | 3.2 |
| H4H13545P2 | 406 ± 1 | 17 | IC | IC |
| H4H12924P2 | 461 ± 0.5 | 133 | 2.67E−03 | 4 |
| H4H12926P2 | 529 ± 2.1 | 25 | 2.79E−02 | 0.4 |
| H4H12913P2 | 318 ± 0.6 | 76 | 8.94E−04 | 13 |
| H4H12922P2 | 548 ± 1.1 | 185 | 6.93E−04 | 17 |
| H4H12857P | 386 ± 0.7 | 111 | 5.53E−04 | 21 |
| H4H12858P | 374 ± 0.9 | 143 | 5.42E−04 | 21 |

TABLE 2-7-continued

Dissociation Rate Constants of Anti-IL-2Rγ mAbs Binding to mfIL-2Rg-MMH at 37° C. in PBS-T-pH 7.4.

| mAb Captured | mAb Capture Level (RU) | 100 nM Ag Bound (RU) | kd (1/s) | t½ (min) |
|---|---|---|---|---|
| H4H12859P | 473 ± 1 | 47 | 3.97E−03 | 2.9 |
| H4H12863P | 542 ± 1 | 177 | 6.06E−04 | 19 |
| H4H12871P | 532 ± 1 | 143 | 1.02E−03 | 11 |
| H4H12874P | 381 ± 0.5 | 92 | 5.41E−04 | 21 |
| H4H12884P | 690 ± 1.3 | 171 | 1.47E−03 | 8 |
| H4H12886P | 418 ± 0.6 | 145 | 4.71E−04 | 25 |
| H4H12889P | 500 ± 1.3 | 147 | 5.78E−04 | 20 |
| H4H12890P | 448 ± 0.1 | 82 | 6.24E−04 | 19 |
| H4H12899P | 458 ± 0.8 | 160 | 5.52E−04 | 21 |
| H4H12900P | 474 ± 1.1 | 166 | 6.23E−04 | 19 |
| H4H12908P | 527 ± 0.8 | 55 | 5.14E−04 | 22 |
| H4H12927P2 | 374 ± 0.4 | 27 | 5.96E−03 | 1.9 |
| H4H12934P2 | 762 ± 1.1 | 70 | 1.24E−02 | 0.9 |

TABLE 2-8

Dissociation Rate Constants of Anti-IL-2Rγ mAbs Binding to mfIL-2Rg-MMH at 37° C. in PBS-T-pH 6.0.

| mAb Captured | mAb Capture Level (RU) | 100 nM Ag Bound (RU) | kd (1/sf) | t½ (min) |
|---|---|---|---|---|
| H4H13538P | 282 ± 0.4 | 122 | 1.39E−03 | 8 |
| H4H13541P | 282 ± 1.4 | 91 | 1.50E−03 | 8 |
| H4H13544P2 | 334 ± 1.1 | 43 | 7.81E−03 | 1.5 |
| H4H13545P2 | 364 ± 0.2 | 13 | IC | IC |
| H4H12924P2 | 506 ± 0.7 | 126 | 1.24E−02 | 0.9 |
| H4H12926P2 | 548 ± 1.5 | 20 | 3.03E−02 | 0.4 |
| H4H12913P2 | 277 ± 1.1 | 54 | 2.96E−03 | 4 |
| H4H12922P2 | 483 ± 1 | 146 | 3.44E−03 | 3.4 |
| H4H12857P | 426 ± 0.6 | 109 | 1.78E−03 | 6 |
| H4H12858P | 369 ± 2.2 | 134 | 1.55E−03 | 7 |
| H4H12859P | 423 ± 1 | 31 | 1.23E−02 | 0.9 |
| H4H12863P | 482 ± 0.8 | 141 | 2.08E−03 | 6 |
| H4H12871P | 565 ± 1.4 | 141 | 2.27E−03 | 5 |
| H4H12874P | 380 ± 0.6 | 82 | 2.55E−03 | 5 |
| H4H12884P | 633 ± 2.4 | 135 | 3.35E−03 | 3.4 |
| H4H12886P | 349 ± 0.7 | 109 | 1.97E−03 | 6 |
| H4H12889P | 537 ± 0.7 | 148 | 1.83E−03 | 6 |
| H4H12890P | 447 ± 0.5 | 71 | 2.76E−03 | 4 |
| H4H12899P | 398 ± 1.4 | 122 | 2.11E−03 | 5 |
| H4H12900P | 390 ± 1.5 | 130 | 2.77E−03 | 4 |
| H4H12908P | 561 ± 0.3 | 52 | 1.31E−03 | 9 |
| H4H12927P2 | 372 ± 0.9 | 22 | 1.29E−02 | 0.9 |
| H4H12934P2 | 711 ± 3.2 | 50 | 2.65E−02 | 0.4 |

Example 3: Binding Kinetics

Equilibrium dissociation constants ($K_D$ values) for IL-2Rγ binding to purified anti-IL2Rγ monoclonal antibodies were determined using a BIACORE 4000 instrument equipped with a real-time surface plasmon resonance biosensor. All binding studies were performed in 10 mM HEPES, 150 mM NaCl, 3 mM EDTA, and 0.05% v/v Surfactant Tween-20, pH 7.4 (HBS-ET) running buffer at 25° C. and 37° C. The BIACORE sensor surface was first derivatized by amine coupling with a monoclonal mouse anti-human Fc antibody (GE, #BR-1008-39) to capture anti-IL2Rγ monoclonal antibodies.

Binding studies were performed on the following IL-2Rγ reagents:

Human IL2Rγ extracellular domain expressed with a C-terminal myc-myc-hexahistidine tag (hIL-2Rg-MMH; SEQ ID NO: 379), comprising Amino acids (1-240): Human IL2Rg ecto (L23-A262 of NP_000197.1)

Amino acids (241-268): Myc-Myc-Hexahistadine tag (underlined)

comprising the amino acid sequence:

```
LNTTILTPNGNEDTTADFFLTTMPTDSLSVSTLPLPEVQCFVFNVEYMNC
TWNSSSEPQPTNLTLHYWYKNSDNDKVQKCSHYLFSEEITSGCQLQKKEI
HLYQTFVVQLQDPREPRRQATQMLKLQNLVIPWAPENLTLHKLSESQLEL
NWNNRFLNHCLEHLVQYRTDWDHSWTEQSVDYRHKFSLPSVDGQKRYTFR
VRSRFNPLCGSAQHWSEWSHPIHWGSNTSKENPFLFALEAEQKLISEEDL
GGEQKLISEEDLHHHHHH
```

*Expressed with mROR signal sequence

*Macaca fascicularis* IL2Rγ extracellular domain expressed with a C-terminal myc-myc-hexahistidine tag (mfIL-2Rg-MMH; SEQ ID NO: 380), comprising Amino acids (1-240): *Macaca fascicularis* IL2Rg ecto (L23-A262 of XP_005593949.1)

Amino acids (241-268): Myc-Myc-Hexahistadine tag (underlined)

comprising the amino acid sequence:

```
LNTTILTPNGNEDATTDFFLTSMPTDSLSVSTLPLPEVQCFVFNVEYMNC
TWNSSSEPQPTNLTLHYWYKNSDNDKVQKCSHYLFSEEITSGCQLQKKEI
HLYQTFVVQLQDPREPRRQATQMLKLQNLVIPWAPENLTLRKLSESQLEL
NWNNRFLNHCLEHLVQYRTDWDHSWTEQSVDYRHKFSLPSVDGQKRYTFR
VRSRFNPLCGSAQHWSEWSHPIHWGSNSSKENPFLFALEAEQKLISEEDL
GGEQKLISEEDLHHHHHH
```

Human IL2Rγ extracellular domain expressed with a C-terminal mouse IgG2a Fc tag (hIL-2Rg-mFc; SEQ ID NO: 381), comprising Amino acids (1-240): Human IL2Rg ecto (L23-A262 of NP_000197.1)

Amino acids (241-473): Mouse IgG2a Fc tag (underlined)

comprising the amino acid sequence:

```
LNTTILTPNGNEDTTADFFLTTMPTDSLSVSTLPLPEVQCFVFNVEYMNC
TWNSSSEPQPTNLTLHYWYKNSDNDKVQKCSHYLFSEEITSGCQLQKKEI
HLYQTFVVQLQDPREPRRQATQMLKLQNLVIPWAPENLTLHKLSESQLEL
NWNNRFLNHCLEHLVQYRTDWDHSWTEQSVDYRHKFSLPSVDGQKRYTFR
VRSRFNPLCGSAQHWSEWSHPIHWGSNTSKENPFLFALEAEPRGPTIKPC
PPCKCPAPNLLGGPSVFIFPPKIKDVLMISLSPIVTCVVVDVSEDDPDVQ
ISWFVNNVEVHTAQTQTHREDYNSTLRVVSALPIQHQDWMSGKEFKCKVN
NKDLPAPIERTISKPKGSVRAPQVYVLPPPEEEMTKKQVTLTCMVTDFMP
EDIYVEWTNNGKTELNYKNTEPVLDSDGSYFMYSKLRVEKKNWVERNSYS
CSVVHEGLHNHHTTKSFSRTPGK
```

*Expressed with mROR signal sequence

D1 domain of human IL-2Rγ extracellular domain expressed with a C-terminal myc-myc-hexahistidine tag (hIL-2Rg_D1-MMH; SEQ ID NO: 382), comprising Amino acids (1-131): Human IL2Rg domain 1 (L23-1153 of NP_000197.1)

Amino acids (132-159): Myc-Myc-Hexahistadine tag (underlined)

comprising the amino acid sequence:

```
LNTTILTPNGNEDTTADFFLTTMPTDSLSVSTLPLPEVQCFVFNVEYMNC
TWNSSSEPQPTNLTLHYWYKNSDNDKVQKCSHYLFSEEITSGCQLQKKEI
HLYQTFVVQLQDPREPRRQATQMLKLQNLVIEQKLISEEDLGGEQKLISE
EDLHHHHHH
```

*Expressed with mROR signal sequence

D2 domain of human IL2Rγ extracellular domain expressed with a C-terminal myc-myc-hexahistidine tag (hIL-2Rg_D2-MMH; SEQ ID NO: 383), comprising Amino acids (1-88): Human IL2Rg Domain 2 (P154-S241 of NP_000197.1)

Amino acids (89-116): Myc-Myc-Hexahistadine tag (underlined)

comprising the amino acid sequence:

```
PWAPENLTLHKLSESQLELNWNNRFLNHCLEHLVQYRTDWDHSWTEQSVD
YRHKFSLPSVDGQKRYTFRVRSRFNPLCGSAQHWSEWSEQKLISEEDLGG
EQKLISEEDLHHHHHH
```

*Expressed with mROR signal sequence

Mouse IL2Rγ extracellular domain expressed with a C-terminal myc-myc-hexahistidine tag (mIL-2Rg-MMH; SEQ ID NO: 384), comprising Amino acids (1-241): Mouse IL2Rg ecto (W23-A263 of NP_038591.1)

Amino acids (242-269): Myc-Myc-Hexahistadine tag (underlined)

comprising the amino acid sequence:

```
WSSKVLMSSANEDIKADLILTSTAPEHLSAPTLPLPEVQCFVFNIEYMNC
TWNSSSEPQATNLTLHYRYKVSDNNTFQECSHYLFSKEITSGCQIQKEDI
QLYQTFVVQLQDPQKPQRRAVQKLNLQNLVIPRAPENLTLSNLSESQLEL
RWKSRHIKERCLQYLVQYRSNRDRSWTELIVNHEPRFSLPSVDELKRYTF
RVRSRYNPICGSSQQWSKWSQPVHWGSHTVEENPSLFALEAEQKLISEED
LGGEQKLISEEDLHHHHHH
```

Rat IL2Rγ extracellular domain expressed with a C-terminal myc-myc-hexahistidine tag (rIL-2Rg-MMH; SEQ ID NO: 385), comprising Amino acids (1-240): Rat IL2Rg ecto (W23-A262 of NP_543165.1)

Amino acids (241-268): Myc-Myc-Hexahistadine tag (underlined)

comprising the amino acid sequence:

```
WSSKVLMSSGNEDTKSDLLLTSMDLKHLSVPTLPLPEVQCFVFNVEYMNC
TWNSSSEPQPTNLTMHYRYKGSDNNTFQECSHYLFSKEITSGCQIQKEDI
```

-continued

```
QLYQTFVVQLQDPQKPQRRAEQKLNLQNLVIPWAPENLTLYNLSESQVEL

RWKSRYIERCLQYLVQYRSNRDRSWTEQIVDHEPRFSLPSVDEQKLYTFR

VRSRFNPICGSTQQWSKWSQPIHWGSHTAEENPSLFALEAEQKLISEEDL

GGEQKLISEEDLHHHHHH
*Expressed with mROR signal sequence
```

Different concentrations of IL2Rγ reagents were prepared in HBS-ET running buffer (100 nM-6.25 nM; 4-fold serial dilution or 50 nM-3.125 nM; 4-fold serial dilution for hIL-2Rg-mFc) and injected over anti-human Fc captured anti-IL2Rγ monoclonal antibody surface for 4 minutes at a flow rate of 30 L/minute. The dissociation of monoclonal antibody bound IL2Rγ reagents were monitored for 8-10 minutes in HBS-ET running buffer. Kinetic association ($k_a$) and dissociation ($K_d$) rate constants were determined by fitting the real-time sensorgrams to a 1:1 binding model using Scrubber 2.0c curve fitting software. Binding dissociation equilibrium constants ($K_D$) and dissociative half-lives (t½) were calculated from the kinetic rate constants as:

$$K_D(M) = \frac{kd}{ka}, \text{ and } t1/2\ (\text{min}) = \frac{\ln(2)}{60 * kd}$$

The kinetic parameters for binding of various IL-2Rγ reagents to different IL2Rγ monoclonal antibodies at 25° C. and 37° C. are shown in Tables 3-1 through 3-14.

TABLE 3-1

Binding kinetics parameters of hIL-2Rg-MMH binding to IL-2Rγ monoclonal antibodies at 25° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12857P | 183 ± 1 | 56 | 8.19E+04 | 2.25E−04 | 2.75E−09 | 51 |
| H4H12858P | 181 ± 0.3 | 67 | 2.57E+05 | 3.16E−04 | 1.23E−09 | 37 |
| H4H12859P | 195 ± 0.4 | 27 | 3.66E+04 | 3.21E−03 | 8.76E−08 | 4 |
| H4H12863P | 283 ± 4.7 | 91 | 2.26E+05 | 3.84E−04 | 1.70E−09 | 30 |
| H4H12871P | 291 ± 4 | 77 | 1.99E+05 | 1.00E−03 | 5.03E−09 | 12 |
| H4H12874P | 199 ± 0.8 | 57 | 8.52E+04 | 3.05E−04 | 3.57E−09 | 38 |
| H4H12884P | 367 ± 2.1 | 84 | 1.99E+05 | 1.39E−03 | 6.96E−09 | 8 |
| H4H12886P | 166 ± 0.6 | 60 | 1.34E+05 | 2.70E−04 | 2.02E−09 | 43 |
| H4H12889P | 215 ± 0.5 | 64 | 2.98E+05 | 4.20E−04 | 1.41E−09 | 28 |
| H4H12890P | 219 ± 1.8 | 48 | 6.79E+04 | 3.33E−04 | 4.91E−09 | 35 |
| H4H12899P | 189 ± 0.7 | 61 | 1.82E+05 | 4.58E−04 | 2.51E−09 | 25 |
| H4H12900P | 248 ± 1.4 | 79 | 2.93E+05 | 3.79E−04 | 1.29E−09 | 30 |
| H4H12908P | 266 ± 1.1 | 19 | 3.31E+04 | 2.85E−04 | 8.61E−09 | 41 |
| H4H12913P2 | 182 ± 0.5 | 42 | 6.20E+04 | 6.91E−04 | 1.12E−08 | 17 |
| H4H12922P2 | 218 ± 0.7 | 79 | 2.97E+05 | 3.86E−04 | 1.30E−09 | 30 |
| H4H12924P2 | 237 ± 0.5 | 78 | 3.22E+05 | 1.74E−03 | 5.38E−09 | 7 |
| H4H12926P2 | 239 ± 0.5 | 13 | 2.00E+05 | 2.64E−02 | 1.32E−07 | 0.4 |
| H4H12927P2 | 151 ± 0.5 | 18 | 5.75E+04 | 5.55E−03 | 9.65E−08 | 2.1 |
| H4H12934P2 | 363 ± 1.1 | 33 | 9.48E+04 | 1.06E−02 | 1.12E−07 | 1.1 |
| H4H13538P | 154 ± 0.4 | 68 | 2.22E+05 | 2.27E−04 | 1.02E−09 | 51 |
| H4H13541P | 199 ± 1 | 72 | 1.05E+05 | 2.52E−04 | 2.41E−09 | 46 |
| H4H13544P2 | 274 ± 0.9 | 51 | 4.72E+04 | 1.35E−03 | 2.87E−08 | 9 |
| H4H13545P2 | 322 ± 1.1 | 12 | 1.71E+05 | 5.75E−02 | 3.36E−07 | 0.2 |

TABLE 3-2

Binding kinetics parameters of hIL-2Rg-MMH binding to IL-2Rγ monoclonal antibodies at 37° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12857P | 95 ± 0.6 | 23 | 1.54E+05 | 9.86E−04 | 6.42E−09 | 12 |
| H4H12858P | 169 ± 4.5 | 57 | 3.86E+05 | 1.74E−03 | 4.52E−09 | 7 |
| H4H12859P | 177 ± 4.9 | 18 | 6.90E+04 | 1.29E−02 | 1.87E−07 | 0.9 |
| H4H12863P | 273 ± 7 | 77 | 3.67E+05 | 1.51E−03 | 4.11E−09 | 8 |
| H4H12871P | 266 ± 5.5 | 61 | 2.50E+05 | 2.66E−03 | 1.06E−08 | 4 |
| H4H12874P | 184 ± 4.4 | 52 | 1.20E+05 | 1.25E−03 | 1.04E−08 | 9 |
| H4H12884P | 319 ± 6.2 | 62 | 2.57E+05 | 3.36E−03 | 1.31E−08 | 3.4 |
| H4H12886P | 151 ± 4.4 | 52 | 6.19E+04 | 9.56E−04 | 1.54E−08 | 12 |
| H4H12889P | 125 ± 1.6 | 32 | 4.65E+05 | 1.85E−03 | 3.99E−09 | 6 |
| H4H12890P | 134 ± 1.2 | 27 | 9.51E+04 | 1.33E−03 | 1.40E−08 | 9 |
| H4H12899P | 114 ± 1.7 | 36 | 3.42E+05 | 2.49E−03 | 7.27E−09 | 5 |
| H4H12900P | 183 ± 2.2 | 43 | 5.03E+05 | 1.84E−03 | 3.66E−09 | 6 |
| H4H12908P | 169 ± 2 | 16 | 4.83E+04 | 1.41E−03 | 2.92E−08 | 8 |
| H4H12913P2 | 114 ± 1.6 | 24 | 1.04E+05 | 3.48E−03 | 3.34E−08 | 3.3 |
| H4H12922P2 | 130 ± 1.7 | 44 | 4.07E+05 | 1.05E−03 | 2.58E−09 | 11 |
| H4H12924P2 | 142 ± 2.1 | 26 | 8.71E+05 | 1.57E−02 | 1.80E−08 | 0.7 |
| H4H12926P2 | 105 ± 1.5 | 2 | NB * | NB * | NB * | NB * |
| H4H12927P2 | 74 ± 1.1 | 5 | NB * | NB * | NB * | NB * |

TABLE 3-2-continued

Binding kinetics parameters of hIL-2Rg-MMH binding to IL-2Rγ monoclonal antibodies at 37° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12934P2 | 221 ± 2.3 | 9 | 2.16E+05 | 7.63E−02 | 3.53E−07 | 0.2 |
| H4H13538P | 231 ± 1.5 | 99 | 3.19E+05 | 1.08E−03 | 3.40E−09 | 11 |
| H4H13541P | 282 ± 2.1 | 103 | 1.56E+05 | 7.80E−04 | 5.01E−09 | 15 |
| H4H13544P2 | 366 ± 1.8 | 49 | 7.60E+04 | 7.82E−03 | 1.03E−07 | 1.5 |
| H4H13545P2 | 410 ± 1.9 | 7 | 6.11E+05 | 6.91E−02 | 1.13E−07 | 0.2 |

* NB indicates that no binding was observed under the current experimental conditions.

TABLE 3-3

Binding kinetics parameters of mfIL-2Rg-MMH binding to IL-2Rγ monoclonal antibodies at 25° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12857P | 183 ± 1.4 | 42 | 7.17E+04 | 2.28E−04 | 3.18E−09 | 51 |
| H4H12858P | 179 ± 0.3 | 58 | 1.14E+05 | 2.69E−04 | 2.36E−09 | 43 |
| H4H12859P | 193 ± 0.3 | 17 | 4.03E+04 | 5.07E−03 | 1.26E−07 | 2.3 |
| H4H12863P | 280 ± 5.1 | 81 | 1.89E+05 | 3.60E−04 | 1.91E−09 | 32 |
| H4H12871P | 288 ± 2.8 | 72 | 1.74E+05 | 9.05E−04 | 5.19E−09 | 13 |
| H4H12874P | 196 ± 0.9 | 50 | 7.15E+04 | 3.06E−04 | 4.28E−09 | 38 |
| H4H12884P | 364 ± 1.7 | 82 | 1.74E+05 | 1.21E−03 | 6.98E−09 | 10 |
| H4H12886P | 165 ± 0.8 | 57 | 1.09E+05 | 2.66E−04 | 2.45E−09 | 43 |
| H4H12889P | 214 ± 0.2 | 59 | 2.33E+05 | 4.04E−04 | 1.74E−09 | 29 |
| H4H12890P | 218 ± 0.4 | 37 | 6.06E+04 | 3.13E−04 | 5.16E−09 | 37 |
| H4H12899P | 188 ± 0.7 | 54 | 1.02E+05 | 4.07E−04 | 4.01E−09 | 28 |
| H4H12900P | 246 ± 1.2 | 71 | 2.32E+05 | 3.35E−04 | 1.44E−09 | 34 |
| H4H12908P | 268 ± 4.1 | 14 | 3.22E+04 | 2.37E−04 | 7.37E−09 | 49 |
| H4H12913P2 | 180 ± 0.8 | 34 | 4.49E+04 | 6.33E−04 | 1.41E−08 | 18 |
| H4H12922P2 | 217 ± 0.3 | 76 | 2.35E+05 | 3.86E−04 | 1.64E−09 | 30 |
| H4H12924P2 | 235 ± 0.6 | 73 | 2.51E+05 | 1.65E−03 | 6.58E−09 | 7 |
| H4H12926P2 | 236 ± 1.2 | 11 | 2.44E+05 | 2.61E−02 | 1.07E−07 | 0.4 |
| H4H12927P2 | 151 ± 0.4 | 12 | 2.88E+04 | 6.86E−03 | 2.38E−07 | 1.7 |
| H4H12934P2 | 362 ± 1.6 | 31 | 9.27E+04 | 1.14E−02 | 1.23E−07 | 1.0 |
| H4H13538P | 154 ± 0.6 | 81 | 1.33E+05 | 3.04E−04 | 2.28E−09 | 38 |
| H4H13541P | 198 ± 0.3 | 82 | 1.70E+05 | 3.15E−04 | 1.85E−09 | 37 |
| H4H13544P2 | 274 ± 0.6 | 60 | 5.17E+04 | 1.27E−03 | 2.46E−08 | 9 |
| H4H13545P2 | 322 ± 1.4 | 26 | 9.78E+04 | 1.40E−02 | 1.43E−07 | 0.8 |

TABLE 3-4

Binding kinetics parameters of mfIL-2Rg-MMH binding to IL-2Rγ monoclonal antibodies at 37 ± C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12857P | 93 ± 1 | 18 | 1.30E+05 | 1.08E−03 | 8.29E−09 | 11 |
| H4H12858P | 155 ± 3.6 | 47 | 3.09E+05 | 1.48E−03 | 4.77E−09 | 8 |
| H4H12859P | 162 ± 3.9 | 10 | 6.28E+04 | 2.01E−02 | 3.20E−07 | 0.6 |
| H4H12863P | 253 ± 2.1 | 63 | 2.66E+05 | 1.47E−03 | 5.51E−09 | 8 |
| H4H12871P | 246 ± 5.1 | 55 | 2.06E+05 | 2.61E−03 | 1.27E−08 | 4 |
| H4H12874P | 169 ± 3.6 | 43 | 9.33E+04 | 1.16E−03 | 1.24E−08 | 10 |
| H4H12884P | 296 ± 5.3 | 59 | 2.00E+05 | 3.21E−03 | 1.61E−08 | 4 |
| H4H12886P | 138 ± 3.2 | 47 | 4.78E+04 | 8.46E−04 | 1.77E−08 | 14 |
| H4H12889P | 118 ± 1.4 | 29 | 3.69E+05 | 1.71E−03 | 4.63E−09 | 7 |
| H4H12890P | 128 ± 1.5 | 20 | 9.36E+04 | 1.31E−03 | 1.40E−08 | 9 |
| H4H12899P | 107 ± 1.6 | 31 | 3.22E+05 | 2.16E−03 | 6.71E−09 | 5 |
| H4H12900P | 175 ± 2.2 | 38 | 4.83E+05 | 1.54E−03 | 3.18E−09 | 8 |
| H4H12908P | 162 ± 2.7 | 13 | 3.71E+04 | 1.48E−03 | 3.98E−08 | 8 |
| H4H12913P2 | 109 ± 1.3 | 20 | 7.93E+04 | 2.96E−03 | 3.73E−08 | 4 |
| H4H12922P2 | 124 ± 1.7 | 44 | 3.08E+05 | 1.29E−03 | 4.18E−09 | 9 |

TABLE 3-4-continued

Binding kinetics parameters of mfIL-2Rg-MMH binding to IL-2Rγ monoclonal antibodies at 37 ± C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12924P2 | 135 ± 1.9 | 24 | 6.62E+05 | 1.37E−02 | 2.07E−08 | 0.8 |
| H4H12926P2 | 100 ± 1.2 | 1 | NB * | NB * | NB * | NB * |
| H4H12927P2 | 71 ± 1 | 1 | NB * | NB * | NB * | NB * |
| H4H12934P2 | 212 ± 2.3 | 7 | 5.73E+05 | 7.59E−02 | 1.32E−07 | 0.2 |
| H4H13538P | 231 ± 1.9 | 115 | 1.69E+05 | 9.32E−04 | 5.50E−09 | 12 |
| H4H13541P | 281 ± 0.6 | 111 | 1.06E+05 | 7.55E−04 | 7.10E−09 | 15 |
| H4H13544P2 | 363 ± 1.6 | 60 | 1.18E+05 | 6.12E−03 | 5.21E−08 | 1.9 |
| H4H13545P2 | 409 ± 1.3 | 21 | 1.46E+05 | 1.29E−02 | 8.86E−08 | 0.9 |

* NB indicates that no binding was observed under the current experimental conditions.

TABLE 3-5

Binding kinetics parameters of hIL-2Rg-mFc binding to IL-2Rγ monoclonal antibodies at 25° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12857P | 180 ± 0.5 | 20 | 3.11E+04 | 7.62E−05 | 2.45E−09 | 152 |
| H4H12858P | 175 ± 1.2 | 46 | 1.16E+05 | 9.94E−05 | 8.55E−10 | 116 |
| H4H12859P | 190 ± 1.1 | 5 | NB * | NB * | NB * | NB * |
| H4H12863P | 280 ± 0.6 | 115 | 3.99E+05 | 3.41E−05 | 8.53E−11 | 339 |
| H4H12871P | 284 ± 2.7 | 103 | 3.63E+05 | 5.22E−05 | 1.44E−10 | 221 |
| H4H12874P | 193 ± 0.9 | 15 | 2.00E+04 | 8.35E−05 | 4.18E−09 | 138 |
| H4H12884P | 359 ± 2 | 112 | 3.55E+05 | 4.02E−05 | 1.13E−10 | 287 |
| H4H12886P | 162 ± 1.1 | 23 | 5.34E+04 | 6.70E−05 | 1.26E−09 | 172 |
| H4H12889P | 209 ± 0.9 | 69 | 3.47E+05 | 1.55E−05 | 4.47E−11 | 746 |
| H4H12890P | 213 ± 0.2 | 12 | NB * | NB * | NB * | NB * |
| H4H12899P | 184 ± 0.6 | 1 | NB * | NB * | NB * | NB * |
| H4H12900P | 241 ± 2.6 | 4 | NB * | NB * | NB * | NB * |
| H4H12908P | 261 ± 1.5 | 11 | 7.62E+04 | 1.00E−05 # | 1.31E−10 | 1155 |
| H4H12913P2 | 177 ± 0.3 | 12 | 4.12E+04 | 5.34E−05 | 1.30E−09 | 216 |
| H4H12922P2 | 213 ± 1 | 82 | 3.10E+05 | 1.75E−05 | 5.64E−11 | 661 |
| H4H12924P2 | 232 ± 1.8 | 28 | 7.26E+04 | 4.11E−04 | 5.66E−09 | 28 |
| H4H12926P2 | 232 ± 0.9 | 46 | 1.85E+05 | 9.62E−04 | 5.21E−09 | 12 |
| H4H12927P2 | 147 ± 0.2 | 7 | NB * | NB * | NB * | NB * |
| H4H12934P2 | 357 ± 1.7 | 75 | 1.67E+05 | 3.94E−04 | 2.36E−09 | 29 |
| H4H13538P | 157 ± 0.1 | 38 | 1.17E+05 | 1.16E−04 | 9.96E−10 | 99 |
| H4H13541P | 199 ± 0.5 | 24 | 4.92E+04 | 8.84E−05 | 1.80E−09 | 131 |
| H4H13544P2 | 274 ± 0.3 | 63 | 1.11E+05 | 2.46E−04 | 2.21E−09 | 47 |
| H4H13545P2 | 321 ± 1.1 | 64 | 1.75E+05 | 2.11E−03 | 1.20E−08 | 5 |

* NB indicates that no binding was observed under the current experimental conditions.

# indicates no dissociation was observed under the current experimental condition and the $k_d$ value was manually fixed at 1.00E−05 $s^{-1}$

TABLE 3-6

Binding kinetics parameters of hIL-2Rg-mFc binding to IL-2Rγ monoclonal antibodies at 37° C.

| mAb Captured | mAb Capture Level (RU) | 50 nM Ag Bound | ka (1/Ms) | kd (1/s) | $K_D$ (M) | t½ (min) |
|---|---|---|---|---|---|---|
| H4H12857P | 83 ± 0.8 | 12 | IC $ | IC $ | IC $ | IC $ |
| H4H12858P | 126 ± 2.1 | 37 | 1.67E+05 | 2.50E−04 | 1.49E−09 | 46 |
| H4H12859P | 130 ± 2.2 | 5 | NB * | NB * | NB * | NB * |
| H4H12863P | 216 ± 4.1 | 93 | 5.37E+05 | 1.00E−05 # | 1.86E−11 | 1155 |
| H4H12871P | 205 ± 2.9 | 81 | 4.73E+05 | 2.39E−05 | 5.05E−11 | 484 |
| H4H12874P | 138 ± 2.3 | 14 | 3.30E+04 | 1.00E−05 # | 3.03E−10 | 1155 |
| H4H12884P | 246 ± 3.6 | 85 | 4.86E+05 | 2.69E−05 | 5.54E−11 | 429 |
| H4H12886P | 111 ± 2 | 19 | 7.08E+03 | 9.09E−05 | 1.28E−08 | 127 |
| H4H12889P | 101 ± 1.5 | 39 | 2.38E+05 | 1.00E05 # | 4.20E−11 | 1155 |
| H4H12890P | 112 ± 1.2 | 8 | NB * | NB * | NB * | NB * |
| H4H12899P | 91 ± 1.6 | 2 | NB * | NB * | NB * | NB * |

TABLE 3-6-continued

Binding kinetics parameters of hIL-2Rg-mFc binding to IL-2Rγ monoclonal antibodies at 37° C.

| mAb Captured | mAb Capture Level (RU) | 50 nM Ag Bound | ka (1/Ms) | kd (1/s) | $K_D$ (M) | t½ (min) |
|---|---|---|---|---|---|---|
| H4H12900P | 158 ± 2.1 | 4 | NB * | NB * | NB * | NB * |
| H4H12908P | 140 ± 2.3 | 8 | 1.93E+04 | 1.00E−05 # | 5.18E−10 | 1155 |
| H4H12913P2 | 95 ± 1 | 9 | 7.32E+04 | 1.85E−04 | 2.53E−09 | 62 |
| H4H12922P2 | 107 ± 1 | 47 | 2.23E+05 | 1.00E−05 # | 4.48E−11 | 1155 |
| H4H12924P2 | 118 ± 1.3 | 13 | 1.50E+04 | 1.83E−04 | 1.22E−08 | 63 |
| H4H12926P2 | 87 ± 1.1 | 11 | 2.04E+05 | 3.26E−03 | 1.60E−08 | 4 |
| H4H12927P2 | 63 ± 0.7 | 4 | NB * | NB * | NB * | NB * |
| H4H12934P2 | 189 ± 1.5 | 39 | 1.85E+05 | 5.90E−04 | 3.19E−09 | 20 |
| H4H13538P | 233 ± 0.9 | 70 | 1.44E+05 | 1.87E−04 | 1.29E−09 | 62 |
| H4H13541P | 281 ± 0.5 | 42 | 5.60E+04 | 1.22E−04 | 2.18E−09 | 94 |
| H4H13544P2 | 361 ± 2.6 | 88 | 1.26E+05 | 8.01E−04 | 6.33E−09 | 14 |
| H4H13545P2 | 408 ± 1.5 | 59 | 2.46E+05 | 7.37E−03 | 3.00E−08 | 1.6 |

* NB indicates that no binding was observed under the current experimental conditions.

# indicates no dissociation was observed under the current experimental condition and the $k_d$ value was manually fixed at 1.00E−05 $s^{-1}$ $ indicates that the binding data was inconclusive to generate reliable binding kinetic values and $K_D$

TABLE 3-7

Binding kinetics parameters of mIL-2Rg-MMH binding to IL-2Rγ monoclonal antibodies at 25° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12857P | 178 ± 0.1 | 5 | NB * | NB * | NB * | NB * |
| H4H12858P | 175 ± 0.4 | 2 | NB * | NB * | NB * | NB * |
| H4H12859P | 190 ± 1.1 | 2 | NB * | NB * | NB * | NB * |
| H4H12863P | 271 ± 3 | 2 | NB * | NB * | NB * | NB * |
| H4H12871P | 281 ± 88 | 0 | NB * | NB * | NB * | NB * |
| H4H12874P | 191 ± 05 | 1 | NB * | NB * | NB * | NB * |
| H4H12884P | 357 ± 3 | 2 | NB * | NB * | NB * | NB * |
| H4H12886P | 160 ± 1.2 | 2 | NB * | NB * | NB * | NB * |
| H4H12889P | 208 ± 0.3 | 1 | NB * | NB * | NB * | NB * |
| H4H12890P | 212 ± 0.8 | 1 | NB * | NB * | NB * | NB * |
| H4H12899P | 183 ± 0 | 51 | 9.06E+04 | 1.67E−03 | 1.84E−08 | 7 |
| H4H12900P | 240 ± 0.6 | 76 | 1.24E+05 | 4.67E−04 | 3.76E−09 | 25 |
| H4H12908P | 262 ± 6.7 | 25 | 3.41E+04 | 3.67E−03 | 1.08E−07 | 3.1 |
| H4H12913P2 | 176 ± 0.5 | 1 | NB * | NB * | NB * | NB * |
| H4H12922P2 | 213 ± 1.8 | 2 | NB * | NB * | NB * | NB * |
| H4H12924P2 | 230 ± 0.3 | 2 | NB * | NB * | NB * | NB * |
| H4H12926P2 | 231 ± 04 | 0 | NB * | NB * | NB * | NB * |
| H4H12927P2 | 147 ± 0.2 | 1 | NB * | NB * | NB * | NB * |
| H4H12934P2 | 354 ± 2.1 | 0 | NB * | NB * | NB * | NB * |
| H4H13538P | 157 ± 0.5 | 4 | NB * | NB * | NB * | NB * |
| H4H13541P | 199 ± 0.7 | 5 | NB * | NB * | NB * | NB * |
| H4H13544P2 | 273 ± 0.3 | 3 | NB * | NB * | NB * | NB * |
| H4H13545P2 | 322 ± 0.6 | 4 | NB * | NB * | NB * | NB * |

* NB indicates that no binding was observed under the current experimental conditions.

TABLE 3-8

Binding kinetics parameters of mIL-2Rg-MMH binding to IL-2Rγ monoclonal antibodies at 37° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12857P | 80 ± 0.2 | 1 | NB * | NB * | NB * | NB * |
| H4H12858P | 120 ± 0.8 | 0 | NB * | NB * | NB * | NB * |
| H4H12859P | 123 ± 0.5 | 0 | NB * | NB * | NB * | NB * |
| H4H12863P | 208 ± 2.1 | 0 | NB * | NB * | NB * | NB * |
| H4H12871P | 196 ± 1.3 | −1 | NB * | NB * | NB * | NB * |
| H4H12874P | 132 ± 1.3 | 0 | NB * | NB * | NB * | NB * |
| H4H12884P | 235 ± 1.3 | 1 | NB * | NB * | NB * | NB * |
| H4H12886P | 105 ± 0.8 | −2 | NB * | NB * | NB * | NB * |

TABLE 3-8-continued

Binding kinetics parameters of mIL-2Rg-MMH binding to IL-2Rγ monoclonal antibodies at 37° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12889P | 97 ± 0.8 | 0 | NB * | NB * | NB * | NB * |
| H4H12890P | 108 ± 0.9 | 1 | NB * | NB * | NB * | NB * |
| H4H12899P | 87 ± 0.4 | 19 | 1.93E+05 | 1.08E−02 | 5.59E−08 | 1.1 |
| H4H12900P | 154 ± 0.6 | 32 | 5.19E+05 | 3.17E−03 | 6.11E−09 | 4 |
| H4H12908P | 135 ± 0.1 | 6 | 7.57E+04 | 2.93E−02 | 3.87E−07 | 0.4 |
| H4H12913P2 | 91 ± 0 | 0 | NB * | NB * | NB * | NB * |
| H4H12922P2 | 104 ± 0.9 | 2 | NB * | NB * | NB * | NB * |
| H4H12924P2 | 114 ± 0.5 | −1 | NB * | NB * | NB * | NB * |
| H4H12926P2 | 84 ± 0.5 | 0 | NB * | NB * | NB * | NB * |
| H4H12927P2 | 61 ± 0 | 1 | NB * | NB * | NB * | NB * |
| H4H12934P2 | 182 ± 0.5 | −1 | NB * | NB * | NB * | NB * |
| H4H13538P | 232 ± 0.8 | 5 | NB * | NB * | NB * | NB * |
| H4H13541P | 281 ± 0.4 | 4 | NB * | NB * | NB * | NB * |
| H4H13544P2 | 361 ± 2.7 | 4 | NB * | NB * | NB * | NB * |
| H4H13545P2 | 407 ± 0.4 | 2 | NB * | NB * | NB * | NB * |

* NB indicates that no binding was observed under the current experimental conditions.

TABLE 3-9

Binding kinetics parameters of rat IL-2Rg-MMH binding to IL-2Rγ monoclonal antibodies at 25° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12857P | 178 ± 0.5 | 1 | NB * | NB * | NB * | NB * |
| H4H12858P | 174 ± 0 | 0 | NB * | NB * | NB * | NB * |
| H4H12859P | 190 ± 1 | 2 | NB * | NB * | NB * | NB * |
| H4H12863P | 279 ± 1.6 | 1 | NB * | NB * | NB * | NB * |
| H4H12871P | 283 ± 0.4 | 1 | NB * | NB * | NB * | NB * |
| H4H12874P | 191 ± 0.6 | 1 | NB * | NB * | NB * | NB * |
| H4H12884P | 355 ± 1.3 | 4 | NB * | NB * | NB * | NB * |
| H4H12886P | 160 ± 0.9 | 3 | NB * | NB * | NB * | NB * |
| H4H12889P | 208 ± 0.2 | 1 | NB * | NB * | NB * | NB * |
| H4H12890P | 211 ± 0.2 | 0 | NB * | NB * | NB * | NB * |
| H4H12899P | 183 ± 0.4 | 39 | 7.04E+04 | 1.53E−03 | 2.17E−08 | 8 |
| H4H12900P | 239 ± 0.8 | 57 | 1.03E+05 | 6.19E−04 | 6.02E−09 | 19 |
| H4H12908P | 261 ± 0.3 | 19 | 2.98E+04 | 2.37E−03 | 7.93E−08 | 5 |
| H4H12913P2 | 176 ± 0.3 | 1 | NB * | NB * | NB * | NB * |
| H4H12922P2 | 213 ± 0.1 | 3 | NB * | NB * | NB * | NB * |
| H4H12924P2 | 229 ± 0.8 | 3 | NB * | NB * | NB * | NB * |
| H4H12926P2 | 230 ± 0.6 | 2 | NB * | NB * | NB * | NB * |
| H4H12927P2 | 147 ± 0 | 2 | NB * | NB * | NB * | NB * |
| H4H12934P2 | 354 ± 6.6 | 1 | NB * | NB * | NB * | NB * |
| H4H13538P | 157 ± 0.2 | 3 | NB * | NB * | NB * | NB * |
| H4H13541P | 198 ± 0 | 4 | NB * | NB * | NB * | NB * |
| H4H13544P2 | 274 ± 0.1 | 3 | NB * | NB * | NB * | NB * |
| H4H13545P2 | 320 ± 1 | 4 | NB * | NB * | NB * | NB * |

* NB indicates that no binding was observed under the current experimental conditions.

TABLE 3-10

Binding kinetics parameters of rat IL-2Rg-MMH binding to IL-2Rγ monoclonal antibodies at 37° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12857P | 79 ± 0.8 | 1 | NB * | NB * | NB * | NB * |
| H4H12858P | 117 ± 1.2 | 0 | NB * | NB * | NB * | NB * |
| H4H12859P | 121 ± 1.3 | 1 | NB * | NB * | NB * | NB * |
| H4H12863P | 199 ± 3.7 | 0 | NB * | NB * | NB * | NB * |
| H4H12871P | 190 ± 3.4 | 1 | NB * | NB * | NB * | NB * |
| H4H12874P | 128 ± 0.9 | 3 | NB * | NB * | NB * | NB * |
| H4H12884P | 231 ± 1.5 | 4 | NB * | NB * | NB * | NB * |

TABLE 3-10-continued

Binding kinetics parameters of rat IL-2Rg-MMH binding to IL-2Rγ monoclonal antibodies at 37° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12886P | 103 ± 0.6 | 4 | NB * | NB * | NB * | NB * |
| H4H12889P | 95 ± 0.7 | 2 | NB * | NB * | NB * | NB * |
| H4H12890P | 107 ± 0.6 | 0 | NB * | NB * | NB * | NB * |
| H4H12899P | 86 ± 1.3 | 16 | 1.46E+05 | 7.53E−03 | 5.16E−08 | 1.5 |
| H4H12900P | 152 ± 0.3 | 27 | 4.17E+05 | 3.63E−03 | 8.70E−09 | 3.2 |
| H4H12908P | 134 ± 1.3 | 8 | 3.89E+04 | 8.35E−03 | 2.15E−07 | 1.4 |
| H4H12913P2 | 90 ± 0.5 | 3 | NB * | NB * | NB * | NB * |
| H4H12922P2 | 102 ± 0.3 | 5 | NB * | NB * | NB * | NB * |
| H4H12924P2 | 113 ± 0.7 | 3 | NB * | NB * | NB * | NB * |
| H4H12926P2 | 83 ± 0.8 | 2 | NB * | NB * | NB * | NB * |
| H4H12927P2 | 60 ± 0.2 | 1 | NB * | NB * | NB * | NB * |
| H4H12934P2 | 180 ± 1.4 | 0 | NB * | NB * | NB * | NB * |
| H4H13538P | 233 ± 0.3 | 5 | NB * | NB * | NB * | NB * |
| H4H13541P | 282 ± 0.1 | 5 | NB * | NB * | NB * | NB * |
| H4H13544P2 | 361 ± 2.2 | 4 | NB * | NB * | NB * | NB * |
| H4H13545P2 | 408 ± 0.7 | 3 | NB * | NB * | NB * | NB * |

* NB indicates that no binding was observed under the current experimental conditions.

TABLE 3-11

Binding kinetics parameters of hIL-2Rg_D1-MMH binding to IL-2Rγ monoclonal antibodies at 25° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12857P | 181 ± 0.7 | 0 | NB * | NB * | NB * | NB * |
| H4H12858P | 178 ± 0.2 | 1 | NB * | NB * | NB * | NB * |
| H4H12859P | 192 ± 0.4 | 0 | NB * | NB * | NB * | NB * |
| H4H12863P | 291 ± 4.5 | 55 | 1.14E+05 | 5.38E−04 | 4.74E−09 | 21 |
| H4H12871P | 287 ± 3.2 | 47 | 9.40E+04 | 1.11E−03 | 1.18E−08 | 10 |
| H4H12874P | 196 ± 1.2 | 0 | NB * | NB * | NB * | NB * |
| H4H12884P | 364 ± 0.5 | 51 | 1.66E+05 | 1.96E−03 | 1.18E−08 | 6 |
| H4H12886P | 164 ± 0.7 | 0 | NB * | NB * | NB * | NB * |
| H4H12889P | 213 ± 0.6 | 38 | 2.00E+05 | 1.07E−03 | 5.34E−09 | 11 |
| H4H12890P | 217 ± 0.6 | 1 | NB * | NB * | NB * | NB * |
| H4H12899P | 187 ± 0.4 | 0 | NB * | NB * | NB * | NB * |
| H4H12900P | 246 ± 1.9 | 0 | NB * | NB * | NB * | NB * |
| H4H12908P | 264 ± 2.5 | 1 | NB * | NB * | NB * | NB * |
| H4H12913P2 | 180 ± 0.6 | 0 | NB * | NB * | NB * | NB * |
| H4H12922P2 | 216 ± 0.4 | 50 | 2.52E+05 | 8.39E−04 | 3.32E−09 | 14 |
| H4H12924P2 | 234 ± 1 | 1 | NB * | NB * | NB * | NB * |
| H4H12926P2 | 235 ± 0.5 | 8 | 1.40E+05 | 2.73E−02 | 1.95E−07 | 0.4 |
| H4H12927P2 | 150 ± 0.4 | 0 | NB * | NB * | NB * | NB * |
| H4H12934P2 | 359 ± 2.9 | 15 | 5.53E+04 | 1.09E−02 | 1.97E−07 | 1.1 |
| H4H13538P | 155 ± 0.8 | 2 | NB * | NB * | NB * | NB * |
| H4H13541P | 199 ± 0.2 | 2 | NB * | NB * | NB * | NB * |
| H4H13544P2 | 273 ± 0.7 | 24 | 3.58E+04 | 2.07E−03 | 5.78E−08 | 6 |
| H4H13545P2 | 322 ± 0.6 | 8 | NB * | NB * | NB * | NB * |

* NB indicates that no binding was observed under the current experimental conditions.

TABLE 3-12

Binding kinetics parameters of hIL-2Rg_D1-MMH binding to IL-2Rγ monoclonal antibodies at 37° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12857P | 88 ± 0.5 | 1 | NB * | NB * | NB * | NB * |
| H4H12858P | 143 ± 2.7 | 1 | NB * | NB * | NB * | NB * |
| H4H12859P | 149 ± 3.4 | 0 | NB * | NB * | NB * | NB * |
| H4H12863P | 237 ± 7.1 | 39 | 2.54E+05 | 2.21E−03 | 8.69E−09 | 5 |
| H4H12871P | 231 ± 3.5 | 33 | 1.70E+05 | 3.60E−03 | 2.12E−08 | 3.2 |
| H4H12874P | 157 ± 3.2 | 1 | NB * | NB * | NB * | NB * |

TABLE 3-12-continued

Binding kinetics parameters of hIL-2Rg_D1-MMH binding to IL-2Rγ monoclonal antibodies at 37° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12884P | 276 ± 5.1 | 32 | 1.34E+05 | 4.42E−03 | 3.29E−08 | 2.6 |
| H4H12886P | 127 ± 2.5 | 0 | NB * | NB * | NB * | NB * |
| H4H12889P | 112 ± 1.3 | 16 | 2.54E+05 | 5.07E−03 | 2.00E−08 | 2.3 |
| H4H12890P | 122 ± 1.1 | 2 | NB * | NB * | NB * | NB * |
| H4H12899P | 101 ± 1.4 | 1 | NB * | NB * | NB * | NB * |
| H4H12900P | 169 ± 1.7 | 2 | NB * | NB * | NB * | NB * |
| H4H12908P | 153 ± 1.8 | 0 | NB * | NB * | NB * | NB * |
| H4H12913P2 | 104 ± 1.2 | 1 | NB * | NB * | NB * | NB * |
| H4H12922P2 | 118 ± 1.4 | 26 | 4.07E+05 | 1.68E−03 | 4.13E−09 | 7 |
| H4H12924P2 | 129 ± 1.6 | −1 | NB * | NB * | NB * | NB * |
| H4H12926P2 | 96 ± 1.3 | 2 | NB * | NB * | NB * | NB * |
| H4H12927P2 | 68 ± 0.7 | 1 | NB * | NB * | NB * | NB * |
| H4H12934P2 | 204 ± 1.8 | 4 | 9.21E+05 | 1.09E−01 | 1.19E−07 | 0.1 |
| H4H13538P | 231 ± 0.6 | 2 | NB * | NB * | NB * | NB * |
| H4H13541P | 282 ± 0.3 | 2 | NB * | NB * | NB * | NB * |
| H4H13544P2 | 363 ± 1.8 | 22 | 4.64E+04 | 1.05E−02 | 2.25E−07 | 1.1 |
| H4H13545P2 | 408 ± 0.9 | 4 | NB * | NB * | NB * | NB * |

* NB indicates that no binding was observed under the current experimental conditions.

TABLE 3-13

Binding kinetics parameters of hIL-2Rg_D2-MMH binding to IL-2Rγ monoclonal antibodies at 25° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12857P | 181 ± 1 | 6 | 2.60E+05 | 7.56E−02 | 2.91E−07 | 0.2 |
| H4H12858P | 177 ± 0.3 | 0 | NB * | NB * | NB * | NB * |
| H4H12859P | 191 ± 0.6 | −1 | NB * | NB * | NB * | NB * |
| H4H12863P | 281 ± 1.7 | 0 | NB * | NB * | NB * | NB * |
| H4H12871P | 285 ± 1.2 | 0 | NB * | NB * | NB * | NB * |
| H4H12874P | 194 ± 1.3 | 10 | 2.03E+05 | 4.35E−02 | 2.14E−07 | 0.3 |
| H4H12884P | 360 ± 1.2 | 1 | NB * | NB * | NB * | NB * |
| H4H12886P | 162 ± 0.5 | 35 | 2.76E+05 | 1.48E−04 | 5.35E−10 | 78 |
| H4H12889P | 211 ± 0.5 | 0 | NB * | NB * | NB * | NB * |
| H4H12890P | 215 ± 0.4 | −1 | NB * | NB * | NB * | NB * |
| H4H12899P | 186 ± 1 | −1 | NB * | NB * | NB * | NB * |
| H4H12900P | 244 ± 0.6 | −1 | NB * | NB * | NB * | NB * |
| H4H12908P | 263 ± 1.5 | −1 | NB * | NB * | NB * | NB * |
| H4H12913P2 | 179 ± 0.4 | 37 | 2.56E+05 | 7.08E−04 | 2.76E−09 | 16 |
| H4H12922P2 | 215 ± 1 | 2 | NB * | NB * | NB * | NB * |
| H4H12924P2 | 233 ± 1.1 | 1 | NB * | NB * | NB * | NB * |
| H4H12926P2 | 233 ± 0.4 | 0 | NB * | NB * | NB * | NB * |
| H4H12927P2 | 149 ± 0.5 | 14 | 2.38E+05 | 1.66E−02 | 6.99E−08 | 0.7 |
| H4H12934P2 | 358 ± 0.6 | −1 | NB * | NB * | NB * | NB * |
| H4H13538P | 156 ± 0.5 | 6 | NB * | NB * | NB * | NB * |
| H4H13541P | 199 ± 0.2 | 10 | NB * | NB * | NB * | NB * |
| H4H13544P2 | 273 ± 0.3 | 5 | NB * | NB * | NB * | NB * |
| H4H13545P2 | 321 ± 0.3 | 5 | NB * | NB * | NB * | NB * |

* NB indicates that no binding was observed under the current experimental conditions.

TABLE 3-14

Binding kinetics parameters of hIL-2Rg_D2-MMH binding to IL-2Rγ monoclonal antibodies at 37° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12857P | 85 ± 0.5 | 0 | NB * | NB * | NB * | NB * |
| H4H12858P | 134 ± 2 | −1 | NB * | NB * | NB * | NB * |
| H4H12859P | 140 ± 2 | −1 | NB * | NB * | NB * | NB * |
| H4H12863P | 226 ± 4.4 | −1 | NB * | NB * | NB * | NB * |
| H4H12871P | 217 ± 3.4 | −1 | NB * | NB * | NB * | NB * |

TABLE 3-14-continued

Binding kinetics parameters of hIL-2Rg_D2-MMH binding to IL-2Rγ monoclonal antibodies at 37° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12874P | 147 ± 2.4 | 2 | NB * | NB * | NB * | NB * |
| H4H12884P | 261 ± 3.8 | 2 | NB * | NB * | NB * | NB * |
| H4H12886P | 119 ± 1.9 | 26 | 3.31E+04 | 3.77E−04 | 1.14E−08 | 31 |
| H4H12889P | 106 ± 1.2 | 0 | NB * | NB * | NB * | NB * |
| H4H12890P | 117 ± 1.5 | 1 | NB * | NB * | NB * | NB * |
| H4H12899P | 96 ± 1.4 | 0 | NB * | NB * | NB * | NB * |
| H4H12900P | 164 ± 2.3 | 1 | NB * | NB * | NB * | NB * |
| H4H12908P | 145 ± 2.6 | −1 | NB * | NB * | NB * | NB * |
| H4H12913P2 | 99 ± 0.9 | 16 | 2.66E+05 | 3.37E−03 | 1.27E−08 | 3.4 |
| H4H12922P2 | 113 ± 1.4 | 3 | NB * | NB * | NB * | NB * |
| H4H12924P2 | 124 ± 1.6 | 0 | NB * | NB * | NB * | NB * |
| H4H12926P2 | 91 ± 1.3 | 0 | NB * | NB * | NB * | NB * |
| H4H12927P2 | 66 ± 0.5 | 2 | NB * | NB * | NB * | NB * |
| H4H12934P2 | 196 ± 2.9 | −1 | NB * | NB * | NB * | NB * |
| H4H13538P | 234 ± 4.8 | 6 | NB * | NB * | NB * | NB * |
| H4H13541P | 282 ± 0.6 | 7 | NB * | NB * | NB * | NB * |
| H4H13544P2 | 363 ± 2 | 4 | NB * | NB * | NB * | NB * |
| H4H13545P2 | 409 ± 0.6 | 3 | NB * | NB * | NB * | NB * |

* NB indicates that no binding was observed under the current experimental conditions.

Example 4: OCTET Cross-Competition Between Different Anti-IL-2Rγ Monoclonal Antibodies Binding competition between a panel of anti-IL2Rγ monoclonal antibodies was determined using a real time, label-free bio-layer interferometry assay on the OCTET HTX biosensor platform (Pall ForteBio Corp.). The entire experiment was performed at 25° C. in 10 mM HEPES, 150 mM NaCl, 3 mM EDTA, and 0.05% v/v Surfactant Tween-20, 1 mg/mL BSA, pH 7.4 (HBS-EBT) buffer using a plate shaker speed of 1000 rpm. To assess whether 2 antibodies competed with one another for binding to their respective epitopes on human IL2Rγ extracellular domain expressed with a C-terminal myc-myc-hexahistidine tag (hIL-2Rg-MMH; SEQ ID: 379), anti-Penta-His antibody coated OCTET biosensor tips (Fortebio Inc, #18-5122) were used to capture ~0.27 nM hIL-2Rg-MMH by submerging the biosensor tips for 3 minutes in wells containing 10 μg/mL hIL-2Rg-MMH. The antigen captured biosensor tips were then saturated with a first anti-IL2Rγ monoclonal antibody (subsequently referred to as mAb-1) by dipping into wells containing 50 μg/mL mAb-1 for 300 seconds. The biosensor tips were then subsequently dipped into wells containing 50 μg/mL of a second anti-IL2Rγ monoclonal antibody (subsequently referred to as mAb-2) for 240 seconds. Biosensor tips were washed in HBS-ETB buffer between every step of the experiment. The real-time binding response was monitored over the entire course of the experiment and the binding response at the end of every step was recorded. The response of mAb-2 binding to hIL-2Rg-MMH pre-complexed with mAb-1 was compared and competitive/non-competitive behavior of different anti-IL2Rγ monoclonal antibodies was determined as shown in Table 4-1.

TABLE 4-1

Cross-competition between anti-IL-2Rg monoclonal antibodies.

| mAb-1 | mAb-2 Competing with mAb-1 |
|---|---|
| H4H12889P | H4H12922P2 |
| H4H12922P2 | H4H12889P |

TABLE 4-1-continued

Cross-competition between anti-IL-2Rg monoclonal antibodies.

| mAb-1 | mAb-2 Competing with mAb-1 |
|---|---|
| H4H12863P | H4H12871P |
| | H4H12884P |
| | H4H12926P2 |
| | H4H12934P2 |
| H4H12871P | H4H12863P |
| | H4H12884P |
| | H4H12926P2 |
| | H4H12934P2 |
| H4H12884P | H4H12863P |
| | H4H12871P |
| | H4H12926P2 |
| | H4H12934P2 |
| H4H12926P2 | H4H12863P |
| | H4H12871P |
| | H4H12884P |
| | H4H12934P2 |
| H4H12934P2 | H4H12863P |
| | H4H12871P |
| | H4H12884P |
| | H4H12926P2 |
| H4H12899P | H4H12900P |
| | H4H12908P |
| | H4H12858P |
| H4H12900P | H4H12899P |
| | H4H12908P |
| | H4H12858P |
| H4H12908P | H4H12899P |
| | H4H12900P |
| | H4H12858P |
| H4H12858P | H4H12899P |
| | H4H12900P |
| | H4H12908P |
| H4H12924P2 | H4H12899P |
| | H4H12900P |
| | H4H12908P |
| | H4H12858P |
| | H4H12890P |
| | H4H12859P |
| | H4H12857P |
| | H4H12874P |
| | H4H12886P |
| | H4H12913P2 |
| | H4H12927P2 |

TABLE 4-1-continued

Cross-competition between anti-IL-2Rg monoclonal antibodies.

| mAb-1 | mAb-2 Competing with mAb-1 |
|---|---|
| H4H12890P | H4H12924P2 |
| | H4H12859P |
| | H4H12857P |
| | H4H12874P |
| | H4H12886P |
| | H4H12913P2 |
| | H4H12927P2 |
| H4H12859P | H4H12924P2 |
| | H4H12890P |
| | H4H12857P |
| | H4H12874P |
| | H4H12886P |
| | H4H12913P2 |
| | H4H12927P2 |
| H4H12857P | H4H12924P2 |
| | H4H12890P |
| | H4H12859P |
| | H4H12874P |
| | H4H12886P |
| | H4H12913P2 |
| | H4H12927P2 |
| H4H12874P | H4H12924P2 |
| | H4H12890P |
| | H4H12859P |
| | H4H12857P |
| | H4H12886P |
| | H4H12913P2 |
| | H4H12927P2 |
| H4H12886P | H4H12924P2 |
| | H4H12890P |
| | H4H12859P |
| | H4H12857P |
| | H4H12874P |
| | H4H12913P2 |
| | H4H12927P2 |
| H4H12913P2 | H4H12924P2 |
| | H4H12890P |
| | H4H12859P |
| | H4H12857P |
| | H4H12874P |
| | H4H12886P |
| | H4H12927P2 |
| H4H12927P2 | H4H12924P2 |
| | H4H12890P |
| | H4H12859P |
| | H4H12857P |
| | H4H12874P |
| | H4H12886P |
| | H4H12913P2 |

Example 5: Flow Cytometry Analysis of STAT Phosphorylation in Human CD4+ T Cells (Human PBMCs)

To assess the in vitro characteristics of IL2Rγ antibodies of the invention, their ability to block CD4+ T cell activation induced by IL-2, IL-4, IL-7, IL-15 and IL-21 was measured by flow cytometry (BD PHOSFLOW assay). BD PHOSFLOW allows simultaneous analysis of intracellular phosphoprotein (such as STAT proteins) and cell surface markers to analyze cell signaling in discrete subpopulations of cells. This technology was used to analyze STAT phosphorylation in human CD4+ T cells upon stimulation with cytokines from the gamma c family.

Human peripheral blood mononuclear cells (PBMCs) were isolated from fresh whole blood (Bioreclammation-IVT) by density gradient centrifugation. K2 EDTA whole blood was diluted 1:1 in X-VIVO 15 media (Lonza), added to SEPMATE tubes (StemCell) containing FICOLL-PAQUE PLUS (Healthcare) and centrifuged to separate PBMCs. The above layer containing the PBMCs was transferred to a new tube and washed twice with DPBS (Life Technologies). PBMCs were then resuspended in X-VIVO 15 media at a concentration of ~$5.0\times10^6$ cells/mL, plated in 96-well plates (50 uL of cells/well; ~250,000 cells/well) and incubated at 37° C. for 2 hours before adding the cytokines and antibodies.

Serial dilutions of antibodies (1:5) were prepared in pre-warmed X-VIVO15 media and were added to the cells (50 uL), with final antibody concentrations starting from 400 nM. Fixed cytokine concentrations were prepared in pre-warmed X-VIVO15 media and were added to the cells (100 uL), with a final concentration of 1 pM for IL-7 (R&D Systems), 50 pM for IL-4 (R&D Systems) and IL-21 (eBioscience), 0.5 nM for IL-15 (R&D Systems) and 10 nM IL-2 (R&D Systems); with a final volume per well of 200 uL.

For cytokine dose responses, serial dilutions for each cytokine (1:5) were also prepared in pre-warmed X-VIVO 15 media, with final cytokine concentrations starting from 5 nM for IL-4, IL-7 and IL-21, or from 50 nM for IL-2 and IL-15. First, 50 uL of X-VIVO 15 media were added to the cells followed by 100 uL of serial dilutions of cytokines, for a total volume per well of 200 uL. After addition of cytokines and antibodies to the cells, they were incubated at 37° C. for 15 minutes to allow PBMCs activation (STAT phosphorylation). The stimulation was then stopped by addition of 200 uL of warm BD CYTOFIX (BD) to each well, and cells were incubated for 10 minutes at 37° C. (fixation step). Cells were then washed twice with BD PHARMIGEN Stain Buffer (BD) and kept overnight at 4° C. The next day, cells were centrifuged and permeabilized by slowly adding 100 uL of cold BD PHOSFLOW Perm Buffer III (BD) to the pellets. Cells were incubated at 4° C. for 30 minutes, then washed twice with BD PHARMIGEN Stain Buffer. To enable the analysis of the CD4+ T cell population used to measure STAT phosphorylation, cells were stained with a mix of human FcR binding inhibitor (eBioscience; 1/10), anti-CD33-PE (BD; 1/200) anti-CD4-PacificBlue (BD; 1/200), anti-CD3-PECy7 (BD; 1/200) and the relevant anti-phospho-STAT-AlexaFluor647 (BD), prepared in BD PHARMIGEN Stain Buffer:

Anti-phosphoSTAT3 (1/10): for cells stimulated with IL-21,

Anti-phosphoSTAT5 (1/20): for cells stimulated with IL-2, IL-7 and IL-15,

Anti-phosphoSTAT6 (1/10): for cells stimulated with IL-4.

The samples were held at room temperature for 1 hour in the dark. The cells were then centrifuged and washed twice with BD PHARMIGEN Stain Buffer. Sample data were acquired on a LSR FORTESSA X-20 cell analyzer using the HTS attachment (BD). Data analysis was performed using FLOWJO X Software (Tree Star, OR). CD4+ T cells were defined as intact cells, singlets, CD33−, CD3+, CD4+; and STAT phosphorylation was analyzed within this cell population (MFI=mean fluorescence intensity).

Both H4H12889P and H4H12922P2 similarly and efficiently blocked STAT phosphorylation induced by all the cytokines tested in this assay (IL-2, IL-4, IL-7, IL-15 and IL-21), while H4H12874P, H4H12886P, H4H12857P as well as the comparator antibody COMP1499 (anti-IL2Rγ antibody CP.B8, see US2002/0028202) only partially blocked or didn't block cytokine-induced STAT phosphorylation.

TABLE 5-1

Anti-IL-2Rγ antibodies H4H12889P and H4H12922P2 blocking human IL-2-, IL-4-, IL7-, IL-15- and IL-21-induced STAT phosphorylation in human CD4+ T cells.

| IC50 [M] | IL-2 | IL-4 | IL-7 | IL-15 | IL-21 |
|---|---|---|---|---|---|
| Constant | 10 nM | 50 pM | 1 pM | 0.5 nM | 50 pM |
| H4H12889P | 2.06E−09 | 1.10E−09 | 8.92E−10 | 2.55E−09 | 2.28E−09 |
| H4H12922P2 | 1.87E−09 | 8.54E−10 | 5.80E−10 | 2.46E−09 | 2.21E−09 |

*IC50 values measured for two antibodies are shown with various interleukins at the indicated concentrations.

See also FIG. 1 (A-E) wherein the level of STAT phosphorylation at each concentration of antibody tested is determined.

Example 6: Flow Cytometry Analysis of STAT3 Phosphorylation in In Vitro Differentiated Human Mast Cells To assess the in vitro characteristics of anti-IL2Rγ antibodies of the invention, their ability to block human mast cell activation induced by IL-9 was measured by flow cytometry (BD PHOSFLOW assay). We used this technology to look at STAT3 phosphorylation in in vitro differentiated human mast cells upon stimulation with human IL-9.

Briefly, human mast cells were in vitro generated from bone marrow $CD133^+$ progenitor cells cultured in StemSpan serum free medium supplemented with human SCF, IL-6 and IL-3 for 6 weeks.

Human mast cells were resuspended in X-VIVO 15 media at a concentration of ~$4.0\times10^6$ cells/mL, plated in 96-well plates (50 uL of cells/well; ~200,000 cells/well) and incubated at 37° C. for 2 hours before adding the cytokines and antibodies.

Serial dilutions of antibodies (1:5) were prepared in pre-warmed X-VIVO15 media and were added to the cells (50 uL), with final antibody concentrations starting from 400 nM. A fixed IL-9 (R&D) concentration was prepared in pre-warmed X-VIVO 15 media and was added to the cells (100 uL), with a final concentration of 2 nM; with a final volume per well of 200 uL.

For the cytokine dose response, serial dilutions of IL-9 (1:5) were also prepared in pre-warmed X-VIVO 15 media with final cytokine concentrations starting from 100 nM. First, 50 uL of X-VIVO15 media were added to the cells followed by 100 uL of serial dilutions of cytokines, for a total volume per well of 200 uL.

After addition of cytokines and antibodies to the cells, they were incubated at 37° C. for 15 minutes to allows mast cell activation (as measured by STAT3 phosphorylation). The stimulation was then stopped by addition of 200 uL of warm BD CYTOFIX (BD) to each well, and cells were incubated for 10 minutes at 37° C. (fixation step). Cells were then washed twice with BD PHARMIGEN Stain Buffer (BD) and kept overnight at 4° C. The next day, cells were centrifuged and permeabilized by slowly adding 100 uL of cold BD PHOSFLOW Perm Buffer III (BD) to the pellets. Cells were incubated at 4° C. for 30 minutes, then washed twice with BD PHARMIGEN Stain Buffer. Mast cells were then stained with a mix of human FcR binding inhibitor (eBioscience; 1/10), anti-c-Kit-PE (BD; 1/100) and anti-phospho-STAT3-AlexaFluor647 (BD; 1/10), prepared in BD PHARMIGEN Stain Buffer.

The samples were held at room temperature for 1 hour in the dark. The cells were then centrifugated and washed twice with BD PHARMIGEN Stain Buffer. Sample data were acquired on a BD LSR FORTESSA X-20 cell analyzer using the HTS attachment (BD). Data analysis was performed using FLOWJO X Software (Tree Star, OR). Mast cells were defined as intact cells, singlets, c-Kit+; and STAT3 phosphorylation was analyzed within this cell population (MFI=mean fluorescence intensity).

Both H4H12889P and H4H12922P2 similarly and efficiently blocked STAT3 phosphorylation induced by IL-9.

TABLE 6-1

Anti-IL-2Ry antibodies H4H12889P and H4H12922P2 blocking human IL-9- induced STAT3 phosphorylation in in vitro differentiated human mast cells.

| IC50 [M] | IL-9 |
|---|---|
| Constant | 2 nM |
| H4H12889P | 4.41E−10 |
| H4H12922P2 | 4.16E−10 |

*IC50 values measured for two antibodies are shown when IL-9 concentration was 2 nM.

Figure 2:
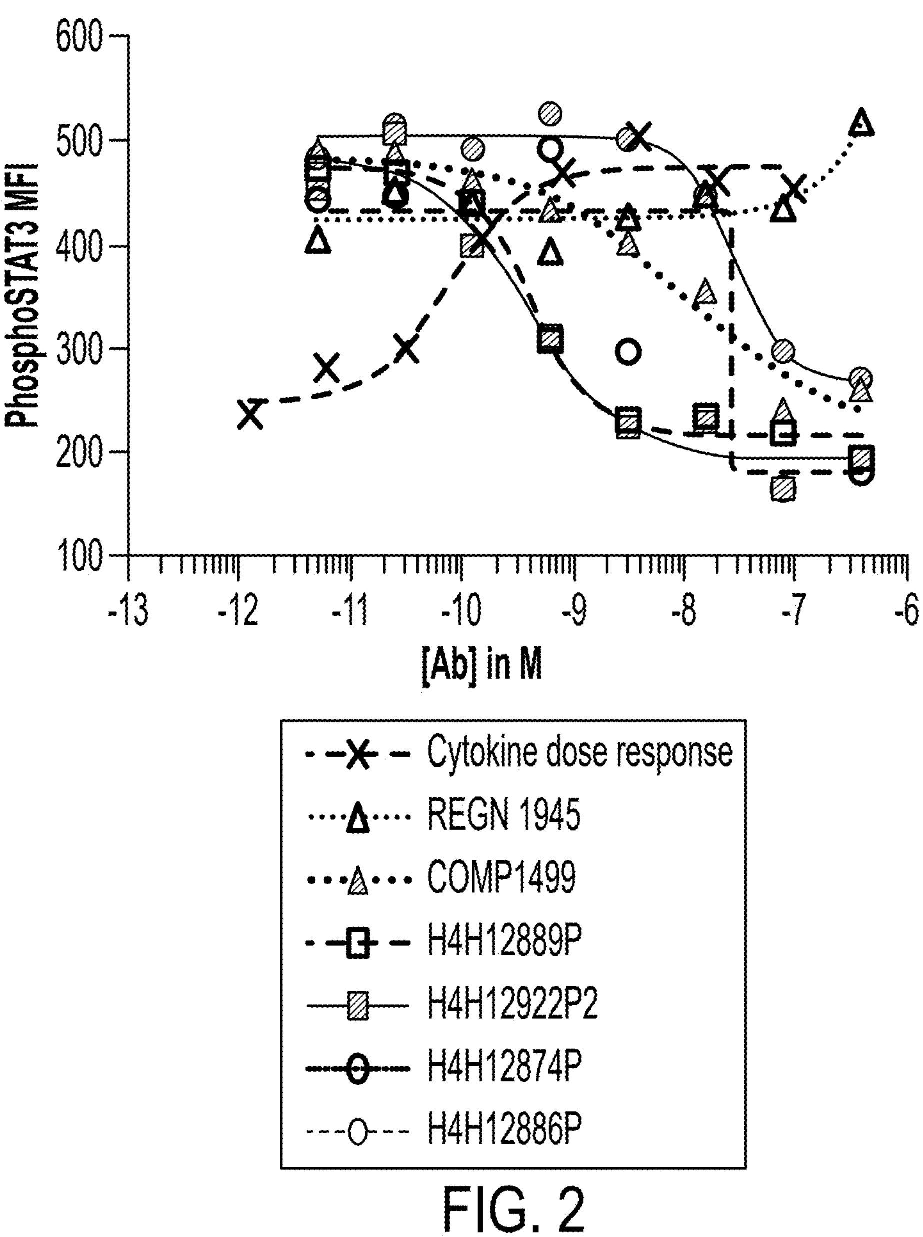
FIG. 2. Blocking human IL-9-induced STAT3 phosphorylation in in vitro differentiated human mast cells by anti-IL-2Rgamma antibodies H4H12874P, H4H12886P, H4H12889P, H4H12922P2; and antibodies COMP1499 and REGN1945.

See also FIG. 2 wherein the level of IL-9 induced STAT phosphorylation at each concentration of antibody tested is determined.

Example 7: Monoclonal Antibody Testing in In Vivo Model; Xenogeneic Acute Graft-Versus-Host Disease Model to Assess the Blocking Activity of IL-2Rgamma Antibodies as a Therapeutic Treatment To determine the effect of our anti-IL2Rγ antibodies, H4H12889P and H4H12922P2, along with the comparator IL-2Rγ antibody COMP1499, in a relevant in vivo model, a xenogeneic acute Graft-versus-Host Disease (GvHD) study was conducted. Briefly, to induce GvHD in mice, human peripheral blood mononuclear cells (huPBMCs) were injected into NOD-scid IL2$r\gamma^{null}$ (NSG) mice (Jackson Lab). Upon engraftment, human immune cells recognize the mouse host as xenogeneic and mount a vigorous immune response against its tissues.

In this experiment, NSG mice (Jackson Lab) were retro-orbitally injected with 10 million huPBMCs (ReachBio) resuspended in DPBS (10 million cells/100 uL; 5 groups of 10 mice each). Briefly, human PBMCs were thawed the day of the injection in IMDM medium (Irvine Scientific) supplemented with 10% FBS (Seradigm) and incubated 2 h at 37° C. in this supplemented medium. Cells were then washed in DPBS (Life Technologies) and resuspended at 10 million cells/100 uL for injection. A control group (10 mice) was retro-orbitally injected with 100 uL of PBS. Four groups of huPBMC-engrafted NSG mice were injected subcutaneously with 25 mg/kg of either H4H12889P, H4H12922P2, COMP1499, or an isotype control antibody (REGN1945; a human anti-*Felis domesticus* Fel d1 antibody (IgG4

(S108P)/kappa)) starting 3 weeks after huPBMC injection and then twice per week for 6 weeks. The experiment was terminated at day 161 post-huPBMC engraftment by sacrificing the remaining mice. Experimental dosing and treatment protocol for groups of mice are shown in Table 7-1.

TABLE 7-1

Experimental dosing and treatment protocol for groups of mice.

| Group | NSG mice | huPBMC injection | Antibody |
|---|---|---|---|
| 1 | 10 | None | None |
| 2 | 10 | 10 million | None |
| 3 | 10 | 10 million | Isotype control antibody (REGN1945) |
| 4 | 10 | 10 million | IL-2Ry antibody (COMP1499) |
| 5 | 10 | 10 million | IL-2Ry antibody (H4H12889P) |
| 6 | 10 | 10 million | IL-2Ry antibody (H4H12922P2) |

During the full length of the experiment, mice were monitored twice weekly for weight loss and death (to assess the effect of therapeutic antibodies on survival). Human cell engraftment in blood as well as serum mouse and human cytokine levels were assessed at different timepoints, as shown in Table 7-2.

TABLE 7-2

Blood/serum collection dates and readouts.

| Day post huPBMC injection | Serum cytokine levels | Blood human cells |
|---|---|---|
| 14 | | + |
| 20 | + | |
| 35 | | + |
| 42 | + | |
| 56 | | + |
| 62 | + | |
| 104 | | + |
| 112 | + | |
| 148 | + | |
| 168 | | + |

Figure 3E:
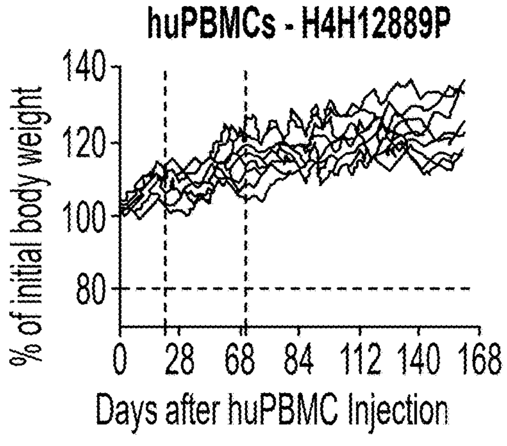
FIG. 3(E) is a graph showing percentage of initial body weight of mice, having human PBMCs, administered anti-IL2R gamma antibody H4H12889P over time. The start of antibody injection on day 21 and the end of antibody injection on day 59 are indicated by dashed lines.
Figure 3F:
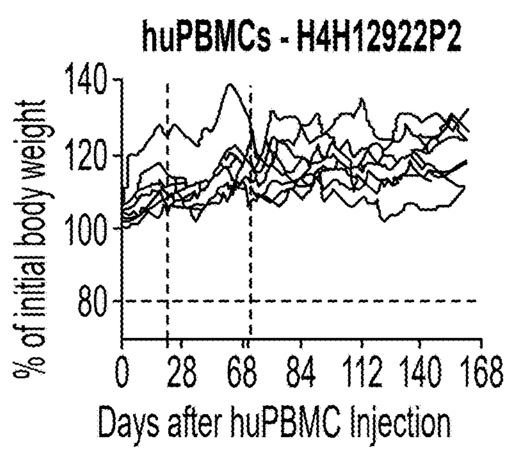
FIG. 3(F) is a graph showing percentage of initial body weight of mice, having human PBMCs, administered anti-IL2R gamma antibody H4H12922P2 over time. The start of antibody injection on day 21 and the end of antibody injection on day 59 are indicated by dashed lines.
Figure 4:
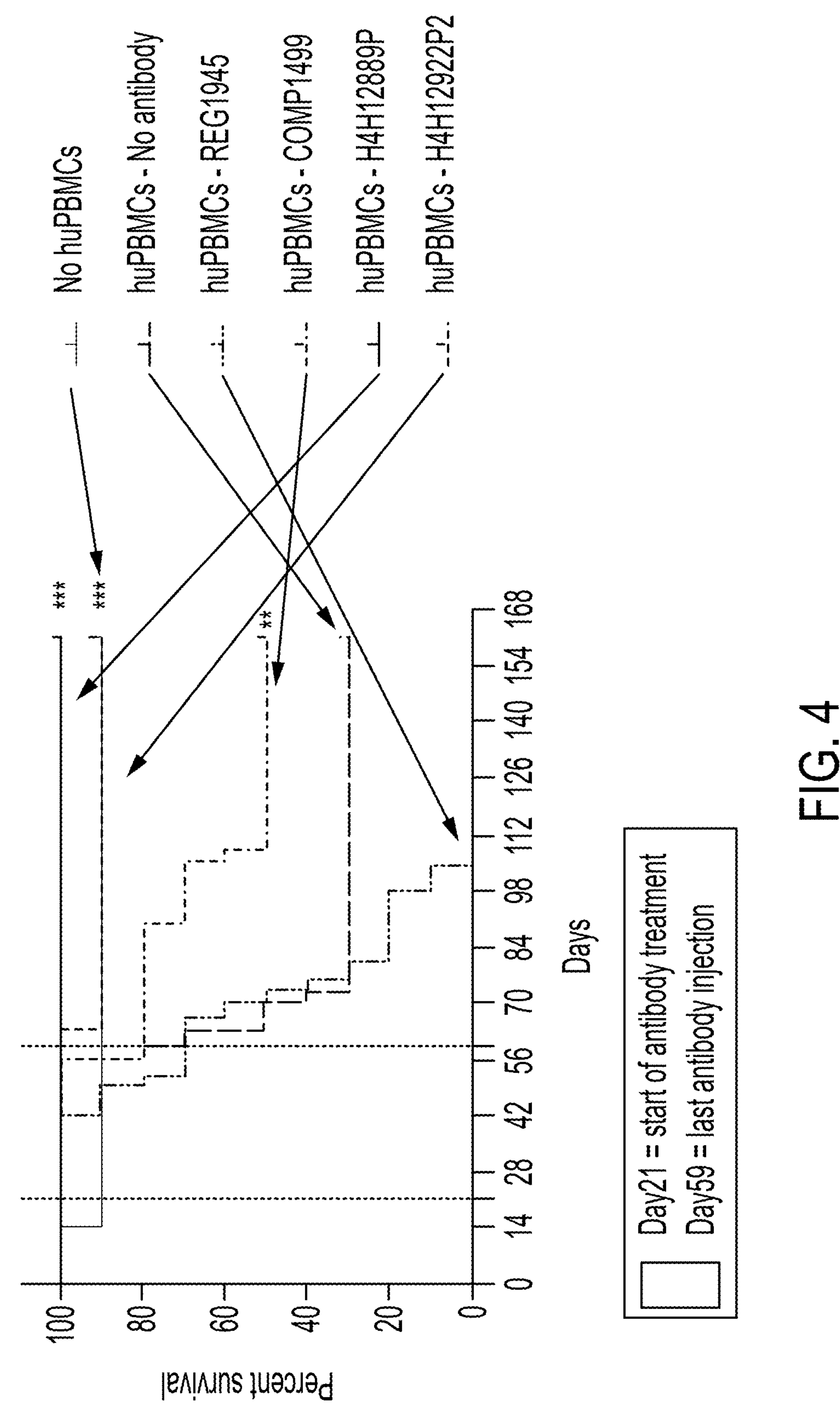
FIG. 4. Survival over time of mice injected with anti-IL2Rgamma antibodies H4H12889P and H4H12922P2, antibody COMP1499, antibody REGN1945 and no antibody are shown. No huPBMCs group is not depicted. Differences in animal survival relative to the isotype control antibody group were analyzed by a Mantel-Cox log-rank test. A P value<0.05 was considered statistically significant. , P value<0.0021; **, P value<0.0001. The start of antibody injection on day 21 and the end of antibody injection on day 59 are indicated by dashed lines.

During the full length of the experiment, mice were monitored twice weekly for weight loss (FIG. 3 (A-F); % of initial body weight at the day of huPBMC engraftment) and death (FIG. 4; to assess the effect of therapeutic antibodies on survival). Animals showing a weight loss of 20% of initial body weight were euthanized.

Blood samples from mice were collected into MICROTAINER tubes (BD, Cat #3659740) at different timepoints after huPBMC injection and human cell engraftment was assessed by looking at human absolute cell numbers in the blood by flow cytometry. Briefly, 50 uL of each blood sample were incubated in ACK lysis buffer (Gibco) for 5 min at room temperature to lyse red blood cells. Cells were then washed in DPBS, stained with LIVE/DEAD fixable dead stain (Invitrogen), washed in MACS buffer (Miltenyi Biotec), and labelled with a mix of antibodies (anti-human CD45, anti-human CD3, anti-human CD4 and anti-human CD8 [BD] diluted 1/50 in brilliant stain buffer [BD], together with human and mouse Fc inhibitor antibodies [eBioscience and BD, respectively]) used to identify human $CD45^+$ cells, T cells, $CD4^+$ T cells and $CD8^+$ T cells. Finally, samples were washed in MACS buffer, fixed in BD CYTOFIX (BD) and then resuspended in MACS buffer containing COUNTBRIGHT beads (Life Technologies) in order to calculate absolute cell numbers in each sample. Sample data were acquired on a LSR FORTESSA X-20 cell analyzer using the HTS attachment (BD). Data analysis was performed using FLOWJO X Software (Tree Star, OR). Human $CD45^+$ T cells were defined as live cells, singlets, $CD45^+$, and within this population $CD4^+$ T cells and $CD8^+$ T cells were further defined as $CD3^+$, $CD4^+$ and $CD3^+$, $CD8^+$, respectively.

TABLE 7-3

Blood human immune cells at day 35 and 56 post huPBMC injection (Mean ± SD in cells/uL of blood).

| | $CD45^+$ cells | | T cells | | $CD4^+$ T cells | | $CD8^+$ T cells | |
|---|---|---|---|---|---|---|---|---|
| Group: | D35 | D56 | D35 | D56 | D35 | D56 | D35 | D56 |
| 1. No huPBMCs | 0.07 ± 0.11 (n = 8) *** | 0.29 ± 0.37 (n = 8) *** | 0.02 ± 0.04 (n = 8) *** | 0.15 ± 0.36 (n = 8) *** | 0.01 ± 0.03 (n = 8) *** | 0.10 ± 0.28 (n = 8) *** | 0 ± 0 (n = 8) *** | 0.03 ± 0.08 (n = 8) *** |
| 2. huPBMCs-No antibody | 1801 ± 1910 (n = 8) | 5047 ± 6745 (n = 8) | 1722 ± 1784 (n = 8) | 5037 ± 6732 (n = 8) | 724 ± 800 (n = 8) | 3053 ± 4427 (n = 8) | 772.6 ± 865.2 (n = 8) | 1446 ± 1856 (n = 8) |
| 3. huPBMCs-Isotype control antibody | 2626 ± 2648 (n = 9) | 2549 ± 2094 (n = 6) | 2622 ± 2646 (n = 9) | 2544 ± 2090 (n = 6) | 1810 ± 2005 (n = 9) | 1505 ± 1354 (n = 6) | 638.6 ± 622 (n = 9) | 830.3 ± 706.1 (n = 6) |
| 4. huPBMCs-COMP1499 | 549.5 ± 637.5 (n = 10) | 2526 ± 5130 (n = 8) | 547.7 ± 636.1 (n = 10) | 2524 ± 5127 (n = 8) | 354.1 ± 415.2 (n = 10) | 2018 ± 4633 (n = 8) | 123.9 ± 130 (n = 10) | 370.1 ± 341.6 (n = 8) |
| 5. huPBMCs-H4H12889P | 7.79 ± 8.32 (n = 9) *** | 9.29 ± 18.16 (n = 10) ** | 7.57 ± 8.10 (n = 9) *** | 9.13 ± 18.16 (n = 10) ** | 5.33 ± 5.57 (n = 9) *** | 3.28 ± 3.57 (n = 10) ** | 1.49 ± 2.05 (n = 9) ** | 5.41 ± 14.71 (n = 10) ** |

TABLE 7-3-continued

| Blood human immune cells at day 35 and 56 post huPBMC injection (Mean ± SD in cells/uL of blood). | | | | | | | | |
|---|---|---|---|---|---|---|---|---|
| | CD45⁺ cells | | T cells | | CD4⁺ T cells | | CD8⁺ T cells | |
| Group: | D35 | D56 | D35 | D56 | D35 | D56 | D35 | D56 |
| 6. huPBMCs-H4H12922P2 | 48.4 ± 65.76 (n = 10) * | 119.1 ± 301.5 (n = 10) | 48.14 ± 65.71 (n = 10) * | 118.8 ± 301.1 (n = 10) | 39.33 ± 57.03 (n = 10) * | 43.73 ± 82.06 (n = 10) | 6.71 ± 8.50 (n = 10) * | 73.6 ± 217.7 (n = 10) |

Note:

Statistical significance determined by Kruskal-Wallis One-way ANOVA with Dunn's multiple comparison post-hoc test is indicated (* = p < 0.05,  = p < 0.01, * = p < 0.001, compared to groups 3: huPBMCs-Isotype control antibody).

n = number of mice analyzed.

Figures 5A, 5B, 5C, 5D:
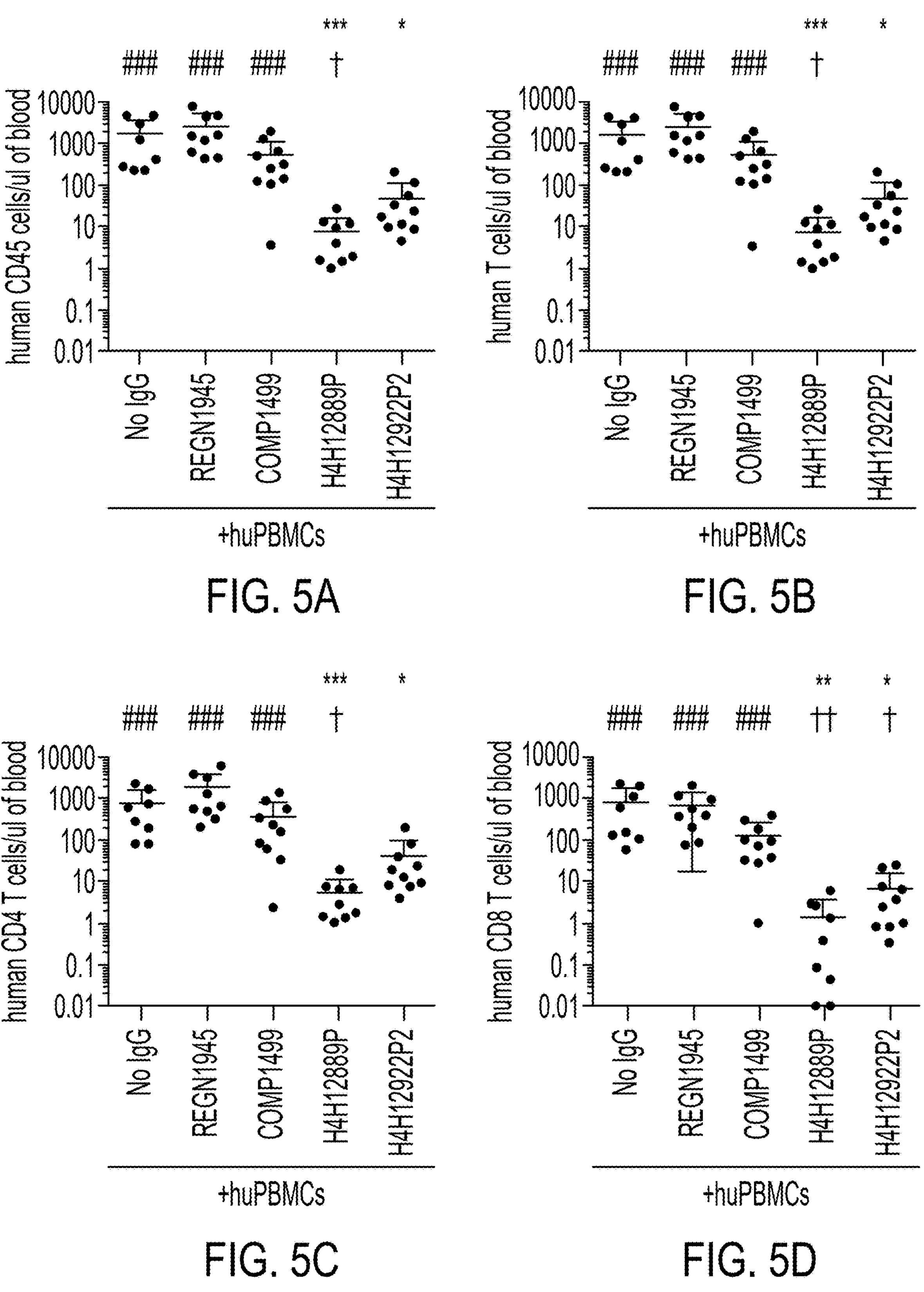
FIG. 5(A) is a graph showing absolute human cell numbers of human CD45 cells in the blood at day 35 post huPBMC injection of mice administered no antibody (No IgG), REGN1945, COMP1499 or anti-IL2R gamma antibody H4H12889P or H4H12922P2. Group "No huPBMCs" is not shown; #, significantly different from group "No huPBMCs"; †, significantly different from group "huPBMCs-No IgG"; *, significantly different from group "huPBMCs-REGN1945". Each symbol represents a mouse. Zero values were arbitrarily changed by a value of 0.01 for graphing purposes (logarithmic scale).
FIG. 5(B) is a graph showing absolute human cell numbers of human T-cells in the blood at day 35 post huPBMC injection of mice administered no antibody (No IgG), REGN1945, COMP1499 or anti-IL2R gamma antibody H4H12889P or H4H12922P2. Group "No huPBMCs" is not shown; #, significantly different from group "No huPBMCs"; †, significantly different from group "huPBMCs-No IgG"; *, significantly different from group "huPBMCs-REGN1945". Each symbol represents a mouse. Zero values were arbitrarily changed by a value of 0.01 for graphing purposes (logarithmic scale).
FIG. 5(C) is a graph showing absolute human cell numbers of human CD4 T-cells cells in the blood at day 35 post huPBMC injection of mice administered no antibody (No IgG), REGN1945, COMP1499 or anti-IL2R gamma antibody H4H12889P or H4H12922P2. Group "No huPBMCs" is not shown; #, significantly different from group "No huPBMCs"; †, significantly different from group "huPBMCs-No IgG"; *, significantly different from group "huPBMCs-REGN1945". Each symbol represents a mouse. Zero values were arbitrarily changed by a value of 0.01 for graphing purposes (logarithmic scale).
FIG. 5(D) is a graph showing absolute human cell numbers of human CD8 T-cells in the blood at day 35 post huPBMC injection of mice administered no antibody (No IgG), REGN1945, COMP1499 or anti-IL2R gamma antibody H4H12889P or H4H12922P2. Group "No huPBMCs" is not shown; #, significantly different from group "No huPBMCs"; †, significantly different from group "huPBMCs-No IgG"; *, significantly different from group "huPBMCs-REGN1945". Each symbol represents a mouse. Zero values were arbitrarily changed by a value of 0.01 for graphing purposes (logarithmic scale).
Figures 6A, 6B, 6C, 6D:
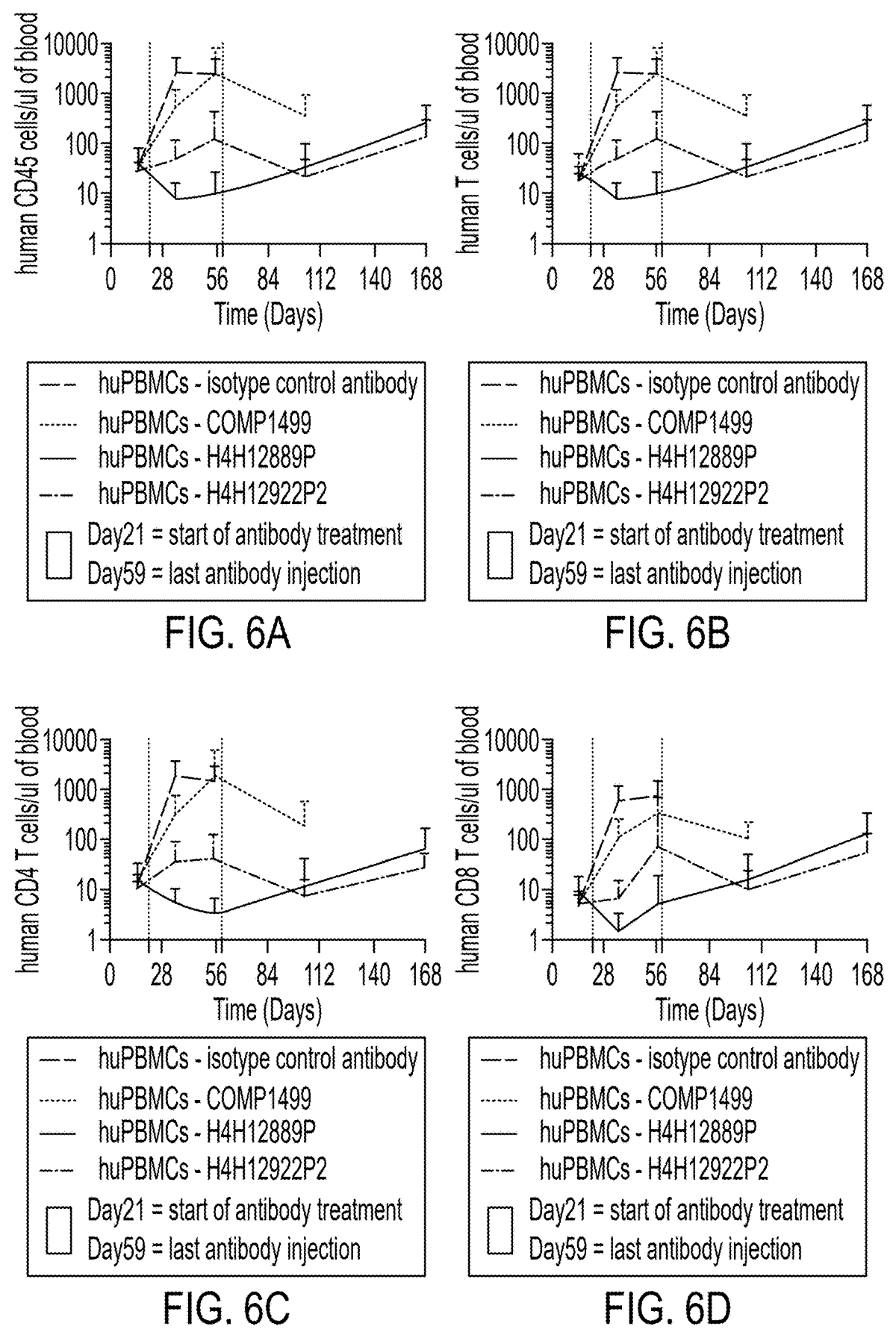

As an example, absolute human cell numbers in the blood at day 35 post huPBMC injection are shown in FIG. 5 (A-D). Blood counts of human CD45+ cells, T cells, CD4+ T cells and CD8⁺ T cells during time are shown in FIG. 6 (A-D).

Serum from mice was collected at different days after huPBMC injection and serum levels of mouse and human cytokines were assessed. Briefly, whole blood was collected into MICROTAINER tubes (BD, Cat #365967) and was allowed to clot by leaving it undisturbed at room temperature for at least 30 minutes. Clotted blood and cells were pelleted by centrifuging at 15,000×g for 10 minutes at 4° C. The resulting supernatant, designated serum, was transferred into clean plates and cytokine concentrations in the serum were measured using two Proinflammatory (mouse and human) multiplex immunoassay kits (Meso Scale Discovery), according to the manufacturer's instructions. PBS containing 0.05% (w/v) Tween-20 (Life Technologies) was used to wash the plates. Electrochemiluminescence was immediately read on a MSD Spector instrument. Data analysis was performed using FLOWJO X Software (Tree Star, OR).

TABLE 7-4

| Serum human cytokine concentrations at day 42 and 62 post huPBMC injection (Mean ± SD in pg/mL). | | | | | | | | | | |
|---|---|---|---|---|---|---|---|---|---|---|
| | hIFN-γ | | hTNFα | | hIL-6 | | hIL-8 | | hIL-10 | |
| Group: | D42 | D62 | D42 | D62 | D42 | D62 | D42 | D62 | D42 | D62 |
| 1. No huPBMCs | 0.62 ± 0.74 (n = 9) *** | 0.50 ± 0.94 (n = 9) *** | 0.04 ± 0.13 (n = 9) *** | 0.09 ± 0.15 (n = 9) ** | 0.02 ± 0.03 (n = 9) *** | 0.06 ± 0.04 (n = 9) ** | 0.05 ± 0.06 (n = 9) *** | 0.06 ± 0.10 (n = 9) *** | 0.00 ± 0.00 (n = 9) *** | 0.04 ± 0.05 (n = 9) *** |
| 2. huPBMCs-No antibody | 14617 ± 14370 (n = 10) | 18851 ± 11943 (n = 7) | 14.8 ± 10.09 (n = 10) | 13.25 ± 7.33 (n = 7) | 0.79 ± 0.58 (n = 10) | 0.32 ± 0.22 (n = 7) | 10.36 ± 10.1 (n = 10) | 4.70 ± 4.42 (n = 7) | 12.57 ± 7.70 (n = 10) | 8.17 ± 4.08 (n = 7) |
| 3. huPBMCs-Isotype control antibody | 14143 ± 6273 (n = 10) | 15369 ± 7915 (n = 7) | 14.2 ± 6.38 (n = 10) | 12.33 ± 5.86 (n = 7) | 2.28 ± 3.99 (n = 10) | 0.74 ± 0.49 (n = 7) | 8.89 ± 3.91 (n = 10) | 5.38 ± 2.97 (n = 7) | 16.39 ± 9.93 (n = 10) | 9.11 ± 4.25 (n = 7) |
| 4. huPBMCs-COMP1499 | 8891 ± 10438 (n = 10) | 8568 ± 8388 (n = 8) | 7.18 ± 6.16 (n = 10) | 6.61 ± 6.35 (n = 8) | 0.85 ± 0.65 (n = 10) | 0.25 ± 0.20 (n = 8) | 5.64 ± 5.06 (n = 10) | 2.73 ± 2.52 (n = 8) | 6.74 ± 4.41 (n = 10) | 8.17 ± 5.59 (n = 8) |
| 5. huPBMCs-H4H12889P | 418.6 ± 1315 (n = 10) *** | 126.1 ± 361.2 (n = 10) ** | 0.53 ± 1.67 (n = 10) *** | 0.20 ± 0.38 (n = 10) ** | 0.08 ± 0.12 (n = 10) *** | 0.05 ± 0.04 (n = 10) *** | 1.65 ± 1.61 (n = 10) ** | 0.3 ± 0.36 (n = 10) ** | 0.57 ± 1.79 (n = 10) *** | 0.49 ± 0.88 (n = 10) ** |
| 6. huPBMCs-H4H12922P2 | 31.66 ± 32.61 (n = 10) * | 42.86 ± 33.48 (n = 10) | 0.08 ± 0.18 (n = 10) *** | 0.22 ± 0.25 (n = 10) * | 0.12 ± 0.06 (n = 10) * | 0.06 ± 0.06 (n = 10) ** | 0.59 ± 0.43 (n = 10) | 0.42 ± 0.35 (n = 10) | 0.48 ± 0.55 (n = 10) ** | 0.65 ± 0.38 (n = 10) |

Note:

Statistical significance determined by Kruskal-Wallis One-way ANOVA with Dunn's multiple comparison post-hoc test is indicated (* = p < 0.05,  = p < 0.01, * = p < 0.001, compared to groups 3: huPBMCs-Isotype control antibody).

n = number of mice analyzed.

TABLE 7-5

| Serum mouse cytokine concentrations at day 42 and 62 post huPBMC injection (Mean ± SD in pg/mL). | | | | | | | | |
|---|---|---|---|---|---|---|---|---|
| | mTNFα | | mIL-6 | | mKC/GRO | | mIL-10 | |
| Group: | D42 | D62 | D42 | D62 | D42 | D62 | D42 | D62 |
| 1. No huPBMCs | 5.31 ± 1.35 (n = 9) * | 9.44 ± 9.63 (n = 9) | 13.14 ± 4.24 (n = 9) ** | 16.09 ± 7.01 (n = 9) * | 33.02 ± 6.72 (n = 9) *** | 57.47 ± 21.14 (n = 9) | 6.16 ± 1.65 (n = 9) ** | 7.01 ± 1.96 (n = 9) ** |
| 2. huPBMCs-No antibody | 20.68 ± 10.72 (n = 10) | 25.83 ± 11.95 (n = 7) | 91.12 ± 48.9 (n = 10) | 50.42 ± 29.96 (n = 7) | 129.5 ± 51.28 (n = 10) | 76.51 ± 33.48 (n = 7) | 14.11 ± 5.75 (n = 10) | 18.3 ± 7.64 (n = 7) |
| 3. huPBMCs-Isotype control antibody | 20.7 ± 9.30 (n = 10) | 25.44 ± 11.31 (n = 7) | 77.91 ± 55.73 (n = 10) | 95.06 ± 35.59 (n = 7) | 106.8 ± 35.56 (n = 10) | 128.7 ± 93.29 (n = 7) | 15.47 ± 10.12 (n = 10) | 17.98 ± 4.05 (n = 7) |
| 4. huPBMCs-COMP1499 | 13.82 ± 6.96 (n = 10) | 20.96 ± 21 (n = 8) | 69.83 ± 49.04 (n = 10) | 32.67 ± 29.2 (n = 8) | 101 ± 60.19 (n = 10) | 88.56 ± 30.26 (n = 8) | 10.1 ± 4.67 (n = 10) | 12.21 ± 3.64 (n = 8) |
| 5. huPBMCs-H4H12889P | 4.43 ± 1.16 (n = 10) *** | 12.02 ± 13.94 (n = 10) | 12.4 ± 3.96 (n = 10) ** | 13.24 ± 7.64 (n = 10) *** | 40.22 ± 15.65 (n = 10) ** | 55.33 ± 34.05 (n = 10) * | 6.46 ± 1.21 (n = 10) ** | 7.22 ± 2.42 (n = 10) ** |
| 6. huPBMCs-H4H12922P2 | 6.45 ± 3.37 (n = 10) ** | 7.77 ± 5.28 (n = 10) * | 17.89 ± 8.94 (n = 10) | 14.78 ± 8.12 (n = 10) ** | 40.83 ± 8.6 (n = 10) * | 65.77 ± 74.79 (n = 10) * | 5.93 ± 0.90 (n = 10) *** | 8.69 ± 5.13 (n = 10) * |

Note:

Statistical significance determined by Kruskal-Wallis One-way ANOVA with Dunn's multiple comparison post-hoc test is indicated (* = $p < 0.05$,  = $p < 0.01$, * = $p < 0.001$, compared to groups 3: huPBMCs-Isotype control antibody).

n = number of mice analyzed.

Figures 7F, 7G, 7H, 7I:
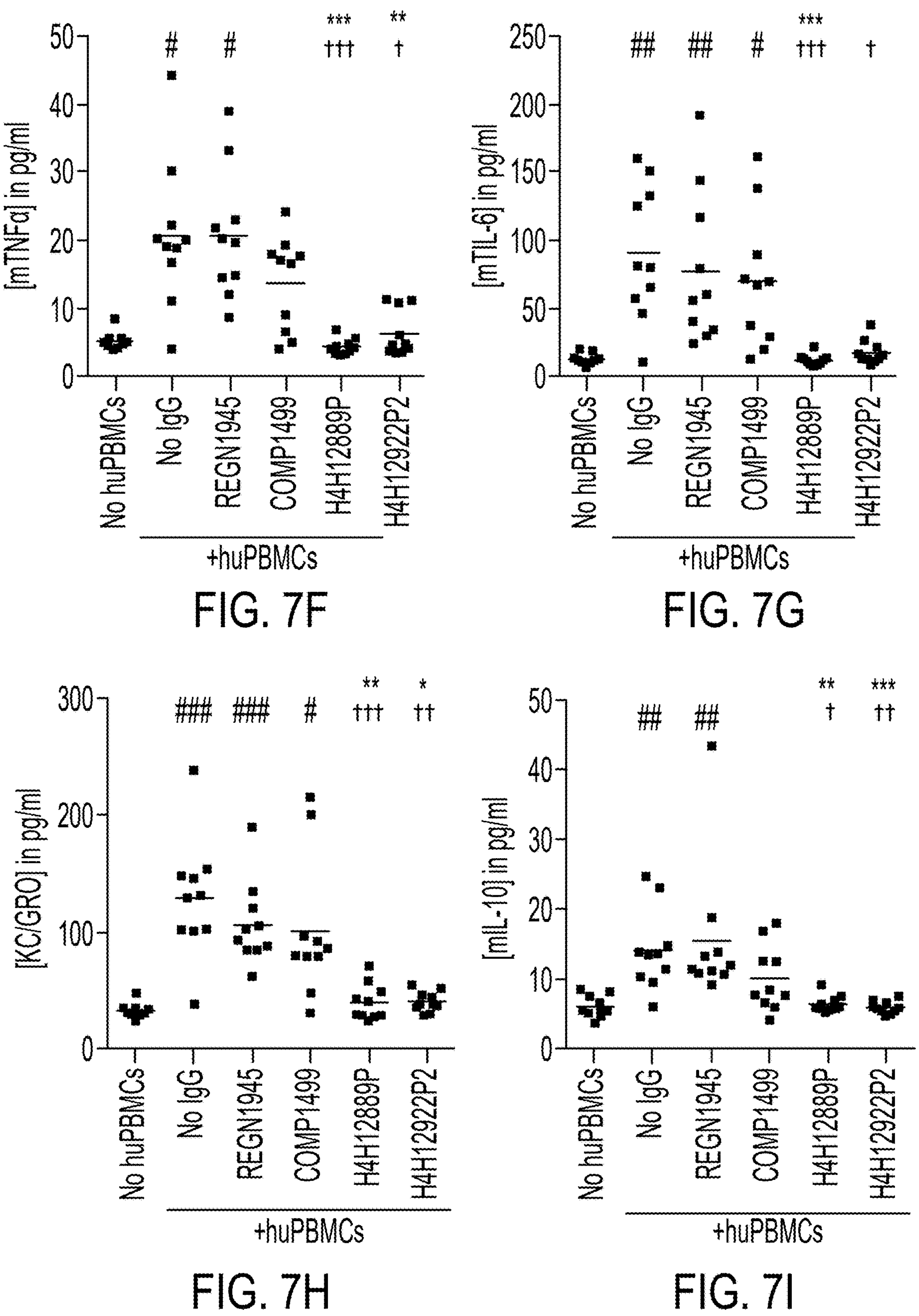
FIG. 7(F) is a graph showing serum levels of mouse TNF-alpha cytokine at day 42 post-huPBMC injection in mice administered no antibody (No IgG), REGN1945, COMP1499 or anti-IL2Rgamma antibody H4H12889P or H4H12922P2 or in mice with no human PBMCs. #, significantly different from group "No huPBMCs"; †, significantly different from group "huPBMCs-No IgG"; *, significantly different from group "huPBMCs-REGN1945". Each symbol represents a mouse.
FIG. 7(G) is a graph showing serum levels of mouse IL-6 cytokine at day 42 post-huPBMC injection in mice administered no antibody (No IgG), REGN1945, COMP1499 or anti-IL2Rgamma antibody H4H12889P or H4H12922P2 or in mice with no human PBMCs. #, significantly different from group "No huPBMCs"; †, significantly different from group "huPBMCs-No IgG"; *, significantly different from group "huPBMCs-REGN1945". Each symbol represents a mouse.
FIG. 7(H) is a graph showing serum levels of mouse KC/GRO cytokine at day 42 post-huPBMC injection in mice administered no antibody (No IgG), REGN1945, COMP1499 or anti-IL2Rgamma antibody H4H12889P or H4H12922P2 or in mice with no human PBMCs. #, significantly different from group "No huPBMCs"; †, significantly different from group "huPBMCs-No IgG"; *, significantly different from group "huPBMCs-REGN1945". Each symbol represents a mouse.
FIG. 7(I) is a graph showing serum levels of mouse IL-10 cytokine at day 42 post-huPBMC injection in mice administered no antibody (No IgG), REGN1945, COMP1499 or anti-IL2Rgamma antibody H4H12889P or H4H12922P2 or in mice with no human PBMCs. #, significantly different from group "No huPBMCs"; †, significantly different from group "huPBMCs-No IgG"; *, significantly different from group "huPBMCs-REGN1945". Each symbol represents a mouse.
Figure 9A:
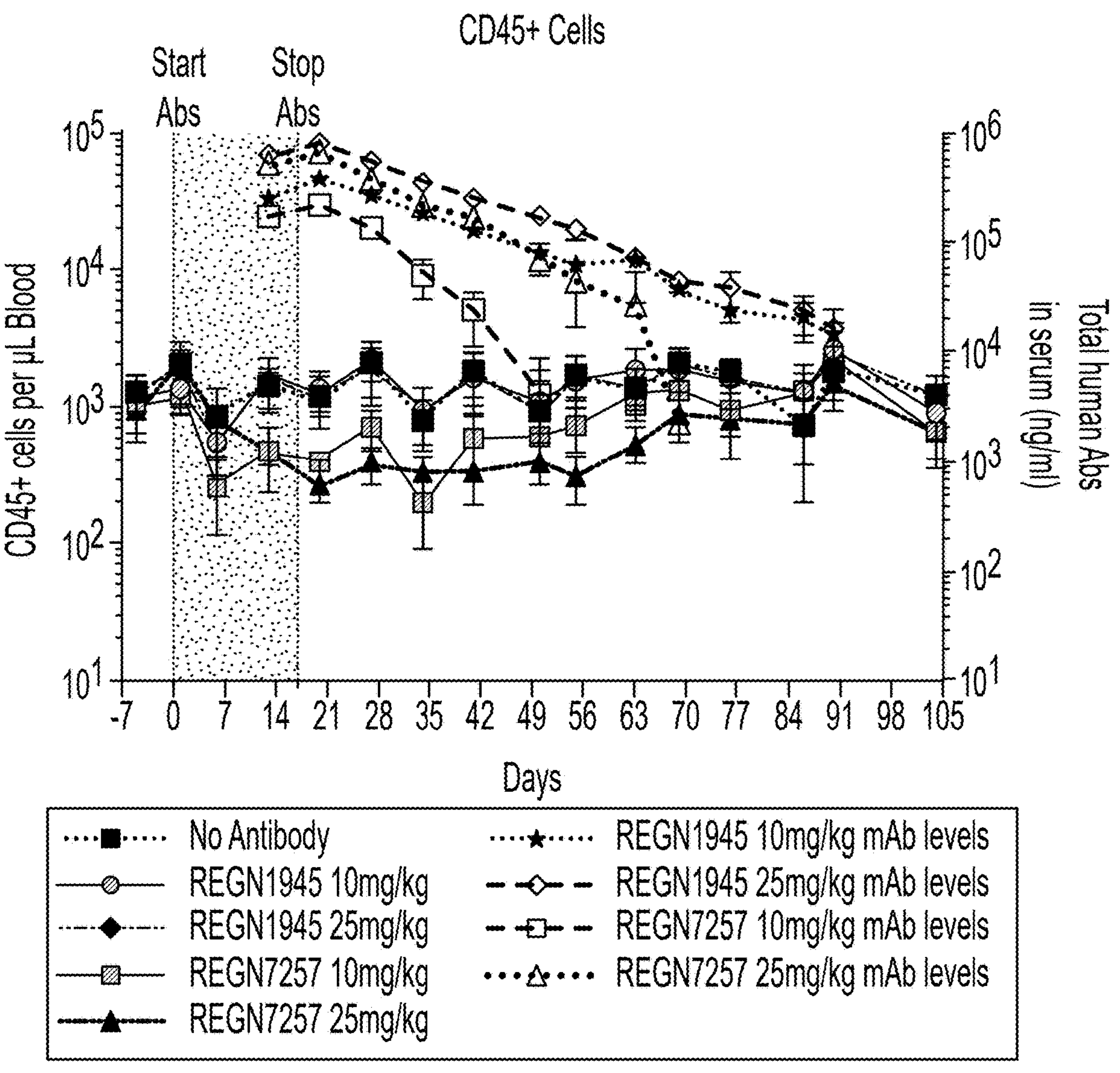
FIG. 9(A) is a graph showing levels of total human antibodies or CD45+ immune cells in blood of mice treated with various doses of antibody REGN1945 or H4H12889P.
Figure 9B:
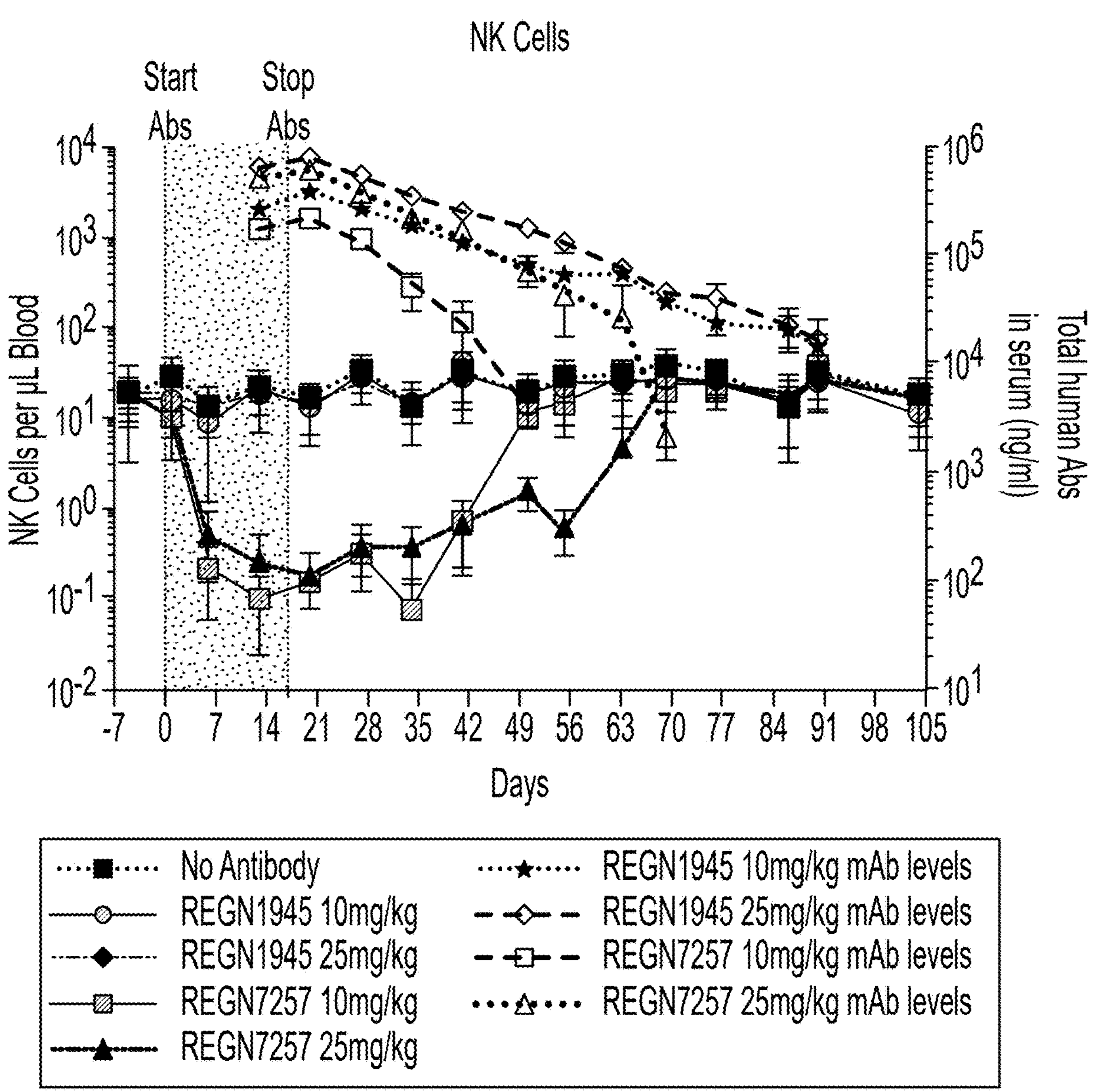
FIG. 9(B) is a graph showing levels of total human antibodies or NK cells in blood of mice treated with various doses of antibody REGN1945 or H4H12889P.
Figure 9C:
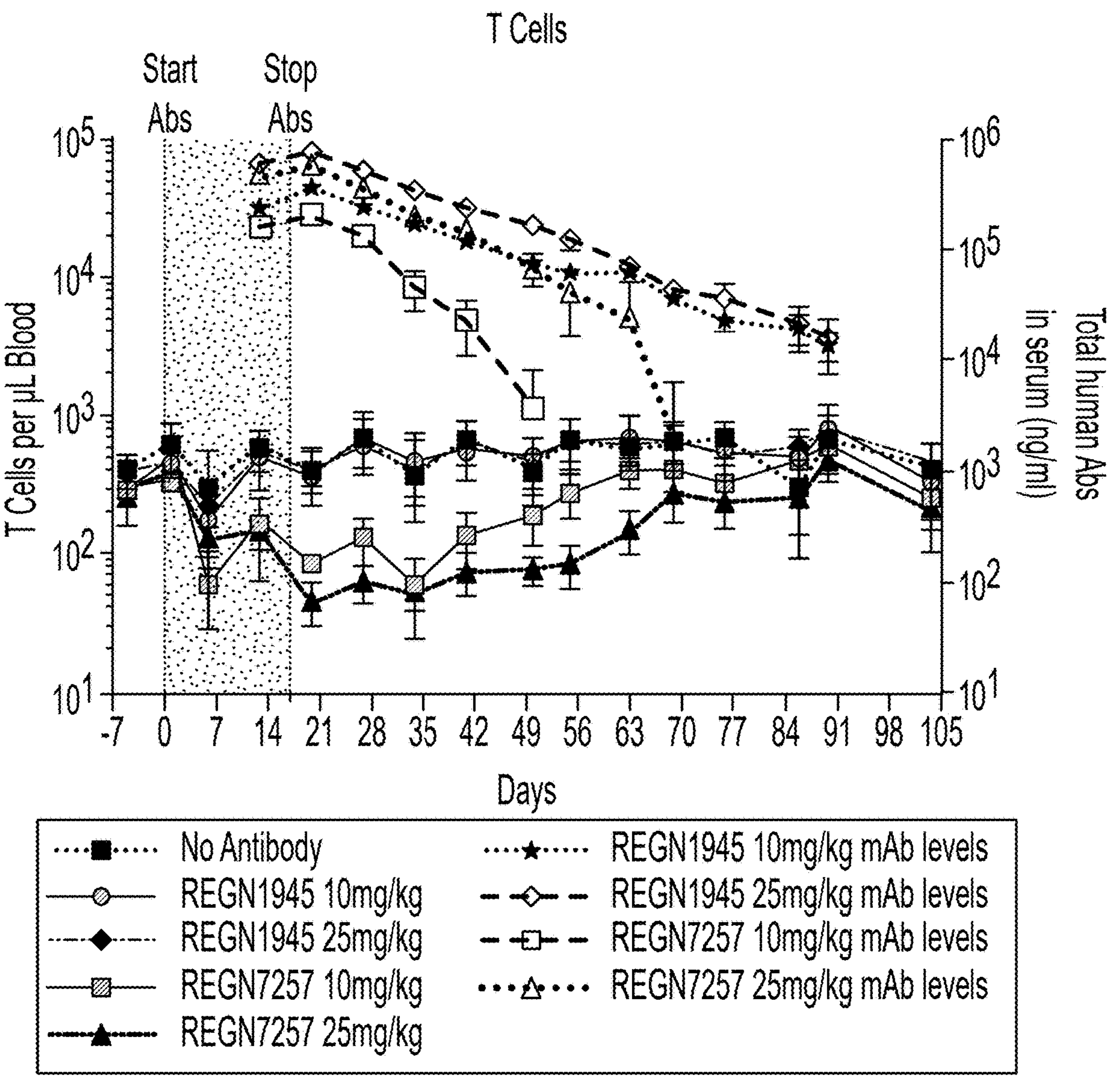
FIG. 9(C) is a graph showing levels of total human antibodies or T cells in blood of mice treated with various doses of antibody REGN1945 or H4H12889P.
Figure 9D:
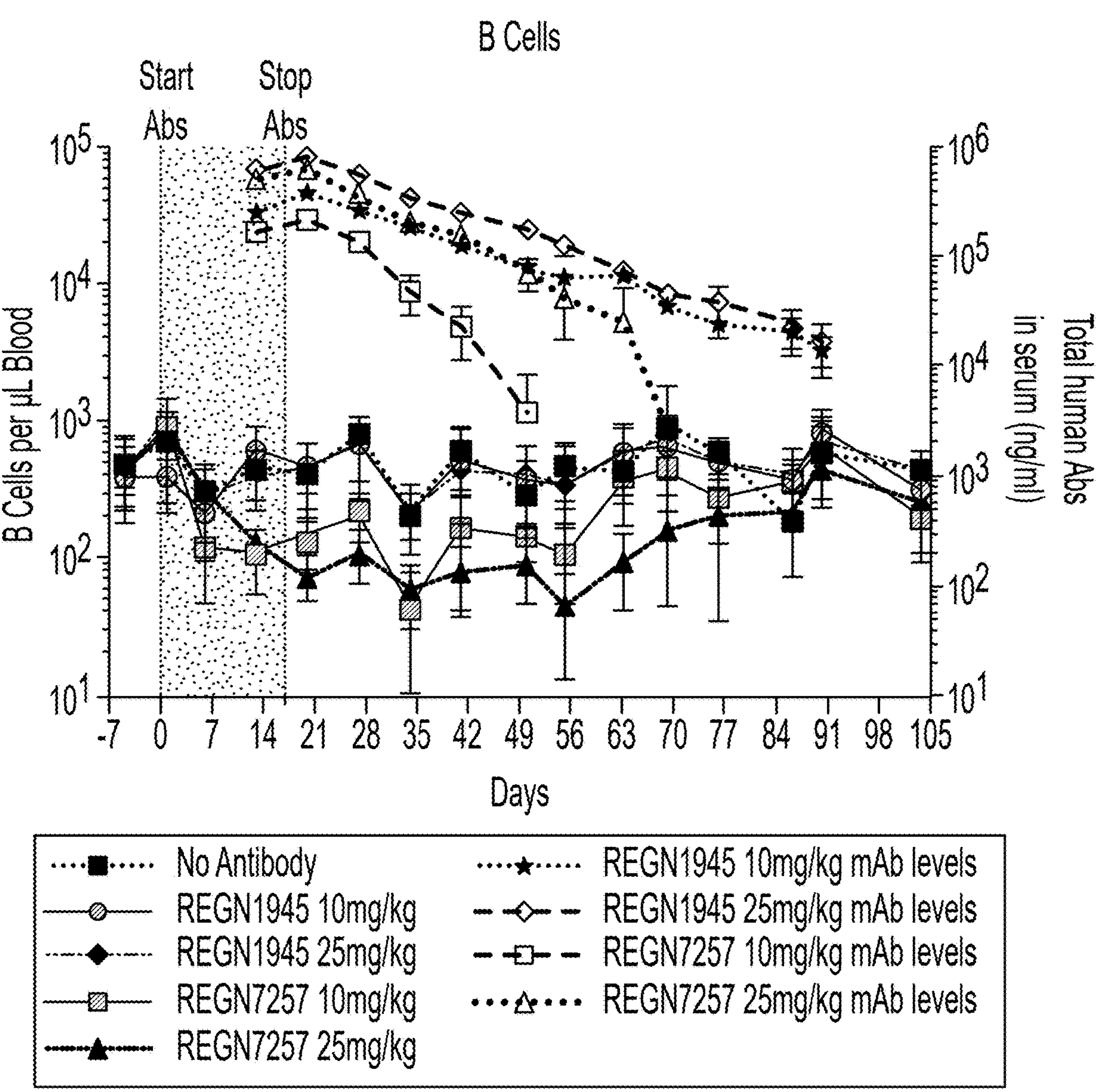
FIG. 9(D) is a graph showing levels of total human antibodies or B cells in blood of mice treated with various doses of antibody REGN1945 or H4H12889P.
Figure 9E:
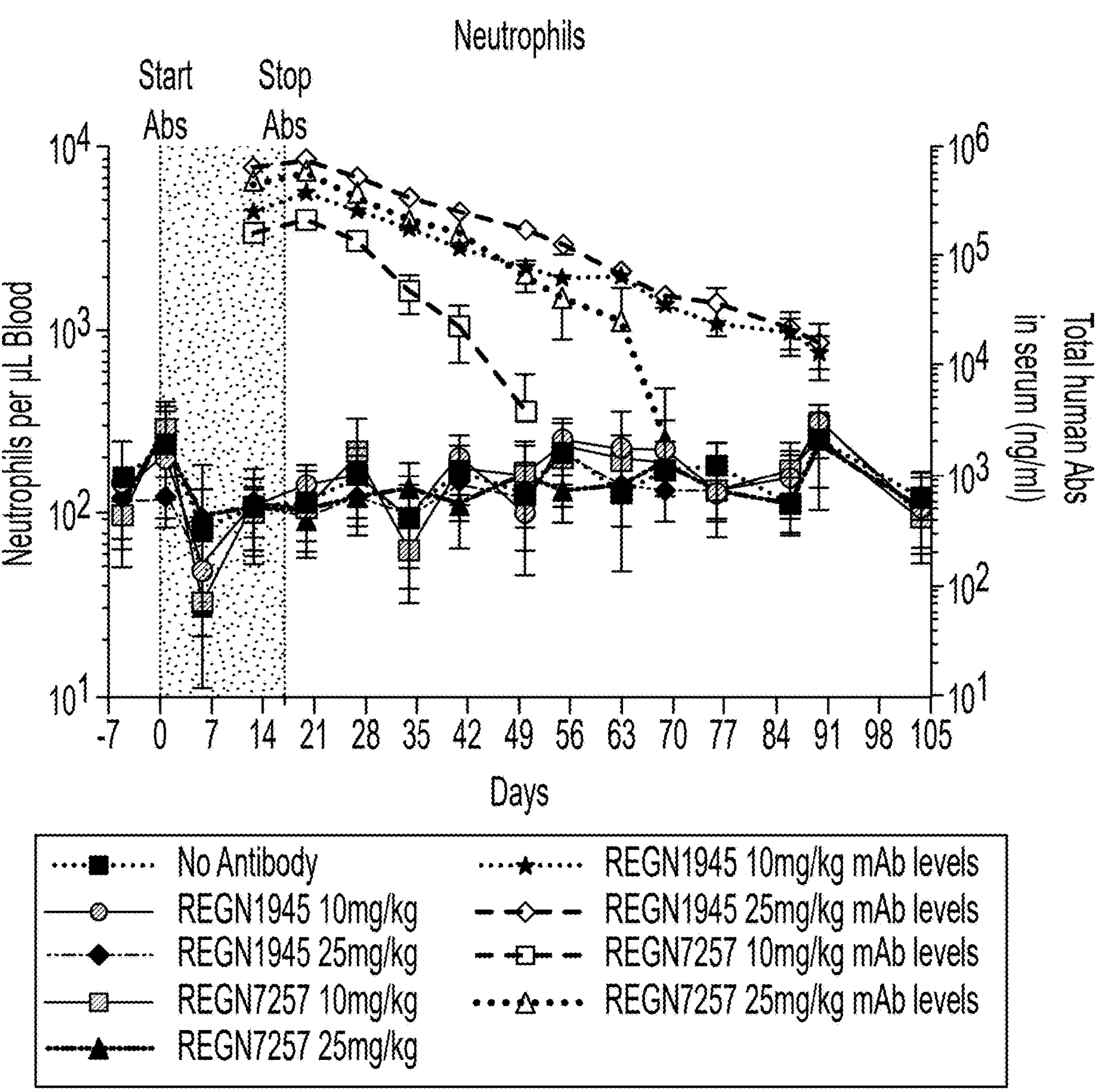
FIG. 9(E) is a graph showing levels of total human antibodies or neutrophils in blood of mice treated with various doses of antibody REGN1945 or H4H12889P.

Also, as an example, serum human and mouse cytokine levels at day 42 post huPBMC injection are shown in FIG. 7 (A-I). Serum levels of human IFN-γ, human TNFα, mouse TNFα and mouse IL-6 during time are shown in FIG. 8 (A-D).

This in vivo study demonstrated the efficacy of anti-IL2Rγ antibodies, H4H12889P and H4H12922P2, when administered therapeutically in a model of Graft-versus-Host Disease. Both H4H12889P and H4H12922P2, but not COMP1499, efficiently blocked the development of GvHD in mice. Mice therapeutically treated with either of these two antibodies were protected from weight loss and death, and this was associated with drastic reductions in both mouse and human serum cytokine levels and human T cell numbers in the blood. See Tables 7-3, 7-4 and 7-5.

Example 8: Bioassay Using NK92/hIL7R/STAT3-Luc and Ramos.2G6.4C10/STAT3-Luc Cells The IL2Rγ family of cytokines, IL-2, IL-4, IL-7, IL-9, IL-15 and IL-21, signal through the JAK-STAT (Janus kinases-Signal Transducer and Activator of Transcription) pathway (Rochman et al., New insights into the regulation of T cells by gamma (c) family cytokines. Nat Rev Immunol. 2009 July; 9(7): 480-90). In order to assess the inhibition of cytokine signaling by anti-IL2Rγ antibodies, a bioassay was developed using NK-92 cells (human natural killer cell line, ATCC) that stably expressed a luciferase reporter (STAT3-Luc; SABiosciences, #CLS-6028L). NK-92 endogenously expressed IL2Rγ and the ligand-selective receptors that mediated signaling of IL-2, IL-9, IL-15 and IL-21. In order to also assess the regulation of IL-7 signaling, NK-92 cells were transduced with lentivirus containing human IL-7R and stably expressing cells were selected and maintained in G418. The resulting cell line is referred to hereafter as NK-92/hIL7R/STAT3-Luc. To test the regulation of IL-4 mediated signaling, Ramos.2G6.4C10 (human B-lymphocytic cell line, ATCC) cells that endogenously expressed IL2Rγ and IL-4R receptor were transduced with STAT3-luc reporter and the resulting cell line is referred to as Ramos.2G6.4C10/STAT3-Luc.

Anti-IL2γ antibodies of the invention were tested for the inhibition of human IL-2 (hIL-2), human IL-7 (hIL-7), human IL-9 (hIL-9), human IL-15 (hIL-15), or human IL-21 (hIL-21) signaling by plating 20,000 NK-92/hIL7R/STAT3-Luc cells per well in growth media (prepared according to instructions by ATCC, but without IL-2) in a 96-well plate and incubated overnight at 37° C. in 5% $CO_2$. The following day, anti-IL2Rγ antibodies or an isotype control were serially diluted from 500-0.008 nM in assay buffer (plus a sample containing buffer alone without test molecule), added to the cells and incubated for 30 minutes. After the incubation, ligands were added to the cells at the following final concentrations: 30 PM hIL-2, 50 PM hIL-7, 20 PM hIL-9, 60 pM or 100 pM hIL-15, or 5 pM or 3 pM hIL-21. Dose-dependent activation was determined using serial dilution of the ligands, from 10 nM to 0.2 pM (plus a sample containing buffer alone without ligand), added to cells. After a 5 hour incubation at 37° C. in 5% $CO_2$, luciferase activity was measured with ONEGLO reagent (Promega, #E6031) and VICTOR X multilabel plate reader (Perkin Elmer).

To test the anti-IL2γ antibodies of the invention in the inhibition of human IL-4 (hIL-4) signaling, Ramos.2G6.4C10/STAT3-Luc cells were plated in growth media (prepared according to instructions by ATCC) at a density of 100,000 cells per well in a 96-well plate. The anti-IL2Rγ antibodies or an isotype control were serially diluted from 500-0.008 nM in assay buffer (plus a sample containing buffer alone without test molecule), added to the cells and incubated for 20 minutes. After the incubation, hIL-4 was added to cells at a final concentration of 250 pM or 200 pM. Dose-dependent activation was determined using serial dilution of hIL-4, from 10 nM to 0.2 pM (plus a sample containing buffer alone without ligand), added to cells. After an overnight incubation at 37° C. in 5% $CO_2$, luciferase activity was measured with ONEGLO reagent (Promega, #E6031) and VICTOR X multilabel plate reader (Perkin Elmer).

The results were analyzed using nonlinear regression (4-parameter logistics) with Prism 5 software (GraphPad) to obtain $EC_{50}$ and $IC_{50}$ values. The percentage of inhibition was calculated with the RLU values by using the following equation:

$$\% \text{ Inhibition} = 100 \times \frac{RLU_{Baseline} - RLU_{Inhibition}}{RLU_{Baseline} - RLU_{Background}}$$

In this equation, "$RLU_{Baseline}$" is the luminescence value from the cells treated with constant amount of ligand without antibodies, "$RLU_{Inhibition}$" is the minimum luminescence value from cells treated with a dose response of a particular antibody at a particular ligand concentration, and "$RLU_{Background}$" is the luminescence value from cells treated without any ligand or antibody.

TABLE 8-1

Inhibition of IL2Rγ signaling by nineteen anti-IL2γ antibodies in bioassay using NK-92/hIL7R/STAT3-Luc and Ramos.2G6.4C10/STAT3-Luc cells.

| | Cells | | | | | | | | | | | |
|---|---|---|---|---|---|---|---|---|---|---|---|---|
| | NK92/hIL7R/ STAT3-luc | | Ramos.2G6.4C10/ STAT3-luc | | NK92/hIL7R/ STAT3-luc | | NK92/hIL7R/ STAT3-luc | | NK92/hIL7R/ STAT3-luc | | NK92/hIL7R/ STAT3-luc | |
| | Ligand | | | | | | | | | | | |
| | IL-2 | | IL-4 | | IL-7 | | IL-9 | | IL-15 | | IL-21 | |
| | EC50 [M] | | | | | | | | | | | |
| | 3.3E−11 | | 1.6E−10 | | 3.9E−11 | | 2.0E−11 | | 1.5E−10 | | 3.1E−12 | |
| | Constant Ligand | | | | | | | | | | | |
| | 30 pM | | 250 pM | | 50 pM | | 20 pM | | 60 pM | | 5 pM | |
| Ab PID # | IC50 [M] | Max Inhibition (%) | IC50 [M] | Max Inhibition (%) | IC50 [M] | Max Inhibition (%) | IC50 [M] | Max Inhibition (%) | IC50 [M] | Max Inhibition (%) | IC50 [M] | Max Inhibition (%) |
| H4H12857P | >1.0E−07 | 44 | 3.8E−08 | 96 | 1.6E−08 | 94 | >1.0E−07 | 83 | >1.0E−07 | 78 | NB | NB |
| H4H12858P | NB | NB | NB | NB | NB | NB | NB | NB | NB | NB | NB | NB |
| H4H12859P | WB | 29 | NB | NB | NB | NB | NB | NB | NB | NB | NB | NB |
| H4H12863P | 4.3E−10 | 48 | 3.6E−10 | 70 | 1.5E−09 | 42 | 4.7E−10 | 38 | WB | 30 | >1.0E−07 | 28 |
| H4H12871P | NB | NB | WB | 31 | 8.2E−10 | 36 | NB | NB | NB | NB | NB | NB |
| H4H12874P | WB | 26 | >1.0E−07 | 70 | 4.1E−08 | 93 | >1.0E−07 | 50 | >1.0E−07 | 55 | NB | NB |
| H4H12884P | WB | 13 | WB | 19 | 2.3E−09 | 34 | NB | NB | NB | NB | NB | NB |
| H4H12886P | WB | 27 | >1.0E−07 | 92 | >1.0E−07 | 81 | >1.0E−07 | 84 | >1.0E−07 | 64 | WB | 18 |
| H4H12889P | 2.7E−08 | 81 | 1.9E−09 | 101 | 3.0E−09 | 100 | 7.1E−09 | 100 | 8.5E−09 | 92 | >1.0E−07 | 35 |
| H4H12890P | WB | 15 | >1.0E−07 | 54 | >1.0E−07 | 66 | WB | 36 | WB | 35 | NB | NB |
| H4H12899P | NB | NB | NB | NB | NB | NB | NB | NB | NB | NB | NB | NB |
| H4H12900P | NB | NB | NB | NB | NB | NB | NB | NB | NB | NB | NB | NB |
| H4H12908P | NB | NB | NB | NB | NB | NB | NB | NB | NB | NB | NB | NB |
| H4H12913P2 | WB | 24 | >1.0E−07 | 55 | >1.0E−07 | 77 | >1.0E−07 | 57 | >1.0E−07 | 58 | NB | NB |
| H4H12922P2 | 1.6E−08 | 85 | 1.3E−09 | 100 | 2.6E−09 | 98 | 3.1E−09 | 99 | 9.3E−09 | 91 | >1.0E−07 | 49 |
| H4H12924P2 | NB | NB | NB | NB | NB | NB | NB | NB | NB | NB | NB | NB |
| H4H12926P2 | NB | NB | NB | NB | NB | NB | NB | NB | NB | NB | NB | NB |
| H4H12927P2 | WB | 18 | WB | 33 | >1.0E−07 | 46 | NB | NB | WB | 34 | NB | NB |
| H4H12934P2 | NB | NB | WB | 22 | WB | 12 | NB | NB | NB | NB | NB | NB |
| Isotype Control mAb | NB | NB | NB | NB | NB | NB | NB | NB | NB | NB | NB | NB |

NB: No blocking

WB: Weak blocking

TABLE 8-2

Inhibition of IL2Rγ signaling by four anti-IL2γ antibodies in bioassay using NK-92/hIL7R/STAT3-Luc and Ramos.2G6.4C10/STAT3-Luc cells.

| | Cells | | | | | | | | | | | |
|---|---|---|---|---|---|---|---|---|---|---|---|---|
| | NK92/hIL7R/ STAT3-luc | | Ramos.2G6.4C10/ STAT3-luc | | NK92/hIL7R/ STAT3-luc | | NK92/hIL7R/ STAT3-luc | | NK92/hIL7R/ STAT3-luc | | NK92/hIL7R/ STAT3-luc | |
| | Ligand | | | | | | | | | | | |
| | IL-2 | | IL-4 | | IL-7 | | IL-9 | | IL-15 | | IL-21 | |
| | EC50 [M] | | | | | | | | | | | |
| | 4.5E−11 | | 3.3E−10 | | 3.9E−11 | | 3.3E−11 | | 2.3E−10 | | 6.0E−12 | |
| | Constant Ligand | | | | | | | | | | | |
| | 30 pM | | 200 pM | | 50 pM | | 20 pM | | 100 pM | | 3 pM | |
| Ab PID # | IC50 [M] | Max Inhibition (%) | IC50 [M] | Max Inhibition (%) | IC50 [M] | Max Inhibition (%) | IC50 [M] | Max Inhibition (%) | IC50 [M] | Max Inhibition (%) | IC50 [M] | Max Inhibition (%) |
| H4H13538P | NB | NB | NB | NB | NB | NB | NB | NB | NB | NB | NB | NB |
| H4H13841P | NB | NB | NB | NB | NB | NB | NB | NB | NB | NB | NB | NB |
| H4H13544P2 | NB | NB | NB | NB | NB | NB | NB | NB | NB | NB | NB | NB |
| H4H13545P2 | NB | NB | NB | NB | NB | NB | NB | NB | NB | NB | NB | NB |
| Isotype Control mAb | NB | NB | NB | NB | NB | NB | NB | NB | NB | NB | NB | NB |

Twenty-three anti-IL2γ antibodies of the invention were tested for their ability to inhibit signaling by the IL2Rγ family of cytokines using a bioassay. As shown in Table 8-1, nineteen out of twenty-three anti-IL2γ antibodies inhibited the activation of IL2Rγ to different extents, and as shown in Table 8-2, four out of twenty-three anti-IL2γ antibodies showed no inhibition of IL2Rγ activation by ligands.

Example 9: Cell Binding Analysis by Flow Cytometry with NK-92, Jurkat, NIH/3T3, MC/9 and HEK293 Cells In order to assess the binding of anti-IL2Rγ antibodies to human and mouse IL-2Rγ expressed on cells, flow cytometry analyses were performed with cell lines that endogenously express IL-2Rγ: NK-92 (human natural killer cell line), Jurkat (human T-lymphocytic cell line), and MC/9 (mouse mast cell line) cells. NIH/3T3 (mouse fibroblast) and HEK293 (human embryonic kidney) cell lines were included as negative controls.

For flow cytometry analyses, the cells were pre-incubated with mouse IgG at 100 μg/ml for 15 minutes at room temperature (RT) to block the binding of the antibodies to Fc receptors. The anti-IL2Rγ antibodies of the invention and an isotype control antibody were used at 10 μg/ml with 0.5-1×$10^6$ cells/well of each cell type in PBS (without calcium and magnesium) containing 1% FBS for Jurkat, NIH/3T3, and HEK293 cells or in growth media (prepared according to instruction by ATCC) for NK-92 and MC/9 for 30-45 minutes at RT. Cells were washed and incubated with an anti-human antibody conjugated to allophycocyanin (APC) (Jackson ImmunoResearch, #109-136-170) for 30 minutes on ice. Cells were washed, fixed using BD CYTOFIX (BD biosciences, #554655) and analyzed on an IQUE (INTELLICYT) Flow Cytometer or ACCURI Flow cytometer (BD). Unstained and secondary antibody alone controls were also included for all cell lines. The results were analyzed using FORECYT (INTELLICYT) software to determine the geometric means of fluorescence (MFI) for viable cells. Binding ratios were calculated by normalizing the MFI of the test sample by the MFI of the unstained sample.

As shown in Table 9-1, nineteen out of twenty-three anti-IL2Rγ antibodies of the invention tested at 10 μg/ml demonstrated binding to Jurkat and NK-92 cells with binding ratios of 1-19 and 1-94, respectively. The anti-IL2Rγ antibodies demonstrated binding to NIH/3T3 and MC/9 cells with binding ratios of 1-13 and 1. The human isotype control antibody, REGN1945, and secondary only control condition exhibited binding ratios of 1-13 to all cell lines tested.

As shown in Table 9-2, four out of twenty-three anti-IL2Rγ antibodies of the invention tested at 10 μg/ml demonstrated binding to NK-92 cells with binding ratios of 1-37 and to HEK293 cells with binding ratios of 1-3. The human isotype control antibody, REGN1945, and secondary only control condition exhibited binding ratios of 1-2 to NK-92 and HEK293 cells.

TABLE 9-1

Flow cytometry analysis with nineteen of twenty-three anti-IL2Rγ antibodies binding to NIH/3T3, MC/9, Jurkat, and NK-92 cells.

| | Raw MFI | | | | Binding Ratio (Sample over unstained MFIs) | | | |
|---|---|---|---|---|---|---|---|---|
| Conditions | NIH/3T3 | MC/9 | Jurkat | NK92 | NIH/3T3 | MC/9 | Jurkat | NK92 |
| H4H12857P | 461 | 198 | 103 | 5494 | 2 | 1 | 1 | 37 |
| H4H12858P | 2951 | 199 | 99 | 228 | 13 | 1 | 1 | 2 |

TABLE 9-1-continued

Flow cytometry analysis with nineteen of twenty-three anti-IL2Rγ antibodies binding to NIH/3T3, MC/9, Jurkat, and NK-92 cells.

| | Raw MFI | | | | Binding Ratio (Sample over unstained MFIs) | | | |
|---|---|---|---|---|---|---|---|---|
| Conditions | NIH/3T3 | MC/9 | Jurkat | NK92 | NIH/3T3 | MC/9 | Jurkat | NK92 |
| H4H12859P | 153 | 201 | 89 | 176 | 1 | 1 | 1 | 1 |
| H4H12863P | 452 | 185 | 1171 | 12991 | 2 | 1 | 13 | 87 |
| H4H12871P | 840 | 184 | 1619 | 13713 | 4 | 1 | 18 | 92 |
| H4H12874P | 366 | 202 | 507 | 6583 | 2 | 1 | 6 | 44 |
| H4H12884P | 744 | 172 | 1425 | 13517 | 3 | 1 | 16 | 90 |
| H4H12886P | 368 | 185 | 488 | 4720 | 2 | 1 | 6 | 32 |
| H4H12889P | 502 | 91 | 1661 | 14092 | 2 | 1 | 19 | 94 |
| H4H12890P | 486 | 170 | 500 | 4569 | 2 | 1 | 6 | 30 |
| H4H12899P | 941 | 167 | 114 | 2670 | 4 | 1 | 1 | 18 |
| H4H12900P | 1602 | 128 | 110 | 4195 | 7 | 1 | 1 | 28 |
| H4H12908P | 831 | 154 | 86 | 2539 | 4 | 1 | 1 | 17 |
| H4H12913P2 | 436 | 178 | 472 | 4912 | 2 | 1 | 5 | 33 |
| H4H12922P2 | 587 | 187 | 1570 | 12518 | 3 | 1 | 18 | 84 |
| H4H12924P2 | 502 | 192 | 104 | 231 | 2 | 1 | 1 | 2 |
| H4H12926P2 | 526 | 175 | 179 | 1853 | 2 | 1 | 2 | 12 |
| H4H12927P2 | 436 | 191 | 315 | 3494 | 2 | 1 | 4 | 23 |
| H4H12934P2 | 1391 | 164 | 295 | 6441 | 6 | 1 | 3 | 43 |
| REGN1945 (hIgG$_4$ control) | 396 | 196 | 92 | 1890 | 2 | 1 | 1 | 13 |
| Anti-hIgG-APC | 205 | 173 | 80 | 210 | 1 | 1 | 1 | 1 |
| Unstained | 231 | 146 | 88 | 150 | 1 | 1 | 1 | 1 |

TABLE 9-2

Flow cytometry analysis with four of twenty-three anti-IL2Rγ antibodies binding to HEK293 and NK-92 cells.

| | Raw MFI | | Binding Ratio (Sample over unstained MFIs) | |
|---|---|---|---|---|
| Conditions | HEK293 | NK92 | HEK293 | NK92 |
| H4H13538P | 571 | 235 | 3 | 1 |
| H4H13841P | 274 | 7051 | 1 | 37 |
| H4H13544P2 | 334 | 4647 | 2 | 24 |
| H4H13545P2 | 295 | 592 | 1 | 3 |
| Isotype control (REGN1945) | 509 | 223 | 2 | 1 |
| anti-hIgG-APC | 260 | 234 | 1 | 1 |
| Unstained | 219 | 190 | 1 | 1 |

Example 10: In Vivo Immunosuppression Experiment to Assess the Effects of the Anti-IL2Rγ Antibody H4H12889P on Immune Cell Populations in the Blood Experimental Procedure. VELOCIGENE (VG) background mice (C57BL/6NTac (75%)/129S6SvEvTac (25%)) from the Regeneron VELOCIGENE breeding colony that were genetically modified to replace the endogenous IL2RG ectodomain with the corresponding human sequences were administered or not an isotype control (REGN1945) or H4H12889P subcutaneously at doses 10 mg/kg or 25 mg/kg at a frequency of 2 times per week for 3 weeks (6 doses total).

TABLE 10-1

Experimental dosing and treatment protocol for groups of mice

| Group | Recipient Strain | n | mAb Treatment |
|---|---|---|---|
| A | Il2rg$^{hu/hu}$ | 8 | No mAb |
| B | Il2rg$^{hu/hu}$ | 8 | REGN1945 (Isotype), 10 mg/kg |
| C | Il2rg$^{hu/hu}$ | 8 | REGN1945 (Isotype), 25 mg/kg |
| D | Il2rg$^{hu/hu}$ | 8 | H4H12889P (anti-hIL2RG), 10 mg/kg |
| E | Il2rg$^{hu/hu}$ | 8 | H4H12889P (anti-hIL2RG), 25 mg/kg |

Analysis of immune cell populations in blood during time by flow cytometry. Total immune cell, B cell, T cell, NK cell, and neutrophil counts in the peripheral blood were analyzed at various timepoints (once a week) via flow cytometry to assess the effects of H4H12889P on the absolute numbers of these cell types. Briefly, at each timepoint, blood samples from mice were collected into MICROTAINER tubes with K2EDTA [BD #365974] and 30-75 uL of each blood sample were incubated in red blood cell lysis buffer [Sigma #R7757] for 5 min at room temperature to lyse red blood cells. A second round of lysis was performed if needed. Cells were then washed in DPBS [Gibco #14190-144], stained for 20 min with LIVE/DEAD Fixable Near-IR Dead Cell Stain [Invitrogen #L34962] diluted 1:500 in DPBS, washed again in DPBS, then blocked with purified anti-mouse CD16/CD32 (Fc Shield) [TONBO Biosciences, #70-0161-M001] diluted 1:50 in MACS buffer [autoMACS Running Buffer; Miltenyi Biotec, #130-091-221]. Subsequently, cells were stained for cell surface markers to identify CD45$^+$ cells, T cells, B cells, NK cells, and neutrophils by the addition of mix of fluorescently labeled antibodies (described in Table 2) diluted in BD HORIZON brilliant stain buffer [BD #566349]. Finally, samples were washed in MACS buffer, fixed in BD CYTOFIX [BD #554655] diluted 1:4 in DPBS, then washed and resuspended in MACS buffer prior to acquisition. Sample data was acquired on a FACSYMPHONY A5 analyzer using the HTS attachment [BD]. A fixed volume of each sample was run. Data analysis was performed using FLOWJO v10 Software [Tree Star, OR].

CD45$^+$ immune cells were defined as singlets, live cells, CD45$^+$; within this population, T cells were further defined as CD3$^+$, B cells as CD3$^-$CD19$^+$, NK cells as CD3$^{-CD}$19$^-$ NKp46$^+$, and neutrophils as F4/80$^-$Ly6G$^+$. Absolute numbers of each cell type run through the analyzer, sample volume run, and the volume of blood originally stained were used to calculate cells/μL blood counts for each sample.

TABLE 10-2

| Antibodies Used for Flow Cytometry Analysis | | | |
|---|---|---|---|
| Antibody | Fluorochrome | Manufacturer | Final dilution |
| NKp46 | FITC | ebioscience | 1:200 |
| Ly6G | BB700 | BD | 1:100 |
| F4/80 | PE | BD | 1:500 |
| CD3 | PE-Cy7 | BD | 1:200 |
| CD4 | BV786 | BD | 1:200 |
| CD8a | BUV395 | BD | 1:200 |
| CD19 | BUV737 | BD | 1:200 |
| CD45 | Alexa Fluor 700 | BioLegend | 1:200 |

Analysis of Serum Therapeutic Antibody Levels During Time by Antigen Capture ELISA.

Serum levels of IL2Rγ antibody or isotype control antibody were measured once a week by Human total IgG Platinum ELISA kit. Serial dilutions were made of each antibody in 0.5% solution of BSA in PBS to generate a standard curve from 1.56-100 ng/mL of H4H12889P and REGN1945. Absorbance at 450 nm measured on a SPECTRAMAX M5 plate reader [Molecular Devices]. Data analysis was performed using Prism 8.1.2 [GraphPad].

Results summary and conclusions. Treatment with H4H12889P (10 mg/kg and 25 mg/kg) resulted in a marked reduction in the numbers of total CD45$^+$ immune cells (FIG. 9 (A)), NK cells (FIG. 9 (B)), T cells ((FIG. 9 (C)) and B cells (FIG. 9 (D)) in blood while neutrophil counts (FIG. 9 (E)) were unaffected. After the 3-week dosing period ended, the serum concentration of H4H12889P decreased over time. This decrease in the concentration of H4H12889P was associated with a continuous increase in the numbers of total CD45$^+$ immune cells (FIG. 9 (A)), NK cells (FIG. 9 (B)), T cells (FIG. 9 (C)) and B cells (FIG. 9 (D)). By the end of the study, all these populations recovered to similar levels as observed pre-treatment, and levels observed in untreated or mice treated with REGN1945 (isotype control).

Example 11: In Vivo Skin Graft Rejection Model to Assess the Blocking Activity of the IL2Rγ Antibody H4H12889P Experimental Procedure. BALB/cJ mice obtained from The Jackson Laboratory (Bar Harbor, ME) were used as skin graft donors, and MHC mismatched VELOCIGENE (VG) background mice (C57BL/6NTac (75%)/129S6SvEvTac (25%)) from the Regeneron VELOCIGENE breeding colony that were genetically modified to replace the endogenous IL2RG ectodomain with the corresponding human sequences were used as recipients. The skin graft was obtained from the tail of the donor mice. The skin was the peeled off using forceps and punched with a 10 mm diameter biopsy punch. VG mice (humanized for IL2Rγ), used as graft recipients, were administered or not an isotype control (REGN1945) or H4H12889P subcutaneously at doses 25 mg/kg at a frequency of 2× per week starting 3 weeks prior to transplant, and continuing until rejection. Recipients with the surgical site shaved were anesthetized by isoflurane via a nose cone and administered an analgesic (buprenorphine-sustained release) (ZooPharm). The shaved dorsal area was swabbed with applications of povidone-iodine and alcohol. The graft bed was created midway laterally between the dorsal and ventral sides of the mouse by pinching skin with forceps followed by skin excision utilizing a sterile 10 mm diameter biopsy skin punch. The graft was then placed down on the graft bed and covered with an adhesive bandage that was secured with two sterile surgical staples to the skin. Aseptic technique was practiced during the entire procedure. After 5 days, the bandages and staples were removed and monitoring ensued.

TABLE 11-1

| Experimental dosing and treatment protocol for groups of mice | | | | | |
|---|---|---|---|---|---|
| Group | Recipient Strain | n | Donor Strain | Donor Tissue | mAb Treatment |
| A | Il2rg$^{hu/hu}$ | 10 | BALB/cJ | Tail skin | No mAb |
| B | Il2rg$^{hu/hu}$ | 10 | BALB/cJ | Tail skin | REGN1945 (Isotype) |
| C | Il2rg$^{hu/hu}$ | 10 | BALB/cJ | Tail skin | H4H12889P (anti-hIL2Rγ) |

Figure 10:
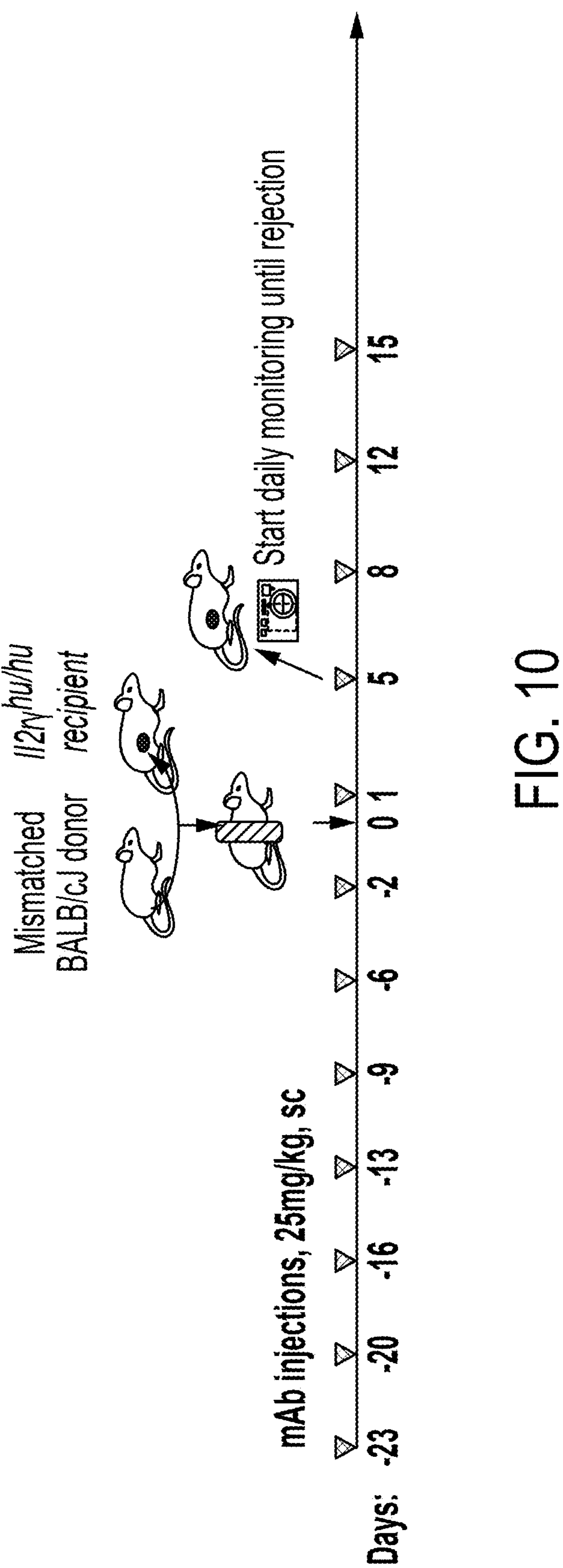
FIG. 10. Experimental layout for in vivo skin graft rejection experiments.

The experiment layout is set forth in FIG. 10.

Figure 11:
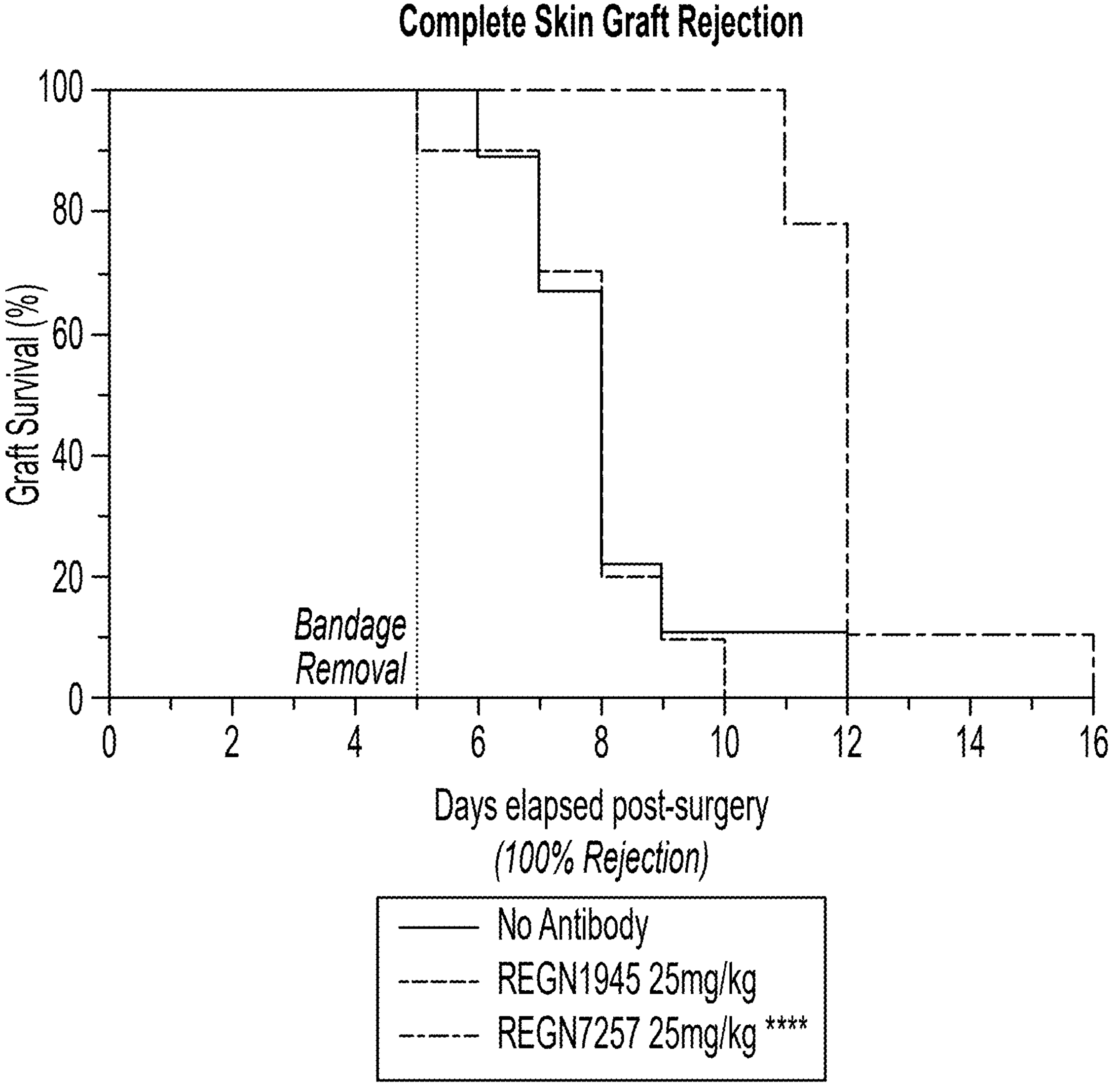
FIG. 11. Time of onset of skin graft rejection in mice administered no antibody, REGN1945 or H4H12889P.
Figure 12:
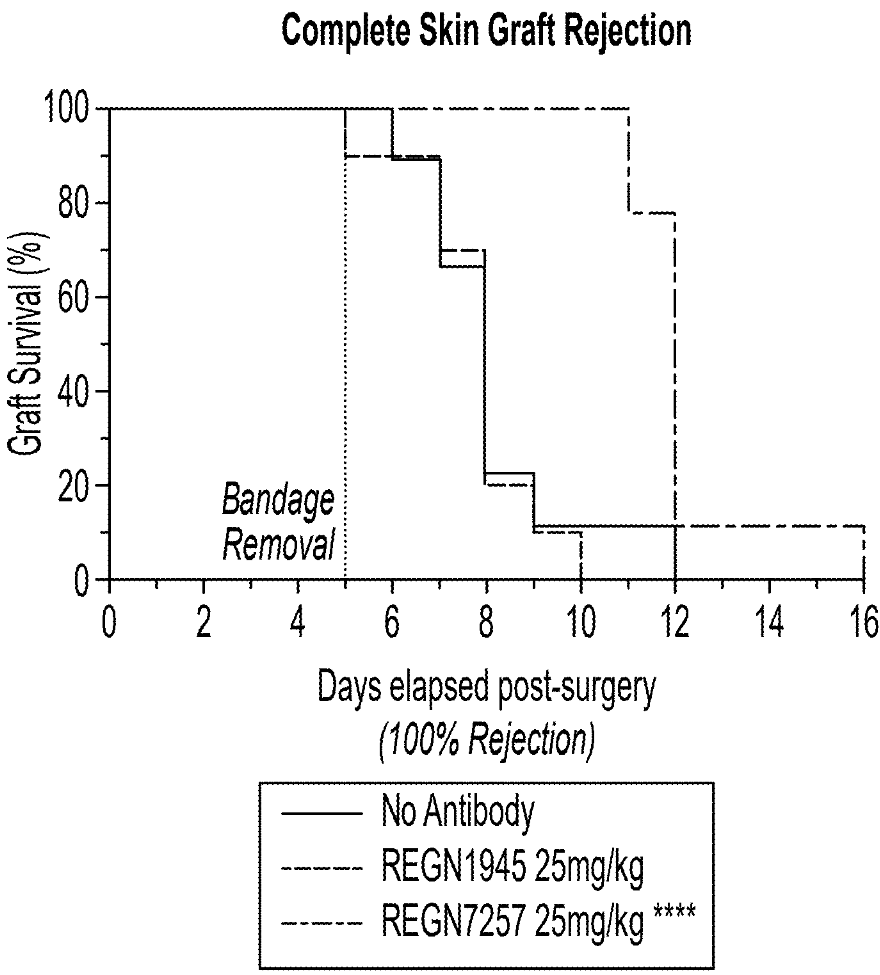
FIG. 12. Time of complete rejection of skin graft in mice administered no antibody, REGN1945 or H4H12889P.

Monitoring of skin graft rejection. Monitoring of the skin grafts included the following criteria: (1) Skin grafts that failed to vascularize properly were considered technical failures and excluded from analysis. These grafts will display scabbing and contraction several hours from bandage removal. (2) "Scabbing" and contraction of the graft at later times was used as indicators of graft rejection. The complete rejection timepoint is recorded as the first day where 100% of the graft tissue was necrotic (FIG. 12). Rejection onset was recorded as the first day where there were signs of rejection (i.e., redness) (FIG. 11). Significance was determined by Log-rank (Mantel-Cox) test with Bonferroni correction (adjusted p value 0.005, K=9).

Figure 13:
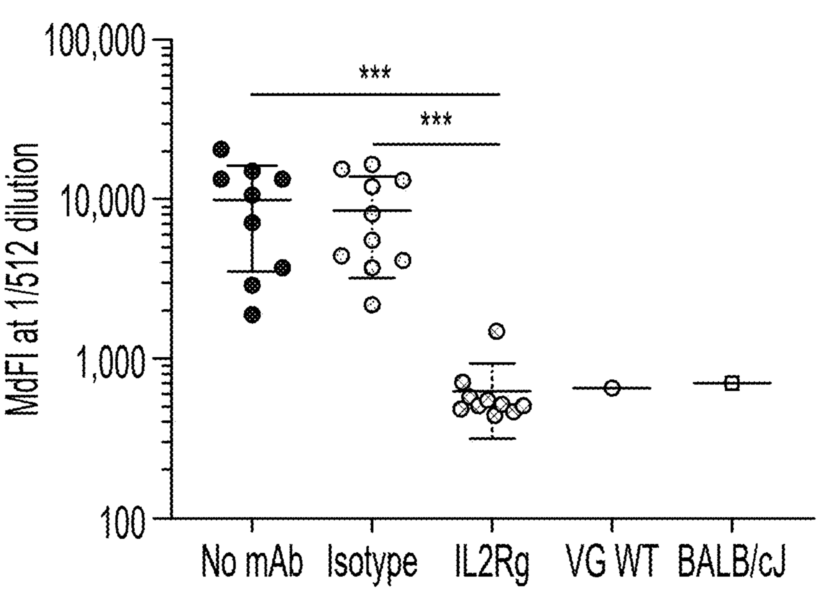
FIG. 13. Total donor specific IgG antibodies in non-engrafted mice or grafted mice administered no antibody, REGN1945 or H4H12889P.

Detection of donor specific antibodies by flow cytometry. Blood was sampled at the day 56 post-transplant timepoint to assess formation of donor-specific antibodies (FIG. 13).

CT26.WT (ATCC CRL-2638) cells were cultured in tissue culture flasks to 80% confluent. Cells were washed with 1×DPBS and dissociated with TrypLE Express reagent (Gibco) by incubating at room temperature for 5 minutes and washing flask with complete RPMI 1640 media. Cells were then centrifuged (500 g, 10 minutes), and resuspended at 5 million cells/ml with 1×DPBS with 1:50 dilution of 4 ug/ml of Fc block (TONBO) for 15 minutes at room temperature. The suspension was plated at 250,000 cells/well (50 uL) in a 384 well V-bottom plate.

50 ul of serially diluted sample serum from transplanted mice and from non-engrafted wild type VG mouse (C57BL/6NTac (75%)/129S6SvEvTac (25%)) and wild type BALB/cJ mouse obtained from The Jackson Laboratory was added to its respective well and incubate at 37° C. for 45 minutes. Following 2 washes with MACS buffer (500 g, 4 minutes), the cells were resuspended in 50 ul of LIVE/DEAD Fixable Blue Dead Cell Stain Kit (Invitrogen) diluted 1:500 in 1×DPBS at 50 ul total volume per well and incubate at room temperature for 15 minutes. After centrifugation at 500 g for 4 minutes, the supernatant was discarded, and the cells were resuspended in 25 ul of Fc Block (TONBO) and incubated at 4° C. for 15 minutes. 25 ul of 2× antibody cocktail (Table 11-2) was then added and incubated at 4° C. for 25 minutes. Cells were washed in MACS buffer following centrifugation (500 g, 4 minutes) by adding 100 ul of MACS buffer to each well. Cells were fixed by resuspending cells in 100 ul of CYTOFIX Fixation Buffer (BD) diluted 1:4 in 1×DPBS and incubated at 4° C. for 15 minutes. The samples were then resuspended in MACS buffer after centrifuging and discarding the fixative. Cells were acquired on a BD Fortessa X-20. Acquired events were analyzed with FlowJo (BD). MFIs were derived from cells that were doublet discriminated (FSC-H, FSC-A) and then Live/Dead dye negative. Results plotted were median fluorescent intensity values at the 1/512 dilution of sample serum.

TABLE 11-2

| Antibodies used in flow cytometry staining cocktail | | | | |
|---|---|---|---|---|
| Antigen | Conjugate | Clone | Supplier | Dilution (1/) |
| CD45 | BV421 | 30-F11 | BioLegend | 200 |
| IgG | APC | Poly4053 | BioLegend | 200 |
| B220 | BUV395 | RA3-6B2 | BD | 200 |
| IgG1 | PE-Cy7 | RMG1-1 | BioLegend | 200 |
| IgM | APC-Cy7 | RMM-1 | BioLegend | 200 |
| IgG2a | FITC | R19-15 | BD | 200 |
| IgG2c | FITC | Goat polyclonal IgG | Bio-Rad | 200 |

Results summary and conclusions. In a skin transplant model (BALB/cJ to VG mice), H4H12889P (anti-IL2Rγ Ab) treatment delayed onset of skin graft rejection and improved overall skin graft survival. H4H12889P treatment also prevented generation of donor-specific antibodies in this transplant model.

SEQUENCE LISTING

The sequence listing of the present application is submitted electronically as ST.26 formatted sequence listing with a file name "10561SeqList_ST26.xml," a creation date of Nov. 29, 2022, and a size of 392.6 KB. This sequence listing submitted is part of the specification and is hereby incorporated by reference in its entirety. Sequences disclosed herein and having a length that is below the minimum length permitted under ST.26 format are provided in the table below:

| SEQ ID NO. | Sequence |
|---|---|
| 13 | tgggcatct |
| 14 | Trp Ala Ser |
| 33 | aaggcgtct |
| 34 | Lys Ala Ser |
| 53 | gctgcgtcc |
| 54 | Ala Ala Ser |
| 73 | gctgcatcc |
| 92 | gatgcatcc |
| 93 | Asp Ala Ser |
| 130 | gctgcatct |
| 229 | ggggcaagt |
| 230 | Gly Ala Ser |
| 249 | gaggtttct |
| 250 | Glu Val Ser |
| 307 | ggtgcatcc |
| 326 | aaagtttct |
| 327 | Lys Val Ser |
| 371 | tctgcatcc |
| 372 | Ser Ala Ser |

```
                              SEQUENCE LISTING

Sequence total quantity: 386
SEQ ID NO: 1              moltype = DNA  length = 369
FEATURE                   Location/Qualifiers
source                    1..369
                          mol_type = unassigned DNA
                          organism = Homo sapiens
SEQUENCE: 1
caggtgcagc tggtgcagtc tggggctgag gtgaagaagc ctggggcctc agtgcgggtc  60
tcctgcaagg cttctggata caccttcacc gactacgata ttcactgggt gcgacaggcc  120
cctggacatg ggcttgagtg gatggggtgg atcaacccta acagtggtgg cacaaactat  180
gcacagaagt ttcagggcag ggtcaccatg accagggaca cgtccatcag tacagtctac  240
atggacctga gcaggctgag atctgacgac acggccgtgt attactgtgc gagagctgat  300
tatagtagtt cgtattatta ttacggtatg gacgtctggg gccaagggac cacggtcacc  360
gtctcctca                                                          369

SEQ ID NO: 2              moltype = AA  length = 123
FEATURE                   Location/Qualifiers
source                    1..123
                          mol_type = protein
                          organism = Homo sapiens
SEQUENCE: 2
QVQLVQSGAE VKKPGASVRV SCKASGYTFT DYDIHWVRQA PGHGLEWMGW INPNSGGTNY  60
AQKFQGRVTM TRDTSISTVY MDLSRLRSDD TAVYYCARAD YSSSYYYYGM DVWGQGTTVT  120
VSS                                                                123

SEQ ID NO: 3              moltype = DNA  length = 24
FEATURE                   Location/Qualifiers
source                    1..24
                          mol_type = unassigned DNA
                          organism = Homo sapiens
SEQUENCE: 3
ggatacacct tcaccgacta cgat                                         24

SEQ ID NO: 4              moltype = AA  length = 8
FEATURE                   Location/Qualifiers
source                    1..8
                          mol_type = protein
                          organism = Homo sapiens
```

```
SEQUENCE: 4
GYTFTDYD                                                          8

SEQ ID NO: 5            moltype = DNA  length = 24
FEATURE                 Location/Qualifiers
source                  1..24
                        mol_type = unassigned DNA
                        organism = Homo sapiens
SEQUENCE: 5
atcaacccta acagtggtgg caca                                        24

SEQ ID NO: 6            moltype = AA  length = 8
FEATURE                 Location/Qualifiers
source                  1..8
                        mol_type = protein
                        organism = Homo sapiens
SEQUENCE: 6
INPNSGGT                                                          8

SEQ ID NO: 7            moltype = DNA  length = 48
FEATURE                 Location/Qualifiers
source                  1..48
                        mol_type = unassigned DNA
                        organism = Homo sapiens
SEQUENCE: 7
gcgagagctg attatagtag ttcgtattat tattacggta tggacgtc              48

SEQ ID NO: 8            moltype = AA  length = 16
FEATURE                 Location/Qualifiers
source                  1..16
                        mol_type = protein
                        organism = Homo sapiens
SEQUENCE: 8
ARADYSSSYY YYGMDV                                                 16

SEQ ID NO: 9            moltype = DNA  length = 339
FEATURE                 Location/Qualifiers
source                  1..339
                        mol_type = unassigned DNA
                        organism = Homo sapiens
SEQUENCE: 9
gacatcgtga tgacccagtc tccagactcc ctggctgtgt ctctgggcga gagggccacc  60
atcaactgca agtccagcca gagtgtttta tacagctcca agaataagaa ctacttatct  120
tggtaccagc agaaaccagg acagcctcct aagttgctca tttactgggc atctacccgg  180
gaattcgggg tccctgaccg attcagtggc cgcgggtctg ggacagattt cactctcacc  240
atcagcagcc tgcaggctga agatgtggca gtttattact gtcaacaata ttatactact  300
ccgtacactt ttggccaggg gaccaagctg gagatcaaa                        339

SEQ ID NO: 10           moltype = AA  length = 113
FEATURE                 Location/Qualifiers
source                  1..113
                        mol_type = protein
                        organism = Homo sapiens
SEQUENCE: 10
DIVMTQSPDS LAVSLGERAT INCKSSQSVL YSSKNKNYLS WYQQKPGQPP KLLIYWASTR  60
EFGVPDRFSG RGSGTDFTLT ISSLQAEDVA VYYCQQYYTT PYTFGQGTKL EIK         113

SEQ ID NO: 11           moltype = DNA  length = 36
FEATURE                 Location/Qualifiers
source                  1..36
                        mol_type = unassigned DNA
                        organism = Homo sapiens
SEQUENCE: 11
cagagtgttt tatacagctc caagaataag aactac                           36

SEQ ID NO: 12           moltype = AA  length = 12
FEATURE                 Location/Qualifiers
source                  1..12
                        mol_type = protein
                        organism = Homo sapiens
SEQUENCE: 12
QSVLYSSKNK NY                                                     12

SEQ ID NO: 13           moltype =   length =
SEQUENCE: 13
000

SEQ ID NO: 14           moltype =   length =
SEQUENCE: 14
```

```
000

SEQ ID NO: 15           moltype = DNA  length = 27
FEATURE                 Location/Qualifiers
source                  1..27
                        mol_type = unassigned DNA
                        organism = Homo sapiens
SEQUENCE: 15
caacaatatt atactactcc gtacact                                       27

SEQ ID NO: 16           moltype = AA  length = 9
FEATURE                 Location/Qualifiers
source                  1..9
                        mol_type = protein
                        organism = Homo sapiens
SEQUENCE: 16
QQYYTTPYT                                                           9

SEQ ID NO: 17           moltype = DNA  length = 1353
FEATURE                 Location/Qualifiers
source                  1..1353
                        mol_type = unassigned DNA
                        organism = Homo sapiens
SEQUENCE: 17
caggtgcagc tggtgcagtc tggggctgag gtgaagaagc ctggggcctc agtgcgggtc  60
tcctgcaagg cttctggata caccttcacc gactacgata ttcactgggt gcgacaggcc  120
cctggacatg ggcttgagtg gatggggtgg atcaacccta acagtggtgg cacaaactat  180
gcacagaagt ttcagggcag ggtcaccatg accagggaca cgtccatcag tacagtctac  240
atggacctga gcaggctgag atctgacgac acggccgtgt attactgtgc gagagctgat  300
tatagtagtt cgtattatta ttacggtatg gacgtctggg gccaagggac cacggtcacc  360
gtctcctcag cctccaccaa gggcccatcg gtcttccccc tggcgccctg ctccaggagc  420
acctccgaga gcacagccgc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acgaagacct acacctgcaa cgtagatcac aagcccagca acaccaaggt ggacaagaga  660
gttgagtcca aatatggtcc cccatgccca ccctgcccag cacctgagtt cctgggggga  720
ccatcagtct tcctgttccc cccaaaaccc aaggacactc tcatgatctc ccggacccct  780
gaggtcacgt gcgtggtggt ggacgtgagc caggaagacc ccgaggtcca gttcaactgg  840
tacgtggatg gcgtggaggt gcataatgcc aagacaaagc cgcgggagga gcagttcaac  900
agcacgtacc gtgtggtcag cgtcctcacc gtcctgcacc aggactggct gaacggcaag  960
gagtacaagt gcaaggtctc caacaaaggc ctcccgtcct ccatcgagaa aaccatctcc  1020
aaagccaaag ggcagccccg agagccacag gtgtacaccc tgcccccatc ccaggaggag  1080
atgaccaaga accaggtcag cctgacctgc ctggtcaaag gcttctaccc cagcgacatc  1140
gccgtggagt gggagagcaa tgggcagccg gagaacaact acaagaccac gcctcccgtg  1200
ctggactccg acggctcctt cttcctctac agcaggctca ccgtggacaa gagcaggtgg  1260
caggagggga atgtcttctc atgctccgtg atgcatgagg ctctgcacaa ccactacaca  1320
cagaagtccc tctccctgtc tctgggtaaa tga                                1353

SEQ ID NO: 18           moltype = AA  length = 450
FEATURE                 Location/Qualifiers
source                  1..450
                        mol_type = protein
                        organism = Homo sapiens
SEQUENCE: 18
QVQLVQSGAE VKKPGASVRV SCKASGYTFT DYDIHWVRQA PGHGLEWMGW INPNSGGTNY  60
AQKFQGRVTM TRDTSISTVY MDLSRLRSDD TAVYYCARAD YSSSYYYYGM DVWGQGTTVT  120
VSSASTKGPS VFPLAPCSRS TSESTAALGC LVKDYFPEPV TVSWNSGALT SGVHTFPAVL  180
QSSGLYSLSS VVTVPSSSLG TKTYTCNVDH KPSNTKVDKR VESKYGPPCP PCPAPEFLGG  240
PSVFLFPPKP KDTLMISRTP EVTCVVVDVS QEDPEVQFNW YVDGVEVHNA KTKPREEQFN  300
STYRVVSVLT VLHQDWLNGK EYKCKVSNKG LPSSIEKTIS KAKGQPREPQ VYTLPPSQEE  360
MTKNQVSLTC LVKGFYPSDI AVEWESNGQP ENNYKTTPPV LDSDGSFFLY SRLTVDKSRW  420
QEGNVFSCSV MHEALHNHYT QKSLSLSLGK                                    450

SEQ ID NO: 19           moltype = DNA  length = 663
FEATURE                 Location/Qualifiers
source                  1..663
                        mol_type = unassigned DNA
                        organism = Homo sapiens
SEQUENCE: 19
gacatcgtga tgacccagtc tccagactcc ctggctgtgt ctctgggcga gagggccacc  60
atcaactgca agtccagcca gagtgtttta tacagctcca agaataagaa ctacttatct  120
tggtaccagc agaaaccagg acagcctcct aagttgctca tttactgggc atctacccgg  180
gaattcgggg tccctgaccg attcagtggc cgcgggtctg ggacagattt cactctcacc  240
atcagcagcc tgcaggctga agatgtggca gtttattact gtcaacaata ttatactact  300
ccgtacactt ttggccaggg gaccaagctg gagatcaaac gaactgtggc tgcaccatct  360
gtcttcatct tcccgccatc tgatgagcag ttgaaatctg gaactgcctc tgttgtgtgc  420
ctgctgaata acttctatcc cagagaggcc aaagtacagt ggaaggtgga taacgccctc  480
caatcgggta actcccagga gagtgtcaca gagcaggaca gcaaggacag cacctacagc  540
ctcagcagca ccctgacgct gagcaaagca gactacgaga aacacaaagt ctacgcctgc  600
```

```
gaagtcaccc atcagggcct gagctcgccc gtcacaaaga gcttcaacag gggagagtgt  660
tag                                                                663

SEQ ID NO: 20          moltype = AA  length = 220
FEATURE                Location/Qualifiers
source                 1..220
                       mol_type = protein
                       organism = Homo sapiens
SEQUENCE: 20
DIVMTQSPDS LAVSLGERAT INCKSSQSVL YSSKNKNYLS WYQQKPGQPP KLLIYWASTR  60
EFGVPDRFSG RGSGTDFTLT ISSLQAEDVA VYYCQQYYTT PYTFGQGTKL EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220

SEQ ID NO: 21          moltype = DNA  length = 363
FEATURE                Location/Qualifiers
source                 1..363
                       mol_type = unassigned DNA
                       organism = Homo sapiens
SEQUENCE: 21
caggtgcagc tggtggagtc tgggggaggc gtggtccagc ctgggaggtc cctgagactc  60
tcctgtacag cctctggatt caccttcaga agttatgaca tgtactgggt ccgccaggct  120
ccaggcaagg ggctggagtg ggtgtcagtt ataacatatg atggaaataa taaatactat  180
gcagactccg tgaagggccg attcaccatc tccagagaca attccaagaa cacgctattt  240
ctgcaaatga gcagcctgag acctgaggac acggctgttt attactgtgc gaaaaggggc  300
ttaatatggg tcggggagtc ctttgactac tggggccagg gaaccctggt caccgtctcc  360
tca                                                                363

SEQ ID NO: 22          moltype = AA  length = 121
FEATURE                Location/Qualifiers
source                 1..121
                       mol_type = protein
                       organism = Homo sapiens
SEQUENCE: 22
QVQLVESGGG VVQPGRSLRL SCTASGFTFR SYDMYWVRQA PGKGLEWVSV ITYDGNNKYY  60
ADSVKGRFTI SRDNSKNTLF LQMSSLRPED TAVYYCAKRG LIWVGESFDY WGQGTLVTVS  120
S                                                                  121

SEQ ID NO: 23          moltype = DNA  length = 24
FEATURE                Location/Qualifiers
source                 1..24
                       mol_type = unassigned DNA
                       organism = Homo sapiens
SEQUENCE: 23
ggattcacct tcagaagtta tgac                                         24

SEQ ID NO: 24          moltype = AA  length = 8
FEATURE                Location/Qualifiers
source                 1..8
                       mol_type = protein
                       organism = Homo sapiens
SEQUENCE: 24
GFTFRSYD                                                           8

SEQ ID NO: 25          moltype = DNA  length = 24
FEATURE                Location/Qualifiers
source                 1..24
                       mol_type = unassigned DNA
                       organism = Homo sapiens
SEQUENCE: 25
ataacatatg atggaaataa taaa                                         24

SEQ ID NO: 26          moltype = AA  length = 8
FEATURE                Location/Qualifiers
source                 1..8
                       mol_type = protein
                       organism = Homo sapiens
SEQUENCE: 26
ITYDGNNK                                                           8

SEQ ID NO: 27          moltype = DNA  length = 42
FEATURE                Location/Qualifiers
source                 1..42
                       mol_type = unassigned DNA
                       organism = Homo sapiens
SEQUENCE: 27
gcgaaaaggg gcttaatatg ggtcggggag tcctttgact ac                     42

SEQ ID NO: 28          moltype = AA  length = 14
```

```
FEATURE                Location/Qualifiers
source                 1..14
                       mol_type = protein
                       organism = Homo sapiens
SEQUENCE: 28
AKRGLIWVGE SFDY                                                14

SEQ ID NO: 29          moltype = DNA  length = 321
FEATURE                Location/Qualifiers
source                 1..321
                       mol_type = unassigned DNA
                       organism = Homo sapiens
SEQUENCE: 29
gacatccaga tgacccagtc tccttccacc ctgtctgcat ctgtaggaga cagagtcacc  60
atcacttgcc gggccagtca gagtattaat agctggttgg cctggtatca gcagaaacca  120
gggaaagccc ctaacctcct gatctataag gcgtctagtt tagaaagtgg ggtcccatca  180
aggttcagcg gcagtggatc tgggacagaa ttcactctca ccatcagcag cctgcagcct  240
gatgattttg caacttatta ctgccaacag tataagagtt attcgtggac gttcggccaa  300
gggaccaagg tggaaatcaa a                                        321

SEQ ID NO: 30          moltype = AA  length = 107
FEATURE                Location/Qualifiers
source                 1..107
                       mol_type = protein
                       organism = Homo sapiens
SEQUENCE: 30
DIQMTQSPST LSASVGDRVT ITCRASQSIN SWLAWYQQKP GKAPNLLIYK ASSLESGVPS  60
RFSGSGSGTE FTLTISSLQP DDFATYYCQQ YKSYSWTFGQ GTKVEIK             107

SEQ ID NO: 31          moltype = DNA  length = 18
FEATURE                Location/Qualifiers
source                 1..18
                       mol_type = unassigned DNA
                       organism = Homo sapiens
SEQUENCE: 31
cagagtatta atagctgg                                            18

SEQ ID NO: 32          moltype = AA  length = 6
FEATURE                Location/Qualifiers
source                 1..6
                       mol_type = protein
                       organism = Homo sapiens
SEQUENCE: 32
QSINSW                                                         6

SEQ ID NO: 33          moltype =   length =
SEQUENCE: 33
000

SEQ ID NO: 34          moltype =   length =
SEQUENCE: 34
000

SEQ ID NO: 35          moltype = DNA  length = 27
FEATURE                Location/Qualifiers
source                 1..27
                       mol_type = unassigned DNA
                       organism = Homo sapiens
SEQUENCE: 35
caacagtata agagttattc gtggacg                                  27

SEQ ID NO: 36          moltype = AA  length = 9
FEATURE                Location/Qualifiers
source                 1..9
                       mol_type = protein
                       organism = Homo sapiens
SEQUENCE: 36
QQYKSYSWT                                                      9

SEQ ID NO: 37          moltype = DNA  length = 1347
FEATURE                Location/Qualifiers
source                 1..1347
                       mol_type = unassigned DNA
                       organism = Homo sapiens
SEQUENCE: 37
caggtgcagc tggtggagtc tgggggaggc gtggtccagc ctgggaggtc cctgagactc  60
tcctgtacag cctctggatt caccttcaga agttatgaca tgtactgggt ccgccaggct  120
ccaggcaagg ggctggagtg ggtgtcagtt ataacatatg atggaaataa taaatactat  180
gcagactccg tgaagggccg attcaccatc tccagagaca attccaagaa cacgctattt  240
```

```
ctgcaaatga gcagcctgag acctgaggac acggctgttt attactgtgc gaaaaggggc  300
ttaatatggg tcggggagtc ctttgactac tggggccagg gaaccctggt caccgtctcc  360
tcagcctcca ccaagggccc atcggtcttc cccctggcgc cctgctccag gagcacctcc  420
gagagcacag ccgccctggg ctgcctggtc aaggactact tccccgaacc ggtgacggtg  480
tcgtggaact caggcgccct gaccagcggc gtgcacacct tcccggctgt cctacagtcc  540
tcaggactct actccctcag cagcgtggtg accgtgccct ccagcagctt gggcacgaag  600
acctacacct gcaacgtaga tcacaagccc agcaacacca aggtggacaa gagagttgag  660
tccaaatatg gtcccccatg cccaccctgc ccagcacctg agttcctggg gggaccatca  720
gtcttcctgt tcccccaaa acccaaggac actctcatga tctcccggac ccctgaggtc  780
acgtgcgtgg tggtggacgt gagccaggaa gaccccgagg tccagttcaa ctggtacgtg  840
gatggcgtgg aggtgcataa tgccaagaca aagccgcggg aggagcagtt caacagcacg  900
taccgtgtgg tcagcgtcct caccgtcctg caccaggact ggctgaacgg caaggagtac  960
aagtgcaagg tctccaacaa aggcctcccg tcctccatcg agaaaaccat ctccaaagcc  1020
aaagggcagc cccgagagcc acaggtgtac accctgcccc catcccagga ggagatgacc  1080
aagaaccagg tcagcctgac ctgcctggtc aaaggcttct accccagcga catcgccgtg  1140
gagtgggaga gcaatgggca gccggagaac aactacaaga ccacgcctcc cgtgctggac  1200
tccgacggct ccttcttcct ctacagcagg ctcaccgtgg acaagagcag gtggcaggag  1260
gggaatgtct tctcatgctc cgtgatgcat gaggctctgc acaaccacta cacacagaag  1320
tccctctccc tgtctctggg taaatga                                      1347

SEQ ID NO: 38           moltype = AA  length = 448
FEATURE                 Location/Qualifiers
source                  1..448
                        mol_type = protein
                        organism = Homo sapiens
SEQUENCE: 38
QVQLVESGGG VVQPGRSLRL SCTASGFTFR SYDMYWVRQA PGKGLEWVSV ITYDGNNKYY  60
ADSVKGRFTI SRDNSKNTLF LQMSSLRPED TAVYYCAKRG LIWVGESFDY WGQGTLVTVS  120
SASTKGPSVF PLAPCSRSTS ESTAALGCLV KDYFPEPVTV SWNSGALTSG VHTFPAVLQS  180
SGLYSLSSVV TVPSSSLGTK TYTCNVDHKP SNTKVDKRVE SKYGPPCPPC PAPEFLGGPS  240
VFLFPPKPKD TLMISRTPEV TCVVVDVSQE DPEVQFNWYV DGVEVHNAKT KPREEQFNST  300
YRVVSVLTVL HQDWLNGKEY KCKVSNKGLP SSIEKTISKA KGQPREPQVY TLPPSQEEMT  360
KNQVSLTCLV KGFYPSDIAV EWESNGQPEN NYKTTPPVLD SDGSFFLYSR LTVDKSRWQE  420
GNVFSCSVMH EALHNHYTQK SLSLSLGK                                     448

SEQ ID NO: 39           moltype = DNA  length = 645
FEATURE                 Location/Qualifiers
source                  1..645
                        mol_type = unassigned DNA
                        organism = Homo sapiens
SEQUENCE: 39
gacatccaga tgacccagtc tccttccacc ctgtctgcat ctgtaggaga cagagtcacc  60
atcacttgcc gggccagtca gagtattaat agctggttgg cctggtatca gcagaaacca  120
gggaaagccc ctaacctcct gatctataag gcgtctagtt tagaaagtgg ggtcccatca  180
aggttcagcg gcagtggatc tgggacagaa ttcactctca ccatcagcag cctgcagcct  240
gatgattttg caacttatta ctgccaacag tataagagtt attcgtggac gttcggccaa  300
gggaccaagg tggaaatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 40           moltype = AA  length = 214
FEATURE                 Location/Qualifiers
source                  1..214
                        mol_type = protein
                        organism = Homo sapiens
SEQUENCE: 40
DIQMTQSPST LSASVGDRVT ITCRASQSIN SWLAWYQQKP GKAPNLLIYK ASSLESGVPS  60
RFSGSGSGTE FTLTISSLQP DDFATYYCQQ YKSYSWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 41           moltype = DNA  length = 360
FEATURE                 Location/Qualifiers
source                  1..360
                        mol_type = unassigned DNA
                        organism = Homo sapiens
SEQUENCE: 41
caggtgcagc tggtggagtc tgggggaggc gtggtccagc ctgggaggtc cctgagactc  60
tcctgtgcag cctctggatt caacttcaga aactttggca tgcactgggt ccgccaggct  120
ccaggcaagg ggctggaatg ggtggcaggt atattatatg atggaagtag taaatactat  180
gcagactccg tgaaggaccg attcaccatc tccagagaca attccaagaa cacgctgttt  240
ctgcaaatga acagcctgag agctgaggac acggctatgt attactgtgc gaaagaggag  300
gacacagcca tggttccttt tgattcctgg ggcccgggaa ccctggtcac cgtctcctca  360

SEQ ID NO: 42           moltype = AA  length = 120
FEATURE                 Location/Qualifiers
```

```
source                 1..120
                       mol_type = protein
                       organism = Homo sapiens
SEQUENCE: 42
QVQLVESGGG VVQPGRSLRL SCAASGFNFR NFGMHWVRQA PGKGLEWVAG ILYDGSSKYY  60
ADSVKDRFTI SRDNSKNTLF LQMNSLRAED TAMYYCAKEE DTAMVPFDSW GPGTLVTVSS  120

SEQ ID NO: 43          moltype = DNA  length = 24
FEATURE                Location/Qualifiers
source                 1..24
                       mol_type = unassigned DNA
                       organism = Homo sapiens
SEQUENCE: 43
ggattcaact tcagaaactt tggc                                         24

SEQ ID NO: 44          moltype = AA  length = 8
FEATURE                Location/Qualifiers
source                 1..8
                       mol_type = protein
                       organism = Homo sapiens
SEQUENCE: 44
GFNFRNFG                                                           8

SEQ ID NO: 45          moltype = DNA  length = 24
FEATURE                Location/Qualifiers
source                 1..24
                       mol_type = unassigned DNA
                       organism = Homo sapiens
SEQUENCE: 45
atattatatg atggaagtag taaa                                         24

SEQ ID NO: 46          moltype = AA  length = 8
FEATURE                Location/Qualifiers
source                 1..8
                       mol_type = protein
                       organism = Homo sapiens
SEQUENCE: 46
ILYDGSSK                                                           8

SEQ ID NO: 47          moltype = DNA  length = 39
FEATURE                Location/Qualifiers
source                 1..39
                       mol_type = unassigned DNA
                       organism = Homo sapiens
SEQUENCE: 47
gcgaaagagg aggacacagc catggttcct tttgattcc                         39

SEQ ID NO: 48          moltype = AA  length = 13
FEATURE                Location/Qualifiers
source                 1..13
                       mol_type = protein
                       organism = Homo sapiens
SEQUENCE: 48
AKEEDTAMVP FDS                                                     13

SEQ ID NO: 49          moltype = DNA  length = 321
FEATURE                Location/Qualifiers
source                 1..321
                       mol_type = unassigned DNA
                       organism = Homo sapiens
SEQUENCE: 49
gacatccagt tgacccagtc tccatccttc ctgtctgctt ctgtaggaga cagagtcacc  60
atcacttgct gggccagtca gggcattagt agttatttag cctggtatca gcaaaaacca  120
gggaaagccc ctaccctcct gatctatgct gcgtccactt tgcaaagtgg ggtcccatca  180
aggttcagcg gcagtggatc tgggacagaa ttcactctca caatcagcag cctgcagcct  240
gaagattttg caagttatta ctgtcaacag cttaagagtt acccgctcac tttcggcgga  300
gggaccaagg tggagatcaa a                                            321

SEQ ID NO: 50          moltype = AA  length = 107
FEATURE                Location/Qualifiers
source                 1..107
                       mol_type = protein
                       organism = Homo sapiens
SEQUENCE: 50
DIQLTQSPSF LSASVGDRVT ITCWASQGIS SYLAWYQQKP GKAPTLLIYA ASTLQSGVPS  60
RFSGSGSGTE FTLTISSLQP EDFASYYCQQ LKSYPLTFGG GTKVEIK                107

SEQ ID NO: 51          moltype = DNA  length = 18
FEATURE                Location/Qualifiers
```

```
source                  1..18
                        mol_type = unassigned DNA
                        organism = Homo sapiens
SEQUENCE: 51
cagggcatta gtagttat                                                18

SEQ ID NO: 52           moltype = AA  length = 6
FEATURE                 Location/Qualifiers
source                  1..6
                        mol_type = protein
                        organism = Homo sapiens
SEQUENCE: 52
QGISSY                                                             6

SEQ ID NO: 53           moltype =   length =
SEQUENCE: 53
000

SEQ ID NO: 54           moltype =   length =
SEQUENCE: 54
000

SEQ ID NO: 55           moltype = DNA  length = 27
FEATURE                 Location/Qualifiers
source                  1..27
                        mol_type = unassigned DNA
                        organism = Homo sapiens
SEQUENCE: 55
caacagctta agagttaccc gctcact                                      27

SEQ ID NO: 56           moltype = AA  length = 9
FEATURE                 Location/Qualifiers
source                  1..9
                        mol_type = protein
                        organism = Homo sapiens
SEQUENCE: 56
QQLKSYPLT                                                          9

SEQ ID NO: 57           moltype = DNA  length = 1344
FEATURE                 Location/Qualifiers
source                  1..1344
                        mol_type = unassigned DNA
                        organism = Homo sapiens
SEQUENCE: 57
caggtgcagc tggtggagtc tgggggaggc gtggtccagc ctgggaggtc cctgagactc  60
tcctgtgcag cctctggatt caacttcaga aactttggca tgcactgggt ccgccaggct  120
ccaggcaagg ggctggaatg ggtggcaggt atattatatg atggaagtag taaatactat  180
gcagactccg tgaaggaccg attcaccatc tccagagaca attccaagaa cacgctgttt  240
ctgcaaatga acagcctgag agctgaggac acggctatgt attactgtgc gaaagaggag  300
gacacagcca tggttccttt tgattcctgg ggcccgggaa ccctggtcac cgtctcctca  360
gcctccacca agggcccatc ggtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc accctgccca gcacctgagt tcctgggggg accatcagtc  720
ttcctgttcc ccccaaaacc caaggacact ctcatgatct cccggacccc tgaggtcacg  780
tgcgtggtgg tggacgtgag ccaggaagac cccgaggtcc agttcaactg gtacgtggat  840
ggcgtggagg tgcataatgc caagacaaag ccgcgggagg agcagttcaa cagcacgtac  900
cgtgtggtca gcgtcctcac cgtcctgcac caggactggc tgaacggcaa ggagtacaag  960
tgcaaggtct ccaacaaagg cctcccgtcc tccatcgaga aaaccatctc caaagccaaa  1020
gggcagcccc gagagccaca ggtgtacacc ctgcccccat cccaggagga gatgaccaag  1080
aaccaggtca gcctgacctg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggctc accgtggaca agagcaggtg gcaggagggg  1260
aatgtcttct catgctccgt gatgcatgag gctctgcaca accactacac acagaagtcc  1320
ctctccctgt ctctgggtaa atga                                         1344

SEQ ID NO: 58           moltype = AA  length = 447
FEATURE                 Location/Qualifiers
source                  1..447
                        mol_type = protein
                        organism = Homo sapiens
SEQUENCE: 58
QVQLVESGGG VVQPGRSLRL SCAASGFNFR NFGMHWVRQA PGKGLEWVAG ILYDGSSKYY  60
ADSVKDRFTI SRDNSKNTLF LQMNSLRAED TAMYYCAKEE DTAMVPFDSW GPGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
```

```
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                      447

SEQ ID NO: 59          moltype = DNA  length = 645
FEATURE                Location/Qualifiers
source                 1..645
                       mol_type = unassigned DNA
                       organism = Homo sapiens
SEQUENCE: 59
gacatccagt tgacccagtc tccatccttc ctgtctgctt ctgtaggaga cagagtcacc  60
atcacttgct gggccagtca gggcattagt agttatttag cctggtatca gcaaaaacca  120
gggaaagccc ctaccctcct gatctatgct gcgtccactt tgcaaagtgg ggtcccatca  180
aggttcagcg gcagtggatc tgggacagaa ttcactctca caatcagcag cctgcagcct  240
gaagattttg caagttatta ctgtcaacag cttaagagtt acccgctcac tttcggcgga  300
gggaccaagg tggagatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 60          moltype = AA  length = 214
FEATURE                Location/Qualifiers
source                 1..214
                       mol_type = protein
                       organism = Homo sapiens
SEQUENCE: 60
DIQLTQSPSF LSASVGDRVT ITCWASQGIS SYLAWYQQKP GKAPTLLIYA ASTLQSGVPS  60
RFSGSGSGTE FTLTISSLQP EDFASYYCQQ LKSYPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 61          moltype = DNA  length = 366
FEATURE                Location/Qualifiers
source                 1..366
                       mol_type = unassigned DNA
                       organism = Homo sapiens
SEQUENCE: 61
caggtgcagc tgcaggagtc gggcccagga ctggtgaagc cttcacagac cctgtccctc  60
acctgcactg tctctggtgg ctccatcagc agtggtggtt actactggag ctggatccgc  120
cagcacccag ggaagggcct ggagtggatt ggtttcatct attacagtgg gaagacctac  180
tacaacccgt ccctcaagag tcgacttacc atctcagtag acacgtctaa gagccagttc  240
tccctgaagc tgaggtctgt gactgccgcg gacacggccg tgtattactg tgcgagactg  300
gggtatacca actcggccgg gtggttcgac ccctggggcc agggaaccct ggtcaccgtc  360
tcctca                                                             366

SEQ ID NO: 62          moltype = AA  length = 122
FEATURE                Location/Qualifiers
source                 1..122
                       mol_type = protein
                       organism = Homo sapiens
SEQUENCE: 62
QVQLQESGPG LVKPSQTLSL TCTVSGGSIS SGGYYWSWIR QHPGKGLEWI GFIYYSGKTY  60
YNPSLKSRLT ISVDTSKSQF SLKLRSVTAA DTAVYYCARL GYTNSAGWFD PWGQGTLVTV  120
SS                                                                 122

SEQ ID NO: 63          moltype = DNA  length = 30
FEATURE                Location/Qualifiers
source                 1..30
                       mol_type = unassigned DNA
                       organism = Homo sapiens
SEQUENCE: 63
ggtggctcca tcagcagtgg tggttactac                                   30

SEQ ID NO: 64          moltype = AA  length = 10
FEATURE                Location/Qualifiers
source                 1..10
                       mol_type = protein
                       organism = Homo sapiens
SEQUENCE: 64
GGSISSGGYY                                                         10

SEQ ID NO: 65          moltype = DNA  length = 21
FEATURE                Location/Qualifiers
source                 1..21
                       mol_type = unassigned DNA
                       organism = Homo sapiens
SEQUENCE: 65
```

```
atctattaca gtgggaagac c                                         21

SEQ ID NO: 66          moltype = AA  length = 7
FEATURE                Location/Qualifiers
source                 1..7
                       mol_type = protein
                       organism = Homo sapiens
SEQUENCE: 66
IYYSGKT                                                         7

SEQ ID NO: 67          moltype = DNA  length = 42
FEATURE                Location/Qualifiers
source                 1..42
                       mol_type = unassigned DNA
                       organism = Homo sapiens
SEQUENCE: 67
gcgagactgg ggtataccaa ctcggccggg tggttcgacc cc                  42

SEQ ID NO: 68          moltype = AA  length = 14
FEATURE                Location/Qualifiers
source                 1..14
                       mol_type = protein
                       organism = Homo sapiens
SEQUENCE: 68
ARLGYTNSAG WFDP                                                 14

SEQ ID NO: 69          moltype = DNA  length = 321
FEATURE                Location/Qualifiers
source                 1..321
                       mol_type = unassigned DNA
                       organism = Homo sapiens
SEQUENCE: 69
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaacctcct gatctatgct gcatccagtt tgcaaagtgg ggtcccatca  180
aggttcagtg gcagtggatc tgggacagat ttcactctca ccatcagcag tctgcaacct  240
gaagatcttg caacttacta ctgtcaacag agttacacaa ccccattcac tttcggccct  300
gggaccaaag tggatatcaa a                                         321

SEQ ID NO: 70          moltype = AA  length = 107
FEATURE                Location/Qualifiers
source                 1..107
                       mol_type = protein
                       organism = Homo sapiens
SEQUENCE: 70
DIQMTQSPSS LSASVGDRVT ITCRASQSIS SYLNWYQQKP GKAPNLLIYA ASSLQSGVPS  60
RFSGSGSGTD FTLTISSLQP EDLATYYCQQ SYTTPFTFGP GTKVDIK             107

SEQ ID NO: 71          moltype = DNA  length = 18
FEATURE                Location/Qualifiers
source                 1..18
                       mol_type = unassigned DNA
                       organism = Homo sapiens
SEQUENCE: 71
cagagcatta gcagctat                                             18

SEQ ID NO: 72          moltype = AA  length = 6
FEATURE                Location/Qualifiers
source                 1..6
                       mol_type = protein
                       organism = Homo sapiens
SEQUENCE: 72
QSISSY                                                          6

SEQ ID NO: 73          moltype =   length =
SEQUENCE: 73
000

SEQ ID NO: 74          moltype = DNA  length = 27
FEATURE                Location/Qualifiers
source                 1..27
                       mol_type = unassigned DNA
                       organism = Homo sapiens
SEQUENCE: 74
caacagagtt acacaacccc attcact                                   27

SEQ ID NO: 75          moltype = AA  length = 9
FEATURE                Location/Qualifiers
source                 1..9
```

```
                        mol_type = protein
                        organism = Homo sapiens
SEQUENCE: 75
QQSYTTPFT                                                                 9

SEQ ID NO: 76           moltype = DNA  length = 1350
FEATURE                 Location/Qualifiers
source                  1..1350
                        mol_type = unassigned DNA
                        organism = Homo sapiens
SEQUENCE: 76
caggtgcagc tgcaggagtc gggcccagga ctggtgaagc cttcacagac cctgtccctc  60
acctgcactg tctctggtgg ctccatcagc agtggtggtt actactggag ctggatccgc  120
cagcacccag ggaagggcct ggagtggatt ggtttcatct attacagtgg gaagacctac  180
tacaacccgt ccctcaagag tcgacttacc atctcagtag acacgtctaa gagccagttc  240
tccctgaagc tgaggtctgt gactgccgcg gacacggccg tgtattactg tgcgagactg  300
gggtatacca actcggccgg gtggttcgac ccctggggcc agggaaccct ggtcaccgtc  360
tcctcagcct ccaccaaggg cccatcggtc ttccccctgg cgccctgctc caggagcacc  420
tccgagagca cagccgccct gggctgcctg gtcaaggact acttccccga accggtgacg  480
gtgtcgtgga actcaggcgc cctgaccagc ggcgtgcaca ccttcccggc tgtcctacag  540
tcctcaggac tctactccct cagcagcgtg gtgaccgtgc cctccagcag cttgggcacg  600
aagacctaca cctgcaacgt agatcacaag cccagcaaca ccaaggtgga caagagagtt  660
gagtccaaat atggtccccc atgcccaccc tgcccagcac ctgagttcct ggggggacca  720
tcagtcttcc tgttcccccc aaaacccaag gacactctca tgatctcccg gacccctgag  780
gtcacgtgcg tggtggtgga cgtgagccag gaagaccccg aggtccagtt caactggtac  840
gtggatggcg tggaggtgca taatgccaag acaaagccgc gggaggagca gttcaacagc  900
acgtaccgtg tggtcagcgt cctcaccgtc ctgcaccagg actggctgaa cggcaaggag  960
tacaagtgca aggtctccaa caaaggcctc ccgtcctcca tcgagaaaac catctccaaa  1020
gccaaagggc agccccgaga gccacaggtg tacaccctgc ccccatccca ggaggagatg  1080
accaagaacc aggtcagcct gacctgcctg gtcaaaggct tctaccccag cgacatcgcc  1140
gtggagtggg agagcaatgg gcagccggag aacaactaca agaccacgcc tcccgtgctg  1200
gactccgacg gctccttctt cctctacagc aggctcaccg tggacaagag caggtggcag  1260
gaggggaatg tcttctcatg ctccgtgatg catgaggctc tgcacaacca ctacacacag  1320
aagtccctct ccctgtctct gggtaaatga                                  1350

SEQ ID NO: 77           moltype = AA  length = 449
FEATURE                 Location/Qualifiers
source                  1..449
                        mol_type = protein
                        organism = Homo sapiens
SEQUENCE: 77
QVQLQESGPG LVKPSQTLSL TCTVSGGSIS SGGYYWSWIR QHPGKGLEWI GFIYYSGKTY  60
YNPSLKSRLT ISVDTSKSQF SLKLRSVTAA DTAVYYCARL GYTNSAGWFD PWGQGTLVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGK                                   449

SEQ ID NO: 78           moltype = DNA  length = 645
FEATURE                 Location/Qualifiers
source                  1..645
                        mol_type = unassigned DNA
                        organism = Homo sapiens
SEQUENCE: 78
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaacctcct gatctatgct gcatccagtt tgcaaagtgg ggtcccatca  180
aggttcagtg gcagtggatc tgggacagat ttcactctca ccatcagcag tctgcaacct  240
gaagatcttg caacttacta ctgtcaacag agttacacaa ccccattcac tttcggccct  300
gggaccaaag tggatatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 79           moltype = AA  length = 214
FEATURE                 Location/Qualifiers
source                  1..214
                        mol_type = protein
                        organism = Homo sapiens
SEQUENCE: 79
DIQMTQSPSS LSASVGDRVT ITCRASQSIS SYLNWYQQKP GKAPNLLIYA ASSLQSGVPS  60
RFSGSGSGTD FTLTISSLQP EDLATYYCQQ SYTTPFTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```

```
SEQ ID NO: 80          moltype = DNA  length = 375
FEATURE                Location/Qualifiers
source                 1..375
                       mol_type = unassigned DNA
                       organism = Homo sapiens
SEQUENCE: 80
gaggtgcagc tggtggagtc ggggggaggt ttggtaaagc ctgggggggtc ccttagactc  60
tcctgtgcag cctctggatt cactttcagt accgcctgga tgagctgggt ccgccagtct  120
ccagggaggg ggctggagtg ggttggccgt atgaaaagca agactgatgg tgggacaaca  180
ttctacgctg cacccgtgaa aggcagattc accatctcaa gagatgattc aaaaaacaca  240
ctgtatctgc aaatgaacag cctgaaaacc gaggacacag ccgtttatta ctgtaccaca  300
ggattagtcc cggccttcta taagtactac ggcgtggacg tctggggcca agggaccacg  360
gtcaccgtct cctca                                                    375

SEQ ID NO: 81          moltype = AA  length = 125
FEATURE                Location/Qualifiers
source                 1..125
                       mol_type = protein
                       organism = Homo sapiens
SEQUENCE: 81
EVQLVESGGG LVKPGGSLRL SCAASGFTFS TAWMSWVRQS PGRGLEWVGR MKSKTDGGTT  60
FYAAPVKGRF TISRDDSKNT LYLQMNSLKT EDTAVYYCTT GLVPAFYKYY GVDVWGQGTT  120
VTVSS                                                               125

SEQ ID NO: 82          moltype = DNA  length = 24
FEATURE                Location/Qualifiers
source                 1..24
                       mol_type = unassigned DNA
                       organism = Homo sapiens
SEQUENCE: 82
ggattcactt tcagtaccgc ctgg                                          24

SEQ ID NO: 83          moltype = AA  length = 8
FEATURE                Location/Qualifiers
source                 1..8
                       mol_type = protein
                       organism = Homo sapiens
SEQUENCE: 83
GFTFSTAW                                                            8

SEQ ID NO: 84          moltype = DNA  length = 30
FEATURE                Location/Qualifiers
source                 1..30
                       mol_type = unassigned DNA
                       organism = Homo sapiens
SEQUENCE: 84
atgaaaagca agactgatgg tgggacaaca                                    30

SEQ ID NO: 85          moltype = AA  length = 10
FEATURE                Location/Qualifiers
source                 1..10
                       mol_type = protein
                       organism = Homo sapiens
SEQUENCE: 85
MKSKTDGGTT                                                          10

SEQ ID NO: 86          moltype = DNA  length = 48
FEATURE                Location/Qualifiers
source                 1..48
                       mol_type = unassigned DNA
                       organism = Homo sapiens
SEQUENCE: 86
accacaggat tagtcccggc cttctataag tactacggcg tggacgtc                48

SEQ ID NO: 87          moltype = AA  length = 16
FEATURE                Location/Qualifiers
source                 1..16
                       mol_type = protein
                       organism = Homo sapiens
SEQUENCE: 87
TTGLVPAFYK YYGVDV                                                   16

SEQ ID NO: 88          moltype = DNA  length = 318
FEATURE                Location/Qualifiers
source                 1..318
                       mol_type = unassigned DNA
                       organism = Homo sapiens
SEQUENCE: 88
gacatccaga tgacccagtc tccatcctcc ctgtctgcat ctgtaggaga cagaatcacc  60
```

```
atcacttgcc aggcgagtca ggacattacc aactatttaa attggtatca gcagaagcca  120
gggaaagccc ctaacctcct gatctacgat gcatccaatt tggttacagg ggtcccatca  180
aggttcagtg gaagtggatc tgggacagat tttactttca ccatcctcag cctgcagcct  240
gaagatattg caacatatta ctgtcaacag tatgatagtc tcctcacttt cggccctggg  300
accaaagtgg atatcaaa                                                318

SEQ ID NO: 89          moltype = AA  length = 106
FEATURE                Location/Qualifiers
source                 1..106
                       mol_type = protein
                       organism = Homo sapiens
SEQUENCE: 89
DIQMTQSPSS LSASVGDRIT ITCQASQDIT NYLNWYQQKP GKAPNLLIYD ASNLVTGVPS  60
RFSGSGSGTD FTFTILSLQP EDIATYYCQQ YDSLLTFGPG TKVDIK                 106

SEQ ID NO: 90          moltype = DNA  length = 18
FEATURE                Location/Qualifiers
source                 1..18
                       mol_type = unassigned DNA
                       organism = Homo sapiens
SEQUENCE: 90
caggacatta ccaactat                                                18

SEQ ID NO: 91          moltype = AA  length = 6
FEATURE                Location/Qualifiers
source                 1..6
                       mol_type = protein
                       organism = Homo sapiens
SEQUENCE: 91
QDITNY                                                             6

SEQ ID NO: 92          moltype =   length =
SEQUENCE: 92
000

SEQ ID NO: 93          moltype =   length =
SEQUENCE: 93
000

SEQ ID NO: 94          moltype = DNA  length = 24
FEATURE                Location/Qualifiers
source                 1..24
                       mol_type = unassigned DNA
                       organism = Homo sapiens
SEQUENCE: 94
caacagtatg atagtctcct cact                                         24

SEQ ID NO: 95          moltype = AA  length = 8
FEATURE                Location/Qualifiers
source                 1..8
                       mol_type = protein
                       organism = Homo sapiens
SEQUENCE: 95
QQYDSLLT                                                           8

SEQ ID NO: 96          moltype = DNA  length = 1359
FEATURE                Location/Qualifiers
source                 1..1359
                       mol_type = unassigned DNA
                       organism = Homo sapiens
SEQUENCE: 96
gaggtgcagc tggtggagtc gggggaggt ttggtaaagc ctgggggtc ccttagactc  60
tcctgtgcag cctctggatt cactttcagt accgcctgga tgagctgggt ccgccagtct  120
ccagggaggg ggctggagtg ggttggccgt atgaaaagca agactgatgg tgggacaaca  180
ttctacgctg cacccgtgaa aggcagattc accatctcaa gagatgattc aaaaaacaca  240
ctgtatctgc aaatgaacag cctgaaaacc gaggacacag ccgtttatta ctgtaccaca  300
ggattagtcc cggccttcta taagtactac ggcgtggacg tctggggcca agggaccacg  360
gtcaccgtct cctcagcctc caccaagggc ccatcggtct tccccctggc gccctgctcc  420
aggagcacct ccgagagcac agccgccctg ggctgcctgg tcaaggacta cttccccgaa  480
ccggtgacgg tgtcgtggaa ctcaggcgcc ctgaccagcg gcgtgcacac cttcccggct  540
gtcctacagt cctcaggact ctactccctc agcagcgtgg tgaccgtgcc ctccagcagc  600
ttgggcacga agacctacac ctgcaacgta gatcacaagc ccagcaacac caaggtggac  660
aagagagttg agtccaaata tggtccccca tgcccaccct gcccagcacc tgagttcctg  720
gggggaccat cagtcttcct gttcccccca aaacccaagg acactctcat gatctcccgg  780
acccctgagg tcacgtgcgt ggtggtggac gtgagccagg aagaccccga ggtccagttc  840
aactggtacg tggatggcgt ggaggtgcat aatgccaaga caaagccgcg ggaggagcag  900
ttcaacagca cgtaccgtgt ggtcagcgtc ctcaccgtcc tgcaccagga ctggctgaac  960
ggcaaggagt acaagtgcaa ggtctccaac aaaggcctcc cgtcctccat cgagaaaacc  1020
atctccaaag ccaaagggca gccccgagag ccacaggtgt acaccctgcc cccatcccag  1080
```

```
gaggagatga ccaagaacca ggtcagcctg acctgcctgg tcaaaggctt ctaccccagc  1140
gacatcgccg tggagtggga gagcaatggg cagccggaga acaactacaa gaccacgcct  1200
cccgtgctgg actccgacgg ctccttcttc ctctacagca ggctcaccgt ggacaagagc  1260
aggtggcagg aggggaatgt cttctcatgc tccgtgatgc atgaggctct gcacaaccac  1320
tacacacaga agtccctctc cctgtctctg ggtaaatga                         1359

SEQ ID NO: 97          moltype = AA  length = 452
FEATURE                Location/Qualifiers
source                 1..452
                       mol_type = protein
                       organism = Homo sapiens
SEQUENCE: 97
EVQLVESGGG LVKPGGSLRL SCAASGFTFS TAWMSWVRQS PGRGLEWVGR MKSKTDGGTT  60
FYAAPVKGRF TISRDDSKNT LYLQMNSLKT EDTAVYYCTT GLVPAFYKYY GVDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLMISR TPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL GK                                452

SEQ ID NO: 98          moltype = DNA  length = 642
FEATURE                Location/Qualifiers
source                 1..642
                       mol_type = unassigned DNA
                       organism = Homo sapiens
SEQUENCE: 98
gacatccaga tgacccagtc tccatcctcc ctgtctgcat ctgtaggaga cagaatcacc  60
atcacttgcc aggcgagtca ggacattacc aactatttaa attggtatca gcagaagcca  120
gggaaagccc ctaacctcct gatctacgat gcatccaatt tggttacagg ggtcccatca  180
aggttcagtg gaagtggatc tgggacagat tttactttca ccatcctcag cctgcagcct  240
gaagatattg caacatatta ctgtcaacag tatgatagtc tcctcacttt cggccctggg  300
accaaagtgg atatcaaacg aactgtggct gcaccatctg tcttcatctt cccgccatct  360
gatgagcagt tgaaatctgg aactgcctct gttgtgtgcc tgctgaataa cttctatccc  420
agagaggcca aagtacagtg gaaggtggat aacgccctcc aatcgggtaa ctcccaggag  480
agtgtcacag agcaggacag caaggacagc acctacagcc tcagcagcac cctgacgctg  540
agcaaagcag actacgagaa acacaaagtc tacgcctgcg aagtcaccca tcagggcctg  600
agctcgcccg tcacaaagag cttcaacagg ggagagtgtt ag                     642

SEQ ID NO: 99          moltype = AA  length = 213
FEATURE                Location/Qualifiers
source                 1..213
                       mol_type = protein
                       organism = Homo sapiens
SEQUENCE: 99
DIQMTQSPSS LSASVGDRIT ITCQASQDIT NYLNWYQQKP GKAPNLLIYD ASNLVTGVPS  60
RFSGSGSGTD FTFTILSLQP EDIATYYCQQ YDSLLTFGPG TKVDIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                                213

SEQ ID NO: 100         moltype = DNA  length = 369
FEATURE                Location/Qualifiers
source                 1..369
                       mol_type = unassigned DNA
                       organism = Homo sapiens
SEQUENCE: 100
gaggtgcagc tggtggagtc tgggggaggc ttggtccagc ctggggggtc cctgagactc  60
tcctgtgcag cctctggatt caccttcaat aactatgcaa tgcactgggt ccgccaggct  120
cccgggaagg gactggaata tgtttcatct attagtagta gtgggggtag cacatattat  180
gaagactctg tgaagggcag attcaccatc tccagagaca attccaagaa cacgctgtat  240
cttcaaatgg gcagcctgag agctgaggac atggctgtgt attactgtgc gagatcattc  300
tatggttcgg ggacttatta tgatactttt gatatgtggg gccaagggac aatggtcacc  360
gtctcttca                                                          369

SEQ ID NO: 101         moltype = AA  length = 123
FEATURE                Location/Qualifiers
source                 1..123
                       mol_type = protein
                       organism = Homo sapiens
SEQUENCE: 101
EVQLVESGGG LVQPGGSLRL SCAASGFTFN NYAMHWVRQA PGKGLEYVSS ISSSGGSTYY  60
EDSVKGRFTI SRDNSKNTLY LQMGSLRAED MAVYYCARSF YGSGTYYDTF DMWGQGTMVT  120
VSS                                                                123

SEQ ID NO: 102         moltype = DNA  length = 24
FEATURE                Location/Qualifiers
source                 1..24
                       mol_type = unassigned DNA
                       organism = Homo sapiens
```

```
SEQUENCE: 102
ggattcacct tcaataacta tgca                                          24

SEQ ID NO: 103         moltype = AA  length = 8
FEATURE                Location/Qualifiers
source                 1..8
                       mol_type = protein
                       organism = Homo sapiens
SEQUENCE: 103
GFTFNNYA                                                            8

SEQ ID NO: 104         moltype = DNA  length = 24
FEATURE                Location/Qualifiers
source                 1..24
                       mol_type = unassigned DNA
                       organism = Homo sapiens
SEQUENCE: 104
attagtagta gtgggggtag caca                                          24

SEQ ID NO: 105         moltype = AA  length = 8
FEATURE                Location/Qualifiers
source                 1..8
                       mol_type = protein
                       organism = Homo sapiens
SEQUENCE: 105
ISSSGGST                                                            8

SEQ ID NO: 106         moltype = DNA  length = 48
FEATURE                Location/Qualifiers
source                 1..48
                       mol_type = unassigned DNA
                       organism = Homo sapiens
SEQUENCE: 106
gcgagatcat tctatggttc ggggacttat tatgatactt ttgatatg                48

SEQ ID NO: 107         moltype = AA  length = 16
FEATURE                Location/Qualifiers
source                 1..16
                       mol_type = protein
                       organism = Homo sapiens
SEQUENCE: 107
ARSFYGSGTY YDTFDM                                                   16

SEQ ID NO: 108         moltype = DNA  length = 321
FEATURE                Location/Qualifiers
source                 1..321
                       mol_type = unassigned DNA
                       organism = Homo sapiens
SEQUENCE: 108
gacatccaga tgacccagtc tccatcctcc ctgtctgcat ctataggaga cagagtcacc  60
atcacttgcc gggcaagtca gagcattagc aggtatttaa attggtatca gcagaaacca  120
gggaaagccc ctaagctcct gatctatgct gcatccagtt tgcaaagtgg ggtcccatca  180
aggttcagtg ccagtggatc tgggacagat ttcactctca ccatcagcag tctgcaacct  240
gaagattttg caacttacta ctgtcaacag agttacagta ccccgttcac ttttggccag  300
gggaccaagc tggagatcaa a                                             321

SEQ ID NO: 109         moltype = AA  length = 107
FEATURE                Location/Qualifiers
source                 1..107
                       mol_type = protein
                       organism = Homo sapiens
SEQUENCE: 109
DIQMTQSPSS LSASIGDRVT ITCRASQSIS RYLNWYQQKP GKAPKLLIYA ASSLQSGVPS  60
RFSASGSGTD FTLTISSLQP EDFATYYCQQ SYSTPFTFGQ GTKLEIK                 107

SEQ ID NO: 110         moltype = DNA  length = 18
FEATURE                Location/Qualifiers
source                 1..18
                       mol_type = unassigned DNA
                       organism = Homo sapiens
SEQUENCE: 110
cagagcatta gcaggtat                                                 18

SEQ ID NO: 111         moltype = AA  length = 6
FEATURE                Location/Qualifiers
source                 1..6
                       mol_type = protein
                       organism = Homo sapiens
SEQUENCE: 111
```

```
QSISRY                                                       6

SEQ ID NO: 112          moltype = DNA  length = 27
FEATURE                 Location/Qualifiers
source                  1..27
                        mol_type = unassigned DNA
                        organism = Homo sapiens
SEQUENCE: 112
caacagagtt acagtacccc gttcact                                27

SEQ ID NO: 113          moltype = AA  length = 9
FEATURE                 Location/Qualifiers
source                  1..9
                        mol_type = protein
                        organism = Homo sapiens
SEQUENCE: 113
QQSYSTPFT                                                    9

SEQ ID NO: 114          moltype = DNA  length = 1353
FEATURE                 Location/Qualifiers
source                  1..1353
                        mol_type = unassigned DNA
                        organism = Homo sapiens
SEQUENCE: 114
gaggtgcagc tggtggagtc tgggggaggc ttggtccagc ctggggggtc cctgagactc  60
tcctgtgcag cctctggatt caccttcaat aactatgcaa tgcactgggt ccgccaggct  120
cccgggaagg gactggaata tgtttcatct attagtagta gtgggggtag cacatattat  180
gaagactctg tgaagggcag attcaccatc tccagagaca attccaagaa cacgctgtat  240
cttcaaatgg gcagcctgag agctgaggac atggctgtgt attactgtgc gagatcattc  300
tatggttcgg ggacttatta tgatactttt gatatgtggg gccaagggac aatggtcacc  360
gtctcttcag cctccaccaa gggcccatcg gtcttccccc tggcgccctg ctccaggagc  420
acctccgaga gcacagccgc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acgaagacct acacctgcaa cgtagatcac aagcccagca acaccaaggt ggacaagaga  660
gttgagtcca aatatggtcc cccatgccca ccctgcccag cacctgagtt cctgggggga  720
ccatcagtct tcctgttccc cccaaaaccc aaggacactc tcatgatctc ccggacccct  780
gaggtcacgt gcgtggtggt ggacgtgagc caggaagacc ccgaggtcca gttcaactgg  840
tacgtggatg gcgtggaggt gcataatgcc aagacaaagc cgcgggagga gcagttcaac  900
agcacgtacc gtgtggtcag cgtcctcacc gtcctgcacc aggactggct gaacggcaag  960
gagtacaagt gcaaggtctc caacaaaggc ctcccgtcct ccatcgagaa aaccatctcc  1020
aaagccaaag ggcagccccg agagccacag gtgtacaccc tgcccccatc ccaggaggag  1080
atgaccaaga accaggtcag cctgacctgc ctggtcaaag gcttctaccc cagcgacatc  1140
gccgtggagt gggagagcaa tgggcagccg gagaacaact acaagaccac gcctcccgtg  1200
ctggactccg acggctcctt cttcctctac agcaggctca ccgtggacaa gagcaggtgg  1260
caggagggga atgtcttctc atgctccgtg atgcatgagg ctctgcacaa ccactacaca  1320
cagaagtccc tctccctgtc tctgggtaaa tga                         1353

SEQ ID NO: 115          moltype = AA  length = 450
FEATURE                 Location/Qualifiers
source                  1..450
                        mol_type = protein
                        organism = Homo sapiens
SEQUENCE: 115
EVQLVESGGG LVQPGGSLRL SCAASGFTFN NYAMHWVRQA PGKGLEYVSS ISSSGGSTYY  60
EDSVKGRFTI SRDNSKNTLY LQMGSLRAED MAVYYCARSF YGSGTYYDTF DMWGQGTMVT  120
VSSASTKGPS VFPLAPCSRS TSESTAALGC LVKDYFPEPV TVSWNSGALT SGVHTFPAVL  180
QSSGLYSLSS VVTVPSSSLG TKTYTCNVDH KPSNTKVDKR VESKYGPPCP PCPAPEFLGG  240
PSVFLFPPKP KDTLMISRTP EVTCVVVDVS QEDPEVQFNW YVDGVEVHNA KTKPREEQFN  300
STYRVVSVLT VLHQDWLNGK EYKCKVSNKG LPSSIEKTIS KAKGQPREPQ VYTLPPSQEE  360
MTKNQVSLTC LVKGFYPSDI AVEWESNGQP ENNYKTTPPV LDSDGSFFLY SRLTVDKSRW  420
QEGNVFSCSV MHEALHNHYT QKSLSLSLGK                             450

SEQ ID NO: 116          moltype = DNA  length = 645
FEATURE                 Location/Qualifiers
source                  1..645
                        mol_type = unassigned DNA
                        organism = Homo sapiens
SEQUENCE: 116
gacatccaga tgacccagtc tccatcctcc ctgtctgcat ctataggaga cagagtcacc  60
atcacttgcc gggcaagtca gagcattagc aggtatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta ccccgttcac ttttggccag  300
gggaccaagc tggagatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
```

```
ctgagctcgc ccgtcacaaa gagcttcaac aggggagagt gttag                645

SEQ ID NO: 117          moltype = AA  length = 214
FEATURE                 Location/Qualifiers
source                  1..214
                        mol_type = protein
                        organism = Homo sapiens
SEQUENCE: 117
DIQMTQSPSS LSASIGDRVT ITCRASQSIS RYLNWYQQKP GKAPKLLIYA ASSLQSGVPS  60
RFSASGSGTD FTLTISSLQP EDFATYYCQQ SYSTPFTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                            214

SEQ ID NO: 118          moltype = DNA  length = 342
FEATURE                 Location/Qualifiers
source                  1..342
                        mol_type = unassigned DNA
                        organism = Homo sapiens
SEQUENCE: 118
caggtgcagc tggtggagtc tgggggagac ttggtcaagc ctgggggtc cctgagactc  60
tcctgtgcaa cctctggatt caccttcagt gacttttaca tgacctggat ccgccaggct  120
ccagggaagg gattggagtg gatttcatat ataagtaata gtgggagtat cgtgaagtac  180
gcagactctg tgaagggccg attcaccatt tccagggata acgccaagaa ctcactgtat  240
ctgcaaatga acagcctgag agccgaggac acggccattt attactgtgc gcggttttat  300
ggtgacagat ggggccaggg aaccctggtc accgtctcct ca                    342

SEQ ID NO: 119          moltype = AA  length = 114
FEATURE                 Location/Qualifiers
source                  1..114
                        mol_type = protein
                        organism = Homo sapiens
SEQUENCE: 119
QVQLVESGGD LVKPGGSLRL SCATSGFTFS DFYMTWIRQA PGKGLEWISY ISNSGSIVKY  60
ADSVKGRFTI SRDNAKNSLY LQMNSLRAED TAIYYCARFY GDRWGQGTLV TVSS        114

SEQ ID NO: 120          moltype = DNA  length = 24
FEATURE                 Location/Qualifiers
source                  1..24
                        mol_type = unassigned DNA
                        organism = Homo sapiens
SEQUENCE: 120
ggattcacct tcagtgactt ttac                                       24

SEQ ID NO: 121          moltype = AA  length = 8
FEATURE                 Location/Qualifiers
source                  1..8
                        mol_type = protein
                        organism = Homo sapiens
SEQUENCE: 121
GFTFSDFY                                                         8

SEQ ID NO: 122          moltype = DNA  length = 24
FEATURE                 Location/Qualifiers
source                  1..24
                        mol_type = unassigned DNA
                        organism = Homo sapiens
SEQUENCE: 122
ataagtaata gtgggagtat cgtg                                       24

SEQ ID NO: 123          moltype = AA  length = 8
FEATURE                 Location/Qualifiers
source                  1..8
                        mol_type = protein
                        organism = Homo sapiens
SEQUENCE: 123
ISNSGSIV                                                         8

SEQ ID NO: 124          moltype = DNA  length = 21
FEATURE                 Location/Qualifiers
source                  1..21
                        mol_type = unassigned DNA
                        organism = Homo sapiens
SEQUENCE: 124
gcgcggtttt atggtgacag a                                          21

SEQ ID NO: 125          moltype = AA  length = 7
FEATURE                 Location/Qualifiers
source                  1..7
                        mol_type = protein
```

```
                        organism = Homo sapiens
SEQUENCE: 125
ARFYGDR                                                             7

SEQ ID NO: 126          moltype = DNA  length = 321
FEATURE                 Location/Qualifiers
source                  1..321
                        mol_type = unassigned DNA
                        organism = Homo sapiens
SEQUENCE: 126
gacatccagt tgacccagtc tccatctttc ctgtctgcat ctgtaggaga cagagtcacc  60
atcacttgct gggccagtca gggcattagc actttttttag cctggtatca gcaaaagccg  120
ggtaaagccc ctaagctcct gatctatgct gcatctactt tacaaagtgg ggtcccatcg  180
cgattcagcg gcagcggatc tgggacagat ttcactctca caatcagcag cctgcagcct  240
gaagattttg caacttatca ctgtcaacaa cttaataatt acccgtggac gttcggccaa  300
gggaccaagg tggaaatcaa a                                             321

SEQ ID NO: 127          moltype = AA  length = 107
FEATURE                 Location/Qualifiers
source                  1..107
                        mol_type = protein
                        organism = Homo sapiens
SEQUENCE: 127
DIQLTQSPSF LSASVGDRVT ITCWASQGIS TFLAWYQQKP GKAPKLLIYA ASTLQSGVPS  60
RFSGSGSGTD FTLTISSLQP EDFATYHCQQ LNNYPWTFGQ GTKVEIK                107

SEQ ID NO: 128          moltype = DNA  length = 18
FEATURE                 Location/Qualifiers
source                  1..18
                        mol_type = unassigned DNA
                        organism = Homo sapiens
SEQUENCE: 128
cagggcatta gcactttt                                                 18

SEQ ID NO: 129          moltype = AA  length = 6
FEATURE                 Location/Qualifiers
source                  1..6
                        mol_type = protein
                        organism = Homo sapiens
SEQUENCE: 129
QGISTF                                                              6

SEQ ID NO: 130          moltype =   length =
SEQUENCE: 130
000

SEQ ID NO: 131          moltype = DNA  length = 27
FEATURE                 Location/Qualifiers
source                  1..27
                        mol_type = unassigned DNA
                        organism = Homo sapiens
SEQUENCE: 131
caacaactta ataattaccc gtggacg                                       27

SEQ ID NO: 132          moltype = AA  length = 9
FEATURE                 Location/Qualifiers
source                  1..9
                        mol_type = protein
                        organism = Homo sapiens
SEQUENCE: 132
QQLNNYPWT                                                           9

SEQ ID NO: 133          moltype = DNA  length = 1326
FEATURE                 Location/Qualifiers
source                  1..1326
                        mol_type = unassigned DNA
                        organism = Homo sapiens
SEQUENCE: 133
caggtgcagc tggtggagtc tgggggagac ttggtcaagc ctgggggggtc cctgagactc  60
tcctgtgcaa cctctggatt caccttcagt gacttttaca tgacctggat ccgccaggct  120
ccagggaagg gattggagtg gatttcatat ataagtaata gtgggagtat cgtgaagtac  180
gcagactctg tgaagggccg attcaccatt tccagggata acgccaagaa ctcactgtat  240
ctgcaaatga acagcctgag agccgaggac acggccattt attactgtgc gcggttttat  300
ggtgacagat ggggccaggg aaccctggtc accgtctcct cagcctccac caagggccca  360
tcggtcttcc ccctggcgcc ctgctccagg agcacctccg agagcacagc cgccctgggc  420
tgcctggtca aggactactt ccccgaaccg gtgacggtgt cgtggaactc aggcgccctg  480
accagcggcg tgcacacctt cccggctgtc ctacagtcct caggactcta ctccctcagc  540
agcgtggtga ccgtgccctc cagcagcttg ggcacgaaga cctacacctg caacgtagat  600
cacaagccca gcaacaccaa ggtggacaag agagttgagt ccaaatatgg tcccccatgc  660
```

```
ccaccctgcc cagcacctga gttcctgggg ggaccatcag tcttcctgtt ccccccaaaa  720
cccaaggaca ctctcatgat ctcccggacc cctgaggtca cgtgcgtggt ggtggacgtg  780
agccaggaag accccgaggt ccagttcaac tggtacgtgg atggcgtgga ggtgcataat  840
gccaagacaa agccgcggga ggagcagttc aacagcacgt accgtgtggt cagcgtcctc  900
accgtcctgc accaggactg gctgaacggc aaggagtaca agtgcaaggt ctccaacaaa  960
ggcctcccgt cctccatcga gaaaaccatc tccaaagcca aagggcagcc ccgagagcca  1020
caggtgtaca ccctgccccc atcccaggag gagatgacca agaaccaggt cagcctgacc  1080
tgcctggtca aaggcttcta ccccagcgac atcgccgtgg agtgggagag caatgggcag  1140
ccggagaaca actacaagac cacgcctccc gtgctggact ccgacggctc cttcttcctc  1200
tacagcaggc tcaccgtgga caagagcagg tggcaggagg ggaatgtctt ctcatgctcc  1260
gtgatgcatg aggctctgca caaccactac acacagaagt ccctctccct gtctctgggt  1320
aaatga                                                             1326

SEQ ID NO: 134          moltype = AA  length = 441
FEATURE                 Location/Qualifiers
source                  1..441
                        mol_type = protein
                        organism = Homo sapiens
SEQUENCE: 134
QVQLVESGGD LVKPGGSLRL SCATSGFTFS DFYMTWIRQA PGKGLEWISY ISNSGSIVKY  60
ADSVKGRFTI SRDNAKNSLY LQMNSLRAED TAIYYCARFY GDRWGQGTLV TVSSASTKGP  120
SVFPLAPCSR STSESTAALG CLVKDYFPEP VTVSWNSGAL TSGVHTFPAV LQSSGLYSLS  180
SVVTVPSSSL GTKTYTCNVD HKPSNTKVDK RVESKYGPPC PPCPAPEFLG GPSVFLFPPK  240
PKDTLMISRT PEVTCVVVDV SQEDPEVQFN WYVDGVEVHN AKTKPREEQF NSTYRVVSVL  300
TVLHQDWLNG KEYKCKVSNK GLPSSIEKTI SKAKGQPREP QVYTLPPSQE EMTKNQVSLT  360
CLVKGFYPSD IAVEWESNGQ PENNYKTTPP VLDSDGSFFL YSRLTVDKSR WQEGNVFSCS  420
VMHEALHNHY TQKSLSLSLG K                                            441

SEQ ID NO: 135          moltype = DNA  length = 645
FEATURE                 Location/Qualifiers
source                  1..645
                        mol_type = unassigned DNA
                        organism = Homo sapiens
SEQUENCE: 135
gacatccagt tgacccagtc tccatctttc ctgtctgcat ctgtaggaga cagagtcacc  60
atcacttgct gggccagtca gggcattagc actttttag cctggtatca gcaaaagccg  120
ggtaaagccc ctaagctcct gatctatgct gcatctactt tacaaagtgg ggtcccatcg  180
cgattcagcg gcagcggatc tgggacagat ttcactctca caatcagcag cctgcagcct  240
gaagattttg caacttatca ctgtcaacaa cttaataatt acccgtggac gttcggccaa  300
gggaccaagg tggaaatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 136          moltype = AA  length = 214
FEATURE                 Location/Qualifiers
source                  1..214
                        mol_type = protein
                        organism = Homo sapiens
SEQUENCE: 136
DIQLTQSPSF LSASVGDRVT ITCWASQGIS TFLAWYQQKP GKAPKLLIYA ASTLQSGVPS  60
RFSGSGSGTD FTLTISSLQP EDFATYHCQQ LNNYPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 137          moltype = DNA  length = 342
FEATURE                 Location/Qualifiers
source                  1..342
                        mol_type = unassigned DNA
                        organism = Homo sapiens
SEQUENCE: 137
caggtgcagc tggtggagtc tgggggaggc ttggtcaagc ctggagggtc cctgagactc  60
tcctgtgaag cctctggatt caccttcaat gacttctata tgacctggat ccgccaggct  120
ccagggaagg ggctggagtg gattgcatac atttctaaga gtggtgataa aatgcgttat  180
gcagactctg tgaagggccg attcagcacc tccagggaca acgccaagaa ttcactatcc  240
ttgcaaatga atagcctgag agccgaggac acggccgtgt attattgtgc gagattctac  300
ggtgatatat ggggccaggg aaccctggtc accgtctcct ca                     342

SEQ ID NO: 138          moltype = AA  length = 114
FEATURE                 Location/Qualifiers
source                  1..114
                        mol_type = protein
                        organism = Homo sapiens
SEQUENCE: 138
QVQLVESGGG LVKPGGSLRL SCEASGFTFN DFYMTWIRQA PGKGLEWIAY ISKSGDKMRY  60
ADSVKGRFST SRDNAKNSLS LQMNSLRAED TAVYYCARFY GDIWGQGTLV TVSS        114
```

```
SEQ ID NO: 139          moltype = DNA  length = 24
FEATURE                 Location/Qualifiers
source                  1..24
                        mol_type = unassigned DNA
                        organism = Homo sapiens
SEQUENCE: 139
ggattcacct tcaatgactt ctat                                          24

SEQ ID NO: 140          moltype = AA  length = 8
FEATURE                 Location/Qualifiers
source                  1..8
                        mol_type = protein
                        organism = Homo sapiens
SEQUENCE: 140
GFTFNDFY                                                            8

SEQ ID NO: 141          moltype = DNA  length = 24
FEATURE                 Location/Qualifiers
source                  1..24
                        mol_type = unassigned DNA
                        organism = Homo sapiens
SEQUENCE: 141
atttctaaga gtggtgataa aatg                                          24

SEQ ID NO: 142          moltype = AA  length = 8
FEATURE                 Location/Qualifiers
source                  1..8
                        mol_type = protein
                        organism = Homo sapiens
SEQUENCE: 142
ISKSGDKM                                                            8

SEQ ID NO: 143          moltype = DNA  length = 21
FEATURE                 Location/Qualifiers
source                  1..21
                        mol_type = unassigned DNA
                        organism = Homo sapiens
SEQUENCE: 143
gcgagattct acggtgatat a                                             21

SEQ ID NO: 144          moltype = AA  length = 7
FEATURE                 Location/Qualifiers
source                  1..7
                        mol_type = protein
                        organism = Homo sapiens
SEQUENCE: 144
ARFYGDI                                                             7

SEQ ID NO: 145          moltype = DNA  length = 321
FEATURE                 Location/Qualifiers
source                  1..321
                        mol_type = unassigned DNA
                        organism = Homo sapiens
SEQUENCE: 145
gacatccagt tgacccagtc tccatccttc ctgtctgcat ctgtaggaga cagagtcacc  60
atcacttgct gggccagtca ggacattagc agttttttag tctggtatca gcaaaaacca  120
gggaaagccc ctaacctcct gatctatgct gcatccgctt tgcagagtgg ggtcccatca  180
aggttcagcg gcagtggatc tgggacagaa ttcactctca caatcagcag cctgcagcct  240
gaagattttg caagttatta ctgtgaacag cttaataatt atccgtggac gttcggccaa  300
gggaccaagg tggaaatcaa a                                             321

SEQ ID NO: 146          moltype = AA  length = 107
FEATURE                 Location/Qualifiers
source                  1..107
                        mol_type = protein
                        organism = Homo sapiens
SEQUENCE: 146
DIQLTQSPSF LSASVGDRVT ITCWASQDIS SFLVWYQQKP GKAPNLLIYA ASALQSGVPS  60
RFSGSGSGTE FTLTISSLQP EDFASYYCEQ LNNYPWTFGQ GTKVEIK                107

SEQ ID NO: 147          moltype = DNA  length = 18
FEATURE                 Location/Qualifiers
source                  1..18
                        mol_type = unassigned DNA
                        organism = Homo sapiens
SEQUENCE: 147
caggacatta gcagtttt                                                 18

SEQ ID NO: 148          moltype = AA  length = 6
```

```
FEATURE                Location/Qualifiers
source                 1..6
                       mol_type = protein
                       organism = Homo sapiens
SEQUENCE: 148
QDISSF                                                         6

SEQ ID NO: 149         moltype = DNA  length = 27
FEATURE                Location/Qualifiers
source                 1..27
                       mol_type = unassigned DNA
                       organism = Homo sapiens
SEQUENCE: 149
gaacagctta ataattatcc gtggacg                                  27

SEQ ID NO: 150         moltype = AA  length = 9
FEATURE                Location/Qualifiers
source                 1..9
                       mol_type = protein
                       organism = Homo sapiens
SEQUENCE: 150
EQLNNYPWT                                                      9

SEQ ID NO: 151         moltype = DNA  length = 1326
FEATURE                Location/Qualifiers
source                 1..1326
                       mol_type = unassigned DNA
                       organism = Homo sapiens
SEQUENCE: 151
caggtgcagc tggtggagtc tgggggaggc ttggtcaagc ctggagggtc cctgagactc  60
tcctgtgaag cctctggatt caccttcaat gacttctata tgacctggat ccgccaggct  120
ccagggaagg ggctggagtg gattgcatac atttctaaga gtggtgataa aatgcgttat  180
gcagactctg tgaagggccg attcagcacc tccagggaca acgccaagaa ttcactatcc  240
ttgcaaatga atagcctgag agccgaggac acggccgtgt attattgtgc gagattctac  300
ggtgatatat ggggccaggg aaccctggtc accgtctcct cagcctccac caagggccca  360
tcggtcttcc ccctggcgcc ctgctccagg agcacctccg agagcacagc cgccctgggc  420
tgcctggtca aggactactt ccccgaaccg gtgacggtgt cgtggaactc aggcgccctg  480
accagcggcg tgcacacctt cccggctgtc ctacagtcct caggactcta ctccctcagc  540
agcgtggtga ccgtgccctc cagcagcttg ggcacgaaga cctacacctg caacgtagat  600
cacaagccca gcaacaccaa ggtggacaag agagttgagt ccaaatatgg tcccccatgc  660
ccaccctgcc cagcacctga gttcctgggg ggaccatcag tcttcctgtt ccccccaaaa  720
cccaaggaca ctctcatgat ctcccggacc cctgaggtca cgtgcgtggt ggtggacgtg  780
agccaggaag accccgaggt ccagttcaac tggtacgtgg atggcgtgga ggtgcataat  840
gccaagacaa agccgcggga ggagcagttc aacagcacgt accgtgtggt cagcgtcctc  900
accgtcctgc accaggactg gctgaacggc aaggagtaca agtgcaaggt ctccaacaaa  960
ggcctcccgt cctccatcga gaaaaccatc tccaaagcca aagggcagcc ccgagagcca  1020
caggtgtaca ccctgccccc atcccaggag gagatgacca agaaccaggt cagcctgacc  1080
tgcctggtca aaggcttcta ccccagcgac atcgccgtgg agtgggagag caatgggcag  1140
ccggagaaca actacaagac cacgcctccc gtgctggact ccgacggctc cttcttcctc  1200
tacagcaggc tcaccgtgga caagagcagg tggcaggagg ggaatgtctt ctcatgctcc  1260
gtgatgcatg aggctctgca caaccactac acacagaagt ccctctccct gtctctgggt  1320
aaatga                                                         1326

SEQ ID NO: 152         moltype = AA  length = 441
FEATURE                Location/Qualifiers
source                 1..441
                       mol_type = protein
                       organism = Homo sapiens
SEQUENCE: 152
QVQLVESGGG LVKPGGSLRL SCEASGFTFN DFYMTWIRQA PGKGLEWIAY ISKSGDKMRY  60
ADSVKGRFST SRDNAKNSLS LQMNSLRAED TAVYYCARFY GDIWGQGTLV TVSSASTKGP  120
SVFPLAPCSR STSESTAALG CLVKDYFPEP VTVSWNSGAL TSGVHTFPAV LQSSGLYSLS  180
SVVTVPSSSL GTKTYTCNVD HKPSNTKVDK RVESKYGPPC PPCPAPEFLG GPSVFLFPPK  240
PKDTLMISRT PEVTCVVVDV SQEDPEVQFN WYVDGVEVHN AKTKPREEQF NSTYRVVSVL  300
TVLHQDWLNG KEYKCKVSNK GLPSSIEKTI SKAKGQPREP QVYTLPPSQE EMTKNQVSLT  360
CLVKGFYPSD IAVEWESNGQ PENNYKTTPP VLDSDGSFFL YSRLTVDKSR WQEGNVFSCS  420
VMHEALHNHY TQKSLSLSLG K                                        441

SEQ ID NO: 153         moltype = DNA  length = 645
FEATURE                Location/Qualifiers
source                 1..645
                       mol_type = unassigned DNA
                       organism = Homo sapiens
SEQUENCE: 153
gacatccagt tgacccagtc tccatccttc ctgtctgcat ctgtaggaga cagagtcacc  60
atcacttgct gggccagtca ggacattagc agtttttttag tctggtatca gcaaaaacca  120
gggaaagccc ctaacctcct gatctatgct gcatccgctt tgcagagtgg ggtcccatca  180
aggttcagcg gcagtggatc tgggacagaa ttcactctca caatcagcag cctgcagcct  240
gaagattttg caagttatta ctgtgaacag cttaataatt atccgtggac gttcggccaa  300
```

-continued

```
gggaccaagg tggaaatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 154          moltype = AA  length = 214
FEATURE                 Location/Qualifiers
source                  1..214
                        mol_type = protein
                        organism = Homo sapiens
SEQUENCE: 154
DIQLTQSPSF LSASVGDRVT ITCWASQDIS SFLVWYQQKP GKAPNLLIYA ASALQSGVPS  60
RFSGSGSGTE FTLTISSLQP EDFASYYCEQ LNNYPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 155          moltype = DNA  length = 375
FEATURE                 Location/Qualifiers
source                  1..375
                        mol_type = unassigned DNA
                        organism = Homo sapiens
SEQUENCE: 155
gaggtgcagc tggtggagtc cgggggacgc ttggtacagc ctggggggtc cctgagactc  60
tcctgtgaag cctctggatt cacgtttagt aattatggca tgacctgggt ccgccaggct  120
ccagggaagg ggctggaatg ggtctcagtt attagtggca gtgataatag aaaatactat  180
gcagagtccg tgaagggccg gttcaccatc tccagagaca attccaaaaa cacactatat  240
ctgcaaatga atagcctgag agccgaggac acggccgtct attactgtgc aaaattggga  300
tatagtcgtt cgtccaagga cttctactac ggaatggacg tctggggcca agggaccacg  360
gtcaccgtct cctca                                                   375

SEQ ID NO: 156          moltype = AA  length = 125
FEATURE                 Location/Qualifiers
source                  1..125
                        mol_type = protein
                        organism = Homo sapiens
SEQUENCE: 156
EVQLVESGGR LVQPGGSLRL SCEASGFTFS NYGMTWVRQA PGKGLEWVSV ISGSDNRKYY  60
AESVKGRFTI SRDNSKNTLY LQMNSLRAED TAVYYCAKLG YSRSSKDFYY GMDVWGQGTT  120
VTVSS                                                              125

SEQ ID NO: 157          moltype = DNA  length = 24
FEATURE                 Location/Qualifiers
source                  1..24
                        mol_type = unassigned DNA
                        organism = Homo sapiens
SEQUENCE: 157
ggattcacgt ttagtaatta tggc                                         24

SEQ ID NO: 158          moltype = AA  length = 8
FEATURE                 Location/Qualifiers
source                  1..8
                        mol_type = protein
                        organism = Homo sapiens
SEQUENCE: 158
GFTFSNYG                                                           8

SEQ ID NO: 159          moltype = DNA  length = 24
FEATURE                 Location/Qualifiers
source                  1..24
                        mol_type = unassigned DNA
                        organism = Homo sapiens
SEQUENCE: 159
attagtggca gtgataatag aaaa                                         24

SEQ ID NO: 160          moltype = AA  length = 8
FEATURE                 Location/Qualifiers
source                  1..8
                        mol_type = protein
                        organism = Homo sapiens
SEQUENCE: 160
ISGSDNRK                                                           8

SEQ ID NO: 161          moltype = DNA  length = 54
FEATURE                 Location/Qualifiers
source                  1..54
                        mol_type = unassigned DNA
                        organism = Homo sapiens
```

```
SEQUENCE: 161
gcaaaattgg gatatagtcg ttcgtccaag gacttctact acggaatgga cgtc       54

SEQ ID NO: 162          moltype = AA  length = 18
FEATURE                 Location/Qualifiers
source                  1..18
                        mol_type = protein
                        organism = Homo sapiens
SEQUENCE: 162
AKLGYSRSSK DFYYGMDV                                               18

SEQ ID NO: 163          moltype = DNA  length = 339
FEATURE                 Location/Qualifiers
source                  1..339
                        mol_type = unassigned DNA
                        organism = Homo sapiens
SEQUENCE: 163
gacatcgtga tgacccagtc tccagactcc ctggctgtgt ctctgggcga gagggccacc  60
atcaactgca agtccagcca gagtgtttta tacaattcca ataataggaa ctacttagtt  120
tggtaccagc agaaaccagg acagtctcct aagttgctca tttactgggc atctacccgg  180
gaatccgggg tccctgaccg gttcagtggc agcgggtctg ggacagattt cactctcacc  240
atcagcagcc tgcaggctga agatgtggca gtgtattact gtcagcaata ttataatgtt  300
ccgtacactt ttggccaggg gaccaagctg gagatcaaa                        339

SEQ ID NO: 164          moltype = AA  length = 113
FEATURE                 Location/Qualifiers
source                  1..113
                        mol_type = protein
                        organism = Homo sapiens
SEQUENCE: 164
DIVMTQSPDS LAVSLGERAT INCKSSQSVL YNSNNRNYLV WYQQKPGQSP KLLIYWASTR  60
ESGVPDRFSG SGSGTDFTLT ISSLQAEDVA VYYCQQYYNV PYTFGQGTKL EIK         113

SEQ ID NO: 165          moltype = DNA  length = 36
FEATURE                 Location/Qualifiers
source                  1..36
                        mol_type = unassigned DNA
                        organism = Homo sapiens
SEQUENCE: 165
cagagtgttt tatacaattc caataatagg aactac                           36

SEQ ID NO: 166          moltype = AA  length = 12
FEATURE                 Location/Qualifiers
source                  1..12
                        mol_type = protein
                        organism = Homo sapiens
SEQUENCE: 166
QSVLYNSNNR NY                                                     12

SEQ ID NO: 167          moltype = DNA  length = 27
FEATURE                 Location/Qualifiers
source                  1..27
                        mol_type = unassigned DNA
                        organism = Homo sapiens
SEQUENCE: 167
cagcaatatt ataatgttcc gtacact                                     27

SEQ ID NO: 168          moltype = AA  length = 9
FEATURE                 Location/Qualifiers
source                  1..9
                        mol_type = protein
                        organism = Homo sapiens
SEQUENCE: 168
QQYYNVPYT                                                         9

SEQ ID NO: 169          moltype = DNA  length = 1359
FEATURE                 Location/Qualifiers
source                  1..1359
                        mol_type = unassigned DNA
                        organism = Homo sapiens
SEQUENCE: 169
gaggtgcagc tggtggagtc cgggggacgc ttggtacagc ctggggggtc cctgagactc  60
tcctgtgaag cctctggatt cacgtttagt aattatggca tgacctgggt ccgccaggct  120
ccagggaagg ggctggaatg ggtctcagtt attagtggca gtgataatag aaaatactat  180
gcagagtccg tgaagggccg gttcaccatc tccagagaca attccaaaaa cacactatat  240
ctgcaaatga atagcctgag agccgaggac acggccgtct attactgtgc aaaattggga  300
tatagtcgtt cgtccaagga cttctactac ggaatggacg tctggggcca agggaccacg  360
gtcaccgtct cctcagcctc caccaagggc ccatcggtct tccccctggc gccctgctcc  420
aggagcacct ccgagagcac agccgccctg ggctgcctgg tcaaggacta cttccccgaa  480
```

```
ccggtgacgg tgtcgtggaa ctcaggcgcc ctgaccagcg gcgtgcacac cttcccggct  540
gtcctacagt cctcaggact ctactccctc agcagcgtgg tgaccgtgcc ctccagcagc  600
ttgggcacga agacctacac ctgcaacgta gatcacaagc ccagcaacac caaggtggac  660
aagagagttg agtccaaata tggtccccca tgcccaccct gcccagcacc tgagttcctg  720
gggggaccat cagtcttcct gttcccccca aaacccaagg acactctcat gatctcccgg  780
acccctgagg tcacgtgcgt ggtggtggac gtgagccagg aagaccccga ggtccagttc  840
aactggtacg tggatggcgt ggaggtgcat aatgccaaga caaagccgcg ggaggagcag  900
ttcaacagca cgtaccgtgt ggtcagcgtc ctcaccgtcc tgcaccagga ctggctgaac  960
ggcaaggagt acaagtgcaa ggtctccaac aaaggcctcc cgtcctccat cgagaaaacc  1020
atctccaaag ccaaagggca gccccgagag ccacaggtgt acaccctgcc cccatcccag  1080
gaggagatga ccaagaacca ggtcagcctg acctgcctgg tcaaaggctt ctaccccagc  1140
gacatcgccg tggagtggga gagcaatggg cagccggaga acaactacaa gaccacgcct  1200
cccgtgctgg actccgacgg ctccttcttc ctctacagca ggctcaccgt ggacaagagc  1260
aggtggcagg aggggaatgt cttctcatgc tccgtgatgc atgaggctct gcacaaccac  1320
tacacacaga agtccctctc cctgtctctg ggtaaatga                          1359

SEQ ID NO: 170         moltype = AA  length = 452
FEATURE                Location/Qualifiers
source                 1..452
                       mol_type = protein
                       organism = Homo sapiens
SEQUENCE: 170
EVQLVESGGR LVQPGGSLRL SCEASGFTFS NYGMTWVRQA PGKGLEWVSV ISGSDNRKYY  60
AESVKGRFTI SRDNSKNTLY LQMNSLRAED TAVYYCAKLG YSRSSKDFYY GMDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLMISR TPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL GK                                452

SEQ ID NO: 171         moltype = DNA  length = 663
FEATURE                Location/Qualifiers
source                 1..663
                       mol_type = unassigned DNA
                       organism = Homo sapiens
SEQUENCE: 171
gacatcgtga tgacccagtc tccagactcc ctggctgtgt ctctgggcga gagggccacc  60
atcaactgca agtccagcca gagtgtttta tacaattcca ataataggaa ctacttagtt  120
tggtaccagc agaaaccagg acagtctcct aagttgctca tttactgggc atctacccgg  180
gaatccgggg tccctgaccg gttcagtggc agcgggtctg ggacagattt cactctcacc  240
atcagcagcc tgcaggctga agatgtggca gtgtattact gtcagcaata ttataatgtt  300
ccgtacactt ttggccaggg gaccaagctg gagatcaaac gaactgtggc tgcaccatct  360
gtcttcatct tcccgccatc tgatgagcag ttgaaatctg gaactgcctc tgttgtgtgc  420
ctgctgaata acttctatcc cagagaggcc aaagtacagt ggaaggtgga taacgccctc  480
caatcgggta actcccagga gagtgtcaca gagcaggaca gcaaggacag cacctacagc  540
ctcagcagca ccctgacgct gagcaaagca gactacgaga aacacaaagt ctacgcctgc  600
gaagtcaccc atcagggcct gagctcgccc gtcacaaaga gcttcaacag gggagagtgt  660
tag                                                                663

SEQ ID NO: 172         moltype = AA  length = 220
FEATURE                Location/Qualifiers
source                 1..220
                       mol_type = protein
                       organism = Homo sapiens
SEQUENCE: 172
DIVMTQSPDS LAVSLGERAT INCKSSQSVL YNSNNRNYLV WYQQKPGQSP KLLIYWASTR  60
ESGVPDRFSG SGSGTDFTLT ISSLQAEDVA VYYCQQYYNV PYTFGQGTKL EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220

SEQ ID NO: 173         moltype = DNA  length = 348
FEATURE                Location/Qualifiers
source                 1..348
                       mol_type = unassigned DNA
                       organism = Homo sapiens
SEQUENCE: 173
gaggtgcagc tggtggagtc tgggggaggt gtggtacggc ctgggggggtc cctgagactc  60
tcctgtgcag cctctggatt cacctttgat gattatggca tgagctgggt ccgccaagct  120
ccagggaagg ggctggagtg gatctcttct attaatagga atggtggtag cgcagattat  180
gcagactctg tgaagggccg attcaccatc tccagagaca acgccaagaa ctccctcttt  240
ctgcaaatga gcagtctgag agccgaggac acggccctct atcactgtgc gagcggggag  300
tttcgctttg actactgggg ccagggaacc ctggtcaccg tctcctca               348

SEQ ID NO: 174         moltype = AA  length = 116
FEATURE                Location/Qualifiers
source                 1..116
                       mol_type = protein
                       organism = Homo sapiens
```

```
SEQUENCE: 174
EVQLVESGGG VVRPGGSLRL SCAASGFTFD DYGMSWVRQA PGKGLEWISS INRNGGSADY  60
ADSVKGRFTI SRDNAKNSLF LQMSSLRAED TALYHCASGE FRFDYWGQGT LVTVSS      116

SEQ ID NO: 175          moltype = DNA  length = 24
FEATURE                 Location/Qualifiers
source                  1..24
                        mol_type = unassigned DNA
                        organism = Homo sapiens
SEQUENCE: 175
ggattcacct ttgatgatta tggc                                        24

SEQ ID NO: 176          moltype = AA  length = 8
FEATURE                 Location/Qualifiers
source                  1..8
                        mol_type = protein
                        organism = Homo sapiens
SEQUENCE: 176
GFTFDDYG                                                          8

SEQ ID NO: 177          moltype = DNA  length = 24
FEATURE                 Location/Qualifiers
source                  1..24
                        mol_type = unassigned DNA
                        organism = Homo sapiens
SEQUENCE: 177
attaatagga atggtggtag cgca                                        24

SEQ ID NO: 178          moltype = AA  length = 8
FEATURE                 Location/Qualifiers
source                  1..8
                        mol_type = protein
                        organism = Homo sapiens
SEQUENCE: 178
INRNGGSA                                                          8

SEQ ID NO: 179          moltype = DNA  length = 27
FEATURE                 Location/Qualifiers
source                  1..27
                        mol_type = unassigned DNA
                        organism = Homo sapiens
SEQUENCE: 179
gcgagcgggg agtttcgctt tgactac                                     27

SEQ ID NO: 180          moltype = AA  length = 9
FEATURE                 Location/Qualifiers
source                  1..9
                        mol_type = protein
                        organism = Homo sapiens
SEQUENCE: 180
ASGEFRFDY                                                         9

SEQ ID NO: 181          moltype = DNA  length = 324
FEATURE                 Location/Qualifiers
source                  1..324
                        mol_type = unassigned DNA
                        organism = Homo sapiens
SEQUENCE: 181
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccgtca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                        324

SEQ ID NO: 182          moltype = AA  length = 108
FEATURE                 Location/Qualifiers
source                  1..108
                        mol_type = protein
                        organism = Homo sapiens
SEQUENCE: 182
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPPITFG QGTRLEIK              108

SEQ ID NO: 183          moltype = DNA  length = 30
FEATURE                 Location/Qualifiers
source                  1..30
                        mol_type = unassigned DNA
                        organism = Homo sapiens
```

```
SEQUENCE: 183
caacagagtt acagtacccc tccgatcacc                                   30

SEQ ID NO: 184         moltype = AA  length = 10
FEATURE                Location/Qualifiers
source                 1..10
                       mol_type = protein
                       organism = Homo sapiens
SEQUENCE: 184
QQSYSTPPIT                                                         10

SEQ ID NO: 185         moltype = DNA  length = 1332
FEATURE                Location/Qualifiers
source                 1..1332
                       mol_type = unassigned DNA
                       organism = Homo sapiens
SEQUENCE: 185
gaggtgcagc tggtggagtc tgggggaggt gtggtacggc ctgggggtc cctgagactc  60
tcctgtgcag cctctggatt cacctttgat gattatggca tgagctgggt ccgccaagct  120
ccagggaagg ggctggagtg gatctcttct attaatagga atggtggtag cgcagattat  180
gcagactctg tgaagggccg attcaccatc tccagagaca acgccaagaa ctccctcttt  240
ctgcaaatga gcagtctgag agccgaggac acggccctct atcactgtgc gagcggggag  300
tttcgctttg actactgggg ccagggaacc ctggtcaccg tctcctcagc ctccaccaag  360
ggcccatcgg tcttcccct ggcgccctgc tccaggagca cctccgagag cacagccgcc  420
ctgggctgcc tggtcaagga ctacttcccc gaaccggtga cggtgtcgtg gaactcaggc  480
gccctgacca gcggcgtgca caccttcccg gctgtcctac agtcctcagg actctactcc  540
ctcagcagcg tggtgaccgt gccctccagc agcttgggca cgaagaccta cacctgcaac  600
gtagatcaca agcccagcaa caccaaggtg gacaagagag ttgagtccaa atatggtccc  660
ccatgcccac cctgcccagc acctgagttc ctggggggac catcagtctt cctgttcccc  720
ccaaaaccca aggacactct catgatctcc cggacccctg aggtcacgtg cgtggtggtg  780
gacgtgagcc aggaagaccc cgaggtccag ttcaactggt acgtggatgg cgtggaggtg  840
cataatgcca agacaaagcc gcgggaggag cagttcaaca gcacgtaccg tgtggtcagc  900
gtcctcaccg tcctgcacca ggactggctg aacggcaagg agtacaagtg caaggtctcc  960
aacaaaggcc tcccgtcctc catcgagaaa accatctcca aagccaaagg gcagccccga  1020
gagccacagg tgtacaccct gcccccatcc caggaggaga tgaccaagaa ccaggtcagc  1080
ctgacctgcc tggtcaaagg cttctacccc agcgacatcg ccgtggagtg ggagagcaat  1140
gggcagccgg agaacaacta caagaccacg cctcccgtgc tggactccga cggctccttc  1200
ttcctctaca gcaggctcac cgtggacaag agcaggtggc aggaggggaa tgtcttctca  1260
tgctccgtga tgcatgaggc tctgcacaac cactacacac agaagtccct ctccctgtct  1320
ctgggtaaat ga                                                      1332

SEQ ID NO: 186         moltype = AA  length = 443
FEATURE                Location/Qualifiers
source                 1..443
                       mol_type = protein
                       organism = Homo sapiens
SEQUENCE: 186
EVQLVESGGG VVRPGGSLRL SCAASGFTFD DYGMSWVRQA PGKGLEWISS INRNGGSADY  60
ADSVKGRFTI SRDNAKNSLF LQMSSLRAED TALYHCASGE FRFDYWGQGT LVTVSSASTK  120
GPSVFPLAPC SRSTSESTAA LGCLVKDYFP EPVTVSWNSG ALTSGVHTFP AVLQSSGLYS  180
LSSVVTVPSS SLGTKTYTCN VDHKPSNTKV DKRVESKYGP PCPPCPAPEF LGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLPSSIEK TISKAKGQPR EPQVYTLPPS QEEMTKNQVS  360
LTCLVKGFYP SDIAVEWESN GQPENNYKTT PPVLDSDGSF FLYSRLTVDK SRWQEGNVFS  420
CSVMHEALHN HYTQKSLSLS LGK                                          443

SEQ ID NO: 187         moltype = DNA  length = 648
FEATURE                Location/Qualifiers
source                 1..648
                       mol_type = unassigned DNA
                       organism = Homo sapiens
SEQUENCE: 187
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccgtca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaacgaact gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgttag               648

SEQ ID NO: 188         moltype = AA  length = 215
FEATURE                Location/Qualifiers
source                 1..215
                       mol_type = protein
                       organism = Homo sapiens
```

```
SEQUENCE: 188
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPPITFG QGTRLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215

SEQ ID NO: 189          moltype = DNA  length = 348
FEATURE                 Location/Qualifiers
source                  1..348
                        mol_type = unassigned DNA
                        organism = Homo sapiens
SEQUENCE: 189
gaagtgcagc tggtggagtc tgggggaggc ttggtacagc ctggcaggtc cctgagactc  60
tcctgtgcag cctctggatt cacccttgaa gattatgcca tgcactgggt ccggcaagct  120
ccagggaagg gcctggaatg ggtctcaggt attagttgga atagaggtag cacaggctat  180
gcggactctg tgaagggccg attcaccatc tcaagagaca acgccaagaa ctccctgtat  240
ctgcaaatga ccagtctgag agctgaggac acggccttgt attactgtgc aaaaggattc  300
tacagtatgg acgtctgggg ccaagggacc acggtcaccg tctcctca              348

SEQ ID NO: 190          moltype = AA  length = 116
FEATURE                 Location/Qualifiers
source                  1..116
                        mol_type = protein
                        organism = Homo sapiens
SEQUENCE: 190
EVQLVESGGG LVQPGRSLRL SCAASGFTLE DYAMHWVRQA PGKGLEWVSG ISWNRGSTGY  60
ADSVKGRFTI SRDNAKNSLY LQMTSLRAED TALYYCAKGF YSMDVWGQGT TVTVSS      116

SEQ ID NO: 191          moltype = DNA  length = 24
FEATURE                 Location/Qualifiers
source                  1..24
                        mol_type = unassigned DNA
                        organism = Homo sapiens
SEQUENCE: 191
ggattcaccc ttgaagatta tgcc                                        24

SEQ ID NO: 192          moltype = AA  length = 8
FEATURE                 Location/Qualifiers
source                  1..8
                        mol_type = protein
                        organism = Homo sapiens
SEQUENCE: 192
GFTLEDYA                                                          8

SEQ ID NO: 193          moltype = DNA  length = 24
FEATURE                 Location/Qualifiers
source                  1..24
                        mol_type = unassigned DNA
                        organism = Homo sapiens
SEQUENCE: 193
attagttgga atagaggtag caca                                        24

SEQ ID NO: 194          moltype = AA  length = 8
FEATURE                 Location/Qualifiers
source                  1..8
                        mol_type = protein
                        organism = Homo sapiens
SEQUENCE: 194
ISWNRGST                                                          8

SEQ ID NO: 195          moltype = DNA  length = 27
FEATURE                 Location/Qualifiers
source                  1..27
                        mol_type = unassigned DNA
                        organism = Homo sapiens
SEQUENCE: 195
gcaaaaggat tctacagtat ggacgtc                                     27

SEQ ID NO: 196          moltype = AA  length = 9
FEATURE                 Location/Qualifiers
source                  1..9
                        mol_type = protein
                        organism = Homo sapiens
SEQUENCE: 196
AKGFYSMDV                                                         9

SEQ ID NO: 197          moltype = DNA  length = 1332
FEATURE                 Location/Qualifiers
source                  1..1332
```

```
                        mol_type = unassigned DNA
                        organism = Homo sapiens
SEQUENCE: 197
gaagtgcagc tggtggagtc tgggggaggc ttggtacagc ctggcaggtc cctgagactc  60
tcctgtgcag cctctggatt cacccttgaa gattatgcca tgcactgggt ccggcaagct  120
ccagggaagg gcctggaatg ggtctcaggt attagttgga atagaggtag cacaggctat  180
gcggactctg tgaagggccg attcaccatc tcaagagaca acgccaagaa ctccctgtat  240
ctgcaaatga ccagtctgag agctgaggac acggccttgt attactgtgc aaaaggattc  300
tacagtatgg acgtctgggg ccaagggacc acggtcaccg tctcctcagc ctccaccaag  360
ggcccatcgg tcttccccct ggcgccctgc tccaggagca cctccgagag cacagccgcc  420
ctgggctgcc tggtcaagga ctacttcccc gaaccggtga cggtgtcgtg gaactcaggc  480
gccctgacca gcggcgtgca caccttcccg gctgtcctac agtcctcagg actctactcc  540
ctcagcagcg tggtgaccgt gccctccagc agcttgggca cgaagaccta cacctgcaac  600
gtagatcaca agcccagcaa caccaaggtg gacaagagag ttgagtccaa atatggtccc  660
ccatgcccac cctgcccagc acctgagttc ctggggggac catcagtctt cctgttcccc  720
ccaaaaccca aggacactct catgatctcc cggacccctg aggtcacgtg cgtggtggtg  780
gacgtgagcc aggaagaccc cgaggtccag ttcaactggt acgtggatgg cgtggaggtg  840
cataatgcca agacaaagcc gcgggaggag cagttcaaca gcacgtaccg tgtggtcagc  900
gtcctcaccg tcctgcacca ggactggctg aacggcaagg agtacaagtg caaggtctcc  960
aacaaaggcc tcccgtcctc catcgagaaa accatctcca aagccaaagg gcagccccga  1020
gagccacagg tgtacaccct gcccccatcc caggaggaga tgaccaagaa ccaggtcagc  1080
ctgacctgcc tggtcaaagg cttctacccc agcgacatcg ccgtggagtg ggagagcaat  1140
gggcagccgg agaacaacta caagaccacg cctcccgtgc tggactccga cggctccttc  1200
ttcctctaca gcaggctcac cgtggacaag agcaggtggc aggaggggaa tgtcttctca  1260
tgctccgtga tgcatgaggc tctgcacaac cactacacac agaagtccct ctccctgtct  1320
ctgggtaaat ga                                                     1332

SEQ ID NO: 198          moltype = AA  length = 443
FEATURE                 Location/Qualifiers
source                  1..443
                        mol_type = protein
                        organism = Homo sapiens
SEQUENCE: 198
EVQLVESGGG LVQPGRSLRL SCAASGFTLE DYAMHWVRQA PGKGLEWVSG ISWNRGSTGY  60
ADSVKGRFTI SRDNAKNSLY LQMTSLRAED TALYYCAKGF YSMDVWGQGT TVTVSSASTK  120
GPSVFPLAPC SRSTSESTAA LGCLVKDYFP EPVTVSWNSG ALTSGVHTFP AVLQSSGLYS  180
LSSVVTVPSS SLGTKTYTCN VDHKPSNTKV DKRVESKYGP PCPPCPAPEF LGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLPSSIEK TISKAKGQPR EPQVYTLPPS QEEMTKNQVS  360
LTCLVKGFYP SDIAVEWESN GQPENNYKTT PPVLDSDGSF FLYSRLTVDK SRWQEGNVFS  420
CSVMHEALHN HYTQKSLSLS LGK                                         443

SEQ ID NO: 199          moltype = DNA  length = 363
FEATURE                 Location/Qualifiers
source                  1..363
                        mol_type = unassigned DNA
                        organism = Homo sapiens
SEQUENCE: 199
caggtacagc tgcagcagtc aggtccagga ctggtgaagc cctcgcagac cctctcactc  60
acctgtgcca tctccggtga cagtgtctct agcaacattg ctgcttggaa ctggatcagg  120
ctgtccccat cgagaggcct tgagtggctg ggaaggacat tcttcaggtc cacgtggttt  180
tatgattatt cactatctgt gaaaggtcgc ataaccatca acccagacac atccaagaac  240
cagttctccc tgcacctgaa ctctgtgact cccgaggacg cggctgtgta ttattgtgca  300
agaacggggc gacggtggtc tcttgactac tggggccagg gaaccctggt caccgtctcc  360
tca                                                               363

SEQ ID NO: 200          moltype = AA  length = 121
FEATURE                 Location/Qualifiers
source                  1..121
                        mol_type = protein
                        organism = Homo sapiens
SEQUENCE: 200
QVQLQQSGPG LVKPSQTLSL TCAISGDSVS SNIAAWNWIR LSPSRGLEWL GRTFFRSTWF  60
YDYSLSVKGR ITINPDTSKN QFSLHLNSVT PEDAAVYYCA RTGRRWSLDY WGQGTLVTVS  120
S                                                                 121

SEQ ID NO: 201          moltype = DNA  length = 30
FEATURE                 Location/Qualifiers
source                  1..30
                        mol_type = unassigned DNA
                        organism = Homo sapiens
SEQUENCE: 201
ggtgacagtg tctctagcaa cattgctgct                                  30

SEQ ID NO: 202          moltype = AA  length = 10
FEATURE                 Location/Qualifiers
source                  1..10
                        mol_type = protein
                        organism = Homo sapiens
```

```
SEQUENCE: 202
GDSVSSNIAA                                                  10

SEQ ID NO: 203          moltype = DNA  length = 27
FEATURE                 Location/Qualifiers
source                  1..27
                        mol_type = unassigned DNA
                        organism = Homo sapiens
SEQUENCE: 203
acattcttca ggtccacgtg gttttat                               27

SEQ ID NO: 204          moltype = AA  length = 9
FEATURE                 Location/Qualifiers
source                  1..9
                        mol_type = protein
                        organism = Homo sapiens
SEQUENCE: 204
TFFRSTWFY                                                   9

SEQ ID NO: 205          moltype = DNA  length = 33
FEATURE                 Location/Qualifiers
source                  1..33
                        mol_type = unassigned DNA
                        organism = Homo sapiens
SEQUENCE: 205
gcaagaacgg ggcgacggtg gtctcttgac tac                        33

SEQ ID NO: 206          moltype = AA  length = 11
FEATURE                 Location/Qualifiers
source                  1..11
                        mol_type = protein
                        organism = Homo sapiens
SEQUENCE: 206
ARTGRRWSLD Y                                                11

SEQ ID NO: 207          moltype = DNA  length = 1347
FEATURE                 Location/Qualifiers
source                  1..1347
                        mol_type = unassigned DNA
                        organism = Homo sapiens
SEQUENCE: 207
caggtacagc tgcagcagtc aggtccagga ctggtgaagc cctcgcagac cctctcactc  60
acctgtgcca tctccggtga cagtgtctct agcaacattg ctgcttggaa ctggatcagg  120
ctgtccccat cgagaggcct tgagtggctg ggaaggacat tcttcaggtc cacgtggttt  180
tatgattatt cactatctgt gaaaggtcgc ataaccatca acccagacac atccaagaac  240
cagttctccc tgcacctgaa ctctgtgact cccgaggacg cggctgtgta ttattgtgca  300
agaacggggc gacggtggtc tcttgactac tggggccagg gaaccctggt caccgtctcc  360
tcagcctcca ccaagggccc atcggtcttc cccctggcgc cctgctccag gagcacctcc  420
gagagcacag ccgccctggg ctgcctggtc aaggactact tccccgaacc ggtgacggtg  480
tcgtggaact caggcgccct gaccagcggc gtgcacacct tcccggctgt cctacagtcc  540
tcaggactct actccctcag cagcgtggtg accgtgccct ccagcagctt gggcacgaag  600
acctacacct gcaacgtaga tcacaagccc agcaacacca aggtggacaa gagagttgag  660
tccaaatatg gtcccccatg cccaccctgc ccagcacctg agttcctggg gggaccatca  720
gtcttcctgt tccccccaaa acccaaggac actctcatga tctcccggac ccctgaggtc  780
acgtgcgtgg tggtggacgt gagccaggaa gaccccgagg tccagttcaa ctggtacgtg  840
gatggcgtgg aggtgcataa tgccaagaca aagccgcggg aggagcagtt caacagcacg  900
taccgtgtgg tcagcgtcct caccgtcctg caccaggact ggctgaacgg caaggagtac  960
aagtgcaagg tctccaacaa aggcctcccg tcctccatcg agaaaaccat ctccaaagcc  1020
aaagggcagc cccgagagcc acaggtgtac accctgcccc catcccagga ggagatgacc  1080
aagaaccagg tcagcctgac ctgcctggtc aaaggcttct accccagcga catcgccgtg  1140
gagtgggaga gcaatgggca gccggagaac aactacaaga ccacgcctcc cgtgctggac  1200
tccgacggct ccttcttcct ctacagcagg ctcaccgtgg acaagagcag gtggcaggag  1260
gggaatgtct tctcatgctc cgtgatgcat gaggctctgc acaaccacta cacacagaag  1320
tccctctccc tgtctctggg taaatga                               1347

SEQ ID NO: 208          moltype = AA  length = 448
FEATURE                 Location/Qualifiers
source                  1..448
                        mol_type = protein
                        organism = Homo sapiens
SEQUENCE: 208
QVQLQQSGPG LVKPSQTLSL TCAISGDSVS SNIAAWNWIR LSPSRGLEWL GRTFFRSTWF  60
YDYSLSVKGR ITINPDTSKN QFSLHLNSVT PEDAAVYYCA RTGRRWSLDY WGQGTLVTVS  120
SASTKGPSVF PLAPCSRSTS ESTAALGCLV KDYFPEPVTV SWNSGALTSG VHTFPAVLQS  180
SGLYSLSSVV TVPSSSLGTK TYTCNVDHKP SNTKVDKRVE SKYGPPCPPC PAPEFLGGPS  240
VFLFPPKPKD TLMISRTPEV TCVVVDVSQE DPEVQFNWYV DGVEVHNAKT KPREEQFNST  300
YRVVSVLTVL HQDWLNGKEY KCKVSNKGLP SSIEKTISKA KGQPREPQVY TLPPSQEEMT  360
KNQVSLTCLV KGFYPSDIAV EWESNGQPEN NYKTTPPVLD SDGSFFLYSR LTVDKSRWQE  420
GNVFSCSVMH EALHNHYTQK SLSLSLGK                              448
```

```
SEQ ID NO: 209          moltype = DNA  length = 348
FEATURE                 Location/Qualifiers
source                  1..348
                        mol_type = unassigned DNA
                        organism = Homo sapiens
SEQUENCE: 209
gaggtgcagc tggtggagtc tggggggaggt gtggtacggc ctgggggggtc cctgagactc  60
tcctgtgcaa cctctggatt cacctttgat gattatggca tgagctgggt ccgccaagtt  120
ccagggaagg ggctggagtg ggtctctagt gttaatagga atggtggtac cacagattat  180
gcagactctg tgaagggccg attcaccatc tccagagaca atgccaagag gtcccttttt  240
ctgcaaatga atagtctgag agccgaagac acggccttgt atcactgtgc gacaggggaa  300
cttttctttg actattgggg ccagggaacc ctggtcaccg tctcctca              348

SEQ ID NO: 210          moltype = AA  length = 116
FEATURE                 Location/Qualifiers
source                  1..116
                        mol_type = protein
                        organism = Homo sapiens
SEQUENCE: 210
EVQLVESGGG VVRPGGSLRL SCATSGFTFD DYGMSWVRQV PGKGLEWVSS VNRNGGTTDY  60
ADSVKGRFTI SRDNAKRSLF LQMNSLRAED TALYHCATGE LFFDYWGQGT LVTVSS      116

SEQ ID NO: 211          moltype = DNA  length = 24
FEATURE                 Location/Qualifiers
source                  1..24
                        mol_type = unassigned DNA
                        organism = Homo sapiens
SEQUENCE: 211
gttaatagga atggtggtac caca                                        24

SEQ ID NO: 212          moltype = AA  length = 8
FEATURE                 Location/Qualifiers
source                  1..8
                        mol_type = protein
                        organism = Homo sapiens
SEQUENCE: 212
VNRNGGTT                                                          8

SEQ ID NO: 213          moltype = DNA  length = 27
FEATURE                 Location/Qualifiers
source                  1..27
                        mol_type = unassigned DNA
                        organism = Homo sapiens
SEQUENCE: 213
gcgacagggg aacttttctt tgactat                                     27

SEQ ID NO: 214          moltype = AA  length = 9
FEATURE                 Location/Qualifiers
source                  1..9
                        mol_type = protein
                        organism = Homo sapiens
SEQUENCE: 214
ATGELFFDY                                                         9

SEQ ID NO: 215          moltype = DNA  length = 1332
FEATURE                 Location/Qualifiers
source                  1..1332
                        mol_type = unassigned DNA
                        organism = Homo sapiens
SEQUENCE: 215
gaggtgcagc tggtggagtc tggggggaggt gtggtacggc ctgggggggtc cctgagactc  60
tcctgtgcaa cctctggatt cacctttgat gattatggca tgagctgggt ccgccaagtt  120
ccagggaagg ggctggagtg ggtctctagt gttaatagga atggtggtac cacagattat  180
gcagactctg tgaagggccg attcaccatc tccagagaca atgccaagag gtcccttttt  240
ctgcaaatga atagtctgag agccgaagac acggccttgt atcactgtgc gacaggggaa  300
cttttctttg actattgggg ccagggaacc ctggtcaccg tctcctcagc ctccaccaag  360
ggcccatcgg tcttccccct ggcgccctgc tccaggagca cctccgagag cacagccgcc  420
ctgggctgcc tggtcaagga ctacttcccc gaaccggtga cggtgtcgtg gaactcaggc  480
gccctgacca gcggcgtgca caccttcccg gctgtcctac agtcctcagg actctactcc  540
ctcagcagcg tggtgaccgt gccctccagc agcttgggca cgaagaccta cacctgcaac  600
gtagatcaca agcccagcaa caccaaggtg gacaagagag ttgagtccaa atatggtccc  660
ccatgcccac cctgcccagc acctgagttc ctggggggac catcagtctt cctgttcccc  720
ccaaaaccca aggacactct catgatctcc cggacccctg aggtcacgtg cgtggtggtg  780
gacgtgagcc aggaagaccc cgaggtccag ttcaactggt acgtggatgg cgtggaggtg  840
cataatgcca agacaaagcc gcgggaggag cagttcaaca gcacgtaccg tgtggtcagc  900
gtcctcaccg tcctgcacca ggactggctg aacggcaagg agtacaagtg caaggtctcc  960
aacaaaggcc tcccgtcctc catcgagaaa accatctcca aagccaaagg gcagccccga  1020
gagccacagg tgtacaccct gcccccatcc caggaggaga tgaccaagaa ccaggtcagc  1080
```

```
ctgacctgcc tggtcaaagg cttctacccc agcgacatcg ccgtggagtg ggagagcaat  1140
gggcagccgg agaacaacta caagaccacg cctcccgtgc tggactccga cggctccttc  1200
ttcctctaca gcaggctcac cgtggacaag agcaggtggc aggaggggaa tgtcttctca  1260
tgctccgtga tgcatgaggc tctgcacaac cactacacac agaagtccct ctccctgtct  1320
ctgggtaaat ga                                                      1332

SEQ ID NO: 216          moltype = AA  length = 443
FEATURE                 Location/Qualifiers
source                  1..443
                        mol_type = protein
                        organism = Homo sapiens
SEQUENCE: 216
EVQLVESGGG VVRPGGSLRL SCATSGFTFD DYGMSWVRQV PGKGLEWVSS VNRNGGTTDY  60
ADSVKGRFTI SRDNAKRSLF LQMNSLRAED TALYHCATGE LFFDYWGQGT LVTVSSASTK  120
GPSVFPLAPC SRSTSESTAA LGCLVKDYFP EPVTVSWNSG ALTSGVHTFP AVLQSSGLYS  180
LSSVVTVPSS SLGTKTYTCN VDHKPSNTKV DKRVESKYGP PCPPCPAPEF LGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLPSSIEK TISKAKGQPR EPQVYTLPPS QEEMTKNQVS  360
LTCLVKGFYP SDIAVEWESN GQPENNYKTT PPVLDSDGSF FLYSRLTVDK SRWQEGNVFS  420
CSVMHEALHN HYTQKSLSLS LGK                                          443

SEQ ID NO: 217          moltype = DNA  length = 357
FEATURE                 Location/Qualifiers
source                  1..357
                        mol_type = unassigned DNA
                        organism = Homo sapiens
SEQUENCE: 217
caggtccagc tggtacagtc tggggctgag gtgaagaagc ctggggcctc agtgaaggtc  60
tcctgcaagg cttctggata caccttcacc ggccactata tgcactgggt gcgacaggcc  120
cctggacaag ggcttgagtg gatgggatgg atctaccctc acagtggtca cacaaattat  180
gcaaagaggt ttcagggcag ggtcaccatg accagggaca cgtccatcac tacagcctac  240
atggagctga tcaggctgag atctgacgac acggccgtgt attactgtgc gagaaggagt  300
gggaggtcct ggtatttcga tctgtggggc cgtggcaccc tggtcactgt ctcctca    357

SEQ ID NO: 218          moltype = AA  length = 119
FEATURE                 Location/Qualifiers
source                  1..119
                        mol_type = protein
                        organism = Homo sapiens
SEQUENCE: 218
QVQLVQSGAE VKKPGASVKV SCKASGYTFT GHYMHWVRQA PGQGLEWMGW IYPHSGHTNY  60
AKRFQGRVTM TRDTSITTAY MELIRLRSDD TAVYYCARRS GRSWYFDLWG RGTLVTVSS   119

SEQ ID NO: 219          moltype = DNA  length = 24
FEATURE                 Location/Qualifiers
source                  1..24
                        mol_type = unassigned DNA
                        organism = Homo sapiens
SEQUENCE: 219
ggatacacct tcaccggcca ctat                                         24

SEQ ID NO: 220          moltype = AA  length = 8
FEATURE                 Location/Qualifiers
source                  1..8
                        mol_type = protein
                        organism = Homo sapiens
SEQUENCE: 220
GYTFTGHY                                                           8

SEQ ID NO: 221          moltype = DNA  length = 24
FEATURE                 Location/Qualifiers
source                  1..24
                        mol_type = unassigned DNA
                        organism = Homo sapiens
SEQUENCE: 221
atctaccctc acagtggtca caca                                         24

SEQ ID NO: 222          moltype = AA  length = 8
FEATURE                 Location/Qualifiers
source                  1..8
                        mol_type = protein
                        organism = Homo sapiens
SEQUENCE: 222
IYPHSGHT                                                           8

SEQ ID NO: 223          moltype = DNA  length = 36
FEATURE                 Location/Qualifiers
source                  1..36
                        mol_type = unassigned DNA
```

```
                        organism = Homo sapiens
SEQUENCE: 223
gcgagaagga gtgggaggtc ctggtatttc gatctg                         36

SEQ ID NO: 224          moltype = AA  length = 12
FEATURE                 Location/Qualifiers
source                  1..12
                        mol_type = protein
                        organism = Homo sapiens
SEQUENCE: 224
ARRSGRSWYF DL                                                   12

SEQ ID NO: 225          moltype = DNA  length = 324
FEATURE                 Location/Qualifiers
source                  1..324
                        mol_type = unassigned DNA
                        organism = Homo sapiens
SEQUENCE: 225
gaaatagttt tgacacagag tcccggcaca ctgtcactct ctcccgggga aagagccacc  60
ttgtcatgta gagcaagtca gtcagtctct agctcttatc tcgcctggta ccagcagaag  120
ccgggacagg cccctagact gctgatctac ggggcaagtt ccagggccac cggaatcccc  180
gaccggttca gtggaagcgg aagcggaacc gatttttactt tgacgatttc tagactggag  240
ccagaggatt tcgccgttta ctattgtcaa cagtacggaa gcagcccgtg gacgtttggc  300
cagggcacga aggtagaaat caag                                      324

SEQ ID NO: 226          moltype = AA  length = 108
FEATURE                 Location/Qualifiers
source                  1..108
                        mol_type = protein
                        organism = Homo sapiens
SEQUENCE: 226
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPWTFG QGTKVEIK            108

SEQ ID NO: 227          moltype = DNA  length = 21
FEATURE                 Location/Qualifiers
source                  1..21
                        mol_type = unassigned DNA
                        organism = Homo sapiens
SEQUENCE: 227
cagtcagtct ctagctctta t                                         21

SEQ ID NO: 228          moltype = AA  length = 7
FEATURE                 Location/Qualifiers
source                  1..7
                        mol_type = protein
                        organism = Homo sapiens
SEQUENCE: 228
QSVSSSY                                                         7

SEQ ID NO: 229          moltype =   length =
SEQUENCE: 229
000

SEQ ID NO: 230          moltype =   length =
SEQUENCE: 230
000

SEQ ID NO: 231          moltype = DNA  length = 27
FEATURE                 Location/Qualifiers
source                  1..27
                        mol_type = unassigned DNA
                        organism = Homo sapiens
SEQUENCE: 231
caacagtacg gaagcagccc gtggacg                                   27

SEQ ID NO: 232          moltype = AA  length = 9
FEATURE                 Location/Qualifiers
source                  1..9
                        mol_type = protein
                        organism = Homo sapiens
SEQUENCE: 232
QQYGSSPWT                                                       9

SEQ ID NO: 233          moltype = DNA  length = 1341
FEATURE                 Location/Qualifiers
source                  1..1341
                        mol_type = unassigned DNA
                        organism = Homo sapiens
```

```
SEQUENCE: 233
caggtccagc tggtacagtc tggggctgag gtgaagaagc ctggggcctc agtgaaggtc  60
tcctgcaagg cttctggata caccttcacc ggccactata tgcactgggt gcgacaggcc  120
cctggacaag ggcttgagtg gatgggatgg atctaccctc acagtggtca cacaaattat  180
gcaaagaggt ttcagggcag ggtcaccatg accagggaca cgtccatcac tacagcctac  240
atggagctga tcaggctgag atctgacgac acggccgtgt attactgtgc gagaaggagt  300
gggaggtcct ggtatttcga tctgtggggc cgtggcaccc tggtcactgt ctcctcagcc  360
tccaccaagg gcccatcggt cttccccctg gcgccctgct ccaggagcac ctccgagagc  420
acagccgccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac gaagacctac  600
acctgcaacg tagatcacaa gcccagcaac accaaggtgg acaagagagt tgagtccaaa  660
tatggtcccc catgcccacc ctgcccagca cctgagttcc tggggggacc atcagtcttc  720
ctgttccccc caaaacccaa ggacactctc atgatctccc ggacccctga ggtcacgtgc  780
gtggtggtgg acgtgagcca ggaagacccc gaggtccagt tcaactggta cgtggatggc  840
gtggaggtgc ataatgccaa gacaaagccg cgggaggagc agttcaacag cacgtaccgt  900
gtggtcagcg tcctcaccgt cctgcaccag gactggctga acggcaagga gtacaagtgc  960
aaggtctcca acaaaggcct cccgtcctcc atcgagaaaa ccatctccaa agccaaaggg  1020
cagccccgag agccacaggt gtacaccctg cccccatccc aggaggagat gaccaagaac  1080
caggtcagcc tgacctgcct ggtcaaaggc ttctacccca gcgacatcgc cgtggagtgg  1140
gagagcaatg ggcagccgga gaacaactac aagaccacgc ctcccgtgct ggactccgac  1200
ggctccttct tcctctacag caggctcacc gtggacaaga gcaggtggca ggaggggaat  1260
gtcttctcat gctccgtgat gcatgaggct ctgcacaacc actacacaca gaagtccctc  1320
tccctgtctc tgggtaaatg a                                             1341

SEQ ID NO: 234          moltype = AA  length = 446
FEATURE                 Location/Qualifiers
source                  1..446
                        mol_type = protein
                        organism = Homo sapiens
SEQUENCE: 234
QVQLVQSGAE VKKPGASVKV SCKASGYTFT GHYMHWVRQA PGQGLEWMGW IYPHSGHTNY  60
AKRFQGRVTM TRDTSITTAY MELIRLRSDD TAVYYCARRS GRSWYFDLWG RGTLVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPPCPA PEFLGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGK                                        446

SEQ ID NO: 235          moltype = DNA  length = 648
FEATURE                 Location/Qualifiers
source                  1..648
                        mol_type = unassigned DNA
                        organism = Homo sapiens
SEQUENCE: 235
gaaatagttt tgacacagag tcccggcaca ctgtcactct ctcccgggga aagagccacc  60
ttgtcatgta gagcaagtca gtcagtctct agctcttatc tcgcctggta ccagcagaag  120
ccgggacagg cccctagact gctgatctac ggggcaagtt ccagggccac cggaatcccc  180
gaccggttca gtggaagcgg aagcggaacc gattttactt tgacgatttc tagactggag  240
ccagaggatt tcgccgttta ctattgtcaa cagtacggaa gcagcccgtg gacgtttggc  300
cagggcacga aggtagaaat caagcgaact gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgttag                648

SEQ ID NO: 236          moltype = AA  length = 215
FEATURE                 Location/Qualifiers
source                  1..215
                        mol_type = protein
                        organism = Homo sapiens
SEQUENCE: 236
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                               215

SEQ ID NO: 237          moltype = DNA  length = 351
FEATURE                 Location/Qualifiers
source                  1..351
                        mol_type = unassigned DNA
                        organism = Homo sapiens
SEQUENCE: 237
gaggtgcagc tggtggagtc tgggggaggg ttggtacagc ctggggggtc cctgggactc  60
tcctgtgcag cctctggatt cacctttagc aactatgcca tgagctgggt ccgccaggct  120
ccagggaagg ggctggagtg ggtctcagct gttagtggtg gtggtggtgg cacatactac  180
gcagactccg tgaagggccg gttcaccatc tccagagaca attccaagaa cacggttctt  240
```

```
ctgcaaatga acagcctgag agccgaggac acggccgtat attactgtgc gagaggtcgg  300
actgggggcc ttgactactg gggcccggga accctggtca ccgtctcctc a           351

SEQ ID NO: 238          moltype = AA  length = 117
FEATURE                 Location/Qualifiers
source                  1..117
                        mol_type = protein
                        organism = Homo sapiens
SEQUENCE: 238
EVQLVESGGG LVQPGGSLGL SCAASGFTFS NYAMSWVRQA PGKGLEWVSA VSGGGGGTYY  60
ADSVKGRFTI SRDNSKNTVL LQMNSLRAED TAVYYCARGR TGGLDYWGPG TLVTVSS     117

SEQ ID NO: 239          moltype = DNA  length = 24
FEATURE                 Location/Qualifiers
source                  1..24
                        mol_type = unassigned DNA
                        organism = Homo sapiens
SEQUENCE: 239
ggattcacct ttagcaacta tgcc                                         24

SEQ ID NO: 240          moltype = AA  length = 8
FEATURE                 Location/Qualifiers
source                  1..8
                        mol_type = protein
                        organism = Homo sapiens
SEQUENCE: 240
GFTFSNYA                                                           8

SEQ ID NO: 241          moltype = DNA  length = 24
FEATURE                 Location/Qualifiers
source                  1..24
                        mol_type = unassigned DNA
                        organism = Homo sapiens
SEQUENCE: 241
gttagtggtg gtggtggtgg caca                                         24

SEQ ID NO: 242          moltype = AA  length = 8
FEATURE                 Location/Qualifiers
source                  1..8
                        mol_type = protein
                        organism = Homo sapiens
SEQUENCE: 242
VSGGGGGT                                                           8

SEQ ID NO: 243          moltype = DNA  length = 30
FEATURE                 Location/Qualifiers
source                  1..30
                        mol_type = unassigned DNA
                        organism = Homo sapiens
SEQUENCE: 243
gcgagaggtc ggactggggg ccttgactac                                   30

SEQ ID NO: 244          moltype = AA  length = 10
FEATURE                 Location/Qualifiers
source                  1..10
                        mol_type = protein
                        organism = Homo sapiens
SEQUENCE: 244
ARGRTGGLDY                                                         10

SEQ ID NO: 245          moltype = DNA  length = 336
FEATURE                 Location/Qualifiers
source                  1..336
                        mol_type = unassigned DNA
                        organism = Homo sapiens
SEQUENCE: 245
gatgttgtga tgactcagtc tcctctctcc ctgcccgtca tctttggaca gccggcctcc  60
atctcctgca ggtcaagtca aagcctcgta gacagtgatg gaaacaccta cttgaattgg  120
cttcagcaga ggccaggcca atctccaagg cgcctaattt atgaggtttc taaccgggac  180
tctggggtcc cagacagatt cagcggcagt gggtcaggca ctgatttcac actgacaatc  240
agcagggtgg aggctgagga tgttggcatt tattactgca tgcaaggtac gcgctggcct  300
cctactttcg gcggagggac caaggtggag atcaaa                            336

SEQ ID NO: 246          moltype = AA  length = 112
FEATURE                 Location/Qualifiers
source                  1..112
                        mol_type = protein
                        organism = Homo sapiens
SEQUENCE: 246
```

```
DVVMTQSPLS LPVIFGQPAS ISCRSSQSLV DSDGNTYLNW LQQRPGQSPR RLIYEVSNRD  60
SGVPDRFSGS GSGTDFTLTI SRVEAEDVGI YYCMQGTRWP PTFGGGTKVE IK          112

SEQ ID NO: 247         moltype = DNA  length = 33
FEATURE                Location/Qualifiers
source                 1..33
                       mol_type = unassigned DNA
                       organism = Homo sapiens
SEQUENCE: 247
caaagcctcg tagacagtga tggaaacacc tac                               33

SEQ ID NO: 248         moltype = AA  length = 11
FEATURE                Location/Qualifiers
source                 1..11
                       mol_type = protein
                       organism = Homo sapiens
SEQUENCE: 248
QSLVDSDGNT Y                                                       11

SEQ ID NO: 249         moltype =   length =
SEQUENCE: 249
000

SEQ ID NO: 250         moltype =   length =
SEQUENCE: 250
000

SEQ ID NO: 251         moltype = DNA  length = 27
FEATURE                Location/Qualifiers
source                 1..27
                       mol_type = unassigned DNA
                       organism = Homo sapiens
SEQUENCE: 251
atgcaaggta cgcgctggcc tcctact                                      27

SEQ ID NO: 252         moltype = AA  length = 9
FEATURE                Location/Qualifiers
source                 1..9
                       mol_type = protein
                       organism = Homo sapiens
SEQUENCE: 252
MQGTRWPPT                                                          9

SEQ ID NO: 253         moltype = DNA  length = 1335
FEATURE                Location/Qualifiers
source                 1..1335
                       mol_type = unassigned DNA
                       organism = Homo sapiens
SEQUENCE: 253
gaggtgcagc tggtggagtc tgggggaggg ttggtacagc ctggggggtc cctgggactc  60
tcctgtgcag cctctggatt cacctttagc aactatgcca tgagctgggt ccgccaggct  120
ccagggaagg ggctggagtg ggtctcagct gttagtggtg gtggtggtgg cacatactac  180
gcagactccg tgaagggccg gttcaccatc tccagagaca attccaagaa cacggttctt  240
ctgcaaatga acagcctgag agccgaggac acggccgtat attactgtgc gagaggtcgg  300
actgggggcc ttgactactg gggcccggga accctggtca ccgtctcctc agcctccacc  360
aagggcccat cggtcttccc cctggcgccc tgctccagga gcacctccga gagcacagcc  420
gccctgggct gcctggtcaa ggactacttc cccgaaccgg tgacggtgtc gtggaactca  480
ggcgccctga ccagcggcgt gcacaccttc ccggctgtcc tacagtcctc aggactctac  540
tccctcagca gcgtggtgac cgtgccctcc agcagcttgg gcacgaagac ctacacctgc  600
aacgtagatc acaagcccag caacaccaag gtggacaaga gagttgagtc caaatatggt  660
cccccatgcc caccctgccc agcacctgag ttcctggggg gaccatcagt cttcctgttc  720
cccccaaaac ccaaggacac tctcatgatc tcccggaccc ctgaggtcac gtgcgtggtg  780
gtggacgtga gccaggaaga ccccgaggtc cagttcaact ggtacgtgga tggcgtggag  840
gtgcataatg ccaagacaaa gccgcgggag gagcagttca acagcacgta ccgtgtggtc  900
agcgtcctca ccgtcctgca ccaggactgg ctgaacggca aggagtacaa gtgcaaggtc  960
tccaacaaag gcctcccgtc ctccatcgag aaaaccatct ccaaagccaa agggcagccc  1020
cgagagccac aggtgtacac cctgccccca tcccaggagg agatgaccaa gaaccaggtc  1080
agcctgacct gcctggtcaa aggcttctac cccagcgaca tcgccgtgga gtgggagagc  1140
aatgggcagc cggagaacaa ctacaagacc acgcctcccg tgctggactc cgacggctcc  1200
ttcttcctct acagcaggct caccgtggac aagagcaggt ggcaggaggg gaatgtcttc  1260
tcatgctccg tgatgcatga ggctctgcac aaccactaca cacagaagtc cctctccctg  1320
tctctgggta aatga                                                   1335

SEQ ID NO: 254         moltype = AA  length = 444
FEATURE                Location/Qualifiers
source                 1..444
                       mol_type = protein
                       organism = Homo sapiens
SEQUENCE: 254
```

```
EVQLVESGGG LVQPGGSLGL SCAASGFTFS NYAMSWVRQA PGKGLEWVSA VSGGGGGTYY  60
ADSVKGRFTI SRDNSKNTVL LQMNSLRAED TAVYYCARGR TGGLDYWGPG TLVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPE FLGGPSVFLF  240
PPKPKDTLMI SRTPEVTCVV VDVSQEDPEV QFNWYVDGVE VHNAKTKPRE EQFNSTYRVV  300
SVLTVLHQDW LNGKEYKCKV SNKGLPSSIE KTISKAKGQP REPQVYTLPP SQEEMTKNQV  360
SLTCLVKGFY PSDIAVEWES NGQPENNYKT TPPVLDSDGS FFLYSRLTVD KSRWQEGNVF  420
SCSVMHEALH NHYTQKSLSL SLGK                                        444

SEQ ID NO: 255          moltype = DNA  length = 660
FEATURE                 Location/Qualifiers
source                  1..660
                        mol_type = unassigned DNA
                        organism = Homo sapiens
SEQUENCE: 255
gatgttgtga tgactcagtc tcctctctcc ctgcccgtca tctttggaca gccggcctcc  60
atctcctgca ggtcaagtca aagcctcgta gacagtgatg gaaacaccta cttgaattgg  120
cttcagcaga ggccaggcca atctccaagg cgcctaattt atgaggtttc taaccgggac  180
tctggggtcc cagacagatt cagcggcagt gggtcaggca ctgatttcac actgacaatc  240
agcagggtgg aggctgagga tgttggcatt tattactgca tgcaaggtac gcgctggcct  300
cctactttcg gcggagggac caaggtggag atcaaacgaa ctgtggctgc accatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct tcaacagggg agagtgttag  660

SEQ ID NO: 256          moltype = AA  length = 219
FEATURE                 Location/Qualifiers
source                  1..219
                        mol_type = protein
                        organism = Homo sapiens
SEQUENCE: 256
DVVMTQSPLS LPVIFGQPAS ISCRSSQSLV DSDGNTYLNW LQQRPGQSPR RLIYEVSNRD  60
SGVPDRFSGS GSGTDFTLTI SRVEAEDVGI YYCMQGTRWP PTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 257          moltype = DNA  length = 366
FEATURE                 Location/Qualifiers
source                  1..366
                        mol_type = unassigned DNA
                        organism = Homo sapiens
SEQUENCE: 257
gaggtgcagc tggtggagtc tgggggaggt gtggtccggc ctggggggtc cctgagactc  60
tcctgtgcag cctctggatt catctttgat gattatgaca tgagttgggt ccgccaacct  120
ccagggaggg gactggaatg ggtctccggt attgattggt ttggtggtac cagaggttat  180
gcagactcta tgaagggccg attcaccatt tccagagaca acgccaagaa ctccctgtat  240
ctgcaaatga acagcctgag agtcgaggac acggccttct attactgtgc gagagggggg  300
gctatagtgg gagctgttac tccctttgac tactggggcc agggaaccct ggtcactgtc  360
tcctca                                                             366

SEQ ID NO: 258          moltype = AA  length = 122
FEATURE                 Location/Qualifiers
source                  1..122
                        mol_type = protein
                        organism = Homo sapiens
SEQUENCE: 258
EVQLVESGGG VVRPGGSLRL SCAASGFIFD DYDMSWVRQP PGRGLEWVSG IDWFGGTRGY  60
ADSMKGRFTI SRDNAKNSLY LQMNSLRVED TAFYYCARGG AIVGAVTPFD YWGQGTLVTV  120
SS                                                                 122

SEQ ID NO: 259          moltype = DNA  length = 24
FEATURE                 Location/Qualifiers
source                  1..24
                        mol_type = unassigned DNA
                        organism = Homo sapiens
SEQUENCE: 259
ggattcatct ttgatgatta tgac                                         24

SEQ ID NO: 260          moltype = AA  length = 8
FEATURE                 Location/Qualifiers
source                  1..8
                        mol_type = protein
                        organism = Homo sapiens
SEQUENCE: 260
GFIFDDYD                                                           8

SEQ ID NO: 261          moltype = DNA  length = 24
```

```
FEATURE                Location/Qualifiers
source                 1..24
                       mol_type = unassigned DNA
                       organism = Homo sapiens
SEQUENCE: 261
attgattggt ttggtggtac caga                                         24

SEQ ID NO: 262         moltype = AA  length = 8
FEATURE                Location/Qualifiers
source                 1..8
                       mol_type = protein
                       organism = Homo sapiens
SEQUENCE: 262
IDWFGGTR                                                           8

SEQ ID NO: 263         moltype = DNA  length = 45
FEATURE                Location/Qualifiers
source                 1..45
                       mol_type = unassigned DNA
                       organism = Homo sapiens
SEQUENCE: 263
gcgagagggg gggctatagt gggagctgtt actccctttg actac                  45

SEQ ID NO: 264         moltype = AA  length = 15
FEATURE                Location/Qualifiers
source                 1..15
                       mol_type = protein
                       organism = Homo sapiens
SEQUENCE: 264
ARGGAIVGAV TPFDY                                                   15

SEQ ID NO: 265         moltype = DNA  length = 321
FEATURE                Location/Qualifiers
source                 1..321
                       mol_type = unassigned DNA
                       organism = Homo sapiens
SEQUENCE: 265
gacatccaga tgacccagtc tccatcctcc ctgtctgcat ctgttggaaa cagagtcacc  60
ctcagttgcc gggcaagtca gagcattaac acctatttaa gttggtatca gcagagacca  120
ggaaaagccc ctaagctcct gatctatgct gcatccagtt tgcaaagtgg ggtcccctca  180
aggttcagtg gcagtggagc tgggacagat ttcactctca ccatcagcag tctgcaacct  240
gaagattttg caacttacta ctgtcaacag agttacagtg cccctctcac tttcggcggt  300
gggaccaagg tggagatcaa a                                            321

SEQ ID NO: 266         moltype = AA  length = 107
FEATURE                Location/Qualifiers
source                 1..107
                       mol_type = protein
                       organism = Homo sapiens
SEQUENCE: 266
DIQMTQSPSS LSASVGNRVT LSCRASQSIN TYLSWYQQRP GKAPKLLIYA ASSLQSGVPS  60
RFSGSGAGTD FTLTISSLQP EDFATYYCQQ SYSAPLTFGG GTKVEIK                107

SEQ ID NO: 267         moltype = DNA  length = 18
FEATURE                Location/Qualifiers
source                 1..18
                       mol_type = unassigned DNA
                       organism = Homo sapiens
SEQUENCE: 267
cagagcatta acacctat                                                18

SEQ ID NO: 268         moltype = AA  length = 6
FEATURE                Location/Qualifiers
source                 1..6
                       mol_type = protein
                       organism = Homo sapiens
SEQUENCE: 268
QSINTY                                                             6

SEQ ID NO: 269         moltype = DNA  length = 27
FEATURE                Location/Qualifiers
source                 1..27
                       mol_type = unassigned DNA
                       organism = Homo sapiens
SEQUENCE: 269
caacagagtt acagtgcccc tctcact                                      27

SEQ ID NO: 270         moltype = AA  length = 9
FEATURE                Location/Qualifiers
```

```
source                  1..9
                        mol_type = protein
                        organism = Homo sapiens
SEQUENCE: 270
QQSYSAPLT                                                          9

SEQ ID NO: 271          moltype = DNA  length = 1350
FEATURE                 Location/Qualifiers
source                  1..1350
                        mol_type = unassigned DNA
                        organism = Homo sapiens
SEQUENCE: 271
gaggtgcagc tggtggagtc tgggggaggt gtggtccggc ctgggggtc cctgagactc  60
tcctgtgcag cctctggatt catctttgat gattatgaca tgagttgggt ccgccaacct  120
ccagggaggg gactggaatg ggtctccggt attgattggt ttggtggtac cagaggttat  180
gcagactcta tgaagggccg attcaccatt tccagagaca acgccaagaa ctccctgtat  240
ctgcaaatga acagcctgag agtcgaggac acggccttct attactgtgc gagagggggg  300
gctatagtgg gagctgttac tccctttgac tactggggcc agggaaccct ggtcactgtc  360
tcctcagcct ccaccaaggg cccatcggtc ttccccctgg cgccctgctc caggagcacc  420
tccgagagca cagccgccct gggctgcctg gtcaaggact acttccccga accggtgacg  480
gtgtcgtgga actcaggcgc cctgaccagc ggcgtgcaca ccttcccggc tgtcctacag  540
tcctcaggac tctactccct cagcagcgtg gtgaccgtgc cctccagcag cttgggcacg  600
aagacctaca cctgcaacgt agatcacaag cccagcaaca ccaaggtgga caagagagtt  660
gagtccaaat atggtccccc atgcccaccc tgcccagcac ctgagttcct gggggggacca  720
tcagtcttcc tgttcccccc aaaacccaag gacactctca tgatctcccg gacccctgag  780
gtcacgtgcg tggtggtgga cgtgagccag gaagaccccg aggtccagtt caactggtac  840
gtggatggcg tggaggtgca taatgccaag acaaagccgc gggaggagca gttcaacagc  900
acgtaccgtg tggtcagcgt cctcaccgtc ctgcaccagg actggctgaa cggcaaggag  960
tacaagtgca aggtctccaa caaaggcctc ccgtcctcca tcgagaaaac catctccaaa  1020
gccaaagggc agccccgaga gccacaggtg tacaccctgc ccccatccca ggaggagatg  1080
accaagaacc aggtcagcct gacctgcctg gtcaaaggct tctaccccag cgacatcgcc  1140
gtggagtggg agagcaatgg gcagccggag aacaactaca agaccacgcc tcccgtgctg  1200
gactccgacg gctccttctt cctctacagc aggctcaccg tggacaagag caggtggcag  1260
gaggggaatg tcttctcatg ctccgtgatg catgaggctc tgcacaacca ctacacacag  1320
aagtccctct ccctgtctct gggtaaatga                                   1350

SEQ ID NO: 272          moltype = AA  length = 449
FEATURE                 Location/Qualifiers
source                  1..449
                        mol_type = protein
                        organism = Homo sapiens
SEQUENCE: 272
EVQLVESGGG VVRPGGSLRL SCAASGFIFD DYDMSWVRQP PGRGLEWVSG IDWFGGTRGY  60
ADSMKGRFTI SRDNAKNSLY LQMNSLRVED TAFYYCARGG AIVGAVTPFD YWGQGTLVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGK                                    449

SEQ ID NO: 273          moltype = DNA  length = 645
FEATURE                 Location/Qualifiers
source                  1..645
                        mol_type = unassigned DNA
                        organism = Homo sapiens
SEQUENCE: 273
gacatccaga tgacccagtc tccatcctcc ctgtctgcat ctgttggaaa cagagtcacc  60
ctcagttgcc gggcaagtca gagcattaac acctatttaa gttggtatca gcagagacca  120
ggaaaagccc ctaagctcct gatctatgct gcatccagtt tgcaaagtgg ggtcccctca  180
aggttcagtg gcagtggagc tgggacagat ttcactctca ccatcagcag tctgcaacct  240
gaagattttg caacttacta ctgtcaacag agttacagtg cccctctcac tttcggcggt  300
gggaccaagg tggagatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 274          moltype = AA  length = 214
FEATURE                 Location/Qualifiers
source                  1..214
                        mol_type = protein
                        organism = Homo sapiens
SEQUENCE: 274
DIQMTQSPSS LSASVGNRVT LSCRASQSIN TYLSWYQQRP GKAPKLLIYA ASSLQSGVPS  60
RFSGSGAGTD FTLTISSLQP EDFATYYCQQ SYSAPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214
```

```
SEQ ID NO: 275          moltype = DNA  length = 366
FEATURE                 Location/Qualifiers
source                  1..366
                        mol_type = unassigned DNA
                        organism = Homo sapiens
SEQUENCE: 275
cagctgcagc tgcaggagtc gggcccagga ctggtgaagc cttcggagac cctgtccctc  60
acctgcactg tctctggtgg ctccatcagc attaagaatt actactgggg ctggatccgt  120
cagcccccag ggaaggggct ggagtggatt gggagtatct attatagtgg gaccacctac  180
tacaacccgt ccctcaagag tcgagtcacc atatccgtag acacgtccaa gaaccagttc  240
tccctgaagc tgagctctgt gaccgccgca gacacggctg tatatcactg tgcgagacat  300
ggatacagct atggtcacgg ctggttcgac ccctggggcc agggaaccct ggtcaccgtc  360
tcctca                                                             366

SEQ ID NO: 276          moltype = AA  length = 122
FEATURE                 Location/Qualifiers
source                  1..122
                        mol_type = protein
                        organism = Homo sapiens
SEQUENCE: 276
QLQLQESGPG LVKPSETLSL TCTVSGGSIS IKNYYWGWIR QPPGKGLEWI GSIYYSGTTY  60
YNPSLKSRVT ISVDTSKNQF SLKLSSVTAA DTAVYHCARH GYSYGHGWFD PWGQGTLVTV  120
SS                                                                 122

SEQ ID NO: 277          moltype = DNA  length = 30
FEATURE                 Location/Qualifiers
source                  1..30
                        mol_type = unassigned DNA
                        organism = Homo sapiens
SEQUENCE: 277
ggtggctcca tcagcattaa gaattactac                                  30

SEQ ID NO: 278          moltype = AA  length = 10
FEATURE                 Location/Qualifiers
source                  1..10
                        mol_type = protein
                        organism = Homo sapiens
SEQUENCE: 278
GGSISIKNYY                                                        10

SEQ ID NO: 279          moltype = DNA  length = 21
FEATURE                 Location/Qualifiers
source                  1..21
                        mol_type = unassigned DNA
                        organism = Homo sapiens
SEQUENCE: 279
atctattata gtgggaccac c                                           21

SEQ ID NO: 280          moltype = AA  length = 7
FEATURE                 Location/Qualifiers
source                  1..7
                        mol_type = protein
                        organism = Homo sapiens
SEQUENCE: 280
IYYSGTT                                                           7

SEQ ID NO: 281          moltype = DNA  length = 42
FEATURE                 Location/Qualifiers
source                  1..42
                        mol_type = unassigned DNA
                        organism = Homo sapiens
SEQUENCE: 281
gcgagacatg gatacagcta tggtcacggc tggttcgacc cc                    42

SEQ ID NO: 282          moltype = AA  length = 14
FEATURE                 Location/Qualifiers
source                  1..14
                        mol_type = protein
                        organism = Homo sapiens
SEQUENCE: 282
ARHGYSYGHG WFDP                                                   14

SEQ ID NO: 283          moltype = DNA  length = 1350
FEATURE                 Location/Qualifiers
source                  1..1350
                        mol_type = unassigned DNA
                        organism = Homo sapiens
SEQUENCE: 283
```

```
cagctgcagc tgcaggagtc gggcccagga ctggtgaagc cttcggagac cctgtccctc  60
acctgcactg tctctggtgg ctccatcagc attaagaatt actactgggg ctggatccgt  120
cagcccccag ggaaggggct ggagtggatt gggagtatct attatagtgg gaccacctac  180
tacaacccgt ccctcaagag tcgagtcacc atatccgtag acacgtccaa gaaccagttc  240
tccctgaagc tgagctctgt gaccgccgca gacacggctg tatatcactg tgcgagacat  300
ggatacagct atggtcacgg ctggttcgac ccctggggcc agggaaccct ggtcaccgtc  360
tcctcagcct ccaccaaggg cccatcggtc ttccccctgg cgccctgctc caggagcacc  420
tccgagagca cagccgccct gggctgcctg gtcaaggact acttccccga accggtgacg  480
gtgtcgtgga actcaggcgc cctgaccagc ggcgtgcaca ccttcccggc tgtcctacag  540
tcctcaggac tctactccct cagcagcgtg gtgaccgtgc cctccagcag cttgggcacg  600
aagacctaca cctgcaacgt agatcacaag cccagcaaca ccaaggtgga caagagagtt  660
gagtccaaat atggtccccc atgcccaccc tgcccagcac ctgagttcct ggggggacca  720
tcagtcttcc tgttcccccc aaaacccaag gacactctca tgatctcccg gacccctgag  780
gtcacgtgcg tggtggtgga cgtgagccag gaagaccccg aggtccagtt caactggtac  840
gtggatggcg tggaggtgca taatgccaag acaaagccgc gggaggagca gttcaacagc  900
acgtaccgtg tggtcagcgt cctcaccgtc ctgcaccagg actggctgaa cggcaaggag  960
tacaagtgca aggtctccaa caaaggcctc ccgtcctcca tcgagaaaac catctccaaa  1020
gccaaagggc agccccgaga gccacaggtg tacaccctgc ccccatccca ggaggagatg  1080
accaagaacc aggtcagcct gacctgcctg gtcaaaggct tctaccccag cgacatcgcc  1140
gtggagtggg agagcaatgg gcagccggag aacaactaca agaccacgcc tcccgtgctg  1200
gactccgacg gctccttctt cctctacagc aggctcaccg tggacaagag caggtggcag  1260
gaggggaatg tcttctcatg ctccgtgatg catgaggctc tgcacaacca ctacacacag  1320
aagtccctct ccctgtctct gggtaaatga                                  1350

SEQ ID NO: 284          moltype = AA  length = 449
FEATURE                 Location/Qualifiers
source                  1..449
                        mol_type = protein
                        organism = Homo sapiens
SEQUENCE: 284
QLQLQESGPG LVKPSETLSL TCTVSGGSIS IKNYYWGWIR QPPGKGLEWI GSIYYSGTTY  60
YNPSLKSRVT ISVDTSKNQF SLKLSSVTAA DTAVYHCARH GYSYGHGWFD PWGQGTLVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGK                                   449

SEQ ID NO: 285          moltype = DNA  length = 366
FEATURE                 Location/Qualifiers
source                  1..366
                        mol_type = unassigned DNA
                        organism = Homo sapiens
SEQUENCE: 285
caggtacagc tgcagcagtc aggtccagga ctggtaaagc cctcacagac cctctcactc  60
acctgtgaca tctccgggga cagtgtctct agcaacattg ctacttggaa ctggatcagg  120
cagtccccat cgagaggcct tgagtggctg ggaaggacat attacaggtc caagtggtat  180
aaagattatg cagtatctgt gaaaagtcga ataaccatca acccagacac atccaagaac  240
cagttctccc tgcaggtgaa ctctgtgact cccgaggaca cggctgtcta ttactgtgca  300
agaatgactg ggccgcgata ctactttgag tactggggcc agggaaccct ggtcaccgtc  360
tcctca                                                            366

SEQ ID NO: 286          moltype = AA  length = 122
FEATURE                 Location/Qualifiers
source                  1..122
                        mol_type = protein
                        organism = Homo sapiens
SEQUENCE: 286
QVQLQQSGPG LVKPSQTLSL TCDISGDSVS SNIATWNWIR QSPSRGLEWL GRTYYRSKWY  60
KDYAVSVKSR ITINPDTSKN QFSLQVNSVT PEDTAVYYCA RMTGPRYYFE YWGQGTLVTV  120
SS                                                                122

SEQ ID NO: 287          moltype = DNA  length = 30
FEATURE                 Location/Qualifiers
source                  1..30
                        mol_type = unassigned DNA
                        organism = Homo sapiens
SEQUENCE: 287
ggggacagtg tctctagcaa cattgctact                                  30

SEQ ID NO: 288          moltype = AA  length = 10
FEATURE                 Location/Qualifiers
source                  1..10
                        mol_type = protein
                        organism = Homo sapiens
SEQUENCE: 288
GDSVSSNIAT                                                        10
```

```
SEQ ID NO: 289          moltype = DNA  length = 27
FEATURE                 Location/Qualifiers
source                  1..27
                        mol_type = unassigned DNA
                        organism = Homo sapiens
SEQUENCE: 289
acatattaca ggtccaagtg gtataaa                                   27

SEQ ID NO: 290          moltype = AA  length = 9
FEATURE                 Location/Qualifiers
source                  1..9
                        mol_type = protein
                        organism = Homo sapiens
SEQUENCE: 290
TYYRSKWYK                                                       9

SEQ ID NO: 291          moltype = DNA  length = 36
FEATURE                 Location/Qualifiers
source                  1..36
                        mol_type = unassigned DNA
                        organism = Homo sapiens
SEQUENCE: 291
gcaagaatga ctgggccgcg atactacttt gagtac                         36

SEQ ID NO: 292          moltype = AA  length = 12
FEATURE                 Location/Qualifiers
source                  1..12
                        mol_type = protein
                        organism = Homo sapiens
SEQUENCE: 292
ARMTGPRYYF EY                                                   12

SEQ ID NO: 293          moltype = DNA  length = 1350
FEATURE                 Location/Qualifiers
source                  1..1350
                        mol_type = unassigned DNA
                        organism = Homo sapiens
SEQUENCE: 293
caggtacagc tgcagcagtc aggtccagga ctggtaaagc cctcacagac cctctcactc  60
acctgtgaca tctccgggga cagtgtctct agcaacattg ctacttggaa ctggatcagg  120
cagtccccat cgagaggcct tgagtggctg ggaaggacat attacaggtc caagtggtat  180
aaagattatg cagtatctgt gaaaagtcga ataaccatca acccagacac atccaagaac  240
cagttctccc tgcaggtgaa ctctgtgact cccgaggaca cggctgtcta ttactgtgca  300
agaatgactg ggccgcgata ctactttgag tactggggcc agggaaccct ggtcaccgtc  360
tcctcagcct ccaccaaggg cccatcggtc ttccccctgg cgccctgctc caggagcacc  420
tccgagagca cagccgccct gggctgcctg gtcaaggact acttccccga accggtgacg  480
gtgtcgtgga actcaggcgc cctgaccagc ggcgtgcaca ccttcccggc tgtcctacag  540
tcctcaggac tctactccct cagcagcgtg gtgaccgtgc cctccagcag cttgggcacg  600
aagacctaca cctgcaacgt agatcacaag cccagcaaca ccaaggtgga caagagagtt  660
gagtccaaat atggtccccc atgcccaccc tgcccagcac ctgagttcct ggggggacca  720
tcagtcttcc tgttcccccc aaaacccaag gacactctca tgatctcccg gacccctgag  780
gtcacgtgcg tggtggtgga cgtgagccag gaagaccccg aggtccagtt caactggtac  840
gtggatggcg tggaggtgca taatgccaag acaaagccgc gggaggagca gttcaacagc  900
acgtaccgtg tggtcagcgt cctcaccgtc ctgcaccagg actggctgaa cggcaaggag  960
tacaagtgca aggtctccaa caaaggcctc ccgtcctcca tcgagaaaac catctccaaa  1020
gccaaagggc agccccgaga gccacaggtg tacaccctgc ccccatccca ggaggagatg  1080
accaagaacc aggtcagcct gacctgcctg gtcaaaggct tctaccccag cgacatcgcc  1140
gtggagtggg agagcaatgg gcagccggag aacaactaca agaccacgcc tcccgtgctg  1200
gactccgacg gctccttctt cctctacagc aggctcaccg tggacaagag caggtggcag  1260
gaggggaatg tcttctcatg ctccgtgatg catgaggctc tgcacaacca ctacacacag  1320
aagtccctct ccctgtctct gggtaaatga                                1350

SEQ ID NO: 294          moltype = AA  length = 449
FEATURE                 Location/Qualifiers
source                  1..449
                        mol_type = protein
                        organism = Homo sapiens
SEQUENCE: 294
QVQLQQSGPG LVKPSQTLSL TCDISGDSVS SNIATWNWIR QSPSRGLEWL GRTYYRSKWY  60
KDYAVSVKSR ITINPDTSKN QFSLQVNSVT PEDTAVYYCA RMTGPRYYFE YWGQGTLVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGK                                 449

SEQ ID NO: 295          moltype = DNA  length = 366
FEATURE                 Location/Qualifiers
```

```
source                  1..366
                        mol_type = unassigned DNA
                        organism = Homo sapiens
SEQUENCE: 295
gaggtgcagc tggtggagtc tgggggaggt gtggtccggc ctgggggtc cctgagactc  60
tcctgtgcag cctctggatt caccttgat gattttgaca tgagctgggt ccgccaaggt  120
ccagggaagg ggctggagtg ggtctctggt attaattggc atgggagtag tacaggttat  180
gcagactctg tgaagggccg attcaccatc tccagagaca acgccaagaa ctccctgtat  240
ctgcaaatga gcagtctgag ggccgaggac acggccttat atcactgtgt gagagggggg  300
actatagtgg gtgccactac tccccttgac tactggggcc agggaaccct ggtcaccgtc  360
tcctca                                                             366

SEQ ID NO: 296          moltype = AA  length = 122
FEATURE                 Location/Qualifiers
source                  1..122
                        mol_type = protein
                        organism = Homo sapiens
SEQUENCE: 296
EVQLVESGGG VVRPGGSLRL SCAASGFTFD DFDMSWVRQG PGKGLEWVSG INWHGSSTGY  60
ADSVKGRFTI SRDNAKNSLY LQMSSLRAED TALYHCVRGG TIVGATTPLD YWGQGTLVTV  120
SS                                                                 122

SEQ ID NO: 297          moltype = DNA  length = 24
FEATURE                 Location/Qualifiers
source                  1..24
                        mol_type = unassigned DNA
                        organism = Homo sapiens
SEQUENCE: 297
ggattcacct ttgatgattt tgac                                         24

SEQ ID NO: 298          moltype = AA  length = 8
FEATURE                 Location/Qualifiers
source                  1..8
                        mol_type = protein
                        organism = Homo sapiens
SEQUENCE: 298
GFTFDDFD                                                           8

SEQ ID NO: 299          moltype = DNA  length = 24
FEATURE                 Location/Qualifiers
source                  1..24
                        mol_type = unassigned DNA
                        organism = Homo sapiens
SEQUENCE: 299
attaattggc atgggagtag taca                                         24

SEQ ID NO: 300          moltype = AA  length = 8
FEATURE                 Location/Qualifiers
source                  1..8
                        mol_type = protein
                        organism = Homo sapiens
SEQUENCE: 300
INWHGSST                                                           8

SEQ ID NO: 301          moltype = DNA  length = 45
FEATURE                 Location/Qualifiers
source                  1..45
                        mol_type = unassigned DNA
                        organism = Homo sapiens
SEQUENCE: 301
gtgagagggg ggactatagt gggtgccact actccccttg actac                  45

SEQ ID NO: 302          moltype = AA  length = 15
FEATURE                 Location/Qualifiers
source                  1..15
                        mol_type = protein
                        organism = Homo sapiens
SEQUENCE: 302
VRGGTIVGAT TPLDY                                                   15

SEQ ID NO: 303          moltype = DNA  length = 321
FEATURE                 Location/Qualifiers
source                  1..321
                        mol_type = unassigned DNA
                        organism = Homo sapiens
SEQUENCE: 303
gacatccaga tgacccagtc tccatcctcc ctgtctgcat ctgtaggaga cagagtcacc  60
atgacttgcc gggcaagtcg gaccattagc agctatttaa gttggtatca gcagaaatca  120
gggaaagtcc ctaacctcct gatctttggt gcatccagtt tgcaaagtgg ggtcccatca  180
```

```
aggttcagtg ccagtggatc tgggacagat ttcactctca tcatcagcag tctgcaacct  240
gaagattttg caacttacta ctgtcaacag agttacagct cccctctcac tttcggcgga  300
gggaccaagg tggagatcaa a                                             321

SEQ ID NO: 304          moltype = AA  length = 107
FEATURE                 Location/Qualifiers
source                  1..107
                        mol_type = protein
                        organism = Homo sapiens
SEQUENCE: 304
DIQMTQSPSS LSASVGDRVT MTCRASRTIS SYLSWYQQKS GKVPNLLIFG ASSLQSGVPS  60
RFSASGSGTD FTLIISSLQP EDFATYYCQQ SYSSPLTFGG GTKVEIK                107

SEQ ID NO: 305          moltype = DNA  length = 18
FEATURE                 Location/Qualifiers
source                  1..18
                        mol_type = unassigned DNA
                        organism = Homo sapiens
SEQUENCE: 305
cggaccatta gcagctat                                                 18

SEQ ID NO: 306          moltype = AA  length = 6
FEATURE                 Location/Qualifiers
source                  1..6
                        mol_type = protein
                        organism = Homo sapiens
SEQUENCE: 306
RTISSY                                                              6

SEQ ID NO: 307          moltype =   length =
SEQUENCE: 307
000

SEQ ID NO: 308          moltype = DNA  length = 27
FEATURE                 Location/Qualifiers
source                  1..27
                        mol_type = unassigned DNA
                        organism = Homo sapiens
SEQUENCE: 308
caacagagtt acagctcccc tctcact                                       27

SEQ ID NO: 309          moltype = AA  length = 9
FEATURE                 Location/Qualifiers
source                  1..9
                        mol_type = protein
                        organism = Homo sapiens
SEQUENCE: 309
QQSYSSPLT                                                           9

SEQ ID NO: 310          moltype = DNA  length = 1350
FEATURE                 Location/Qualifiers
source                  1..1350
                        mol_type = unassigned DNA
                        organism = Homo sapiens
SEQUENCE: 310
gaggtgcagc tggtggagtc tgggggaggt gtggtccggc ctgggggggtc cctgagactc  60
tcctgtgcag cctctggatt caccttttgat gattttgaca tgagctgggt ccgccaaggt  120
ccagggaagg ggctggagtg ggtctctggt attaattggc atgggagtag tacaggttat  180
gcagactctg tgaagggccg attcaccatc tccagagaca acgccaagaa ctccctgtat  240
ctgcaaatga gcagtctgag ggccgaggac acggccttat atcactgtgt gagaggggggg  300
actatagtgg gtgccactac tccccttgac tactggggcc agggaaccct ggtcaccgtc  360
tcctcagcct ccaccaaggg cccatcggtc ttccccctgg cgccctgctc caggagcacc  420
tccgagagca cagccgccct gggctgcctg gtcaaggact acttccccga accggtgacg  480
gtgtcgtgga actcaggcgc cctgaccagc ggcgtgcaca ccttcccggc tgtcctacag  540
tcctcaggac tctactccct cagcagcgtg gtgaccgtgc cctccagcag cttgggcacg  600
aagacctaca cctgcaacgt agatcacaag cccagcaaca ccaaggtgga caagagagtt  660
gagtccaaat atggtccccc atgcccaccc tgcccagcac ctgagttcct ggggggacca  720
tcagtcttcc tgttcccccc aaaacccaag gacactctca tgatctcccg gacccctgag  780
gtcacgtgcg tggtggtgga cgtgagccag gaagaccccg aggtccagtt caactggtac  840
gtggatggcg tggaggtgca taatgccaag acaaagccgc gggaggagca gttcaacagc  900
acgtaccgtg tggtcagcgt cctcaccgtc ctgcaccagg actggctgaa cggcaaggag  960
tacaagtgca aggtctccaa caaaggcctc ccgtcctcca tcgagaaaac catctccaaa  1020
gccaaagggc agccccgaga gccacaggtg tacaccctgc ccccatccca ggaggagatg  1080
accaagaacc aggtcagcct gacctgcctg gtcaaaggct tctaccccag cgacatcgcc  1140
gtggagtggg agagcaatgg gcagccggag aacaactaca agaccacgcc tcccgtgctg  1200
gactccgacg gctccttctt cctctacagc aggctcaccg tggacaagag caggtggcag  1260
gaggggaatg tcttctcatg ctccgtgatg catgaggctc tgcacaacca ctacacacag  1320
aagtccctct ccctgtctct gggtaaatga                                    1350
```

```
SEQ ID NO: 311         moltype = AA  length = 449
FEATURE                Location/Qualifiers
source                 1..449
                       mol_type = protein
                       organism = Homo sapiens
SEQUENCE: 311
EVQLVESGGG VVRPGGSLRL SCAASGFTFD DFDMSWVRQG PGKGLEWVSG INWHGSSTGY  60
ADSVKGRFTI SRDNAKNSLY LQMSSLRAED TALYHCVRGG TIVGATTPLD YWGQGTLVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGK                                   449

SEQ ID NO: 312         moltype = DNA  length = 645
FEATURE                Location/Qualifiers
source                 1..645
                       mol_type = unassigned DNA
                       organism = Homo sapiens
SEQUENCE: 312
gacatccaga tgacccagtc tccatcctcc ctgtctgcat ctgtaggaga cagagtcacc  60
atgacttgcc gggcaagtcg gaccattagc agctatttaa gttggtatca gcagaaatca  120
gggaaagtcc ctaacctcct gatctttggt gcatccagtt tgcaaagtgg ggtcccatca  180
aggttcagtg ccagtggatc tgggacagat ttcactctca tcatcagcag tctgcaacct  240
gaagattttg caacttacta ctgtcaacag agttacagct cccctctcac tttcggcgga  300
gggaccaagg tggagatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                 645

SEQ ID NO: 313         moltype = AA  length = 214
FEATURE                Location/Qualifiers
source                 1..214
                       mol_type = protein
                       organism = Homo sapiens
SEQUENCE: 313
DIQMTQSPSS LSASVGDRVT MTCRASRTIS SYLSWYQQKS GKVPNLLIFG ASSLQSGVPS  60
RFSASGSGTD FTLIISSLQP EDFATYYCQQ SYSSPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 314         moltype = DNA  length = 351
FEATURE                Location/Qualifiers
source                 1..351
                       mol_type = unassigned DNA
                       organism = Homo sapiens
SEQUENCE: 314
gaggtgcagc tggtggagtc tggggggagac ttggtacagc ctggggggtc cctgagactc  60
tcctgtacag cctctggatt catttttagg aactatgcca tgaactgggt ccgccaggct  120
ccagggaagg ggctggagtg ggttgtcaggt attcttggta gtaatgataa cacatactac  180
gtagactccg tgaagggccg gttcaccatt tctagagaca attccaggaa cacgctgtat  240
ctgcaaatga acagcctgag agccgaggac tcggccgtat attactgtgc aaaaggggac  300
gctgggggct ttgactactg gggccaggga accctggtca ccgtctcctc a          351

SEQ ID NO: 315         moltype = AA  length = 117
FEATURE                Location/Qualifiers
source                 1..117
                       mol_type = protein
                       organism = Homo sapiens
SEQUENCE: 315
EVQLVESGGD LVQPGGSLRL SCTASGFIFR NYAMNWVRQA PGKGLEWLSG ILGSNDNTYY  60
VDSVKGRFTI SRDNSRNTLY LQMNSLRAED SAVYYCAKGD AGGFDYWGQG TLVTVSS     117

SEQ ID NO: 316         moltype = DNA  length = 24
FEATURE                Location/Qualifiers
source                 1..24
                       mol_type = unassigned DNA
                       organism = Homo sapiens
SEQUENCE: 316
ggattcattt ttaggaacta tgcc                                        24

SEQ ID NO: 317         moltype = AA  length = 8
FEATURE                Location/Qualifiers
source                 1..8
                       mol_type = protein
                       organism = Homo sapiens
```

```
SEQUENCE: 317
GFIFRNYA                                                         8

SEQ ID NO: 318          moltype = DNA  length = 24
FEATURE                 Location/Qualifiers
source                  1..24
                        mol_type = unassigned DNA
                        organism = Homo sapiens
SEQUENCE: 318
attcttggta gtaatgataa caca                                       24

SEQ ID NO: 319          moltype = AA  length = 8
FEATURE                 Location/Qualifiers
source                  1..8
                        mol_type = protein
                        organism = Homo sapiens
SEQUENCE: 319
ILGSNDNT                                                         8

SEQ ID NO: 320          moltype = DNA  length = 30
FEATURE                 Location/Qualifiers
source                  1..30
                        mol_type = unassigned DNA
                        organism = Homo sapiens
SEQUENCE: 320
gcaaaagggg acgctggggg ctttgactac                                 30

SEQ ID NO: 321          moltype = AA  length = 10
FEATURE                 Location/Qualifiers
source                  1..10
                        mol_type = protein
                        organism = Homo sapiens
SEQUENCE: 321
AKGDAGGFDY                                                       10

SEQ ID NO: 322          moltype = DNA  length = 336
FEATURE                 Location/Qualifiers
source                  1..336
                        mol_type = unassigned DNA
                        organism = Homo sapiens
SEQUENCE: 322
gatgttgtga tgactcagtc tccactctcc ctgcccgtca tccttggaca gccggcctcc  60
atctcctgca ggtctagtca aagcctcgta tccagtgatg gaaacaccta cttgaattgg  120
tttcagcaga ggccaggcca atctccaagg cgcctaattt ataaagtttc taaccgggac  180
tctggggtcc cagacagatt cagcggcagt gggtcaggca ctgatttcac actgaaaatc  240
agcagggtgg aggctgagga tgttggggct tattactgca tgcaaggttc atactggcct  300
ccgacttttg gccaggggac caagctggag atcaaa                          336

SEQ ID NO: 323          moltype = AA  length = 112
FEATURE                 Location/Qualifiers
source                  1..112
                        mol_type = protein
                        organism = Homo sapiens
SEQUENCE: 323
DVVMTQSPLS LPVILGQPAS ISCRSSQSLV SSDGNTYLNW FQQRPGQSPR RLIYKVSNRD  60
SGVPDRFSGS GSGTDFTLKI SRVEAEDVGA YYCMQGSYWP PTFGQGTKLE IK         112

SEQ ID NO: 324          moltype = DNA  length = 33
FEATURE                 Location/Qualifiers
source                  1..33
                        mol_type = unassigned DNA
                        organism = Homo sapiens
SEQUENCE: 324
caaagcctcg tatccagtga tggaaacacc tac                             33

SEQ ID NO: 325          moltype = AA  length = 11
FEATURE                 Location/Qualifiers
source                  1..11
                        mol_type = protein
                        organism = Homo sapiens
SEQUENCE: 325
QSLVSSDGNT Y                                                     11

SEQ ID NO: 326          moltype =   length =
SEQUENCE: 326
000

SEQ ID NO: 327          moltype =   length =
SEQUENCE: 327
```

000

SEQ ID NO: 328 moltype = DNA length = 27
FEATURE Location/Qualifiers
source 1..27
mol_type = unassigned DNA
organism = Homo sapiens
SEQUENCE: 328
atgcaaggtt catactggcc tccgact 27

SEQ ID NO: 329 moltype = AA length = 9
FEATURE Location/Qualifiers
source 1..9
mol_type = protein
organism = Homo sapiens
SEQUENCE: 329
MQGSYWPPT 9

SEQ ID NO: 330 moltype = DNA length = 1335
FEATURE Location/Qualifiers
source 1..1335
mol_type = unassigned DNA
organism = Homo sapiens
SEQUENCE: 330
gaggtgcagc tggtggagtc tgggggagac ttggtacagc ctggggggtc cctgagactc 60
tcctgtacag cctctggatt catttttagg aactatgcca tgaactgggt ccgccaggct 120
ccagggaagg ggctggagtg gttgtcaggt attcttggta gtaatgataa cacatactac 180
gtagactccg tgaagggccg gttcaccatt tctagagaca attccaggaa cacgctgtat 240
ctgcaaatga acagcctgag agccgaggac tcggccgtat attactgtgc aaaaggggac 300
gctgggggct ttgactactg gggccaggga accctggtca ccgtctcctc agcctccacc 360
aagggcccat cggtcttccc cctggcgccc tgctccagga gcacctccga gagcacagcc 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacgaagac ctacacctgc 600
aacgtagatc acaagcccag caacaccaag gtggacaaga gagttgagtc caaatatggt 660
cccccatgcc caccctgccc agcacctgag ttcctggggg gaccatcagt cttcctgttc 720
cccccaaaac ccaaggacac tctcatgatc tcccggaccc ctgaggtcac gtgcgtggtg 780
gtggacgtga gccaggaaga ccccgaggtc cagttcaact ggtacgtgga tggcgtggag 840
gtgcataatg ccaagacaaa gccgcgggag gagcagttca acagcacgta ccgtgtggtc 900
agcgtcctca ccgtcctgca ccaggactgg ctgaacggca aggagtacaa gtgcaaggtc 960
tccaacaaag gcctcccgtc ctccatcgag aaaaccatct ccaaagccaa agggcagccc 1020
cgagagccac aggtgtacac cctgccccca tcccaggagg agatgaccaa gaaccaggtc 1080
agcctgacct gcctggtcaa aggcttctac cccagcgaca tcgccgtgga gtgggagagc 1140
aatgggcagc cggagaacaa ctacaagacc acgcctcccg tgctggactc cgacggctcc 1200
ttcttcctct acagcaggct caccgtggac aagagcaggt ggcaggaggg gaatgtcttc 1260
tcatgctccg tgatgcatga ggctctgcac aaccactaca cacagaagtc cctctccctg 1320
tctctgggta aatga 1335

SEQ ID NO: 331 moltype = AA length = 444
FEATURE Location/Qualifiers
source 1..444
mol_type = protein
organism = Homo sapiens
SEQUENCE: 331
EVQLVESGGD LVQPGGSLRL SCTASGFIFR NYAMNWVRQA PGKGLEWLSG ILGSNDNTYY 60
VDSVKGRFTI SRDNSRNTLY LQMNSLRAED SAVYYCAKGD AGGFDYWGQG TLVTVSSAST 120
KGPSVFPLAP CSRSTSESTA ALGCLVKDYF PEPVTVSWNS GALTSGVHTF PAVLQSSGLY 180
SLSSVVTVPS SSLGTKTYTC NVDHKPSNTK VDKRVESKYG PPCPPCPAPE FLGGPSVFLF 240
PPKPKDTLMI SRTPEVTCVV VDVSQEDPEV QFNWYVDGVE VHNAKTKPRE EQFNSTYRVV 300
SVLTVLHQDW LNGKEYKCKV SNKGLPSSIE KTISKAKGQP REPQVYTLPP SQEEMTKNQV 360
SLTCLVKGFY PSDIAVEWES NGQPENNYKT TPPVLDSDGS FFLYSRLTVD KSRWQEGNVF 420
SCSVMHEALH NHYTQKSLSL SLGK 444

SEQ ID NO: 332 moltype = DNA length = 660
FEATURE Location/Qualifiers
source 1..660
mol_type = unassigned DNA
organism = Homo sapiens
SEQUENCE: 332
gatgttgtga tgactcagtc tccactctcc ctgcccgtca tccttggaca gccggcctcc 60
atctcctgca ggtctagtca aagcctcgta tccagtgatg gaaacaccta cttgaattgg 120
tttcagcaga ggccaggcca atctccaagg cgcctaattt ataaagtttc taaccgggac 180
tctggggtcc cagacagatt cagcggcagt gggtcaggca ctgatttcac actgaaaatc 240
agcagggtgg aggctgagga tgttggggct tattactgca tgcaaggttc atactggcct 300
ccgacttttg gccaggggac caagctggag atcaaacgaa ctgtggctgc accatctgtc 360
ttcatcttcc cgccatctga tgagcagttg aaatctggaa ctgcctctgt tgtgtgcctg 420
ctgaataact tctatcccag agaggccaaa gtacagtgga aggtggataa cgccctccaa 480
tcgggtaact cccaggagag tgtcacagag caggacagca aggacagcac ctacagcctc 540
agcagcaccc tgacgctgag caaagcagac tacgagaaac acaaagtcta cgcctgcgaa 600

```
gtcacccatc agggcctgag ctcgcccgtc acaaagagct tcaacagggg agagtgttag  660

SEQ ID NO: 333          moltype = AA  length = 219
FEATURE                 Location/Qualifiers
source                  1..219
                        mol_type = protein
                        organism = Homo sapiens
SEQUENCE: 333
DVVMTQSPLS LPVILGQPAS ISCRSSQSLV SSDGNTYLNW FQQRPGQSPR RLIYKVSNRD  60
SGVPDRFSGS GSGTDFTLKI SRVEAEDVGA YYCMQGSYWP PTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 334          moltype = DNA  length = 363
FEATURE                 Location/Qualifiers
source                  1..363
                        mol_type = unassigned DNA
                        organism = Homo sapiens
SEQUENCE: 334
caggtgcagc tggtggagtc tgggggaggc gtggtcaagc ctgggggtc cctgagactc  60
tcctgtgcag cctctggatt caccttcagt aactctggca ttcactgggt ccgccaggct  120
ccaggcaagg ggctggagtg ggtggcactt atatcatatg ctggaagtaa taaatactat  180
gcagactccg tgaagggccg attcaccatc tccagagaca attccaagaa cacgctgtct  240
ctgcaaatga acagcctgag agctgaggac acggctgtgt attactgtgc gaaagaggtt  300
tggactggaa cttatgattc ttttgatatg tggggccgag ggacaatggt caccgtctct  360
tca                                                                363

SEQ ID NO: 335          moltype = AA  length = 121
FEATURE                 Location/Qualifiers
source                  1..121
                        mol_type = protein
                        organism = Homo sapiens
SEQUENCE: 335
QVQLVESGGG VVKPGGSLRL SCAASGFTFS NSGIHWVRQA PGKGLEWVAL ISYAGSNKYY  60
ADSVKGRFTI SRDNSKNTLS LQMNSLRAED TAVYYCAKEV WTGTYDSFDM WGRGTMVTVS  120
S                                                                  121

SEQ ID NO: 336          moltype = DNA  length = 24
FEATURE                 Location/Qualifiers
source                  1..24
                        mol_type = unassigned DNA
                        organism = Homo sapiens
SEQUENCE: 336
ggattcacct tcagtaactc tggc                                         24

SEQ ID NO: 337          moltype = AA  length = 8
FEATURE                 Location/Qualifiers
source                  1..8
                        mol_type = protein
                        organism = Homo sapiens
SEQUENCE: 337
GFTFSNSG                                                           8

SEQ ID NO: 338          moltype = DNA  length = 24
FEATURE                 Location/Qualifiers
source                  1..24
                        mol_type = unassigned DNA
                        organism = Homo sapiens
SEQUENCE: 338
atatcatatg ctggaagtaa taaa                                         24

SEQ ID NO: 339          moltype = AA  length = 8
FEATURE                 Location/Qualifiers
source                  1..8
                        mol_type = protein
                        organism = Homo sapiens
SEQUENCE: 339
ISYAGSNK                                                           8

SEQ ID NO: 340          moltype = DNA  length = 42
FEATURE                 Location/Qualifiers
source                  1..42
                        mol_type = unassigned DNA
                        organism = Homo sapiens
SEQUENCE: 340
gcgaaagagg tttggactgg aacttatgat tcttttgata tg                     42

SEQ ID NO: 341          moltype = AA  length = 14
FEATURE                 Location/Qualifiers
```

```
source                  1..14
                        mol_type = protein
                        organism = Homo sapiens
SEQUENCE: 341
AKEVWTGTYD SFDM                                                    14

SEQ ID NO: 342          moltype = DNA  length = 1347
FEATURE                 Location/Qualifiers
source                  1..1347
                        mol_type = unassigned DNA
                        organism = Homo sapiens
SEQUENCE: 342
caggtgcagc tggtggagtc tgggggaggc gtggtcaagc ctgggggtc cctgagactc  60
tcctgtgcag cctctggatt caccttcagt aactctggca ttcactgggt ccgccaggct  120
ccaggcaagg ggctggagtg ggtggcactt atatcatatg ctggaagtaa taaatactat  180
gcagactccg tgaagggccg attcaccatc tccagagaca attccaagaa cacgctgtct  240
ctgcaaatga acagcctgag agctgaggac acggctgtgt attactgtgc gaaagaggtt  300
tggactggaa cttatgattc ttttgatatg tggggccgag ggacaatggt caccgtctct  360
tcagcctcca ccaagggccc atcggtcttc cccctggcgc cctgctccag gagcacctcc  420
gagagcacag ccgccctggg ctgcctggtc aaggactact tccccgaacc ggtgacggtg  480
tcgtggaact caggcgccct gaccagcggc gtgcacacct tcccggctgt cctacagtcc  540
tcaggactct actccctcag cagcgtggtg accgtgccct ccagcagctt gggcacgaag  600
acctacacct gcaacgtaga tcacaagccc agcaacacca aggtggacaa gagagttgag  660
tccaaatatg gtcccccatg cccaccctgc ccagcacctg agttcctggg gggaccatca  720
gtcttcctgt tccccccaaa acccaaggac actctcatga tctcccggac ccctgaggtc  780
acgtgcgtgg tggtggacgt gagccaggaa gaccccgagg tccagttcaa ctggtacgtg  840
gatggcgtgg aggtgcataa tgccaagaca aagccgcggg aggagcagtt caacagcacg  900
taccgtgtgg tcagcgtcct caccgtcctg caccaggact ggctgaacgg caaggagtac  960
aagtgcaagg tctccaacaa aggcctcccg tcctccatcg agaaaaccat ctccaaagcc  1020
aaagggcagc cccgagagcc acaggtgtac accctgcccc catcccagga ggagatgacc  1080
aagaaccagg tcagcctgac ctgcctggtc aaaggcttct accccagcga catcgccgtg  1140
gagtgggaga gcaatgggca gccggagaac aactacaaga ccacgcctcc cgtgctggac  1200
tccgacggct ccttcttcct ctacagcagg ctcaccgtgg acaagagcag gtggcaggag  1260
gggaatgtct tctcatgctc cgtgatgcat gaggctctgc acaaccacta cacacagaag  1320
tccctctccc tgtctctggg taaatga                                      1347

SEQ ID NO: 343          moltype = AA  length = 448
FEATURE                 Location/Qualifiers
source                  1..448
                        mol_type = protein
                        organism = Homo sapiens
SEQUENCE: 343
QVQLVESGGG VVKPGGSLRL SCAASGFTFS NSGIHWVRQA PGKGLEWVAL ISYAGSNKYY  60
ADSVKGRFTI SRDNSKNTLS LQMNSLRAED TAVYYCAKEV WTGTYDSFDM WGRGTMVTVS  120
SASTKGPSVF PLAPCSRSTS ESTAALGCLV KDYFPEPVTV SWNSGALTSG VHTFPAVLQS  180
SGLYSLSSVV TVPSSSLGTK TYTCNVDHKP SNTKVDKRVE SKYGPPCPPC PAPEFLGGPS  240
VFLFPPKPKD TLMISRTPEV TCVVVDVSQE DPEVQFNWYV DGVEVHNAKT KPREEQFNST  300
YRVVSVLTVL HQDWLNGKEY KCKVSNKGLP SSIEKTISKA KGQPREPQVY TLPPSQEEMT  360
KNQVSLTCLV KGFYPSDIAV EWESNGQPEN NYKTTPPVLD SDGSFFLYSR LTVDKSRWQE  420
GNVFSCSVMH EALHNHYTQK SLSLSLGK                                     448

SEQ ID NO: 344          moltype = DNA  length = 363
FEATURE                 Location/Qualifiers
source                  1..363
                        mol_type = unassigned DNA
                        organism = Homo sapiens
SEQUENCE: 344
gaggtgcagc tggtggagtc tgggggaggc ttggtacagc ctggagggtc cctgagactc  60
tcctgtgcag cctctggatt catcttcagt agttatgaaa tgcattgggt ccgccaggct  120
ccagggaagg ggctggagtg gatttcatac attagtagta gtggtactac catatactac  180
gcagactctg tgaagggccg attcaccatc tccagagaca acgccaagaa ctcactgtat  240
ctgcacatga acagcctgag agccgaggac acggctgttt attactgtac gagagcccgt  300
ataactggaa ctttcgatgt ttttgatatc tggggccaag ggacaatggt caccgtctct  360
tca                                                                363

SEQ ID NO: 345          moltype = AA  length = 121
FEATURE                 Location/Qualifiers
source                  1..121
                        mol_type = protein
                        organism = Homo sapiens
SEQUENCE: 345
EVQLVESGGG LVQPGGSLRL SCAASGFIFS SYEMHWVRQA PGKGLEWISY ISSSGTTIYY  60
ADSVKGRFTI SRDNAKNSLY LHMNSLRAED TAVYYCTRAR ITGTFDVFDI WGQGTMVTVS  120
S                                                                  121

SEQ ID NO: 346          moltype = DNA  length = 24
FEATURE                 Location/Qualifiers
source                  1..24
                        mol_type = unassigned DNA
```

```
                         organism = Homo sapiens
SEQUENCE: 346
ggattcatct tcagtagtta tgaa                                          24

SEQ ID NO: 347           moltype = AA  length = 8
FEATURE                  Location/Qualifiers
source                   1..8
                         mol_type = protein
                         organism = Homo sapiens
SEQUENCE: 347
GFIFSSYE                                                            8

SEQ ID NO: 348           moltype = DNA  length = 24
FEATURE                  Location/Qualifiers
source                   1..24
                         mol_type = unassigned DNA
                         organism = Homo sapiens
SEQUENCE: 348
attagtagta gtggtactac cata                                          24

SEQ ID NO: 349           moltype = AA  length = 8
FEATURE                  Location/Qualifiers
source                   1..8
                         mol_type = protein
                         organism = Homo sapiens
SEQUENCE: 349
ISSSGTTI                                                            8

SEQ ID NO: 350           moltype = DNA  length = 42
FEATURE                  Location/Qualifiers
source                   1..42
                         mol_type = unassigned DNA
                         organism = Homo sapiens
SEQUENCE: 350
acgagagccc gtataactgg aactttcgat gtttttgata tc                      42

SEQ ID NO: 351           moltype = AA  length = 14
FEATURE                  Location/Qualifiers
source                   1..14
                         mol_type = protein
                         organism = Homo sapiens
SEQUENCE: 351
TRARITGTFD VFDI                                                     14

SEQ ID NO: 352           moltype = DNA  length = 321
FEATURE                  Location/Qualifiers
source                   1..321
                         mol_type = unassigned DNA
                         organism = Homo sapiens
SEQUENCE: 352
gacatccaga tgacccagtc tccatcctcc ctgtctgcat ctgtgggaga cagagtcacc  60
atcacttgcc gggcaagtca gagcattagc agctatttaa attggtatca gcagaaacca  120
gggaaagccc ctaagctcct gatctttgct gcatccaatt tacagagtgg ggtcccatca  180
aggttcagtg gcagtagatc tgggacagat ttcactctca ccatcagcag tctgcaacct  240
gaagattttg caacttacta ctgtcaacag aattacaata tcccgtacac ttttggccag  300
gggaccaagc tggagatcaa a                                             321

SEQ ID NO: 353           moltype = AA  length = 107
FEATURE                  Location/Qualifiers
source                   1..107
                         mol_type = protein
                         organism = Homo sapiens
SEQUENCE: 353
DIQMTQSPSS LSASVGDRVT ITCRASQSIS SYLNWYQQKP GKAPKLLIFA ASNLQSGVPS  60
RFSGSRSGTD FTLTISSLQP EDFATYYCQQ NYNIPYTFGQ GTKLEIK                 107

SEQ ID NO: 354           moltype = DNA  length = 27
FEATURE                  Location/Qualifiers
source                   1..27
                         mol_type = unassigned DNA
                         organism = Homo sapiens
SEQUENCE: 354
caacagaatt acaatatccc gtacact                                       27

SEQ ID NO: 355           moltype = AA  length = 9
FEATURE                  Location/Qualifiers
source                   1..9
                         mol_type = protein
                         organism = Homo sapiens
```

```
SEQUENCE: 355
QQNYNIPYT                                                        9

SEQ ID NO: 356          moltype = DNA  length = 1347
FEATURE                 Location/Qualifiers
source                  1..1347
                        mol_type = unassigned DNA
                        organism = Homo sapiens
SEQUENCE: 356
gaggtgcagc tggtggagtc tgggggaggc ttggtacagc ctggagggtc cctgagactc  60
tcctgtgcag cctctggatt catcttcagt agttatgaaa tgcattgggt ccgccaggct  120
ccagggaagg ggctggagtg gatttcatac attagtagta gtggtactac catatactac  180
gcagactctg tgaagggccg attcaccatc tccagagaca acgccaagaa ctcactgtat  240
ctgcacatga acagcctgag agccgaggac acggctgttt attactgtac gagagcccgt  300
ataactggaa ctttcgatgt ttttgatatc tggggccaag ggacaatggt caccgtctct  360
tcagcctcca ccaagggccc atcggtcttc cccctggcgc cctgctccag gagcacctcc  420
gagagcacag ccgccctggg ctgcctggtc aaggactact tccccgaacc ggtgacggtg  480
tcgtggaact caggcgccct gaccagcggc gtgcacacct tcccggctgt cctacagtcc  540
tcaggactct actccctcag cagcgtggtg accgtgccct ccagcagctt gggcacgaag  600
acctacacct gcaacgtaga tcacaagccc agcaacacca aggtggacaa gagagttgag  660
tccaaatatg gtcccccatg cccaccctgc ccagcacctg agttcctggg gggaccatca  720
gtcttcctgt tcccccaaa acccaaggac actctcatga tctcccggac ccctgaggtc  780
acgtgcgtgg tggtggacgt gagccaggaa gaccccgagg tccagttcaa ctggtacgtg  840
gatggcgtgg aggtgcataa tgccaagaca aagccgcggg aggagcagtt caacagcacg  900
taccgtgtgg tcagcgtcct caccgtcctg caccaggact ggctgaacgg caaggagtac  960
aagtgcaagg tctccaacaa aggcctcccg tcctccatcg agaaaaccat ctccaaagcc  1020
aaagggcagc cccgagagcc acaggtgtac accctgcccc catcccagga ggagatgacc  1080
aagaaccagg tcagcctgac ctgcctggtc aaaggcttct accccagcga catcgccgtg  1140
gagtgggaga gcaatgggca gccggagaac aactacaaga ccacgcctcc cgtgctggac  1200
tccgacggct ccttcttcct ctacagcagg ctcaccgtgg acaagagcag gtggcaggag  1260
gggaatgtct tctcatgctc cgtgatgcat gaggctctgc acaaccacta cacacagaag  1320
tccctctccc tgtctctggg taaatga                                    1347

SEQ ID NO: 357          moltype = AA  length = 448
FEATURE                 Location/Qualifiers
source                  1..448
                        mol_type = protein
                        organism = Homo sapiens
SEQUENCE: 357
EVQLVESGGG LVQPGGSLRL SCAASGFIFS SYEMHWVRQA PGKGLEWISY ISSSGTTIYY  60
ADSVKGRFTI SRDNAKNSLY LHMNSLRAED TAVYYCTRAR ITGTFDVFDI WGQGTMVTVS  120
SASTKGPSVF PLAPCSRSTS ESTAALGCLV KDYFPEPVTV SWNSGALTSG VHTFPAVLQS  180
SGLYSLSSVV TVPSSSLGTK TYTCNVDHKP SNTKVDKRVE SKYGPPCPPC PAPEFLGGPS  240
VFLFPPKPKD TLMISRTPEV TCVVVDVSQE DPEVQFNWYV DGVEVHNAKT KPREEQFNST  300
YRVVSVLTVL HQDWLNGKEY KCKVSNKGLP SSIEKTISKA KGQPREPQVY TLPPSQEEMT  360
KNQVSLTCLV KGFYPSDIAV EWESNGQPEN NYKTTPPVLD SDGSFFLYSR LTVDKSRWQE  420
GNVFSCSVMH EALHNHYTQK SLSLSLGK                                   448

SEQ ID NO: 358          moltype = DNA  length = 645
FEATURE                 Location/Qualifiers
source                  1..645
                        mol_type = unassigned DNA
                        organism = Homo sapiens
SEQUENCE: 358
gacatccaga tgacccagtc tccatcctcc ctgtctgcat ctgtgggaga cagagtcacc  60
atcacttgcc gggcaagtca gagcattagc agctatttaa attggtatca gcagaaacca  120
gggaaagccc ctaagctcct gatctttgct gcatccaatt tacagagtgg ggtcccatca  180
aggttcagtg gcagtagatc tgggacagat ttcactctca ccatcagcag tctgcaacct  240
gaagattttg caacttacta ctgtcaacag aattacaata tcccgtacac ttttggccag  300
gggaccaagc tggagatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                645

SEQ ID NO: 359          moltype = AA  length = 214
FEATURE                 Location/Qualifiers
source                  1..214
                        mol_type = protein
                        organism = Homo sapiens
SEQUENCE: 359
DIQMTQSPSS LSASVGDRVT ITCRASQSIS SYLNWYQQKP GKAPKLLIFA ASNLQSGVPS  60
RFSGSRSGTD FTLTISSLQP EDFATYYCQQ NYNIPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 360          moltype = DNA  length = 366
FEATURE                 Location/Qualifiers
```

```
source                  1..366
                        mol_type = unassigned DNA
                        organism = Homo sapiens
SEQUENCE: 360
caggtgcagc tgcaggagtc gggcccagga ctggtgaagc cttcacagac cctgtccctc  60
acctgtactg tctctggtgg ctccatcacc agtggcggtt actactggag ctggatccgc  120
cagtacccag ggcagggcct ggagtggatt ggttacatct attatagtgg gaagacctac  180
tacaatccgt cttttacgag tcgaattacc atatcagtag acacgtctaa gaagcagttc  240
tccctgaaga tgagctctgt gactgccgcg gacacggccg tgtattattg tgcgagagcg  300
ggattcacct ctagtaacgg ctggttcgac ccctggggcc agggaaccct ggtcaccgtc  360
tcctca                                                              366

SEQ ID NO: 361          moltype = AA  length = 122
FEATURE                 Location/Qualifiers
source                  1..122
                        mol_type = protein
                        organism = Homo sapiens
SEQUENCE: 361
QVQLQESGPG LVKPSQTLSL TCTVSGGSIT SGGYYWSWIR QYPGQGLEWI GYIYYSGKTY  60
YNPSFTSRIT ISVDTSKKQF SLKMSSVTAA DTAVYYCARA GFTSSNGWFD PWGQGTLVTV  120
SS                                                                  122

SEQ ID NO: 362          moltype = DNA  length = 30
FEATURE                 Location/Qualifiers
source                  1..30
                        mol_type = unassigned DNA
                        organism = Homo sapiens
SEQUENCE: 362
ggtggctcca tcaccagtgg cggttactac                                   30

SEQ ID NO: 363          moltype = AA  length = 10
FEATURE                 Location/Qualifiers
source                  1..10
                        mol_type = protein
                        organism = Homo sapiens
SEQUENCE: 363
GGSITSGGYY                                                          10

SEQ ID NO: 364          moltype = DNA  length = 21
FEATURE                 Location/Qualifiers
source                  1..21
                        mol_type = unassigned DNA
                        organism = Homo sapiens
SEQUENCE: 364
atctattata gtgggaagac c                                             21

SEQ ID NO: 365          moltype = DNA  length = 42
FEATURE                 Location/Qualifiers
source                  1..42
                        mol_type = unassigned DNA
                        organism = Homo sapiens
SEQUENCE: 365
gcgagagcgg gattcacctc tagtaacggc tggttcgacc cc                      42

SEQ ID NO: 366          moltype = AA  length = 14
FEATURE                 Location/Qualifiers
source                  1..14
                        mol_type = protein
                        organism = Homo sapiens
SEQUENCE: 366
ARAGFTSSNG WFDP                                                     14

SEQ ID NO: 367          moltype = DNA  length = 321
FEATURE                 Location/Qualifiers
source                  1..321
                        mol_type = unassigned DNA
                        organism = Homo sapiens
SEQUENCE: 367
gacatccaga tgacccagtc tccatcctcc ctatctgcat ctgtaggaga cagagtcacc  60
atcacttgcc gggcaagtca gaacattcgc agctatttga attggtatca gcagaaacca  120
gggaaagccc caaaactcct gatctattct gcatccagtt tgcaaagtgg ggtcccatca  180
aggttcagtg gcagtggatc tgggacagat ttcactctca ccatcagcag tctgcaacct  240
gaagattttc caacttacta ctgtcaacag acttacagtt ccccgtggac gttcggccct  300
gggaccaagg tggaaatcaa a                                             321

SEQ ID NO: 368          moltype = AA  length = 107
FEATURE                 Location/Qualifiers
source                  1..107
                        mol_type = protein
```

```
                         organism = Homo sapiens
SEQUENCE: 368
DIQMTQSPSS LSASVGDRVT ITCRASQNIR SYLNWYQQKP GKAPKLLIYS ASSLQSGVPS  60
RFSGSGSGTD FTLTISSLQP EDFPTYYCQQ TYSSPWTFGP GTKVEIK               107

SEQ ID NO: 369           moltype = DNA  length = 18
FEATURE                  Location/Qualifiers
source                   1..18
                         mol_type = unassigned DNA
                         organism = Homo sapiens
SEQUENCE: 369
cagaacattc gcagctat                                                18

SEQ ID NO: 370           moltype = AA  length = 6
FEATURE                  Location/Qualifiers
source                   1..6
                         mol_type = protein
                         organism = Homo sapiens
SEQUENCE: 370
QNIRSY                                                             6

SEQ ID NO: 371           moltype =   length =
SEQUENCE: 371
000

SEQ ID NO: 372           moltype =   length =
SEQUENCE: 372
000

SEQ ID NO: 373           moltype = DNA  length = 27
FEATURE                  Location/Qualifiers
source                   1..27
                         mol_type = unassigned DNA
                         organism = Homo sapiens
SEQUENCE: 373
caacagactt acagttcccc gtggacg                                      27

SEQ ID NO: 374           moltype = AA  length = 9
FEATURE                  Location/Qualifiers
source                   1..9
                         mol_type = protein
                         organism = Homo sapiens
SEQUENCE: 374
QQTYSSPWT                                                          9

SEQ ID NO: 375           moltype = DNA  length = 1350
FEATURE                  Location/Qualifiers
source                   1..1350
                         mol_type = unassigned DNA
                         organism = Homo sapiens
SEQUENCE: 375
caggtgcagc tgcaggagtc gggcccagga ctggtgaagc cttcacagac cctgtccctc  60
acctgtactg tctctggtgg ctccatcacc agtggcggtt actactggag ctggatccgc  120
cagtacccag ggcagggcct ggagtggatt ggttacatct attatagtgg gaagacctac  180
tacaatccgt cttttacgag tcgaattacc atatcagtag acacgtctaa gaagcagttc  240
tccctgaaga tgagctctgt gactgccgcg gacacggccg tgtattattg tgcgagagcg  300
ggattcacct ctagtaacgg ctggttcgac ccctggggcc agggaaccct ggtcaccgtc  360
tcctcagcct ccaccaaggg cccatcggtc ttccccctgg cgccctgctc caggagcacc  420
tccgagagca cagccgccct gggctgcctg gtcaaggact acttccccga accggtgacg  480
gtgtcgtgga actcaggcgc cctgaccagc ggcgtgcaca ccttcccggc tgtcctacag  540
tcctcaggac tctactccct cagcagcgtg gtgaccgtgc cctccagcag cttgggcacg  600
aagacctaca cctgcaacgt agatcacaag cccagcaaca ccaaggtgga caagagagtt  660
gagtccaaat atggtccccc atgcccaccc tgcccagcac ctgagttcct ggggggacca  720
tcagtcttcc tgttcccccc aaaacccaag gacactctca tgatctcccg gacccctgag  780
gtcacgtgcg tggtggtgga cgtgagccag gaagaccccg aggtccagtt caactggtac  840
gtggatggcg tggaggtgca taatgccaag acaaagccgc gggaggagca gttcaacagc  900
acgtaccgtg tggtcagcgt cctcaccgtc ctgcaccagg actggctgaa cggcaaggag  960
tacaagtgca aggtctccaa caaaggcctc ccgtcctcca tcgagaaaac catctccaaa  1020
gccaaagggc agccccgaga gccacaggtg tacaccctgc ccccatccca ggaggagatg  1080
accaagaacc aggtcagcct gacctgcctg gtcaaaggct tctaccccag cgacatcgcc  1140
gtggagtggg agagcaatgg gcagccggag aacaactaca agaccacgcc tcccgtgctg  1200
gactccgacg gctccttctt cctctacagc aggctcaccg tggacaagag caggtggcag  1260
gaggggaatg tcttctcatg ctccgtgatg catgaggctc tgcacaacca ctacacacag  1320
aagtccctct ccctgtctct gggtaaatga                                   1350

SEQ ID NO: 376           moltype = AA  length = 449
FEATURE                  Location/Qualifiers
source                   1..449
                         mol_type = protein
```

```
                         organism = Homo sapiens
SEQUENCE: 376
QVQLQESGPG LVKPSQTLSL TCTVSGGSIT SGGYYWSWIR QYPGQGLEWI GYIYYSGKTY  60
YNPSFTSRIT ISVDTSKKQF SLKMSSVTAA DTAVYYCARA GFTSSNGWFD PWGQGTLVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGK                                   449

SEQ ID NO: 377           moltype = DNA  length = 645
FEATURE                  Location/Qualifiers
source                   1..645
                         mol_type = unassigned DNA
                         organism = Homo sapiens
SEQUENCE: 377
gacatccaga tgacccagtc tccatcctcc ctatctgcat ctgtaggaga cagagtcacc  60
atcacttgcc gggcaagtca gaacattcgc agctatttga attggtatca gcagaaacca  120
gggaaagccc caaaactcct gatctattct gcatccagtt tgcaaagtgg ggtcccatca  180
aggttcagtg gcagtggatc tgggacagat ttcactctca ccatcagcag tctgcaacct  240
gaagattttc caacttacta ctgtcaacag acttacagtt ccccgtggac gttcggccct  300
gggaccaagg tggaaatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                 645

SEQ ID NO: 378           moltype = AA  length = 214
FEATURE                  Location/Qualifiers
source                   1..214
                         mol_type = protein
                         organism = Homo sapiens
SEQUENCE: 378
DIQMTQSPSS LSASVGDRVT ITCRASQNIR SYLNWYQQKP GKAPKLLIYS ASSLQSGVPS  60
RFSGSGSGTD FTLTISSLQP EDFPTYYCQQ TYSSPWTFGP GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 379           moltype = AA  length = 268
FEATURE                  Location/Qualifiers
REGION                   1..268
                         note = Human IL2R extracellular domain expressed with a
                          C-terminalmyc-myc-hexahistidine tag
source                   1..268
                         mol_type = protein
                         organism = synthetic construct
SEQUENCE: 379
LNTTILTPNG NEDTTADFFL TTMPTDSLSV STLPLPEVQC FVFNVEYMNC TWNSSSEPQP  60
TNLTLHYWYK NSDNDKVQKC SHYLFSEEIT SGCQLQKKEI HLYQTFVVQL QDPREPRRQA  120
TQMLKLQNLV IPWAPENLTL HKLSESQLEL NWNNRFLNHC LEHLVQYRTD WDHSWTEQSV  180
DYRHKFSLPS VDGQKRYTFR VRSRFNPLCG SAQHWSEWSH PIHWGSNTSK ENPFLFALEA  240
EQKLISEEDL GGEQKLISEE DLHHHHHH                                    268

SEQ ID NO: 380           moltype = AA  length = 268
FEATURE                  Location/Qualifiers
REGION                   1..268
                         note = Macaca fascicularis IL2R extracellular domain
                          expressed with aC-terminal myc-myc-hexahistidine tag
source                   1..268
                         mol_type = protein
                         organism = synthetic construct
SEQUENCE: 380
LNTTILTPNG NEDATTDFFL TSMPTDSLSV STLPLPEVQC FVFNVEYMNC TWNSSSEPQP  60
TNLTLHYWYK NSDNDKVQKC SHYLFSEEIT SGCQLQKKEI HLYQTFVVQL QDPREPRRQA  120
TQMLKLQNLV IPWAPENLTL RKLSESQLEL NWNNRFLNHC LEHLVQYRTD WDHSWTEQSV  180
DYRHKFSLPS VDGQKRYTFR VRSRFNPLCG SAQHWSEWSH PIHWGSNSSK ENPFLFALEA  240
EQKLISEEDL GGEQKLISEE DLHHHHHH                                    268

SEQ ID NO: 381           moltype = AA  length = 473
FEATURE                  Location/Qualifiers
REGION                   1..473
                         note = Human IL2Rextracellular domain expressed with a
                          C-terminalmouse IgG2a Fc tag
source                   1..473
                         mol_type = protein
                         organism = synthetic construct
SEQUENCE: 381
```

-continued

```
LNTTILTPNG NEDTTADFFL TTMPTDSLSV STLPLPEVQC FVFNVEYMNC TWNSSSEPQP  60
TNLTLHYWYK NSDNDKVQKC SHYLFSEEIT SGCQLQKKEI HLYQTFVVQL QDPREPRRQA  120
TQMLKLQNLV IPWAPENLTL HKLSESQLEL NWNNRFLNHC LEHLVQYRTD WDHSWTEQSV  180
DYRHKFSLPS VDGQKRYTFR VRSRFNPLCG SAQHWSEWSH PIHWGSNTSK ENPFLFALEA  240
EPRGPTIKPC PPCKCPAPNL LGGPSVFIFP PKIKDVLMIS LSPIVTCVVV DVSEDDPDVQ  300
ISWFVNNVEV HTAQTQTHRE DYNSTLRVVS ALPIQHQDWM SGKEFKCKVN NKDLPAPIER  360
TISKPKGSVR APQVYVLPPP EEEMTKKQVT LTCMVTDFMP EDIYVEWTNN GKTELNYKNT  420
EPVLDSDGSY FMYSKLRVEK KNWVERNSYS CSVVHEGLHN HHTTKSFSRT PGK         473

SEQ ID NO: 382          moltype = AA  length = 159
FEATURE                 Location/Qualifiers
REGION                  1..159
                        note = D1 domain of human IL-2R extracellular domain
                         expressed with aC-terminal myc-myc-hexahistidine tag
source                  1..159
                        mol_type = protein
                        organism = synthetic construct
SEQUENCE: 382
LNTTILTPNG NEDTTADFFL TTMPTDSLSV STLPLPEVQC FVFNVEYMNC TWNSSSEPQP  60
TNLTLHYWYK NSDNDKVQKC SHYLFSEEIT SGCQLQKKEI HLYQTFVVQL QDPREPRRQA  120
TQMLKLQNLV IEQKLISEED LGGEQKLISE EDLHHHHHH                        159

SEQ ID NO: 383          moltype = AA  length = 116
FEATURE                 Location/Qualifiers
REGION                  1..116
                        note = D2 domain of human IL2R extracellular domain
                         expressed with aC-terminal myc-myc-hexahistidine tag
source                  1..116
                        mol_type = protein
                        organism = synthetic construct
SEQUENCE: 383
PWAPENLTLH KLSESQLELN WNNRFLNHCL EHLVQYRTDW DHSWTEQSVD YRHKFSLPSV  60
DGQKRYTFRV RSRFNPLCGS AQHWSEWSEQ KLISEEDLGG EQKLISEEDL HHHHHH      116

SEQ ID NO: 384          moltype = AA  length = 269
FEATURE                 Location/Qualifiers
REGION                  1..269
                        note = Mouse IL2R extracellular domain expressed with a
                         C-terminalmyc-myc-hexahistidine tag
source                  1..269
                        mol_type = protein
                        organism = synthetic construct
SEQUENCE: 384
WSSKVLMSSA NEDIKADLIL TSTAPEHLSA PTLPLPEVQC FVFNIEYMNC TWNSSSEPQA  60
TNLTLHYRYK VSDNNTFQEC SHYLFSKEIT SGCQIQKEDI QLYQTFVVQL QDPQKPQRRA  120
VQKLNLQNLV IPRAPENLTL SNLSESQLEL RWKSRHIKER CLQYLVQYRS NRDRSWTELI  180
VNHEPRFSLP SVDELKRYTF RVRSRYNPIC GSSQQWSKWS QPVHWGSHTV EENPSLFALE  240
AEQKLISEED LGGEQKLISE EDLHHHHHH                                   269

SEQ ID NO: 385          moltype = AA  length = 268
FEATURE                 Location/Qualifiers
REGION                  1..268
                        note = Rat IL2R extracellular domain expressed with a
                         C-terminalmyc-myc-hexahistidine tag
source                  1..268
                        mol_type = protein
                        organism = synthetic construct
SEQUENCE: 385
WSSKVLMSSG NEDTKSDLLL TSMDLKHLSV PTLPLPEVQC FVFNVEYMNC TWNSSSEPQP  60
TNLTMHYRYK GSDNNTFQEC SHYLFSKEIT SGCQIQKEDI QLYQTFVVQL QDPQKPQRRA  120
EQKLNLQNLV IPWAPENLTL YNLSESQVEL RWKSRYIERC LQYLVQYRSN RDRSWTEQIV  180
DHEPRFSLPS VDEQKLYTFR VRSRFNPICG STQQWSKWSQ PIHWGSHTAE ENPSLFALEA  240
EQKLISEEDL GGEQKLISEE DLHHHHHH                                    268

SEQ ID NO: 386          moltype = AA  length = 5
FEATURE                 Location/Qualifiers
REGION                  1..5
                        note = G4S linker
source                  1..5
                        mol_type = protein
                        organism = synthetic construct
SEQUENCE: 386
GGGGS                                                             5
```

We claim:

1. A method for treating an interleukin-2 receptor gamma (IL2Rγ)-mediated disease or condition, in a subject in need thereof, comprising administering to the subject an effective amount of an antibody or antigen-binding fragment thereof that specifically binds to IL2Rγ, wherein the antibody or antigen-binding fragment thereof comprises a heavy chain immunoglobulin or variable region thereof comprising a CDR-H1 comprising the amino acid sequence set forth in SEQ ID NO: 347, a CDR-H2 comprising the amino acid sequence set forth in SEQ ID NO: 349, and a CDR-H3 comprising the amino acid sequence set forth in SEQ ID NO: 351; and a light chain immunoglobulin or variable region thereof comprising a CDR-L1 comprising the amino acid sequence set forth in SEQ ID NO: 72, a CDR-L2 comprising the amino acid sequence set forth in SEQ ID NO: 54, and a CDR-L3 comprising the amino acid sequence set forth in SEQ ID NO: 355.

2. The method of claim 1, wherein the IL2Rγ-mediated disease or condition is graft-versus-host disease, organ transplant rejection, b-islet cell graft rejection, skin transplant rejection, heart transplant rejection, lung transplant rejection, kidney transplant rejection, liver transplant rejection, birdshot chorioretinopathy, multiple sclerosis, uveitis, an autoimmune disease, Type I diabetes, multiple sclerosis, rheumatoid arthritis, systemic lupus erythematosus, myasthenia gravis, aplastic anemia, atopic dermatitis, asthma, a mast cell activation disorder, mast cell activation syndrome (MCAS), systemic mastocytosis (SM), or mast cell leukemia (MCL).

3. The method of claim 1, wherein the antibody or antigen-binding fragment thereof is administered by injection into the body of the subject subcutaneously, intravenously or intramuscularly.

4. The method of claim 2, wherein the IL2Rγ-mediated disease or condition is graft-versus-host disease.

5. The method of claim 4, wherein the IL2Rγ-mediated disease or condition is acute graft-versus-host disease.

6. The method of claim 4, wherein the IL2Rγ-mediated disease or condition is chronic graft-versus-host disease.

7. The method of claim 2, wherein the IL2Rγ-mediated disease or condition is aplastic anemia.

8. The method of claim 1, wherein the antibody or antigen-binding fragment thereof is a monoclonal antibody.

9. The method of claim 1, wherein the antibody or antigen-binding fragment thereof is a human antibody.

10. The method of claim 1, wherein the antibody or antigen-binding fragment thereof is an antigen-binding fragment of an antibody.

11. The method of claim 1, wherein the heavy chain variable region comprises the amino acid sequence set forth in SEQ ID NO: 345; and/or the light chain variable region comprises the amino acid sequence set forth in SEQ ID NO: 353.

12. The method of claim 11, wherein the heavy chain variable region comprises the amino acid sequence set forth in SEQ ID NO: 345 and the light chain variable region comprises the amino acid sequence set forth in SEQ ID NO: 353.

13. The method of claim 1, wherein the heavy chain comprises the amino acid sequence set forth in SEQ ID NO: 357; and/or the light chain comprises the amino acid sequence set forth in SEQ ID NO: 359.

14. The method of claim 2, wherein the IL2Rγ-mediated disease or condition is organ transplant rejection.

15. A method of treating graft-versus-host disease in a subject in need thereof, comprising administering to the subject an effective amount of an antibody that specifically binds to interleukin-2 receptor gamma (IL2Rγ), wherein the antibody comprises a heavy chain immunoglobulin comprising a CDR-H1 comprising the amino acid sequence set forth in SEQ ID NO: 347, a CDR-H2 comprising the amino acid sequence set forth in SEQ ID NO: 349, and a CDR-H3 comprising the amino acid sequence set forth in SEQ ID NO: 351; and a light chain immunoglobulin comprising a CDR-L1 comprising the amino acid sequence set forth in SEQ ID NO: 72, a CDR-L2 comprising the amino acid sequence set forth in SEQ ID NO: 54, and a CDR-L3 comprising the amino acid sequence set forth in SEQ ID NO: 355.

16. The method of claim 15, wherein the graft-versus-host disease is acute graft-versus-host disease.

17. The method of claim 15, wherein the graft-versus-host disease is chronic graft-versus-host disease.

18. The method of claim 15, wherein the antibody comprises a heavy chain variable region that comprises the amino acid sequence set forth in SEQ ID NO: 345 and a light chain variable region that comprises the amino acid sequence set forth in SEQ ID NO: 353.

19. The method of claim 18, wherein the antibody comprises a heavy chain that comprises the amino acid sequence set forth in SEQ ID NO: 357 and a light chain that comprises the amino acid sequence set forth in SEQ ID NO: 359.

20. A method of treating aplastic anemia in a subject in need thereof, comprising administering to the subject an effective amount of an antibody that specifically binds to interleukin-2 receptor gamma (IL2Rγ), wherein the antibody comprises a heavy chain immunoglobulin comprising a CDR-H1 comprising the amino acid sequence set forth in SEQ ID NO: 347, a CDR-H2 comprising the amino acid sequence set forth in SEQ ID NO: 349, and a CDR-H3 comprising the amino acid sequence set forth in SEQ ID NO: 351; and a light chain immunoglobulin comprising a CDR-L1 comprising the amino acid sequence set forth in SEQ ID NO: 72, a CDR-L2 comprising the amino acid sequence set forth in SEQ ID NO: 54, and a CDR-L3 comprising the amino acid sequence set forth in SEQ ID NO: 355.

21. The method of claim 20, wherein the antibody comprises a heavy chain variable region that comprises the amino acid sequence set forth in SEQ ID NO: 345 and a light chain variable region comprises that the amino acid sequence set forth in SEQ ID NO: 353.

22. The method of claim 21, wherein the antibody comprises a heavy chain that comprises the amino acid sequence set forth in SEQ ID NO: 357 and a light chain that comprises the amino acid sequence set forth in SEQ ID NO: 359.

23. A method of preventing or delaying the onset of organ transplant rejection in a subject in need thereof, comprising administering to the subject an effective amount of an antibody that specifically binds to interleukin-2 receptor gamma (IL2Rγ), wherein the antibody comprises a heavy chain immunoglobulin comprising a CDR-H1 comprising the amino acid sequence set forth in SEQ ID NO: 347, a CDR-H2 comprising the amino acid sequence set forth in SEQ ID NO: 349, and a CDR-H3 comprising the amino acid sequence set forth in SEQ ID NO: 351; and a light chain immunoglobulin comprising a CDR-L1 comprising the amino acid sequence set forth in SEQ ID NO: 72, a CDR-L2 comprising the amino acid sequence set forth in SEQ ID NO: 54, and a CDR-L3 comprising the amino acid sequence set forth in SEQ ID NO: 355.

24. The method of claim 23, wherein the antibody comprises a heavy chain variable region that comprises the amino acid sequence set forth in SEQ ID NO: 345 and a light chain variable region comprises that the amino acid sequence set forth in SEQ ID NO: 353.

25. The method of claim 23, wherein the antibody comprises a heavy chain that comprises the amino acid sequence set forth in SEQ ID NO: 357 and a light chain that comprises the amino acid sequence set forth in SEQ ID NO: 359.

* * * * *